US006623923B1

(12) United States Patent
Xu et al.

(10) Patent No.: US 6,623,923 B1
(45) Date of Patent: Sep. 23, 2003

(54) COMPOUNDS FOR IMMUNOTHERAPY AND DIAGNOSIS OF COLON CANCER AND METHODS FOR THEIR USE

(75) Inventors: Jiangchun Xu, Bellevue, WA (US); Michael J. Lodes, Seattle, WA (US); Heather Secrist, Seattle, WA (US); Madeleine Joy Meagher, Seattle, WA (US); John Stolk, Bothell, WA (US); Darin R. Benson, Seattle, WA (US); Tongtong Wang, Medina, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/401,064

(22) Filed: Sep. 22, 1999

Related U.S. Application Data

(63) Continuation-in-part of application No. 09/347,496, filed on Jul. 2, 1999, which is a continuation-in-part of application No. 09/221,298, filed on Dec. 23, 1998, now Pat. No. 6,284,241.

(51) Int. Cl.[7] .......................... C12Q 1/68; C07H 21/04
(52) U.S. Cl. ..................... 435/6; 536/23.1; 536/24.3; 536/24.31; 536/24.33
(58) Field of Search .................. 435/6; 536/23.5, 536/24.3, 24.31, 24.33

(56) References Cited

U.S. PATENT DOCUMENTS

| | | | |
|---|---|---|---|
| 5,929,033 A | 7/1999 | Tang et al. ............. 514/12 |
| 5,986,170 A | 11/1999 | Subjeck ................. 800/2 |
| 6,183,968 B1 | 2/2001 | Bandman et al. ........ 435/6 |
| 6,261,562 B1 * | 7/2001 | Xu et al. ............. 424/185.1 |

FOREIGN PATENT DOCUMENTS

| | | |
|---|---|---|
| EP | 0 317 141 | 5/1989 |
| EP | 0478146 A1 * | 8/1991 |
| WO | WO 98/53319 | 11/1998 |
| WO | WO 99/01020 | 1/1999 |
| WO | WO 99/60161 | 11/1999 |
| WO | WO 99/63088 | 12/1999 |
| WO | WO 00/21991 | 4/2000 |
| WO | WO 00/37643 | 6/2000 |
| WO | WO 00/55350 | 9/2000 |
| WO | WO 00/73348 | 12/2000 |
| WO | WO 01/42285 | 6/2001 |

OTHER PUBLICATIONS

Genbank Accession No. AAQ22438, 1995.*
GenBank Accession No. 095362, May 1, 1999.
Sjögren, H., "Therapeutic immunization against cancer antigens using genetically engineered cells," *Immunotechnology* 3:161–172, 1997.

Chan et al., "Identification of novel genes that are differentially expressed in human colorectal carcinoma," *Biochimica et Biophysica Acta*, 1407:200–204, 1998.

Frigerio et al., "Analysis of 2166 clones from a human colorectal cancer cDNA library by partial sequencing," *Human Molecular Genetics*, 4(1):37–43, 1995.

Gelos et al., "Detection of genes differentially expressed in colorectal cancer: comparison of three methods," *2 nd Congress of Molecular Medicine; Berlin, Germany*, 76(6):B13, May, 1998.

Grimm and Johnson, "A modified screening method for pcDNA-1 expression libraries which is applicable to both surface and intracellular antigens Cloning of a colon carcinoma antigen," *Journal of Immunological Methods*, 186:305–312, 1995.

Tortola et al., "Analysis of differential gene expression in human colorectal tumor tissue by RNA arbitrarily primed–PCR: a technical assessment," *Laboratory Investigation*, 78(3):309–317, Mar., 1998.

Yeatman and Mao, "Identification of a differentially–expressed message associated with colon cancer liver metastasis using an improved method of differential display," *Nucleic Acid Research*, 23(19):4007–4008, Mar., 1998.

GenBank Accession No. AA366895, "Initial assessment of human gene diversity and expression patterns based upon 83 million basepairs of cDNA sequence," located at http://www.ncbi.nlm.nih.gov.

GenBank Accession No. AF097021, "Identification and characterization of novel full–length cDNAs differentially expressed in human hematopoietic lineages," located at http://www.ncbi.nlm.nih.gov.

* cited by examiner

*Primary Examiner*—Shin-Lin Chen
(74) *Attorney, Agent, or Firm*—Eric M. Barzee; Cynthia L. Shumate

(57) ABSTRACT

Compositions and methods for the therapy and diagnosis of cancer, such as colon cancer, are disclosed. Compositions may comprise one or more colon tumor proteins, immunogenic portions thereof, or polynucleotides that encode such portions. Alternatively, a therapeutic composition may comprise an antigen presenting cell that expresses a colon tumor protein, or a T cell that is specific for cells expressing such a protein. Such compositions may be used, for example, for the prevention and treatment of diseases such as colon cancer. Diagnostic methods based on detecting a colon tumor protein, or mRNA encoding such a protein, in a sample are also provided.

4 Claims, No Drawings

COMPOUNDS FOR IMMUNOTHERAPY AND DIAGNOSIS OF COLON CANCER AND METHODS FOR THEIR USE

REFERENCE TO RELATED APPLICATIONS

This application is a continuation-in-part of U.S. patent application Ser. No. 09/347,496, filed Jul. 2, 1999, which is a continuation-in-part of U.S. patent application Ser. No. 09/221,298, filed Dec. 23, 1998 now U.S. Pat. No. 6,284,241.

TECHNICAL FIELD

The present invention relates generally to therapy and diagnosis of cancer, such as colon cancer. The invention is more specifically related to polypeptides comprising at least a portion of a colon tumor protein, and to polynucleotides encoding such polypeptides. Such polypeptides and polynucleotides may be used in vaccines and pharmaceutical compositions for prevention and treatment of colon cancer, and for the diagnosis and monitoring of such cancers.

BACKGROUND OF THE INVENTION

Cancer is a significant health problem throughout the world. Although advances have been made in detection and therapy of cancer, no vaccine or other universally successful method for prevention or treatment is currently available. Current therapies, which are generally based on a combination of chemotherapy or surgery and radiation, continue to prove inadequate in many patients.

Colon cancer is the second most frequently diagnosed malignancy in the United States as well as the second most common cause of cancer death. An estimated 95,600 new cases of colon cancer will be diagnosed in 1998, with an estimated 47,700 deaths. The five-year survival rate for patients with colorectal cancer detected in an early localized stage is 92%; unfortunately, only 37% of colorectal cancer is diagnosed at this stage. The survival rate drops to 64% if the cancer is allowed to spread to adjacent organs or lymph nodes, and to 7% in patients with distant metastases.

The prognosis of colon cancer is directly related to the degree of penetration of the tumor through the bowel wall and the presence or absence of nodal involvement, consequently, early detection and treatment are especially important. Currently, diagnosis is aided by the use of screening assays for fecal occult blood, sigmoidoscopy, colonoscopy and double contrast barium enemas. Treatment regimens are determined by the type and stage of the cancer, and include surgery, radiation therapy and/or chemotherapy. Recurrence following surgery (the most common form of therapy) is a major problem and is often the ultimate cause of death. In spite of considerable research into therapies for the disease, colon cancer remains difficult to diagnose and treat. In spite of considerable research into therapies for these and other cancers, colon cancer remains difficult to diagnose and treat effectively. Accordingly, there is a need in the art for improved, methods for detecting and treating such cancers. The present invention fulfills these needs and further provides other related advantages.

SUMMARY OF THE INVENTION

Briefly stated, the present invention provides compositions and methods for the diagnosis and therapy of cancer, such as colon cancer. In one aspect the present invention provides polypeptides comprising at least a portion of a colon tumor protein, or a variant thereof. Certain portions and other variants are immunogenic, such that the ability of the variant to react with antigen-specific antisera is not substantially diminished Within certain embodiments, the polypeptide comprises a sequence that is encoded by a polynucleotide sequence selected from the group consisting of: (a) sequences recited in SEQ ID NO: 2, 8, 15, 16, 22, 24, 30, 32–34, 36, 38, 40, 41, 46–49, 52, 54, 59, 60, 65–69, 79, 89, 90, 93, 99–101, 109–111, 116–119, 123–132, 138–142, 143, 148, 149, 156, 168, 170–182, 184, 189, 191–193, 196, 205, 207, 210–212, 214, 215, 218, 224–226, 228, 233, 234, 236, 238, 241, 242, 245, 246, 248, 250, 253, 254, 256, 259, 260, 262, 263, 266, 267, 270–273, 279 282, 291, 293, 294, 298, 300, 302, 303, 310–313, 315, 317, 320, 322, 324, 332–335, 345, 347, 356, 358, 361, 362, 366, 369 and 371, (b) variants of a sequence recited in SEQ ID NO: 2, 8, 15, 16, 22, 24, 30, 32–34, 36, 38, 40, 41, 46–49, 52, 54, 59, 60, 65–69, 79, 89, 90, 93, 99–101, 109–111, 116–119, 123–132, 138–142, 143, 148, 149, 156, 168, 170–182, 184, 189, 191–193, 196, 205, 207, 210–212, 214, 215, 218, 224–226, 228, 233, 234, 236, 238, 241, 242, 245, 246, 248, 250, 253, 254, 256, 259, 260, 262, 263, 266, 267, 270–273, 279, 282, 291, 293, 294, 298, 300, 302, 303, 310–313, 315, 317, 320, 322, 324, 332–335, 345, 347, 356, 358, 361, 362, 366, 369 and 371; and (c) complements of a sequence of (a) or (b).

The present invention further provides polynucleotides that encode a polypeptide as described above, or a portion thereof (such as a portion encoding at least 15 amino acid residues of a colon tumor protein), expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, vaccines are provided. Such vaccines comprise a polypeptide or polynucleotide as described above and a non-specific immune response enhancer.

The present invention further provides pharmaceutical compositions that comprise: (a) an antibody or antigen-binding fragment thereof that specifically binds to a colon tumor protein; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Antigen presenting cells include dendritic cells, macrophages, monocytes, fibroblasts and B cells.

Within related aspects, vaccines are provided that comprise: (a) an antigen presenting cell that expresses a polypeptide as described above and (b) a non-specific immune response enhancer.

The present invention further provides, in other aspects, fusion proteins that comprise at least one polypeptide as described above, as well as polynucleotides encoding such fusion proteins.

Within related aspects, pharmaceutical compositions comprising a fusion protein, or a polynucleotide encoding a fusion protein, in combination with a physiologically acceptable carrier are provided.

Vaccines are further provided, within other aspects, that comprise a fusion protein, or a polynucleotide encoding a fusion protein, in combination with a non-specific immune response enhancer.

Within further aspects, the present invention provides methods for inhibiting the development of a cancer in a patient, comprising administering to a patient a pharmaceutical composition or vaccine as recited above.

The present invention further provides, within other aspects, methods for removing tumor cells from a biological sample, comprising contacting a biological sample with T cells that specifically react with a colon tumor protein, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a colon tumor protein, comprising contacting T cells with one or more of: (i) a polypeptide as described above, (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells isolated from a patient with one or more of: (i) a polypeptide comprising at least an immunogenic portion of a colon tumor protein; (ii) a polynucleotide encoding such a polypeptide; and (iii) an antigen-presenting cell that expresses such a polypeptide, and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer in a patient, comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody. The cancer may be colon cancer.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating, steps (a) and (b) using a biological sample obtained from the patient at a subsequent point in time; and (d) comparing the amount of polypeptide detected in step (c) with the amount detected step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a colon tumor protein; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a colon tumor protein; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description. All references disclosed herein are hereby incorporated by reference in their entirety as if each was incorporated individually.

BRIEF DESCRIPTION OF THE SEQUENCE IDENTIFIERS

SEQ ID NO: 1 is a first determined cDNA sequence for Contig 1, showing homology to Neutrophil Gelatinase Associated Lipocalin.

SEQ ID NO: 2 is the determined cDNA sequence for Contig 2, showing no significant homology to any known genes.

SEQ ID NO: 3 is the determined cDNA sequence for Contig 4, showing homology to Carcinoembryonic antigen.

SEQ ID NO: 4 is the determined cDNA sequence for Contig 5, showing homology to Carcinoembryonic antigen.

SEQ ID NO: 5 is the determined cDNA sequence for Contig 9, showing homology to Carcinoembryonic antigen.

SEQ ID NO: 6 is the determined cDNA sequence for Contig 52, showing homology to Carcinoembryonic antigen.

SEQ ID NO: 7 is the determined cDNA sequence for Contig 6, showing homology to Villin.

SEQ ID NO: 8 is the determined cDNA sequence for Contig 8, showing no significant homology to any known genes.

SEQ ID NO: 9 is the determined cDNA sequence for Contig 10, showing homology to Transforming Growth Factor (BIGH3).

SEQ ID NO: 10 is the determined cDNA sequence for Contig 19, showing homology to Transforming Growth Factor (BIGH3).

SEQ ID NO: 11 is the determined cDNA sequence for Contig 21, showing homology to Transforming Growth Factor (BIGH3).

SEQ ID NO: 12 is the determined cDNA sequence for Contig 11, showing homology to CO-029.

SEQ ID NO: 13 is the determined cDNA sequence for Contig 55, showing homology to CO-029.

SEQ ID NO: 14 is the determined cDNA sequence for Contig 12, showing homology to Chromosome 17, clone hRPC.1171_I_10, also referred to as C798P.

SEQ ID NO: 15 is the determined cDNA sequence for Contig 13, showing no significant homology to any known gene.

SEQ ID NO: 16 is the determined cDNA sequence for Contig 14, also referred to as 14261, showing no significant homology to any known gene.

SEQ ID NO: 17 is the determined cDNA sequence for Contig 15, showing homology to Ets-Related Transcription Factor (ERT).

SEQ ID NO: 18 is the determined cDNA sequence for Contig 16, showing homology to Chromosome 5, PAC clone 228g9 (LBNL H142).

SEQ ID NO: 19 is the determined cDNA sequence for Contig 24, showing homology to Chromosome 5, PAC clone 228g9 (LBNL H142).

SEQ ID NO: 20 is the determined cDNA sequence for Contig 17, showing homology to Cytokeratin.

SEQ ID NO; 21 is the determined cDNA sequence for Contig 18, showing homology to L1-Cadherin.

SEQ ID NO: 22 is the determined cDNA sequence for Contig 20, showing no significant homology to any known gene.

SEQ ID NO: 23 is the determined cDNA sequence for Contig 22, showing homology to Bumetanide-sensitive Na-K-Cl cotransporter (NKCCl).

SEQ ID NO: 24 is the determined cDNA sequence for Contig 23, showing no significant homology to any known gene.

SEQ ID NO: 25 is the determined cDNA sequence for Contig 25, showing homology to Macrophage Inflammatory Protein 3 alpha.

SEQ ID NO: 26 is the determined cDNA sequence for Contig 26, showing homology to Laminin.

SEQ ID NO: 27 is the determined cDNA sequence for Contig 48, showing homology to Laminin.

SEQ ID NO: 28 is the determined cDNA sequence for Contig 27, showing homology to Mytobularin (MTM1).

SEQ ID NO: 29 is the determined cDNA sequence for Contig 28, showing homology to Chromosome 16 BAC clone CIT987SK-A-363E6.

SEQ ID NO: 30 is the determined cDNA sequence for Contig 29, also referred to as C751P and 14247, showing no significant homology to any known gene, but partial homology to Rat GSK-3β-interacting protein Axil homolog.

SEQ ID NO: 31 is the determined cDNA sequence for Contig 30, showing homology to Zinc-Finger Transcription Factor (ZNF207).

SEQ ID NO: 32 is the determined cDNA sequence for Contig 31, showing no significant homology to any known gene, but partial homology to Mus musculus GOB-4 homolog.

SEQ ID NO: 33 is the determined cDNA sequence for Contig 35, showing no significant homology to any known gene, but partial homology to Mus musculus GOB-4 homolog.

SEQ ID NO: 34 is the determined cDNA sequence for Contig 32, showing no significant homology to any known gene.

SEQ ID NO: 35 is the determined cDNA sequence for Contig 34, showing homology to Desmoglein 2.

SEQ ID NO: 36 is the determined cDNA sequence for Contig 36, showing no significant homology to any known gene.

SEQ ID NO: 37 is the determined cDNA sequence for Contig 37, showing homology to Putative Transmembrane Protein.

SEQ ID NO: 38 is the determined cDNA sequence for Contig 38, also referred to as C796P and 14219, showing no significant homology to any known gene.

SEQ ID NO: 39 is the determined cDNA sequence for Contig 40, showing homology to Nonspecific Cross-reacting Antigen.

SEQ ID NO: 40 is the determined cDNA sequence for Contig 41, also referred to as C799P and 14308, showing no significant homology to any known gene.

SEQ ID NO: 41 is the determined cDNA sequence for Contig 42, also referred to as C794P and 14309, showing no significant homology to any known gene.

SEQ ID NO: 42 is the determined cDNA sequence for Contig 43, showing homology to Chromosome 1 specific transcript KIAA0487.

SEQ ID NO: 43 is the determined cDNA sequence for Contig 45, showing homology to hMCM2.

SEQ ID NO: 44 is the determined cDNA sequence for Contig 46, showing homology to ETS2.

SEQ ID NO: 45 is the determined cDNA sequence for Contig 49, showing homology to Pump-1.

SEQ ID NO: 46 is the determined cDNA sequence for Contig 50, also referred to as C792P and 18323, showing no significant homology to any known gene.

SEQ ID NO: 47 is the determined cDNA sequence for Contig 51, also referred to as C795P and 14317, showing no significant homology to any known gene.

SEQ ID NO: 48 is the determined cDNA sequence for 11092, showing no significant homology to any known gene.

SEQ ID NO: 49 is the determined cDNA sequence for 11093, showing no significant homology to any known gene.

SEQ ID NO: 50 is the determined cDNA sequence for 11094, showing homology Human Putative Enterocyte Differentiation Protein.

SEQ ID NO: 51 is the determined cDNA sequence for 11095, showing homology to Human Transcriptional Corepressor hKAP1/TIF1B mRNA.

SEQ ID NO: 52 is the determined cDNA sequence for 11096, showing no significant homology to any known gene.

SEQ ID NO: 53 is the determined cDNA sequence for 11097, showing homology to Human Nonspecific Antigen.

SEQ ID NO: 54 is the determined cDNA sequence for 11098, showing no significant homology to any known gene.

SEQ ID NO: 55 is the determined cDNA sequence for 11099, showing homology to Human Pancreatic Secretory Inhibitor (PST) mRNA.

SEQ ID NO: 56 is the determined cDNA sequence for 11186, showing homology to Human Pancreatic Secretory Inhibitor (PST) mRNA.

SEQ ID NO: 57 is the determined cDNA sequence for 11101, showing homology to Human Chromosome X.

SEQ ID NO: 58 is the determined cDNA sequence for 11102, showing homology to Human Chromosome X.

SEQ ID NO: 59 is the determined cDNA sequence for 11103, showing no significant homology to any known gene.

SEQ ID NO: 60 is the determined cDNA sequence for 11174, showing no significant homology to any known gene.

SEQ ID NO: 61 is the determined cDNA sequence for 11104, showing homology to Human mRNA for KIAA0154.

SEQ ID NO: 62 is the determined cDNA sequence for 11105, showing homology to Human Apurinic/Apyrimidinic Endonuclease (hap 1)mRNA.

SEQ ID NO: 63 is the determined cDNA sequence for 11106, showing homology to Human Chromosome 12p13.

SEQ ID NO: 64 is the determined cDNA sequence for 11107, showing homology to Human 90 kDa Heat Shock Protein.

SEQ ID NO: 65 is the determined cDNA sequence for 11108, showing no significant homology to any known gene.

SEQ ID NO: 66 is the determined cDNA sequence for 11112, showing no significant homology to any known gene.

SEQ ID NO: 67 is the determined cDNA sequence for 11115, showing no significant homology to any known gene.

SEQ ID NO: 68 is the determined cDNA sequence for 11117, showing no significant homology to any known gene.

SEQ ID NO: 69 is the determined cDNA sequence for 11118, showing no significant homology to any known gene.

SEQ ID NO: 70 is the determined cDNA sequence for 11119, showing homology to Human Elongation Factor 1-alpha.

SEQ ID NO: 71 is the determined cDNA sequence for 11121, showing homology to Human Lamin B Receptor (LBR) mRNA.

SEQ ID NO: 72 is the determined cDNA sequence for 11122, showing homology to *H. sapiens* mRNA for Novel Glucocorticoid.

SEQ ID NO: 73 is the determined cDNA sequence for 11123, showing homology to *H. sapiens* mRNA for snRNA protein B.

SEQ ID NO: 74 is the determined cDNA sequence for 11124, showing homology to Human Cisplatin Resistance Associated Beta-protein.

SEQ ID NO: 75 is the determined cDNA sequence for 11127, showing homology to *M. musculus* Calumenin mRNA.

SEQ ID NO: 76 is the determined cDNA sequence for 11128, showing homology to Human ras-related small GTP binding protein.

SEQ ID NO: 77 is the determined cDNA sequence for 11130, showing homology to Human Cosmid U169d2.

SEQ ID NO: 78 is the determined cDNA sequence for 11131, showing homology to *H. sapiens* mRNA for protein homologous to Elongation 1-g.

SEQ ID NO: 79 is the determined cDNA sequence for 11134, showing no significant homology to any known gene.

SEQ ID NO: 80 is the determined cDNA sequence for 11135, showing homology to *H. sapiens* Nieman-Pick (NPC1) mRNA.

SEQ ID NO: 81 is the determined cDNA sequence for 11137, showing homology to *H. sapiens* mRNA for Niecin b-chain.

SEQ ID NO: 82 is the determined cDNA sequence for 11138, showing homology to Human Endogenous Retroviral Protease mRNA.

SEQ ID NO: 83 is the determined cDNA sequence for 11139, showing homology to *H. sapiens* mRNA for DMBT1 protein.

SEQ ID NO: 84 is the determined cDNA sequence for 11140, showing homology to *H. sapiens* ras GTPase activating-like protein.

SEQ ID NO: 85 is the determined cDNA sequence for 11143, showing homology to Human Acidic Ribosomal Phosphoprotein PO mRNA.

SEQ ID NO: 86 is the determined cDNA sequence for 11144, showing homology to *H. sapiens* U21 mRNA.

SEQ ID NO: 87 is the determined cDNA sequence for 11145, showing homology to Human GTP-binding protein.

SEQ ID NO: 88 is the determined cDNA sequence for 11148, showing homology to *H. sapiens* U21 mRNA.

SEQ ID NO: 89 is the determined cDNA sequence for 11151, showing no significant homology to any known gene.

SEQ ID NO: 90 is the determined cDNA sequence for 11154, showing no significant homology to any known gene.

SEQ ID NO: 91 is the determined cDNA sequence for 11156, showing homology to *H. sapiens* Ribosomal Protein L27.

SEQ ID NO: 92 is the determined cDNA sequence for 11157, showing homology to *H. sapiens* Ribosomal Protein L27.

SEQ ID NO: 93 is the determined cDNA sequence for 11158, showing no significant homology to any known gene.

SEQ ID NO: 94 is the determined cDNA sequence for 11162, showing homology to Ag-X antigen.

SEQ ID NO: 95 is the determined cDNA sequence for 11164, showing homology to *H. sapiens* mRNA for Signal Recognition Protein sub14.

SEQ ID NO: 96 is the determined cDNA sequence for 11165, showing homology to Human PAC 204e5/127h14.

SEQ ID NO: 97 is the determined cDNA sequence for 11166, showing homology to Human mRNA for KIAA0108.

SEQ ID NO: 98 is the determined cDNA sequence for 11167, showing homology to *H. sapiens* mRNA for Neutrophil Gelatinase asset. Lipocalin.

SEQ ID NO: 99 is the determined cDNA sequence for 11168, showing no significant homology to any known gene.

SEQ ID NO: 100 is the determined cDNA sequence for 11172, showing no significant homology to any known gene.

SEQ ID NO: 101 is the determined cDNA sequence for 11175, showing no significant homology to any known gene.

SEQ ID NO: 102 is the determined cDNA sequence for 11176, showing homology to Human maspin mRNA.

SEQ ID NO: 103 is the determined cDNA sequence for 11177, showing homology to Human Carcinoembryonic Antigen.

SEQ ID NO: 104 is the determined cDNA sequence for 11178, showing homology to Human A-Tubulin mRNA.

SEQ ID NO: 105 is the determined cDNA sequence for 11179, showing homology to Human mRNA for proton-ATPase-like protein.

SEQ ID NO: 106 is the determined cDNA sequence for 11180, showing homology to Human HepG2 3' region cDNA clone hmd.

SEQ ID NO: 107 is the determined cDNA sequence for 11182, showing homology to Human MHC homologous to Chicken B-Complex Protein.

SEQ ID NO: 108 is the determined cDNA sequence for 11183, showing homology to Human High Mobility Group Box (SSRP1) mRNA.

SEQ ID NO: 109 is the determined cDNA sequence for 11184, showing no significant homology to any known gene.

SEQ ID NO: 110 is the determined cDNA sequence for 11185, showing no significant homology to any known gene.

SEQ ID NO: 111 is the determined cDNA sequence for 11187, showing no significant homology to any known gene.

SEQ ID NO: 112 is the determined cDNA sequence for 11190, showing homology to Human Replication Protein A 70 kDa.

SEQ ID NO: 113 is the determined cDNA sequence for Contig 47, also referred to as C797P, showing homology to Human Chromosome X clone bWXD342.

SEQ ID NO: 114 is the determined cDNA sequence for Contig 7, showing homology to Equilibrative Nucleoside Transporter 2 (ent2).

SEQ ID NO: 115 is the determined cDNA sequence for 14235.1, also referred to as C791P, showing homology to *H. sapiens* chromosome 21 derived BAC containing ets-2 gene.

SEQ ID NO: 116 is the determined cDNA sequence for 14287.2, showing no significant homology to any known gene, but some degree of homology to Putative Transmembrane Protein.

SEQ ID NO: 117 is the determined cDNA sequence for 14233.1, also referred to as Contig 48, showing no significant homology to any known gene.

SEQ ID NO: 118 is the determined cDNA sequence for 14298.2, also referred to as C793P, showing no significant homology to any known gene.

SEQ ID NO: 119 is the determined cDNA sequence for 14372, also referred to as Contig 44, showing no significant homology to any known gene.

SEQ ID NO: 120 is the determined cDNA sequence for 14295, showing homology to secreted cement gland protein XAG-2 homolog.

SEQ ID NO: 121 is the determined full-length cDNA sequence for a clone showing homology to Beta 1G-H3.

SEQ ID NO: 122 is the predicted amino acid sequence for the clone of SEQ ID NO: 121.

SEQ ID NO: 123 is a longer determined cDNA sequence for C751P.

SEQ ID NO: 124 is a longer determined cDNA sequence for C791P.

SEQ ID NO: 125 is a longer determined cDNA sequence for C792P.

SEQ ID NO: 126 is a longer determined cDNA sequence for C793P.

SEQ ID NO: 127 is a longer determined cDNA sequence for C794P.

SEQ ID NO: 128 is a longer determined cDNA sequence for C795P.

SEQ ID NO: 129 is a longer determined cDNA sequence for C796P.

SEQ ID NO: 130 is a longer determined cDNA sequence for C797P.

SEQ ID NO: 131 is a longer determined cDNA sequence for C798P.

SEQ ID NO: 132 is a longer determined cDNA sequence for C799P.

SEQ ID NO: 133 is a first partial determined cDNA sequence for CoSub-3 (also known as 23569).

SEQ ID NO: 134 is a second partial determined cDNA sequence for CoSub-3 (also known as 23569).

SEQ ID NO: 135 is a first partial determined cDNA sequence for CoSub-13 (also known as 23579).

SEQ ID NO: 136 is a second partial determined cDNA sequence for CoSub-13 (also known as 23579).

SEQ ID NO: 137 is the determined cDNA sequence for CoSub-17 (also known as 23583).

SEQ ID NO: 138 is the determined cDNA sequence for CoSub-19 (also known as 23585).

SEQ ID NO: 139 is the determined cDNA sequence for CoSub-22 (also known as 23714).

SEQ ID NO: 140 is the determined cDNA sequence for CoSub-23 (also known as 23715).

SEQ ID NO: 141 is the determined cDNA sequence for CoSub-26 (also known as 23717).

SEQ ID NO: 142 is the determined cDNA sequence for CoSub-33 (also known as 23724).

SEQ ID NO: 143 is the determined cDNA sequence for CoSub-34 (also known as 23725).

SEQ ID NO: 144 is the determined cDNA sequence for CoSub-35 (also known as 23726).

SEQ ID NO: 145 is the determined cDNA sequence for CoSub-37 (also known as 23728).

SEQ ID NO: 146 is the determined cDNA sequence for CoSub-39 (also known as 23730).

SEQ ID NO: 147 is the determined cDNA sequence for CoSub-42 (also known as 23766).

SEQ ID NO: 148 is the determined cDNA sequence for CoSub-44 (also known as 23768).

SEQ ID NO: 149 is the determined cDNA sequence for CoSub-47 (also known as 23771).

SEQ ID NO: 150 is the determined cDNA sequence for CoSub-54 (also known as 23778).

SEQ ID NO: 151 is the determined cDNA sequence for CoSub-55 (also known as 23779).

SEQ ID NO: 152 is the determined cDNA sequence for CT1 (also known as 24099).

SEQ ID NO: 153 is the determined cDNA sequence for CT2 (also known as 24100).

SEQ ID NO: 154 is the determined cDNA sequence for CF3 (also known as 24101).

SEQ ID NO: 155 is the determined cDNA sequence for CT6 (also known as 24104).

SEQ ID NO: 156 is the determined cDNA sequence for CT7 (also known as 24105).

SEQ ID NO: 157 is the determined cDNA sequence for CT2 (also known as 24110).

SEQ ID NO: 158 is the determined cDNA sequence for CT3 (also known as 24111).

SEQ ID NO: 159 is the determined cDNA sequence for CT14 (also known as 24112).

SEQ ID NO: 160 is the determined cDNA sequence for CT15 (also known as 24113).

SEQ ID NO: 161 is the determined cDNA sequence for CT17 (also known as 24115).

SEQ ID NO: 162 is the determined cDNA sequence for CT18 (also known as 24116).

SEQ ID NO: 163 is the determined cDNA sequence for CT22 (also known as 23848).

SEQ ID NO: 164 is the determined cDNA sequence for CT24 (also known as 23849).

SEQ ID NO: 165 is the determined cDNA sequence for CT31 (also known as 23854).

SEQ ID NO: 166 is the determined cDNA sequence for CT34 (also known as 23856).

SEQ ID NO: 167 is the determined cDNA sequence for CT37 (also known as 23859).

SEQ ID NO: 168 is the determined cDNA sequence for CT39 (also known as 23860).

SEQ ID NO: 169 is the determined cDNA sequence for CT40 (also known as 23861).

SEQ ID NO: 170 is the determined cDNA sequence for CT51 (also known as 24130).

SEQ ID NO: 171 is the determined cDNA sequence for CT53 (also known as 24132).

SEQ ID NO: 172 is the determined cDNA sequence for CT63 (also known as 24595).

SEQ ID NO: 173 is the determined cDNA sequence for CT88 (also known as 24608).

SEQ ID NO: 174 is the determined cDNA sequence for CT92 (also known as 24800).

SEQ ID NO: 175 is the determined cDNA sequence for CT94 (also known as 24802).

SEQ ID NO. 176 is the determined cDNA sequence for CT102 (also known as 24805).

SEQ ID NO: 177 is the determined cDNA sequence for CT103 (also known as 24806).

SEQ ID NO: 178 is the determined cDNA sequence for CT111 (also known as 25520).

SEQ ID NO: 179 is the determined cDNA sequence for CT118 (also known as 25522).

SEQ ID NO: 180 is the determined cDNA sequence for CT121 (also known as 25523).

SEQ ID NO: 181 is the determined cDNA sequence for CT126 (also known as 25527).

SEQ ID NO: 182 is the determined cDNA sequence for CT135 (also known as 25534).

SEQ ID NO: 183 is the determined cDNA sequence for CT140 (also known as 25537).

SEQ ID NO: 184 is the determined cDNA sequence for CT 145 (also known as 25542).

SEQ ID NO: 185 is the determined cDNA sequence for CT147 (also known as 25543).

SEQ ID NO: 186 is the determined cDNA sequence for CT148 (also known as 25544).

SEQ ID NO: 187 is the determined cDNA sequence for CT502 (also known as 26420).

SEQ ID NO: 188 is the determined cDNA sequence for CT507 (also known as 26425).

SEQ ID NO: 189 is the determined cDNA sequence for CT521 (also known as 27366).

SEQ ID NO: 190 is the determined cDNA sequence for CT544 (also known as 27375).

SEQ ID NO: 191 is the determined cDNA sequence for CT577 (also known as 27385).

SEQ ID NO: 192 is the determined cDNA sequence for CT580 (also known as 27387).

SEQ ID NO: 193 is the determined cDNA sequence for CT594 (also known as 27540).

SEQ ID NO: 194 is the determined cDNA sequence for CT606 (also known as 27547).

SEQ ID NO: 195 is the determined cDNA sequence for CT607 (also known as 27548).

SEQ ID NO: 196 is the determined cDNA sequence for CT599 (also known as 27903).

SEQ ID NO: 197 is the determined cDNA sequence for CT632 (also known as 27922).

SEQ ID NO: 198 is the predicted amino acid sequence for CT502 (SEQ ID NO: 187).

SEQ ID NO: 199 is the predicted amino acid sequence for CT507 (SEQ ID NO: 188).

SEQ ID NO: 200 is the predicted amino acid sequence for CT521 (SEQ ID NO: 189).

SEQ ID NO: 201 is the predicted amino acid sequence for CT544 (SEQ ID NO: 190).

SEQ ID NO: 202 is the predicted amino acid sequence for CT606 (SEQ ID NO: 194).

SEQ ID NO: 203 is the predicted amino acid sequence for CT607 (SEQ ID NO: 195).

SEQ ID NO: 204 is the predicted amino acid sequence for CT632 (SEQ ID NO: 197).

SEQ ID NO: 205 is the determined cDNA sequence for clone 25244.

SEQ ID NO: 206 is the determined cDNA sequence for clone 25245.

SEQ ID NO: 207 is the determined cDNA sequence for clone 25246.

SEQ ID NO: 208 is the determined cDNA sequence for clone 25248.

SEQ ID NO: 209 is the determined cDNA sequence for clone 25249.

SEQ ID NO: 210 is the determined cDNA sequence for clone 25250.

SEQ ID NO: 211 is the determined cDNA sequence for clone 25251.

SEQ ID NO: 212 is the determined cDNA sequence for clone 25252.

SEQ ID NO. 213 is the determined cDNA sequence for clone 25253.

SEQ ID NO: 214 is the determined cDNA sequence for clone 25254.

SEQ ID NO: 215 is the determined cDNA sequence for clone 25255.

SEQ ID NO: 216 is the determined cDNA sequence for clone 25256.

SEQ ID NO: 217 is the determined cDNA sequence for clone 25257.

SEQ ID NO: 218 is the determined cDNA sequence for clone 25259.

SEQ ID NO: 219 is the determined cDNA sequence for clone 25260.

SEQ ID NO: 220 is the determined cDNA sequence for clone 25261.

SEQ ID NO: 221 is the determined cDNA sequence for clone 25262.

SEQ ID NO: 222 is the determined cDNA sequence for clone 25263.

SEQ ID NO: 223 is the determined cDNA sequence for clone 25264.

SEQ ID NO: 224 is the determined cDNA sequence for clone 25265.

SEQ ID NO: 225 is the determined cDNA sequence for clone 25266.

SEQ ID NO: 226 is the determined cDNA sequence for clone 25267.

SEQ ID NO: 227 is the determined cDNA sequence for clone 25268.

SEQ ID NO: 228 is the determined cDNA sequence for clone 25269.
SEQ ID NO: 229 is the determined cDNA sequence for clone 25271.
SEQ ID NO: 230 is the determined cDNA sequence for clone 25272.
SEQ ID NO: 231 is the determined cDNA sequence for clone 25273.
SEQ ID NO: 232 is the determined cDNA sequence for clone 25274.
SEQ ID NO: 233 is the determined cDNA sequence for clone 25275.
SEQ ID NO: 234 is the determined cDNA sequence for clone 25276.
SEQ ID NO: 235 is the determined cDNA sequence for clone 25277.
SEQ ID NO: 236 is the determined cDNA sequence for clone 25278.
SEQ ID NO: 237 is the determined cDNA sequence for clone 25280.
SEQ ID NO: 238 is the determined cDNA sequence for clone 25281.
SEQ ID NO: 239 is the determined cDNA sequence for clone 25282.
SEQ ID NO: 240 is the determined cDNA sequence for clone 25283.
SEQ ID NO: 241 is the determined cDNA sequence for clone 25284.
SEQ ID NO: 242 is the determined cDNA sequence for clone 25285.
SEQ ID NO: 243 is the determined cDNA sequence for clone 25286.
SEQ ID NO: 244 is the determined cDNA sequence for clone 25287.
SEQ ID NO: 245 is the determined cDNA sequence for clone 25288.
SEQ ID NO: 246 is the determined cDNA sequence for clone 25289.
SEQ ID NO: 247 is the determined cDNA sequence for clone 25290.
SEQ ID NO: 248 is the determined cDNA sequence for clone 25291.
SEQ ID NO: 249 is the determined cDNA sequence for clone 25292.
SEQ ID NO: 250 is the determined cDNA sequence for clone 25293.
SEQ ID NO: 251 is the determined cDNA sequence for clone 25294.
SEQ ID NO: 252 is the determined cDNA sequence for clone 25295.
SEQ ID NO: 253 is the determined cDNA sequence for clone 25296.
SEQ ID NO: 254 is the determined cDNA sequence for clone 25297.
SEQ ID NO: 255 is the determined cDNA sequence for clone 25418.
SEQ ID NO: 256 is the determined cDNA sequence for clone 25419.
SEQ ID NO: 257 is the determined cDNA sequence for clone 25420.
SEQ ID NO: 258 is the determined cDNA sequence for clone 25421.
SEQ ID NO: 259 is the determined cDNA sequence for clone 25422.
SEQ ID NO: 260 is the determined cDNA sequence for clone 25423.
SEQ ID NO: 261 is the determined cDNA sequence for clone 25424.
SEQ ID NO: 262 is the determined cDNA sequence for clone 25426.
SEQ ID NO: 263 is the determined cDNA sequence for clone 25427.
SEQ ID NO: 264 is the determined cDNA sequence for clone 25428.
SEQ ID NO: 265 is the determined cDNA sequence for clone 25429.
SEQ ID NO: 266 is the determined cDNA sequence for clone 25430.
SEQ ID NO: 267 is the determined cDNA sequence for clone 25431.
SEQ ID NO: 268 is the determined cDNA sequence for clone 25432.
SEQ ID NO: 269 is the determined cDNA sequence for clone 25433.
SEQ ID NO: 270 is the determined cDNA sequence for clone 25434.
SEQ ID NO: 271 is the determined cDNA sequence for clone 25435.
SEQ ID NO: 272 is the determined cDNA sequence for clone 25436.
SEQ ID NO: 273 is the determined cDNA sequence for clone 25437.
SEQ ID NO: 274 is the determined cDNA sequence for clone 25438.
SEQ ID NO: 275 is the determined cDNA sequence for clone 25439.
SEQ ID NO: 276 is the determined cDNA sequence for clone 25440.
SEQ ID NO: 277 is the determined cDNA sequence for clone 25441.
SEQ ID NO: 278 is the determined cDNA sequence for clone 25442.
SEQ ID NO: 279 is the determined cDNA sequence for clone 25443.
SEQ ID NO: 280 is the determined cDNA sequence for clone 25444.
SEQ ID NO: 281 is the determined cDNA sequence for clone 25445.
SEQ ID NO: 282 is the determined cDNA sequence for clone 25446.
SEQ ID NO: 283 is the determined cDNA sequence for clone 25447.
SEQ ID NO: 284 is the determined cDNA sequence for clone 25448.
SEQ ID NO: 285 is the determined cDNA sequence for clone 25844.
SEQ ID NO: 286 is the determined cDNA sequence for clone 25845.
SEQ ID NO: 287 is the determined cDNA sequence for clone 25846.
SEQ ID NO: 288 is the determined cDNA sequence for clone 25847.
SEQ ID NO: 289 is the determined cDNA sequence for clone 25848.

SEQ ID NO: 290 is the determined cDNA sequence for clone 25850.
SEQ ID NO: 291 is the determined cDNA sequence for clone 25851.
SEQ ID NO: 292 is the determined cDNA sequence for clone 25852.
SEQ ID NO: 293 is the determined cDNA sequence for clone 25853.
SEQ ID NO: 294 is the determined cDNA sequence for clone 25854.
SEQ ID NO: 295 is the determined cDNA sequence for clone 25855.
SEQ ID NO: 296 is the determined cDNA sequence for clone 25856.
SEQ ID NO: 297 is the determined cDNA sequence for clone 25857.
SEQ ID NO: 298 is the determined cDNA sequence for clone 25858.
SEQ ID NO: 299 is the determined cDNA sequence for clone 25859.
SEQ ID NO: 300 is the determined cDNA sequence for clone 25860.
SEQ ID NO: 301 is the determined cDNA sequence for clone 25861.
SEQ ID NO: 302 is the determined cDNA sequence for clone 25862.
SEQ ID NO: 303 is the determined cDNA sequence for clone 25863.
SEQ ID NO: 304 is the determined cDNA sequence for clone 25864.
SEQ ID NO: 305 is the determined cDNA sequence for clone 25865.
SEQ ID NO: 306 is the determined cDNA sequence for clone 25866.
SEQ ID NO: 307 is the determined cDNA sequence for clone 25867.
SEQ ID NO: 308 is the determined cDNA sequence for clone 25868.
SEQ ID NO: 309 is the determined cDNA sequence for clone 25869.
SEQ ID NO: 310 is the determined cDNA sequence for clone 25870.
SEQ ID NO: 311 is the determined cDNA sequence for clone 25871.
SEQ ID NO: 312 is the determined cDNA sequence for clone 25872.
SEQ ID NO: 313 is the determined cDNA sequence for clone 25873.
SEQ ID NO: 314 is the determined cDNA sequence for clone 25875.
SEQ ID NO: 315 is the determined cDNA sequence for clone 25876.
SEQ ID NO: 316 is the determined cDNA sequence for clone 25877.
SEQ ID NO: 317 is the determined cDNA sequence for clone 25878.
SEQ ID NO: 318 is the determined cDNA sequence for clone 25879.
SEQ ID NO: 319 is the determined cDNA sequence.for clone 25880.
SEQ ID NO: 320 is the determined cDNA sequence for clone 25881.
SEQ ID NO: 321 is the determined cDNA sequence for clone 25882.
SEQ ID NO: 322 is the determined cDNA sequence for clone 25883.
SEQ ID NO: 323 is the determined cDNA sequence for clone 25884.
SEQ ID NO: 324 is the determined cDNA sequence for clone 25885.
SEQ ID NO: 325 is the determined cDNA sequence for clone 25886.
SEQ ID NO: 326 is the determined cDNA sequence for clone 25887.
SEQ ID NO: 327 is the determined cDNA sequence for clone 25888.
SEQ ID NO: 328 is the determined cDNA sequence for clone 25889.
SEQ ID NO: 329 is the determined cDNA sequence for clone 25890.
SEQ ID NO: 330 is the determined cDNA sequence for clone 25892.
SEQ ID NO: 331 is the determined cDNA sequence for clone 25894.
SEQ ID NO: 332 is the determined cDNA sequence for clone 25895.
SEQ ID NO: 333 is the determined cDNA sequence for clone 25896.
SEQ ID NO: 334 is the determined cDNA sequence for clone 25897.
SEQ ID NO: 335 is the determined cDNA sequence for clone 25899.
SEQ ID NO: 336 is the determined cDNA sequence for clone 25900.
SEQ ID NO: 337 is the determined cDNA sequence for clone 25901.
SEQ ID NO: 338 is the determined cDNA sequence for clone 25902.
SEQ ID NO: 339 is the determined cDNA sequence for clone 25903.
SEQ ID NO: 340 is the determined cDNA sequence for clone 25904.
SEQ ID NO: 341 is the determined cDNA sequence for clone 25906.
SEQ ID NO: 342 is the determined cDNA sequence for clone 25907.
SEQ ID NO: 343 is the determined cDNA sequence for clone 25908.
SEQ ID NO: 344 is the determined cDNA sequence for clone 25909.
SEQ ID NO: 345 is the determined cDNA sequence for clone 25910.
SEQ ID NO: 346 is the determined cDNA sequence for clone 25911.
SEQ ID NO: 347 is the determined cDNA sequence for clone 25912.
SEQ ID NO: 348 is the determined cDNA sequence for clone 25913.
SEQ ID NO: 349 is the determined cDNA sequence for clone 25914.
SEQ ID NO: 350 is the determined cDNA sequence for clone 25915.
SEQ ID NO: 351 is the determined cDNA sequence for clone 25916.

SEQ ID NO: 352 is the determined cDNA sequence for clone 25917.

SEQ ID NO: 353 is the determined cDNA sequence for clone 25918.

SEQ ID NO: 354 is the determined cDNA sequence for clone 25919.

SEQ ID NO: 355 is the determined cDNA sequence for clone 25920.

SEQ ID NO: 356 is the determined cDNA sequence for clone 25921.

SEQ ID NO: 357 is the determined cDNA sequence for clone 25922.

SEQ ID NO: 358 is the determined cDNA sequence for clone 25924.

SEQ ID NO: 359 is the determined cDNA sequence for clone 25925.

SEQ ID NO: 360 is the determined cDNA sequence for clone 25926.

SEQ ID NO: 356 is the determined cDNA sequence for clone 25927.

SEQ ID NO: 362 is the determined cDNA sequence for clone 25928.

SEQ ID NO: 363 is the determined cDNA sequence for clone 25929.

SEQ ID NO: 364 is the determined cDNA sequence for clone 25930.

SEQ ID NO: 365 is the determined cDNA sequence for clone 25931.

SEQ ID NO: 366 is the determined cDNA sequence for clone 25932.

SEQ ID NO: 367 is the determined cDNA sequence for clone 25933.

SEQ ID NO: 368 is the determined cDNA sequence for clone 25934.

SEQ ID NO: 369 is the determined cDNA sequence for clone 25935.

SEQ ID NO: 370 is the determined cDNA sequence for clone 25936.

SEQ ID NO: 371 is the determined cDNA sequence for clone 25939.

DETAILED DESCRIPTION OF THE INVENTION

As noted above, the present invention is generally directed to compositions and methods for the therapy and diagnosis of cancer, such as colon cancer. The compositions described herein may include colon tumor polypeptides, polynucleotides encoding such polypeptides, binding agents such as antibodies, antigen presenting cells (APCs) and/or immune system cells (e.g., T cells). Polypeptides of the present invention generally comprise at least a portion (such as an immunogenic portion) of a colon tumor protein or a variant thereof. A "colon tumor protein" is a protein that is expressed in colon tumor cells at a level that is at least two fold, and preferably at least five fold, greater than the level of expression in a normal tissue, as determined using a representative assay provided herein. Certain colon tumor proteins are tumor proteins that react detectably (within an immunoassay, such as an ELISA or Western blot) with antisera of a patient afflicted with colon cancer. Polynucleotides of the subject invention generally comprise a DNA or RNA sequence that encodes all or a portion of such a polypeptide, or that is complementary to such a sequence.

Antibodies are generally immune system proteins, or antigen-binding fragments thereof, that are capable of binding to a polypeptide as described above. Antigen presenting cells include dendritic cells, macrophages, monocytes, fibroblasts and B-cells that express a polypeptide as described above. T cells that may be employed within such compositions are generally T cells that are specific for a polypeptide as described above.

The present invention is based on the discovery of human colon tumor proteins. Partial sequences of polynucleotides encoding specific tumor proteins are provided in SEQ ID NO: 1–120 and 123–371.

COLON TUMOR PROTEIN POLYNUCLEOTIDES

Any polynucleotide that encodes a colon tumor protein or a portion or other variant thereof as described herein is encompassed by the present invention. Preferred polynucleotides comprise at least 15 consecutive nucleotides, preferably at least 30 consecutive nucleotides and more preferably at least 45 consecutive nucleotides, that encode a portion of a colon tumor protein. More preferably, a polynucleotide encodes an immunogenic portion of a colon tumor protein. Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e. an endogenous sequence that encodes a colon tumor protein or a portion thereof) or may comprise a variant of such a sequence. Polynucleotide variants may contain one or more substitutions, additions, deletions and/or insertions such that the immunogenicity of the encoded polypeptide is not diminished, relative to a native tumor protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native colon tumor protein or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, in which a sequence may be compared to a reference sequence of the same number of contiguous positions after the two sequences are optimally aligned Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff., M. O. (ed.) Atlas of Protein Sequence and Structure, National Biomedical Research Foundation, Washington D.C. Vol. 5, Suppl. 3, pp. 345–358; Hemi J. (1990) Unified Approach to Alignment and Phylogenes pp. 626–645 *Methods in Enzymology* vol. 183, Academic Press. Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxoniomy*, Freeman Press, San Francisco, Calif.; Wilbur, W. J. and Lipman, D. J. (1983) *Proc. Natl. Acad., Sci. USA* 80:726–730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequence (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native colon tumor protein (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques. For example, a polynucleotide may be identified, as described in more detail below, by screening a microarray of cDNAs for tumor-associated expression (i.e., expression that is at least two fold greater in a colon tumor than in normal tissue, as determined using a representative assay provided herein). Such screens may be performed using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polypeptides may be amplified from cDNA prepared from cells expressing the proteins described herein, such as colon tumor cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., a colon tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nucl. Acids Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Certain nucleic acid sequences of cDNA molecules encoding portions of colon tumor proteins are provided in SEQ ID NO: 1–120 and 123–371. These polynucleotides were isolated from colon tumor cDNA libraries using conventional and/or PCR-based subtraction techniques, as described below.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding a colon tumor protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding a colon tumor polypeptide, and administering the transfected cells to the patient).

A portion of a sequence complementary to a coding sequence (i.e., an antisense polynucleotide) may also be used as a probe or to modulate gene expression. cDNA constructs that can be transcribed into antisense RNA may also be introduced into cells of tissues to facilitate the production of antisense RNA. An antisense polynucleotide may be used, as described herein, to inhibit expression of a tumor protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches*, Futura Publishing Co. (Mt. Kisco, N.Y.; 1994)). Alternatively, an antisense molecule may be designed to hybridize with a control region of a gene (e.g., promoter, enhancer or transcription initiation site), and block transcription of the gene; or to block translation by inhibiting binding of a transcript to ribosomes.

A portion of a coding sequence, or of a complementary sequence, may also be designed as a probe or primer to detect gene expression. Probes may be labeled with a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22–30 nucleotides in length.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

COLON TUMOR POLYPEPTIDES

Within the context of the present invention, polypeptides may comprise at least an immunogenic portion of a colon tumor protein or a variant thereof, as described herein. As noted above, a "colon tumor protein" is a protein that is expressed by colon tumor cells. Proteins that are colon tumor proteins also react detectably within an immunoassay (such as an ELISA) with antisera from a patient with colon cancer. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a colon tumor protein or a variant thereof. Certain preferred immunogenic portions include peptides in which an N-terminal leader sequence and/or transmembrane domain have been deleted. Other preferred immunogenic portions may contain a small N- and/or C-terminal deletion (e.g., 1–30 amino acids, preferably 5–15 amino acids), relative to the mature protein.

Immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigten-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native colon tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native colon tumor protein. A polypeptide "variant," as used herein, is a polypeptide that differs from a native colon tumor protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants preferably exhibit at least about 70%, more preferably at least about 90% and most preferably at least about 95% identity (determined as described above) to the identified polypeptides.

Preferably, a variant contains conservative substitutions. A "conservative substitution" is one in which an amino acid is substituted for another amino acid that has similar properties such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine, and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain non-conservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985, Murphy et al., *Proc. Natl Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91, 1997).

Within preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

BINDING AGENTS

The present invention further provides agents, such as antibodies and antigen-binding fragments thereof, that specifically bind to a colon tumor protein. As used herein, an antibody, or antigen-binding fragment thereof, is said to "specifically bind" to a colon tumor protein if it reacts at a detectable level (within, for example, an ELISA) with a colon tumor protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a cancer, such as colon cancer, using the representative assays provided herein. In other words, antibodies or other binding agents that bind to a colon tumor protein will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof Antibodies may be prepared by any of a variety of techniques known to those of ordinary skill in the art. See, e.g. Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{221}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

T CELLS

Immunotherapeutic compositions may also, or alternatively, comprise T cells specific for a colon tumor protein. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the ISOLEX™ system, available from Nexell Therapeutics Inc., Irvine, Calif. Alternatively, T cells may be derived from related or unrelated humans, non-human mammals, cell lines or cultures.

T cells may be stimulated with a colon tumor polypeptide, polynucleotide encoding a colon tumor polypeptide and/or an antigen presenting cell (APC) that expresses such a polypeptide. Such stimulation is performed under conditions and for a time sufficient to permit the generation of T cells that are specific for the polypeptide. Preferably, a colon tumor polypeptide or polynucleotide is present within a delivery vehicle, such as a microsphere, to facilitate the generation of specific T cells.

T cells are considered to be specific for a colon tumor polypeptide if the T cells kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., Cancer Res.. 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a colon tumor polypeptide (100 ng/ml–100 $\mu$g/ml, preferably 200 ng/ml–25 $\mu$g/ml) for 3–7 days should result in at least a two fold increase in proliferation of the T cells. Contact as described above for 2–3 hours should result in activation of the T cells, as measured using standard cytokine assays in which a two fold increase in the level of cytokine release (e.g., TNF or IFN-$\gamma$) is indicative of T cell activation (see Coligan et al., Current Protocols in Immunology, vol. 1, Wiley Interscience (Greene 1998)). T cells that have been activated in response to a colon tumor polypeptide, polynucleotide or polypeptide-expressing APC may be $CD4^+$ and/or $CD8^+$. Colon tumor protein-specific T cells may be expanded using standard techniques. Within preferred embodiments, the T cells are derived from either a patient or a related, or unrelated, donor and are administered to the patient following stimulation and expansion.

For therapeutic purposes, $CD4^+$ or $CD8^+$ T cells that proliferate in response to a colon tumor polypeptide, polynucleotide or APC can be expanded in number either in vitro or in vivo. Proliferation of such T cells in vitro may be accomplished in a variety of ways. For example, the T cells can be re-exposed to a colon tumor polypeptide, or a short peptide corresponding to an immunogenic portion of such a polypeptide, with or without the addition of T cell growth factors, such as interleukin-2, and/or stimulator cells that synthesize a colon tumor polypeptide. Alternatively, one or more T cells that proliferate in the presence of a colon tumor protein can be expanded in number by cloning. Methods for cloning cells are well known in the art, and include limiting dilution.

PHARMACEUTICAL COMPOSITIONS AND VACCINES

Within certain aspects, polypeptides, polynucleotides, T cells and/or binding agents disclosed herein may be incorporated into pharmaceutical compositions or immunogenic compositions (i.e., vaccines). Pharmaceutical compositions comprise one or more such compounds and a physiologically acceptable carrier. Vaccines may comprise one or more such compounds and a non-specific immune response enhancer. A ion-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated, see e.g. Fullerton, U.S. Pat. No. 4,235,877). Vaccine preparation is generally described in, for example, M. F. Powell and M. J. Newman, eds., "Vaccine Design (the subunit and adjuvant approach),"

Plenum Press (NY, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487, WO 89/01973; U.S. Pat. No. 4,777,127; GB 2,200,651; EP 0,345,242; WO 91/02805, Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type-cytokines (e.g., IFN-$\gamma$, IL-2 and IL-12) tend to favor the induction of cell mediated immune responses to an administered antigen. In contrast, high levels of Th2-type cytokines (e.g., IL-4, IL-5, IL-6, IL-10 and TNF-$\beta$) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Ribi ImmunoChem Research Inc. (Hamilton, Mont.) (see U.S. Pat. Nos. 4,436, 727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/3373.9. Other preferred formulations comprises an oil-in-water emulsion and tocopherol. A particularly potent adjuvant formulation involving QS21, 3D-MPL and tocopherol in an oil-in-water emulsion is described in WO 95/17210. Any vaccine provided herein may be prepared using well known methods that result in a combination of antigen, immune response enhancer and a suitable carrier or excipient.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural-killer cells (CD56), as determined using standard assays. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80 and CD86).

APCs may generally be transfected with a polynucleotide encoding a colon tumor protein (or portion or other variant thereof) such that the colon tumor polypeptide, or an immunogenic portion thereof, is expressed on the cell surface. Such transfection may take place ex vivo, and a composition or vaccine comprising-such transfected cells may then be is used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the colon tumor polypeptide, DNA (naked or within a plasmid vector) or RNA, or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

CANCER THERAPY

In further aspects of the present invention, the compositions described herein may be used for immunotherapy of cancer, such as colon cancer. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors with the administration of immune response-modifying agents (such as polypeptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune-system. Examples of effector cells include T cells as discussed above, T lymphocytes (such as CD8⁻ cytotoxic T lymphocytes and CD4⁺ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 15:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions disclosed herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 100 μg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a colon tumor protein generally correlate with an improved clinical outcome. Such immune responses may generally be evaluated using standard proliferation, cytotoxicity or cytokine assays, which may be performed using samples obtained from a patient before and after treatment.

METHODS FOR DETECTING CANCER

In general, a cancer may be detected in a patient based on the presence of one or more colon tumor proteins and/or polynucleotides encoding such proteins in a biological sample (for example, blood, sera, sputum, urine and/or tumor biopsies) obtained from the patient. In other words, such proteins may be used as markers to indicate the presence or absence of a cancer such as colon cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a colon tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length colon tumor proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 $\mu$g, and preferably about 100 ng to about 1 $\mu$g, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a.different site on the polypeptide) containing a reporter.group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with colon cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as colon cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 μg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use colon tumor polypeptides to detect antibodies that bind to such polypeptides in a biological sample. The detection of such colon tumor protein specific antibodies may correlate with the presence of a cancer.

A cancer may also, or alternatively, be detected based on the presence of T cells that specifically react with a colon tumor protein in a biological sample. Within certain methods, a biological sample comprising $CD4^+$ and/or $CD8^+$ T cells isolated from a patient is incubated with a colon tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with one or more representative polypeptides (e.g., 5–25 μg/ml). It may be desirable to incubate another aliquot of a T cell sample in the absence of colon tumor polypeptide to serve as a control. For $CD4^-$ T cells, activation is preferably detected by evaluating proliferation of the T cells For $CD8^-$ T cells, activation is preferably detected by evaluating cytolytic activity. A level of preliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a colon tumor protein in a biological sample. For example, at least two oligonucleotide primers may be employed in a polymerase chain reaction (PCR) based assay to amplify a portion of a colon tumor cDNA derived-from a biological sample, wherein at least one of the oligonucleotide primers is specific for (i.e., hybridizes to) a polynucleotide encoding the colon tumor protein. The amplified cDNA is then separated and detected using techniques well known in the art, such as gel electrophoresis. Similarly, oligonucleotide probes that specifically hybridize to a polynucleotide encoding a colon tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a colon tumor protein that is at least 10 nucleotides, and preferably at least 20 nucleotides, in length. Preferably, oligonucleotide primers and/or probes will hybridize to a polynucleotide encoding a polypeptide disclosed herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence recited in SEQ ID NO: 1–120 and 123–371. Techniques for both PCR based assays and hybridization assays are well known in the art (see, for example, Mullis et al., *Cold Spring Harbor Symp. Quant. Biol.*, 51:263, 1987, Erlich ed., PCR Technology, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the disclosed compositions may be used as markers for the progression of cancer. In this embodiment, assays as described above for the diagnosis of a cancer may be performed over time, and the change in the level of reactive polypeptide(s) or polynucleotide evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple colon tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

DIAGNOSTIC KITS

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a colon tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mPNA encoding a colon tumor protein in a biological sample. Such kits generally comprise at least one oligonucleotide probe or primer, as described above, that hybridizes to a polynucleotide encoding a colon tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a colon tumor protein.

The following Examples are offered by way of illustration and not by way of limitation.

EXAMPLES

Example 1

Isolation and Characterization of Colon Tumor Polypeptides by PCR-Based Subtraction and Microarray Analysis A cDNA library was constructed in the PCR2.1 vector (Invitrogen, Carlsbad, Calif.) by subtracting a pool of three colon tumors with a pool of normal colon, spleen, brain, liver, kidney, lung, stomach and small intestine using PCR subtraction methodologies (Clontech, Palo Alto, Calif.). The subtraction was performed using a PCR-based protocol, which was modified to generate larger fragments. Within this protocol, tester and driver double stranded cDNA were separately digested with five restriction enzymes hat recognize six-nucleotide restriction sites (MitI, MscI, PvuII, SalI and StuI). This digestion resulted in an average cDNA size of 600 bp, rather than the average size of 300 bp that results from digestion with RsaI according to the Clontech protocol. This modification did not affect the subtraction efficiency. Two tester populations were then created with different adapters, and the driver library remained without adapters.

The tester and driver libraries were then hybridized using excess driver cDNA. In the first hybridization step, driver was separately hybridized with each of the two tester cDNA populations. This resulted in populations of (a) unhybridized tester cDNAs, (b) tester cDNAs hybridized to other tester cDNAs, (c) tester cDNAs hybridized to driver cDNAs, and (d) unhybridized driver cDNAs. The two separate hybridization reactions were then combined, and rehybridized in the presence of additional denatured driver cDNA. Following this second hybridization, in addition to populations (a) through (d), a fifth population (e) was generated in which tester cDNA with one adapter hybridized to tester cDNA with the second adapter. Accordingly, the second hybridization step resulted in enrichment of differentially expressed sequences which could be used as templates for PCR amplification with adaptor-specific primers.

The ends were then filled in, and PCR amplification was performed using adaptor-specific primers. Only population (e), which contained tester cDNA that did not hybridize to driver cDNA, was amplified exponentially. A second PCR amplification step was then performed, to reduce background and further enrich differentially expressed sequences.

This PCR-based subtraction technique normalizes differentially expressed cDNAs so that rare transcripts that are over-expressed in colon tumor tissue may be recoverable. Such transcripts would be difficult to recover by traditional subtraction methods.

To characterize the complexity and redundancy of the subtracted library, 96 clones were randomly picked and 65 were sequenced, as previously described. These sequences were further characterized by comparison with the most recent Genbank database (April, 1998) to determine their degree of novelty. No significant homologies were found to 21 of these clones, hereinafter referred to as 11092, 11093, 11096, 11098, 11103, 11174, 11108, 11112, 11115, 11117, 11118, 11134, 11151, 11154, 11158, 11168, 11172, 11175, 11184, 11185 and 11187. The determined cDNA sequences for these clones are provided in SEQ ID NO: 48, 49, 52, 54, 59, 60, 65–69, 79, 89, 90, 93, 99–101 and 109–111, respectively.

Two-thousand clones from the above mentioned cDNA subtraction library were randomly picked and submitted to a round of PCR amplification. Briefly, 0.5 µl of glycerol stock solution was added to 99.5 µl of per MIX (80 µH$_2$O, 10 µl 10× PCR Buffer, 6 µl 25 mM MgCl$_2$, 1 µl 10 mM dNTPs, 1 µl 100 mM M13 forward primer (CAGGAC GTTGTAAAACGACGG;) (SEQ ID NO:688), 1 µl 100 mM M13 reverse primer (CACAGGAAACAGCTATGACC) (SEQ ID NO:689)), and 0.5 µl 5 u/ml Taq polymerase (primers provided by (Operon Technologies, Alameda, Calif.). The PCR amplification was run for thirty cycles under the following conditions: 95° C. for 5 min., 92° C. for 30 sec., 57° C. for 40 sec., 75° C. for 2 min. and 75° C. for 5 minutes.

mRNA expression levels for representative clones were determined using microarray technology (Synteni, Palo Alto, Calif.) in colon tumor tissues (n=25), normal colon tissues (n=6), kidney, lung, liver, brain, heart, esophagus, small intestine, stomach, pancreas, adrenal gland, salivary gland, resting PBMC, activated PBMC, bone marrow, dendritic cells, spinal cord, blood vessels, skeletal muscle, skin, breast and fetal tissues. The number of tissue samples tested in each case was one (n=1), except where specifically noted above; additionally, all the above-mentioned tissues were derived from humans. The PCR amplification products were dotted onto slides in an array format, with each product occupying a unique location in the array. mRNA was extracted from the tissue sample to be tested, and fluorescent-labeled cDNA probes were generated by reverse transcription according to the protocol provided by Synteni. The microarrays were probed with the labeled cDNA probes, the slides scanned, and fluorescence intensity was measured. This intensity correlates with the hybridization intensity.

One hundred and forty nine clones showed two or more fold over-expression in the colon tumor probe group as compared to the normal tissue probe group. These cDNA clones were further characterized by DNA sequencing with a Perkin Elmer/Applied Biosystems Division Automated Sequencer Model 373A and/or Model 377 (Foster City, Calif.). These sequences were compared to known sequences in the most recent GenBank database. No significant homologies to human gene sequences were found in forty nine of these clones, represented by the following sixteen cDNA-consensus sequences SEQ ID NO: 2, 8, 15, 16, 22, 24, 30, 32–34, 36, 38, 40, 41, 46 and 47, hereinafter referred to as Contig 2, 8, 13, 14, 20, 23, 29, 31, 35, 32, 36, 38, 41, 42, 50 and 51, respectively). Contig 29 (SEQ ID NO: 30) was found to be a Rat GSK-3-β-interacting protein Axil homolog. Also, Contigs 31 and 35 (SEQ ID NO: 32 and 33, respectively) were found to be a Mus musculus GOB-4 homolog. The determined cDNA sequences of SEQ ID NO: 1, 3–7, 9–14, 17–21, 23, 25–29, 31, 35, 37, 39, 42–45, 50, 51, 53, 55–58, 61–64, 70–78, 80–88, 91, 92, 94–98, 102–108 and 112 were found to show some homology to previously identified genes sequences.

Microarray analysis demonstrated Contig 2 (SEQ ID NO: 2) showed over-expression in 34% of colon tumors tested, as well as increased expression in normal pancreatic tissue, with no over-expression in normal colon tissues. Upon further analysis, Contigs 2, 8 and 23 were found to share homology to the known gene GW 112. Contigs 4, 5, 9 and 52 showed homology to carcinoembryonic antigen (SEQ ID NO: 3, 4, 5 and 6, respectively). A representative sampling of these fragments showed over-expression in 85% of colon tumors, with over-expression in normal bone marrow and 3/6 normal colon tissues. Contig 6 (SEQ ID NO: 7), showing homology to the known gene sequence for villin, and was over-expressed in about half of all colon tumors tested, with a limited degree of low level over-expression in normal colon. Contig 12 (SEQ ID NO: 14), showing homology to Chromosome 17, clone hRPC.1171_I_10, also referred to as C798P, was over-expressed in approximately 70% of colon tumors tested, with low over-expression in 1/6 normal colon samples. Contig 14, also referred to as 14261 (SEQ ID NO: 16), showing no significant homology to any known gene, showed over-expression in 44% of colon tumors tested, with low level expression in half of normal colon tissues, as well as small intestine and pancreatic tissue. Contig 18 (SEQ ID NO: 21), showing homology to the known gene for L1-cadherin, showed over-expression in approximately half of colon tumors and low level over-expression in 3/6 normal colon tissues tested. Contig 22 (SEQ ID NO: 23), showing homology to Bumetanide-sensitive Na—K—Cl cotransporter was over-expressed in 70% of colon tumors and no over-expression in all normal tissues tested. Contig 25 (SEQ ID NO: 25), showing homology to macrophage inflammatory protein-3α, was over-expressed in over 40% of colon tumors and in activated PBMC. Contigs 26 and 48 (SEQ ID NOS: 25 and 26), showing homology to the sequence for laminin, was over-expressed in 48% of colon tumors and with low over-expression in stomach tissue. Contig 28 (SEQ ID NO: 293) showing homology to the known gene sequence for Chromosome 16 BAC clone CIT987SK-A-363E6, was over-expressed in 33% of colon tumors tested with normal stomach and 2/6 normal colon tissues showing low level over-expression. Contigs 29, 31 and 35 (SEQ ID NOS: 30, 32 and 33, respetively), also referred to as C751P, an unknown sequence showing limited and partial homology to Rat GSK-3β-interacting protein Axil homolog and Mus musculus GOB-4 homolog, was over-expressed in 74% of colon tumors and no over-expression in all normal tissues tested. Contig 34 (SEQ ID NO: 35), showing homology to the known sequence for desmoglein 2, was over-expressed in 56% of colon tumors and showed low level over-expression in 1/6 normal colon tissues. Contig 36 (SEQ ID NO: 36), an unknown sequence also referred to as C793P, showed over-expression in 30% of colon tumor tissues tested. Contig 37 and 14287.2 (SEQ ID NOS: 37 and 116), an unknown sequence, but with limited (89%) homology to the known sequence for putative transmembrane protein was over-expressed in 70% of colon tumors, as well as in normal lung tissue and 3/6 normal colon tissues tested. Contig 38, also referred to as C796P and 14219 (SEQ ID NO: 38), showing no significant homology to any known gene, was over-expressed in 38% in colon tumors and no elevated over-expression in any normal tissues. Contig 41 (SEQ ID NO: 40), also referred to as C799P and 14308, an unknown sequence showing no significant homology to any known gene, was over-expressed in 22% of colon tumors. Contig 42, (SEQ ID NO: 41), also referred to as C794P and 14309, an unknown sequence with no significant homology to any known gene, was over-expressed in 63% of colon tumors tested, as well as in 3/6 normal colon tissues. Contig 43 (SEQ ID NO: 42), showing homology to the known sequence for Chromosome 1 specific transcript KIAA0487 was over-expressed in 85% of colon tumors tested and in normal lung and 4/6 normal colon tissues. Contig 49 (SEQ ID NO: 45), showing homology to the known sequence for pump-1, was over-expressed in 44% of colon tumors and no over-expression in all normal tissues tested. Contig 50 (SEQ ID NO: 46), also referred to as C792P and 18323, showing no significant homology to any known gene, was over-expressed in 33% of colon tumors with no detectable over-expression in any normal tissues tested. Contig 51 (SEQ ID NO: 47), also referred to as C795P and 14317 was over-expressed in 11% of colon tumors.

Additional microarray analysis yielded seven clones showing two or more fold over-expression in the colon tumor probe group as compared to the normal tissue probe group. Three of these clones demonstrated particularly good colon tumor specificity, and are represented by SEQ ID NO: 115, 116 and 120. Specifically, SEQ.ID NO: 115, referred to as C791P or 14235, which shows homology to the known gene sequence for *H. sapiens* chromosome 21 derived BAC containing ets-2 gene, was over-expressed in 89% of colon tumors tested and in 5/6 normal colon tissues, as well as over-expressed at low levels in normal lung and activated PBMC. Microarray analysis for SEQ ID NO: 116 is discussed above. SEQ ID NO: 120, referred to as 14295, showing homology to the known gene sequence for secreted cement gland protein XAG-2 homolog, was over-expressed in 70% of colon tumors and in 5/6 normal colon tissues, as well as low level over-expression in normal small intestine, stomach and lung. All clones showing over-expression in colon tumor were sequenced and these sequences compared to the most recent Genbank database (Feb. 12, 1999). Of the seven clones, three contained sequences that did not share significant homology to any known gene sequences, represented by SEQ ID NO: 116, 117 and 119. To the best of the inventors' knowledge, none of these sequences have been previously shown to be present in colon. The determined cDNA sequences of the remaining clones (SEQ ID NO: 113–115 and 120) were found to show some homology to previously identified genes.

Further analysis identified a clone which was recovered several times by PCR subtraction and by expression screening using a mouse anti-acid antiserum. The determined full length cDNA sequence for this clone is provided in SEQ ID NO: 121, with the corresponding predicted amino acid sequence being provided in SEQ ID NO: 122. This clone is homologous with the known gene Beta IG-H3, as disclosed in U.S. Pat. No. 5,444,164. Microarray analysis demonstrated this clone to be over-expressed in 75 to 80% of colon tumors tested (n=27), with no over-expression in normal colon samples (n=6), but with some low level over-expression in other normal tissues tested.

Further analysis of the PCR-subtraction library described above led to the isolation of longer cDNA sequences for the clones of SEQ ID NO: 30, 115, 46, 118, 41, 47, 138, 113, 14 and 40 (known as C751P, C791P, C792P, C793P, C794P, C795P, C796P, C797P, C798P and C799P, respectively). These determined cDNA sequences are provided in SEQ ID NO: 123–132, respectively.

Using PCR subtraction methodology described above with minor modifications, transcripts from a pool of three moderately differentiated colon adenocarcinoma samples were subtracted with a set of transcripts from normal brain, pancreas, bone marrow, liver, heart, lung, stomach and small intestine. Modifications of the above protocol were included at the cDNA digestion steps and in the tester to drive hybridization ratios. In a first subtraction, the restriction enzymes PvuII, DraI, MscI and StuI were used to digest cDNAs, and the tester to driver ratio was 1:40, as suggested by Clontech. In a second subtraction, DraI, MscI and StuI were used for cDNA digestion and a tester to driver ratio of 1:76 was used. Following the PCR amplification steps, the cDNAs were clones into pCR2.1 plasmid vector. The determined cDNA sequences of 167 isolated clones are provided in SEQ ID NO: 205–371. These sequences were compared to sequenced in the public databases as described above. The sequences of SEQ ID NO: 205, 207, 210–212, 214, 215, 218, 224–226, 228, 233, 234, 236, 238, 241, 242, 245, 246, 248, 250, 253, 254, 256, 259, 260, 262, 263, 266, 267, 270–273, 279, 282, 291, 293, 294, 298, 300, 302, 303, 310–313, 315, 317, 320, 322, 324, 332–335, 345, 347, 356, 358, 361, 362, 366, 369 and 371 were found to show some homology to previously identified ESTs. The remaining sequences were found to show some homology to previously identified genes.

Example 2

Isolation of Tumor Polypeptides Using SCID-Passaged Tumor RNA

Human colon tumor antigens were obtained using SCID mouse passaged colon tumor RNA as follows. Human colon tumor was implanted in SCID mice and harvested, as described in patent application Ser. No. 08/556,659 filed Nov. 11, 1995, now U.S. Pat. No. 5,986,170. First strand cDNA was synthesized from poly A+ RNA from three SCID mouse-passaged colon tumors using a Lambda ZAP Express cDNA synthesis kit (Stratagene). The reactions were pooled and digested with RNase A, T1 and H to cleave the RNA and then treated with NaOH to degrade the RNA. The resulting cDNA was annealed with biotinylated (Vector Labs, Inc., Burlingame, Calif.) cDNA from a normal resting PBMC plasmid library (constructed from Superscript plasmid System, Gibco BRL), and subtracted with streptavidin by phenol/chloroform extraction. Second strand cDNA was synthesized from the subtracted first strand cDNA and digested with S1 nuclease (Gibco BRL). The cDNA was blunted with Pfu polymerase and EcoRI adaptors (Stratagene) were ligated to the ends. The cDNA was phosphorylated with T4 polynucleotide kinase, digested with restriction endonuclease XhoI, and size selected with Sephacryl S-400 (Sigma). Fractions were pooled, ligated to Lambda ZAP Express arms (Stratagene) and packaged with Gigapack Gold III extract (Stratagene). Random plaques were picked, phagemid was excised, transformed into XLOLR cells (Stratagene) and resulting plasmid DNA (Qiagen Inc., Valencia, Calif.) was sequenced as described above. The determined cDNA sequences for 17 clones isolated as described above are provided in SEQ ID NO: 133–151, wherein 133 and 134 represent partial sequences of a clone referred to as CoSub-3 and SEQ ID NO: 135 and 136 represent partial sequences of a clone referred to as CoSub-13. These sequences were compared with those in the public databases as described above. The sequences of SEQ ID NO: 139 and 149 showed no significant homologies to any previously identified sequences. The sequences of SEQ ID NO: 138, 140, 141, 142, 143, 148 and 149 showed some homology to previously isolated expressed sequence tags (ESTs). The sequences of SEQ ID NO: 133–137, 144–147, 150 and 151 showed some homology to previously isolated gene sequences.

Example 3

Use of Mouse Antisera to Identify DNA Sequences Encodein Colon Tumor Antigens

This example illustrates the isolation of cDNA sequences encoding colon tumor antigens by screening of colon tumor cDNA libraries with mouse anti-tumor sera.

A cDNA expression library was prepared from SCID mouse-passaged human colon tumor poly A+ RNA using a Stratagene (La Jolla, Calif.) Lambda ZAP Express kit, following the manufacturer's instructions. Sera was obtained from the colon tumor-bearing SCID mouse. This serum was injected into normal mice to produce anti-colon tumor serum. Approximately 600,000 PFUs were screened from the unamplified library using this antiserum. Using a goat anti-mouse IgG-A-M (H+L) alkaline phosphatase second antibody developed with NBT/BCIP (BRL Labs.), positive plaques were identified. Phage was purified and phagemid excised for several clones with inserts in a pBK-CMV vector for expression in prokaryotic or eukaryotic cells.

The determined cDNA sequences for 46 of the isolated clones are provided in SEQ ID NO: 152–197. The predicted, amino acid sequences for the cDNA sequences of SEQ ID NO: 187, 188, 189, 190, 194, 195 and 197 are provided in SEQ ID NO: 198–204, respectively. The determined cDNA sequences were compared with those in the public database as described above. The sequences of SEQ ID NO: 156, 168, 184, 189, 192 and 196 showed some homology to previously isolated ESTs. The sequences of SEQ ID NO: 152–155, 157–167, 169–182, 183, 185–188, 190, 194, 195 and 197 showed some homology to previously identified genes.

Example 4

Synthesis of Polypeptides

Polypeptides may be synthesized on a Perkin Elmer/Applied Biosystems Division 430A peptide synthesizer using FMOC chemistry with HPTU (O-Benzotriazole-N,N, N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for determining the presence of colon cancer in a patient, comprising the steps of:
   (a) obtaining a biological sample from the patient;
   (b) contacting the biological sample with an oligonucleotide, wherein said oligonucleotide is capable of hybridizing under moderately stringent conditions to a polynucleotide sequence selected from the group consisting of:
      (i) SEQ ID NO:12; and
      (ii) SEQ ID NO:13;
      wherein said moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS;
   (c) detecting in the sample an amount of oligonucleotide that hybridizes to the polynucleotide; and
   (d) comparing the amount of oligonucleotide that hybridizes to the polynucleotide TO a predetermined cut-off value, wherein an increase in the amount of oligonucleotide that hybridizes to the polynucleotide as compared to the predetermined cut-off value indicates the presence of cancer in the patient.

2. A method for monitoring the progression of colon cancer in a patient, comprising:
   (a) obtaining a biological sample from the patient;
   (b) contacting the biological sample with an oligonucleotide, wherein said oligonucleotide is capable of hybridizing under moderately stringent conditions to a polynucleotide sequence selected from the group consisting of:
      (i) SEQ ID NO:12; and
      (ii) SEQ ID NO:13
      wherein said moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS;
   (c) detecting in the sample an amount of oligonucleotide that hybridizes to the polynucleotide;
   (d) repeating steps (a)–(c) wherein the biological sample is obtained from the patient at a subsequent point in time; and
   (e) comparing the amount of oligonucleotide detected in (d) to the amount detected in (c) wherein an increase in the amount of oligonucleotide in step (d) as compared to the amount of oligonucleotide in step (c) indicates progression of said colon cancer and wherein a decrease in the amount of oligonucleotide in step (d) as compared to the amount of oligonucleotide in step (c) indicates a remission of said colon cancer.

3. A method for determining the presence or absence of a colon cancer in a patient, comprising the steps of:
 (a) contacting a biological sample obtained from the patient with at least two oligonucleotide primers specific for a polynucleotide sequence selected from the group consisting of:
  (i) SEQ ID NO:12;
  (ii) SEQ ID NO:13; and
  (iii) The complement of any of the sequences of (i)–(ii); under conditions effective for amplifying an expressed product in an reversed transcription-polymerase chain reaction (RT-PCR) reaction;
 (b) detecting in the sample an amount of said product; and
 (c) comparing the amount of said product to a predetermined cut-off value and therefrom determining the presence of colon cancer in a patient.

4. A method for monitoring the progression of a colon cancer in a patient, comprising the steps of:
 (a) contacting a biological sample obtained from the patient with at least two oligonucleotide primers specific for a polynucleotide sequence selected from the group consisting of:
  (i) SEQ ID NO:12;
  (ii) SEQ ID NO:13; and
  (iii) The complement of any of The sequences of (i)–(ii); under conditions effective for amplifying an expressed product in an reverse transcription-polymerase chain reaction (RT-PCR) reaction;
 (b) detecting in the sample an amount of said product; and
 (c) repeating steps (a) and (b) using a biological sample obtained from the patient at a subsequent point in time; and thereby monitoring the progression of colon cancer in the patient.

* * * * *

SEQUENCE LISTING

<160> NUMBER OF SEQ ID NOS: 371

<210> SEQ ID NO 1
<211> LENGTH: 458
<212> TYPE: DNA
<213> ORGANISM: Homo sapien
<220> FEATURE:
<221> NAME/KEY: misc_feature
<222> LOCATION: (1)...(458)
<223> OTHER INFORMATION: n = A,T,C or G

<400> SEQUENCE: 1

```
ncaggtctgg cggcacctgt gcactcagcc gtcgatacac tggtcgattg ggacagggaa      60
gacgatgtgg ttttcaggga ggcccagaga tttggagaag cggatgaagt tctcctttag    120
ttccgaagtc agctccttgg ttctcccgta gagggtgatc ttgaagtact ccctgttttg    180
agaaactttc ttgaagaaca ccatagcatg ctggttgtag ttggtgctca ccactcggac    240
gaggtaactc gttaatccag ggtaactctt aatgttgccc agcgtgaact cgccgggctg    300
gcaacctgga acaaagtcc tgatccagta gtcacacttc tttttcctaa acaggacgga    360
ggtgacattg tagctcttgt cttctttcag ctcatagatg gtggcataca tcttttgcgg    420
gtctttgtct tctctgagaa ttgcattccc tgccagga                             458
```

<210> SEQ ID NO 2
<211> LENGTH: 423
<212> TYPE: DNA
<213> ORGANISM: Homo sapien

<400> SEQUENCE: 2

```
cagggtccat aggtgatccg caactctcga gcatttatat acaatagcaa atcatccagt      60
gtgttgtaca gtctataata ctccaacagt ctcccatctg tattcaatgg cgccacccaa    120
tacagtcctt tgtttggatg ctggggagag taatccctac cccaagcacc atatagaaa     180 gaaaccctc tccagttgag ctgaaccaca gacggtttgc tgatgttcac cacaccacca    240
tgaccacagc tccctggagt gggaggaggg tggacgacag gggtgttttg atctttagag    300
gcttcacact ctttcagctt ggtcttcaga gccacgattt ctcggcgaat ggcaaggaca    360
ttgtttttgt ctagtgtctc aagcttctct accaagagag tcatatttct tatctccacc    420
tcc                                                                   423
```

<210> SEQ ID NO 3
<211> LENGTH: 538
<212> TYPE: DNA
<213> ORGANISM: Homo sapien

<400> SEQUENCE: 3

```
ggtctgtcca atggcaacag gaccctcact ctaytcartg tcacaagraa tgayrcagsa      60
msctayraat gtgaaaycca gaacccagtg agtgccarsc gcagtgayyc agtcatcctg     120
aatgtcctct atgcccrga tgmccccacc atttcccctc taaacacatm ttaccgwyca     180
ggggaaaatc tgaacctctc ctgccacgca gcctctaacc cacctgcaca gtactcttgg     240
tttrtcaatg ggactttcca gcaatccacm caagagctct ttatcccaa catcactgtg     300 aataatagyg gatcctatac gtgccaagcc cataactcag mcactggcct caataggacc     360
acagtcacga cgatcacagt ctatgcaaga gccacccaaa cccttcatca ccagcaacaa     420
ctccaacccc gtggaggatg aggatgctgt agccttaacc tgtgaacctg agattcagaa     480
cacaacctac ctgtggtggg taaataatca gagcctcccg gtcagtccca ggctgcag       538

<210> SEQ ID NO 4
<211> LENGTH: 309
<212> TYPE: DNA
<213> ORGANISM: Homo sapien

<400> SEQUENCE: 4
tggtaascca aaaagatgct ggggcagatt gtggacaagt agaagaacct ccttcccctc      60
tgcgaacatt gaacggcgtg gattcaatag tgagcttggc agtggtgggc gggttccaga     120
aggttagaag tgaggctgtg agcaggagcc cctgccaggg gatvcacgca mtctgtgggg     180
aggggctgag rggdgwcycc atggtctctg ctgtctgctc tgtcctcctc tgtggagaag     240
agcttgagct ccaggaacgc tttgrtcavg gctgcctgtg acctytgctc tgbtctgcct     300
gcccgggcg                                                             309

<210> SEQ ID NO 5
<211> LENGTH: 412
<212> TYPE: DNA
<213> ORGANISM: Homo sapien

<400> SEQUENCE: 5
gtccaatggc aacaggaccc ctcacttcta ttcaatgtca caagaaatga cgcaagagcc      60
tatgtatgtg gaatccagaa ctkcagtgag tgcaaaccgc agtgacccag tcaccctgga     120
tgtcctctat gggccagaca sccccatca tttcccccc agactcgtct taccttttcgg     180 gagcgaacct caacctctcc tgccactcgg cctctaaccc atcccgcag tattcttggc     240 kgtatcaatg ggataccgca gcaacacaca caagttctct ttatcgccaa aatcacgcca     300
aataataacg ggacctatgc ctgttttgtc tctaacttgg ctactggccc gcaataattc     360
catagtcaag agcatcacag tcttctgcat ctggaacttc tcctggtctt ct             412

<210> SEQ ID NO 6
<211> LENGTH: 332
<212> TYPE: DNA
<213> ORGANISM: Homo sapien

<400> SEQUENCE: 6
gtgcaagggc tttacaaaaa ctgtgccagt krcttctyca tgwsrcwrga tctgactkka      60
ttsaygttkt atgagsysya saatmctgaw gctcmttyts sakgrwsttc kgsatmrgca     120
gtsrattcsa catttgggrt akrtymtctc tsgaagysam tgtcakgcag tgrcayccwr     180
gkktcwgcwt gcwgtgrgtt amcakcmwtr ywtagkgsgm ayatrattta ramrgtayak     240
cymtctcmct cytycmccay wtgcwcaass mkcacacctc ggccgcgacc acgctaagcc     300
```

```
cgaattccag cacactggcg gccgttacta gt                                    332
```

<210> SEQ ID NO 7
<211> LENGTH: 401
<212> TYPE: DNA
<213> ORGANISM: Homo sapien

<400> SEQUENCE: 7

```
tggtgttgtt ggcgccagtt ccctggacct ggaacagccg tgtggagggc ccggtctcca      60
agttgttagt tcgggaggtg cctccctggt agaccaccat gcgtcccttg aagatggaca     120
taagatgagg tggctccttg cccattggga cccggatctg gactggttca ccattgtact     180
tctggtccag gatgacggct tgataagctg atgctgtaat ttcatcttgg ctggcctggc     240
tgccctgcca aacgtagagc aggtaatgct gcttctcgcc gatgaaggta ggtgtaagag     300
cagcaggtaa gcaagttcgc ccccatagaa gtgggcctag ccacttggaa ttccagcaca     360
ctggcggccc gttactagtg ggatcccgag ctcggtacca a                         401
```

<210> SEQ ID NO 8
<211> LENGTH: 1151
<212> TYPE: DNA
<213> ORGANISM: Homo sapien

<400> SEQUENCE: 8

```
ctctctccat aaaactcagc actttacaga tgtagaatat ataagcatgc caaatttact      60
tatctgccac atacaaagca tcattccagg tgctagtgag gggaaaaaaa agttggagat     120
ttggtccctc gaggagctcc agatattaat ctacctaact aagtcccag gtttcttcca     180
ggcatggaag aattagtggt gctacatgga tgaggactag tcattgggca atatttcctg     240
tacaaagaat ccctagacgc catactgagt tttaagttcc ttaattccta atttaaggct     300
tctagtgaag cctcctcaca gtaggcttca ctaggcccac agtgccccta gacctctgac     360
aatcccaccc tagacagact ttattgcaaa atgcgcctga agaggcagat gattcccaag     420
agaactcacc aaatcaagac aaatgtccta gatctctagt gtggtagaac tatgcaccta     480
aacattgctg caaaatgaac acactttag acaccctgc agatatctaa gtaagtggag     540
aagactattt tttcaacaaa cattttctct ttcacccta ctcctaaaca gcttactggg     600
gcttctgcaa gacagaaaga tcataattca gaaggtaacc atcgttatag acataaagtt     660
tctggtcaaa agggtatag ttaatgctct gcacttttc ctgcatctta tgcattacaa     720
tgtctagttt gccctctttc cctgtgtttg tgtcataata gtaaaaaatc tcttctgttc     780
tggtgtttca tagtacgggt ggcatacaga accccacata ccatgaaggc gttagaagca     840
gatggtttat actgcttggt ataccaagtg tttagcacct gaagtgtggt gtcattgagt     900
ttactaatca ccatgttacc agtgctggct tcagttgaat aaataaccca caatccattc     960
tcatccacag caaagtcaat atcttgccaa gcaacattag catatgaaaa gcggttatta    1020
taggcagcat tagggagagt ttgagtcaca gcaatcgtgt tggtggtcag gttaactctg    1080
gcaatattcc cggtgttgta catgttgacg tacatgttgt tgttgtaaac tgctgtacca    1140
ctaccttgga c                                                        1151
```

<210> SEQ ID NO 9
<211> LENGTH: 604
<212> TYPE: DNA
<213> ORGANISM: Homo sapien
<220> FEATURE:
<221> NAME/KEY: misc_feature
<222> LOCATION: (1)...(604)
<223> OTHER INFORMATION: n = A,T,C or G

<400> SEQUENCE: 9

```
ctgtgcaagg gctttacaaa aactgtgcca ggacttccca tgaggctgga ttgcttgatt      60
catgttttat gagccccaca atactgaagc tccttttcca gggacttggc ataggcagtc     120
aattccacat ttgggatagg tcctctctgg aagtgaatgt caggcagtga catccaagtt     180
tctgcatgca gtgggttaac agccatgttt aggggaaca tgatttaaaa agtacatctc      240
tctccctcct cccccacatg cacaaggctc acatctcatt atggtgkcgg cccatgtcac     300
attaaagtgt gatacttkgg ttttgaaaac attcaaacag tctctgtgga aatctggaga     360
gaaattggcg gagagctgcc gtggtgcatt cctcctgtag tgcttcaagn taatgcttca     420
tcctttntta ataacttttg atagacaggg gctagtcgca cagacctctg ggaagccctg     480
gaaaacgctg atgcttgttt gaagatctca agcgcagagt ctgcaagttc atcccctctt     540
tcctgaggtc tgttggctgg aggctgcaga acattggtga tgacatggac cacgccattt     600
gtgg                                                                  604
```

<210> SEQ ID NO 10
<211> LENGTH: 473
<212> TYPE: DNA
<213> ORGANISM: Homo sapien

<400> SEQUENCE: 10

```
tcgagaagat ccctagtgag actttgaacc gtatcctggg cgacccagaa gccctgagag      60
acctgctgaa caaccacatc ttgaagtcag ctatgtgtgc tgaagccatc gttgcggggc     120
tgtctgtgga daccctggag ggcacgacac tggaggtggg ctgcagcggg gacatgctca     180
ctatcaacgg gaaggcgatc atctccaata aagacatcct agccaccaac ggggtgatcc     240
actacattga tgagctactc atcccagact cagccaagac actatttgaa ttggctgcag     300
agtctgatgt gtccacagcc attgaccttt tcagacaagc cggcctcggc aatcatctct     360
ctggaagtga gcggttgacc ctcctgggct cccctgaatt ctgtattcaa agatggaacc     420
cctccaattg atgcccatac aaggaatttg cttcggaacc acataattaa aga            473
```

<210> SEQ ID NO 11
<211> LENGTH: 411
<212> TYPE: DNA
<213> ORGANISM: Homo sapien
<220> FEATURE:
<221> NAME/KEY: misc_feature
<222> LOCATION: (1)...(411)
<223> OTHER INFORMATION: n = A,T,C or G

<400> SEQUENCE: 11

```
tcctcattgg tcggggccaa aagcgtgtac tggccgttac cttcaagcat cgtgttgagc      60
cctgatgcag ccacagcagc ccgaagggtc tcaaaggtgt cctcgatctc aatgatctgc     120
tggatgttgt tggtgatggt ggagatgacc ttatcgatga ggtgcaccac cccgttggtt     180
gcatggtggt cggctttyar carccgggca cagttcacag ttacaatccc attaggatag     240
tggtggatct nggatgttgg aattctggta catagnaggt gaggggtcat gcccgtgttt     300
cagctcatca gtcaggactc gcctgcccac catatggtaa gcsgragggc atttgagcag     360
ctcaatgttt gacattgctg gaccagggga gttccagcac ttctangang a             411
```

<210> SEQ ID NO 12

<210> SEQ ID NO 12
<211> LENGTH: 560
<212> TYPE: DNA
<213> ORGANISM: Homo sapien

<400> SEQUENCE: 12

| | | |
|---|---|---|
| tacttgcctg gagatwgcyt tykckwtmtg ytcwrawgtc cgtggataca gaaatctctg | 60 |
| caggcaagtt gctccagagc atattgcagg acaagcctgt aacgaatagt taaattcacg | 120 |
| gcatctggat tcctaatcct tttccgaaat ggcaggtgtg agtgcctgta taaatattc | 180 |
| tatgtttacc ttcaacttct tgttctggct atgtggtatc ttgatcctag cattagcaat | 240 |
| atgggtacga gtaagcaatg actctcaagc aattttggt tctgaagatg taggctctag | 300 |
| ctcctacgtt gctgtggaca tattgattgc tgtaggtgcc atcatcatga ttctgggctt | 360 |
| cctgggatgc tgcggtgcta taaaagaaag tcgctgcatg cttctgttgt ttttcatagg | 420 |
| cttgcttctg atcctgctcc tgcaggtggg cgacaggtat cctaggagct gttttcaaat | 480 |
| ctaagtctga tcgcattgtg aatgaaactc tctatgaaaa cacaaagctt ttgagcgcca | 540 |
| cagggaaag tgaaaaacaa | 560 |

<210> SEQ ID NO 13
<211> LENGTH: 150
<212> TYPE: DNA
<213> ORGANISM: Homo sapien

<400> SEQUENCE: 13

| | | |
|---|---|---|
| gggcaggctg tcttttaaa atgtctcggc tagctagacc acagatatct tctagacata | 60 |
| ttgaacacat ttaagatttg agggatataa gggaaaatga tatgaatgtg tatttttact | 120 |
| caaaataaaa gtaactgttt acgttggtga | 150 |

<210> SEQ ID NO 14
<211> LENGTH: 403
<212> TYPE: DNA
<213> ORGANISM: Homo sapien

<400> SEQUENCE: 14

| | | |
|---|---|---|
| ctgctgcctg tggcgtgtgt gggctggatc ccttgaaggc tgagttttg agggcagaaa | 60 |
| gctagctatg ggtagccagg tgttacaaag gtgctgctcc ttctccaacc cctacttggt | 120 |
| ttccctcacc ccaagcctca tgttcatacc agccagtggg ttcagcagaa cgcatgacac | 180 |
| cttatcacct ccctccttgg gtgagctctg aacaccagct ttggcccctc cacagtaagg | 240 |
| ctgctacatc agggcaacc ctggctctat cattttcctt ttttgccaaa aggaccagta | 300 |
| gcataggtga gccctgagca ctaaaaggag gggtccctga agctttccca ctatagtgtg | 360 |
| gagttctgtc cctgaggtgg gtacagcagc cttggttcct ctg | 403 |

<210> SEQ ID NO 15
<211> LENGTH: 688
<212> TYPE: DNA
<213> ORGANISM: Homo sapien
<220> FEATURE:
<221> NAME/KEY: misc_feature
<222> LOCATION: (1)...(688)
<223> OTHER INFORMATION: n = A,T,C or G

<400> SEQUENCE: 15

| | | |
|---|---|---|
| caaagcacat tttaatcatt tattttaaaa gggggagtaa agcatttaaa ctgccaatcc | 60 |
| tatagactag gacttgaaca tcaaaggaaa aatagacaaa gactagatga taaagtcatt | 120 |
| caaaagcaca gaagcacatc acatacacca gcaaggtttc caactactgc actgattaac | 180 |

```
tagatactct caatagcttt tctatagctc gtcctagaaa aaaaattaa attttcattt      240 tcttacaagt tccaggctta aacaaaggca aaaattacat gcaacaactg atacactcat      300
aagttgcaca tatgctccaa ggtctttatt agataacaat aaatgctagc actttgtcac      360
tgccatcaga ttttccttat agtcttagag tcatgtaaat aaaagttcca taatgaaatt      420
aaagaaaatt aattttctta atcttagatc agttccatag aaaactatta atttttttaa      480
agtaggcagt agaaggggggt tggtgggggg tggaattggt tagtaagtct ggttctaatc      540
ttctgagctg cctttggaag gaagttatga ggtagaagat tctactgact tttagtaagg      600
tggacaatga gagaaaagaa aaagcaggtg cctcatcnnc agatccttnt ggtatttatn      660
tgccangtnc nanntaatnc atanaaag                                         688

<210> SEQ ID NO 16
<211> LENGTH: 408
<212> TYPE: DNA
<213> ORGANISM: Homo sapien

<400> SEQUENCE: 16
caggtcatca agatgactta caggatgtaa tagggagagc tgtcgagatt ggtgttaaaa       60
agtttatgat tacaggtgga aatctacaag acagtaaaga tgcactgcat ttggcacaaa      120
caaatggtat gttttttcagt acagttggat gtcgtcctac aagatgtggt gaatttgaaa      180
agaataaccc tgatctttac ttaaaggagt tgctaaatct tgctgaaaac aataaaggga      240
aagttgtggc aataggagaa tgcggacttg attttgaccc gactgcagtt ttgtcccaaa      300
gatactcaac tcaaatattt tgaaaaacag tttgaactgt cagaacaaac aaaattacca      360
atgtttcttc attgtccgaa actcacatgc tgaattttg gacataat                   408

<210> SEQ ID NO 17
<211> LENGTH: 407
<212> TYPE: DNA
<213> ORGANISM: Homo sapien

<400> SEQUENCE: 17
ggtcctgggg aggccctagg ggagcaccgt gatggagagg acagagcagg ggctccagca       60
ccttctttct ggactggcgt tcacctccct gctcagtgct gggctccac gggcaggggt      120 cagagcactc cctaatttat gtgctatata aatatgtcag atgtacatag agatctattt      180
tttctaaaac attcccctyc ccactcctct cccacagagt gctggactgt tccaggccct      240
ccagtgggct gatgctggga cccttaggat ggggctccca gctcctttct cctgtgaatg      300
gaggcagaag acctccaata aagtgccttc tgggcttttt ctaaccttttg tcttagctac      360 ctgtgtactg aaatttgggc ctttggatcg aatatggtca agaggtt                   407

<210> SEQ ID NO 18
<211> LENGTH: 405
<212> TYPE: DNA
<213> ORGANISM: Homo sapien

<400> SEQUENCE: 18
tgaagagtca acttgggcct ggaggactga taaagtttgt gattttgagg gcctctaaaa       60
gtattaaagc agcggcagcc gctgcacgca gacatgaggg ctaggttaaa acagtaagat      120
caagttgttt ggacagaaag gctacagagt gtggtcctgg ctcttgtgta agaattacga      180
ccacgctaac catgcctagg aaggaaagga gttattgttt tgtagaaagg tgctggggtt      240
```

```
tgagagatca gtcggacacg attggcaggg agagcacgtg tgtttttatg agaattatgc      300
ccgagatagg taacagatga ggaagaaatt tgggcttgat tgaagtaatg ggggctgtct      360
gtgaagcttt gcagcagtac agcctaggta atttgctgag cctaa                     405

<210> SEQ ID NO 19
<211> LENGTH: 401
<212> TYPE: DNA
<213> ORGANISM: Homo sapien

<400> SEQUENCE: 19
tcctgacatt cctgccttct tatattaata agacaaataa aacaaaatag tgttgaagtg       60
ttggggcagc gaaaatttt ggggggtggt atggagagat aatgggcgat gtttctcagg      120
gctgcttcaa gcgggattag gggcggcgtg ggagcctaga gtgggagaga ttaagctgaa     180
gggaggtctt gtggtaaggg gtgatatcat ggggatgtta aagaaacat ttgtcgtata       240 gaatgattgg tgatggcctg gatacggttt tggatgattt gagaagctaa atggaagata     300
caaggtccga ataaaaggag gagaaaaatg ggtattaaat gtctaagaat tgggaggacc     360
taggacatct gattagagag tgcctaagga gattcagcat a                         401

<210> SEQ ID NO 20
<211> LENGTH: 331
<212> TYPE: DNA
<213> ORGANISM: Homo sapien

<400> SEQUENCE: 20
aggtccagct ctgtctcata cttgactcta aagtcatcag cagcaagacg ggcattgtca       60
atctgcagaa cgatgcgggc attgtccaca gtatttgcga agatctgagc cctcaggtcc     120
tcgatgatct tgaagtaatg gctccagtct ctgacctggg gtcccttctt ctccaagtgc     180
tcccggattt tgctctccag cctccggttc tcggtctcca ggctcctcac tctgtccagg     240
taagaggcca ggcggtcgtt caggctttgc atggtctcct tctcgttctg gatgcctccc     300
attcctgcca gaccccggc tatcccggtg g                                     331

<210> SEQ ID NO 21
<211> LENGTH: 346
<212> TYPE: DNA
<213> ORGANISM: Homo sapien
<220> FEATURE:
<221> NAME/KEY: misc_feature
<222> LOCATION: (1)...(346)
<223> OTHER INFORMATION: n = A,T,C or G

<400> SEQUENCE: 21
ggtccaccac ttgtacccga tatggacttc cggcttctct gtccaatgga gccacactaa       60
agatctcacc agtcacgtgg tcaattttaa gccaacctct tgtgtctccc ctcagtgaat     120
agcttatgtc cagaccttct ggatccttgg cagtcacatt gcccacttta gtgcctatag     180
ctacatcctc actgactttc gcttggaata cgtgttggga aaattgaggt gcttcattca     240
catctgtcac aataagncgt gaacttggca aaagaacttg cattgtactt cacaccaaac     300
actagaggct caggattttc tgctttgaac acaatgttgg aaacag                   346

<210> SEQ ID NO 22
<211> LENGTH: 360
<212> TYPE: DNA
<213> ORGANISM: Homo sapien
<220> FEATURE:
<221> NAME/KEY: misc_feature
```

```
<222> LOCATION: (1)...(360)
<223> OTHER INFORMATION: n = A,T,C or G

<400> SEQUENCE: 22
gaagactccc tctctcggaa gccggatccc gagccgggca ggatggatca ccaccagccg      60
gggactgggc gctaccaggt gcttcttaat gaagaggata actcagaatc atcggctata     120
gagcagccac ctacttcaaa cccagcaccc gcagattgtg caggctgcgt cttcagcacc     180
agcacttgaa actgactctt cccctccacc atatagtagt attactggtg gaagtaccta     240
caacttcaga tacagaagtt tacggtgagt tttatcccgt gccacctccc tatagcgttg     300
ctacctctct tcctacnwta cgatgaaagc tgagaaggct aaagctgctg caatggcatg     360

<210> SEQ ID NO 23
<211> LENGTH: 251
<212> TYPE: DNA
<213> ORGANISM: Homo sapien

<400> SEQUENCE: 23
ggcggagctc cacgacgagc tgaaaaggaa acctttgag gatggctttg caaatgggga      60
agaaagtact ccaaccagag atgctgtggt cacgtatact gcagaaagta aggagtcgt     120 gaagtttggc tggatcaagg gtgtattagt acgttgtatg ttaaacattt ggggtgtgat     180
gcttttcatt agattgtcat ggattgtggg tcaagctgga ataggtctat cagtccttgt     240
aataatgatg g                                                         251

<210> SEQ ID NO 24
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 24
caggtctttc ccaggtgttg actccagctc cagcttcagc tccagctcca ggtcgggctc      60
cagctccagc cgcagcttar gcagcgggag gttctgtgtc ccagttgttt tccaatttca     120
ccggctcccg tggatgamcg ygggacctgy caswgctcct gtktycctgc yagsacacca     180
cnytttyccg tggacacrar kggaaccckct tggaattcac agctyatgtt ctttctcara    240
agtttgagaa agaactttct aaagtgaggg aatatgtcca attaattagt gtgtatgaaa     300
agaaactgtt aaacctaact gtccgaattg acatcatgga raaaggatac catttcttac     360
actgaactgg acttcgagct gatcaaggta gaagtgaagg agatggaaaa actggtcata     420
c                                                                     421

<210> SEQ ID NO 25
<211> LENGTH: 381
<212> TYPE: DNA
<213> ORGANISM: Homo sapien
<220> FEATURE:
<221> NAME/KEY: misc_feature
<222> LOCATION: (1)...(381)
<223> OTHER INFORMATION: n = A,T,C or G

<400> SEQUENCE: 25 gaacttttg tttctttatt ttcaatattt gtcttattaa tattttctt attttataat        60 gcaattacaa caatttagga nacaaaacaa tataaacaaa agaatgttaa atagttttt      120
```

```
ttaaaaaata gcttgttgct tgcaanaaag tccatataat cttattcccc cccaaatata      180
attttatact ttgcactaaa ccaaaatagc ttatggaaaa ttagtattaa atagctaaac      240
acagaaaacc tacagctata aataacataa aatacagttt aactttaatg ngatgcttaa      300
acaaagcaaa ctatgatgca atatgaatca acttcattaa ttggacaagt ccagnggagg      360
cacaaattag ataagcacta a                                                381
```

<210> SEQ ID NO 26
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 26

```
ggaaaaggga ctggcctctc tgaagagtga gatgagggaa gtggaaggag agctggaaag      60
gaaggagctg gagtttgaca cgaatatgga tgcagtacag atggtgatta cagaagccca     120
gaaggttgat accagaagcc aagaacgctg gggttacaat ccaagacaca ctcaacacat     180
tagacgggct cctgcattct gatggaccaa ccttttcang tggtaagatt gaagangggg     240
cctgggctta cctgggaagc aaaaactttt cccganccaa ggaacccagg attcaaccan     300
gcnacttgcn ggccaaggaa ggcanaactn ggaanaaaag gccccttaag caaaagggnc     360
accttcattt gctnggaaan cagcctttan ttggaatctt g                         401
```

<210> SEQ ID NO 27
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 27

```
aattgcaact ggactttat tgggcagtta cnacaacnaa tgttttcana aaatatttg       60 gaaaaaatat accacttcat agctaagtct tacagagaan aggatttgct aataaaactt     120
aagttttgaa aattaagatg cnggtanagc ttctgaacta atgcccacag ctccaaggaa     180
nacatgtcct atttagttat tcaaatacca gttgagggca ttgtgattaa gcaaacaata    240
tatttgttan aactttgntt ttaaattact gntncttgac attacttata aaggagnctc     300
taactttcga tttctaaaac tatgtaatac aaaagtatan ntttcccat tttgataaaa      360 gggccnanga tactgantag gaa                                              383
```

<210> SEQ ID NO 28
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 28

```
ggtcgcgttt ccoctggctc acagtctgcc attatttgca tttttaaatg aagaaaagtt      60
taacgtggat ggatggacag tttacaatcc agtggaagaa tacaggaggc agggcttgcc     120
caatcaccat tggagaataa cttttattaa taagtgctat gagctctgcg acacttaccc     180
```

```
tgctcttttg gtggttccgt atcgtgcctc anatgatgac ctccggagag ttgcaacttt       240
taggtcccga aatcgaattc cagtgctgtc atggattcat ccagaaaata agacggtcat       300
tgtgcgttgc agtcagcctc ttgtcggtat gagtgggaaa cgaaataaag atgatgagaa       360
atatctcgat gttatcaggg agactaataa acaaatttct a                          401
```

<210> SEQ ID NO 29
<211> LENGTH: 401
<212> TYPE: DNA
<213> ORGANISM: Homo sapien

<400> SEQUENCE: 29

```
atatgagttt gccatctcca tggatgccat ttcaatgcct tcagggtaat cattctctcc       60
ccaaagactg cccacggggt catcactcct gtgacgaaat gagggctgga ttgaagatgt       120
tctgctgagc accccctgg tcatctttgg ggtctcagaa gagccataat catgaccatt        180
ctcagcatct gaataatcag gttctctcca agtgcttggc aagttctgat tgtcctcagc      240
actgggatag tctggctccc caaaaaggg tggagagtta ggttgaatgt cagcgcctgg       300
ataatcaggc tttcccagag agtctgcgta tggattgatt ctaaaacttg tatgttccag     360
attctttctg gatcctggat ggttcaaatt ggctctgggt c                          401
```

<210> SEQ ID NO 30
<211> LENGTH: 401
<212> TYPE: DNA
<213> ORGANISM: Homo sapien

<400> SEQUENCE: 30

```
cctgaactat ttattaaaaa catgaccact cttggctatt gaagatgctg cctgtatttg       60
agagactgcc atacataata tatgacttcc tagggatctg aaatccataa actaagagaa      120
actgtgtata gcttacctga acaggaatcc ttactgatat ttatagaaca gttgatttcc     180
cccatcccca gtttatggat atgctgcttt aaacttggaa gggggagaca ggaagtttta     240
attgttctga ctaaacttag gagttgagct aggagtgcgt tcatggtttc ttcactaaca    300
gaggaattat gctttgcact acgtccctcc aagtgaagac agactgtttt agacagactt     360
tttaaaatgg tgccctacca ttgacacatg cagaaattgg t                         401
```

<210> SEQ ID NO 31
<211> LENGTH: 297
<212> TYPE: DNA
<213> ORGANISM: Homo sapien

<400> SEQUENCE: 31

```
acctccatta atgccaggtg ttcctcctct gatgccagga atgccaccag ttatgccagg      60
catgccacct ggattgcatc atcagagaaa atacacccag tcattttgcg gtgaaaacat     120
aatgatgcca atgggtggaa tgatgccacc tggaccagga ataccacctc tgatgcctgg    180
aatgccacca ggtatgcccc cacctgttcc acgtcctgga attcctccaa tgactcaagc    240
acaggctgtt tcagcgccag gtattcttaa tagaccacct gcaccaacag caactgt       297
```

<210> SEQ ID NO 32
<211> LENGTH: 401
<212> TYPE: DNA
<213> ORGANISM: Homo sapien

<400> SEQUENCE: 32

-continued

| caaacctgga gccaaaaagg acacaaagga ctctcgaccc aaactgcccc agaccctctc | 60 |
| cagaggttgg ggtgaccaac tcatctggac tcagacatat gaagaagctc tatataaatc | 120 |
| caagacaagc aacaaaccct tgatgattat tcatcacttg ggtgagtgcc cacacagtca | 180 |
| agctttaaag aaagtgtttg ctgaaaataa agaaatccag aaattggcag agcagtttgt | 240 |
| cctcctcaat ctggtttatg aaacaactga caaacacctt tctcctgatg ccagtatgt | 300 |
| ccccaggatt atgtttgttg acccatctct gacagttaga gcccgatatc actggaagat | 360 |
| attcaaaccg tctctatgct tacgaacctg cagatacagc t | 401 |

<210> SEQ ID NO 33
<211> LENGTH: 401
<212> TYPE: DNA
<213> ORGANISM: Homo sapien

<400> SEQUENCE: 33

| agcagaggga caggaatcat tcggccactg ttcagacggg agccacaccc ttctccaatc | 60 |
| caagcctggc cccagaagat cacaaagagc caaagaaact ggcaggtgtc cacgcgctcc | 120 |
| aggccagtga gttggttgtc acttactttt tctgtgggga agaaattcca taccggagga | 180 |
| tgctgaaggc tcagagcttg accctgggcc actttaaaga gcagctcagc aaaaagggaa | 240 |
| attataggta ttacttcaaa aaagcaagcg atgagtttgc ctgtggagcg gtgtttgagg | 300 |
| agatctggga ggatgagacg gtgctcccga tgtatgaagg ccggattctg gcaaagtgg | 360 |
| agcggatcga ttgagccctg gggtctggct ttggtgaact g | 401 |

<210> SEQ ID NO 34
<211> LENGTH: 401
<212> TYPE: DNA
<213> ORGANISM: Homo sapien

<400> SEQUENCE: 34

| aacaatggct atgaaggcat tgtcgttgca atcgacccca atgtgccaga agatgaaaca | 60 |
| ctcattcaac aaataaagga catggtgacc caggcatctc tgtatctgtt tgaagctaca | 120 |
| ggaaagcgat tttatttcaa aaatgttgcc attttgattc ctgaaacatg gaagacaaag | 180 |
| gctgactatg tgagaccaaa acttgagacc tacaaaaatg ctgatgttct ggttgcttga | 240 |
| gtctactcct ccaggtaatg atgaacccta cactgagcag atggggcaac tgtggagaga | 300 |
| aggggtgaaa ggatcccacc tcactcctga tttcattgca ggaaaaaagt tagcttgaat | 360 |
| atggaccaca aggtaagggc atttgtccat gaatggggct c | 401 |

<210> SEQ ID NO 35
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 35

| catttcttcc tactagactg ccccttgat ccactggcag aaatgatggc accaccttgt | 60 |
| cttcaggtgg tgctccttca ttattccaag gatgcagcat ctctatggtg ccaggtatgg | 120 |
| gggtaaagcc tttggcgccc tttccgcaat ggcacatcag cagtaaaagt ggtaccaata | 180 |
| gcangaacag aaagggcaaa atcatgancg caattgctgc gggtcccaag cccacatagg | 240 |
| aatcatgctg ngcttccctg canccgctgc catgcaagac actnacaaac tgngantgta | 300 |

```
aggacctgct tttcaggaca actaaaaccc tgattgnctg aaatcaggaa ctgaatttca      360
cttctcccaa gcttttctc actttggtgc aacancacac t                          401

<210> SEQ ID NO 36
<211> LENGTH: 401
<212> TYPE: DNA
<213> ORGANISM: Homo sapien

<400> SEQUENCE: 36
cctgctagaa tcactgccgc tgtgctttcg tggaaatgac agttccttgt ttttttttgtt    60 tctgttttg ttttacatta gtcattggac cacagccatt caggaactac cccctgcccc     120
acaaagaaat gaacagttgt agggagaccc agcagcacct ttcctccaca caccttcatt    180
ttgaagttcg ggttttttgtg ttaagttaat ctgtacattc tgtttgccat tgttacttgt   240
actatacatc tgtatatagt gtacggcaaa agagtattaa tccactatct ctagtgcttg    300
actttaaatc agtacagtac ctgtacctgc acggtcaccc gctccgtgtg tcgccctata    360
ttgagggctc aagctttccc ttgttttttg aagggggttt a                        401

<210> SEQ ID NO 37
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 37
cnnctntgna atggantnnt tgnctaaaan ganttgatga tgatgaaaat ccctangang    60
antaagcatg gancntgatc ntttnctnng cactccttta cgacacggaa acangnatca   120
ncatgatggt accaganacc ttatcaccna cgcgcacnga nctgactnat tccaaagagt   180
tgnggttacg gncatccggt cattgctcgt gcccattgct gcagggctga tnctactggt   240
gcttattatg ntggccctga ggatgctcca caatgaatat aagcatgctg catgatcagc   300
ggcaacanat gctctgccgt ttgcactaca tctttcacgg acacnatntc gaaacgggc    360 acnttgcana gttagacttg gaatgcatgg ngccggncan n                        401

<210> SEQ ID NO 38
<211> LENGTH: 401
<212> TYPE: DNA
<213> ORGANISM: Homo sapien

<400> SEQUENCE: 38
aattggctca ctctctcaag gcaagcactg tctcaaggca gtctcaaggc agagatgaca    60
cagcaaaaaa cagaggggga gaaaaaagtc tattattggc ttgtgattta caaaagccaa   120
agtcctttag ataaaaggcc aggagtcgta ccaacataga taccaaatcc aggagaacac   180
agaccagcga taagagggac gcttccccat gacccagacc agcctaaagc ccctgtgggg   240
gcagccagtg gggagctgtc agaccttgga catggtggtc tttgagaatg ggtctgccct   300
tctctccctg accagttggg atagacacct gactggaatc cttgacactg gcaggtgttt   360
ctatgaacag agaggactgt gcctgtcttc ctgaatccca a                        401

<210> SEQ ID NO 39
<211> LENGTH: 401
<212> TYPE: DNA
```

<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 39

| | | | | | |
|---|---|---|---|---|---|
| tctggtangg | agcaattcta | ttatttggca | ttgcatggct | gggttgaatt | aaaacaggga | 60 |
| gtgagaacag | gtgagtctag | aagtccaact | ctgaaaagga | ccactgtaca | tttgaacaca | 120 |
| cggctgtgtt | aaagatgctg | ctaatgtcag | tcactgggtg | cactaaagga | tctcttattt | 180 |
| tatgtaaaac | gttgggaatg | acaagatana | actgatactc | tggtaagtta | ccctctgaag | 240 |
| ctacttcttg | tgaaatacta | atgacagcat | catcctgcca | agcgaaagag | gcaggcataa | 300 |
| gcaaggacaa | attaaaaggg | ggtaagagcc | ttatcatgat | gaggagtctt | gttttgacat | 360 |
| cttgggaaaa | gctgtccata | gtgtgaagtc | gtcaatttct | c | | 401 |

<210> SEQ ID NO 40
<211> LENGTH: 401
<212> TYPE: DNA
<213> ORGANISM: Homo sapien

<400> SEQUENCE: 40

| | | | | | |
|---|---|---|---|---|---|
| tctggtcacc | caactcttgt | ggaagagggg | aattgagatc | gagtactgaa | tatctggcag | 60 |
| agaggctgga | atccttcagc | cccagagccc | agggaccact | ccagtagatg | cagagagggg | 120 |
| cctgcccagg | ggtcagggca | gtgggtatca | ctggtgacat | caagaatatc | agggctgggg | 180 |
| aggcatcttt | gtttcctggt | gccctcctca | aagttgctga | cactttgggg | acgggaaggg | 240 |
| gtagaagtag | ggctgctcct | tttggagctg | gagggaatag | acctggagac | agagttgagg | 300 |
| cagtcgggct | gtccaggttc | taagcatcac | agcttctgca | ctgggctctg | aggagattct | 360 |
| cagccagagg | atcccagcct | cctcctccct | caaatgtcaa | g | | 401 |

<210> SEQ ID NO 41
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 41

| | | | | | |
|---|---|---|---|---|---|
| ctggactaaa | aatgtccact | atggggtgca | ctctacagtt | tttgaaatgc | taggaggcag | 60 |
| aaggggcaga | gagtaaaaaa | catgacctgg | tagaaggaag | agaggcaaag | gaaactaggt | 120 |
| ggggaggatc | aattagagag | gaggcacctg | ggatccacct | tcttccttan | gtcccctcct | 180 |
| ccatcagcaa | aggagcactt | ctctaatcat | gccctcccga | agactggctg | ggagaaggtt | 240 |
| taaaaacaaa | aaatccagga | gtaagagcct | taggtcagtt | tgaaattgga | gacaaactgt | 300 |
| ctggcaaagg | gtgcganagg | gagcttgtgc | tcangagtcc | agcccgtcca | gcctcggggt | 360 |
| gtangtttct | gaagtgtgcc | attggggcct | caccttctct | g | | 401 |

<210> SEQ ID NO 42
<211> LENGTH: 310
<212> TYPE: DNA
<213> ORGANISM: Homo sapien

<400> SEQUENCE: 42

| | | | | | |
|---|---|---|---|---|---|
| ggttcgacaa | atccccaaaa | atggcaaatt | aagccctgtg | acaaaataag | ttattggatc | 60 |

| | |
|---|---|
| atacagaaat agcccaaatc tggaaatttt gaattaaaat tgtaatcctg taaaacaagt | 120 |
| tttggggtga atggatttct ttaataccaa taatatttt aattcccacc acagatggat | 180 |
| ttgctgaata tgctaatgct gtgaatgaga aaacaatttt ggggtaggta tacccacaag | 240 |
| taatctgatg acaaaataaa ccacagactg atgtcaaatg acaaaaaac tgaaatatg | 300 |
| ctgtgagaaa | 310 |

<210> SEQ ID NO 43
<211> LENGTH: 401
<212> TYPE: DNA
<213> ORGANISM: Homo sapien

<400> SEQUENCE: 43

| | |
|---|---|
| aggtcactta cacttgtgac cagtgtgggg cagagaccta ccagccgatc cagtctccca | 60 |
| cttttcatgcc tctgatcatg tgcccaagcc aggagtgcca aaccaaccgc tcaggagggc | 120 |
| ggctgtatct gcagacacgg ggctccagat tcatcaaatt ccaggagatg aagatgcaag | 180 |
| aacatagtga tcaggtgcct gtgggaaata tccctcgtag tatcacggtg ctggtagaag | 240 |
| gagagaacac aaggattgcc cagcctggag accacgtcag cgtcactggt attttcttgc | 300 |
| caatcctgcg cactgggttc cgacaggtgg tacagggttt actctcagaa acctacctgg | 360 |
| aagcccatcg gattgtgaag atgaacaaga gtgaggatga t | 401 |

<210> SEQ ID NO 44
<211> LENGTH: 401
<212> TYPE: DNA
<213> ORGANISM: Homo sapien

<400> SEQUENCE: 44

| | |
|---|---|
| atccctgtaa gtctattaaa tgtaaataat acatacttta caacttctct tagtcggccc | 60 |
| ttggcagatt aaatctttgc aaaattccat atgtgctatt gaaaaatgaa ataaaacctc | 120 |
| agatgtctga attcttattt caaatacagt tatataatta ttttaaatta caatatacaa | 180 |
| tttctgttaa atacaactgt taagggattc tgagaacaat tataagatta taataatata | 240 |
| tacaaactaa cttctgaaat gacatggggtt gtttccttcc caccctccta ccctctcaaa | 300 |
| gagttttgc atttgctgtt cctggttgca aaaggcaaaa gaaaatctaa aaatagtctg | 360 |
| tgtgtgtcca cgacatgctc gctcctttga gaatctcaaa c | 401 |

<210> SEQ ID NO 45
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 45

| | |
|---|---|
| gtgcctgctg cctggcagcc tggccctgcc gctgcctcag gaggcgggag gcatgagtga | 60 |
| gctacagtgg gaacaggctc aggactatct caagagattt tatctctatg actcagaaac | 120 |
| aaaaaatgcc aacagtttag aagccaaact caaggagatg caaaaaattc tttggcctac | 180 |
| ctatactgga atggtaaact cccgcgtcat anaaataatg caannagccc agatgtggag | 240 |
| tgccagatgt tgcagaatac tcactatttc caaatagccc aaaatggact tccaaagtgg | 300 |
| tcacctacag gatcgtatca tatactcgag acttaccgca tattacagtg gatcgattag | 360 |

```
tgtcaaaggc tttaaacatg tggggcaaag agatcccct g                  401
```

<210> SEQ ID NO 46
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 46

```
gtcagaattg tctttctgaa aggaagcact cggaatcctt ccgaactttc caagtccatc    60
catgattcan agatactgcc ttctctctct ctgggatttt atgtgtttct gatagtgaat   120
tgttgatgta tttgctactt tgcttctttt ctctttcaag acttgatcat tttatatgct   180
gnttggagaa aaaaagaact tttggtagca aggaggtttc aagaaatgat tttggatttt   240
ctgctgcgga atttctcggc acctacctgt agtatggggc acttggtttg gttgcagagt   300
aagaaggtgg aagaatgagc tgtacttggt taagcagttg aaaccttttt tgagcaggat   360
ctgtaaaagc ataattgaat ttgtttcacc cccgtggatt c                      401
```

<210> SEQ ID NO 47
<211> LENGTH: 401
<212> TYPE: DNA
<213> ORGANISM: Homo sapien

<400> SEQUENCE: 47

```
ggtctgcagc aatgcacttc aaccatacat actgcttcca ctagctaata ccaaatgcag    60
gttctcagat ccagacaaat ggaggaaaag aacatttatg cttccgtttc agaaagccaa   120
gtcgtagttt tggcccttcc tttctctaaa gtttattccc aaaaacaggt agcattcctg   180
attgggcaga gaagaggata ttttcagccc acatctgctg caggtatgtc attttctccc   240
atcttcactg tgactagtaa agatctcacc acttctcttt ggaatttcca actttgcttg   300
tgattgaatg tcacttcgtg aatttgtatt atgtcagatc acttggcatt gctcttccat   360
atgcatcaag ttgccaggca ctaaacccaa tgttcatgaa c                      401
```

<210> SEQ ID NO 48
<211> LENGTH: 430
<212> TYPE: DNA
<213> ORGANISM: Homo sapien

<400> SEQUENCE: 48

```
acataacttg taaactttt ctgcttgggg gctgtaacag acagaagagt aaagactaca    60
aggattttct gaagatgctt caatgaaaat catcatttcc tctttagtca tcccaagtct   120
tggtttgaaa aacttgggca tggacttata cagaccttga accaccactg acttatcatt   180
gggtggcaga ccttgaaacc aagctctctg tgttacttct gaaagtgcat caattctgat   240
ttggctaaga acagaagaca aatactggga tcgtgattct gtgttatact ctagccacag   300
catagcagct tctcgaacgg tttcttcctt ttctacattt aaattgtcac tactgagaat   360
atctatcagt aggtcatgtg acagacctgc cccggggccg gcccgctcga tgcttgccga   420
atatcatggt                                                         430
```

<210> SEQ ID NO 49
<211> LENGTH: 57
<212> TYPE: DNA
<213> ORGANISM: Homo sapien

<220> FEATURE:
<221> NAME/KEY: misc_feature
<222> LOCATION: (1)...(57)
<223> OTHER INFORMATION: n = A,T,C or G

<400> SEQUENCE: 49
ggtattaaca atatcangca ctcattcttc ccctcttatg aaanggatna attttta         57

<210> SEQ ID NO 50
<211> LENGTH: 327
<212> TYPE: DNA
<213> ORGANISM: Homo sapien
<220> FEATURE:
<221> NAME/KEY: misc_feature
<222> LOCATION: (1)...(327)
<223> OTHER INFORMATION: n = A,T,C or G

<400> SEQUENCE: 50
gatggnggtn tccacaagan tnaangtncn tattaantan nncttgtaga nccacttnna        60
ttaattgnnn tatgnntgnc cttctggtgg ntgtngaagc ttcatatnnt ntttggacat       120
cattacacgt cttagctctt tnaagnacaa ctttaatgct atatgaattt tgccattttn       180
gctaacactg gtatgctccn ngcatccacc atnccacntg gaattattta ttncnttcat       240
attaatnttt tgtttaccaa atctnacttg acccgaacga aactttctgn gtattttang       300
gccccnccat tcttactttt caagcct                                           327

<210> SEQ ID NO 51
<211> LENGTH: 236
<212> TYPE: DNA
<213> ORGANISM: Homo sapien

<400> SEQUENCE: 51
cgtctcgaag aagcgctgca ggccgatgat ggactgcacg tctgccttgt cctcagttaa        60
cttgttgaat tgcttgaaca tgcggcccac atcctgggca aactcctgtg gggagctgta       120
gggaggtgac aacttctcct ggaggcgggc acggatcagg gtcagatcca gggtgccacc       180
gggctggtcc aggagaagg tggagtcgta gccagacctg cccgggcggc cgctcg           236

<210> SEQ ID NO 52
<211> LENGTH: 291
<212> TYPE: DNA
<213> ORGANISM: Homo sapien
<220> FEATURE:
<221> NAME/KEY: misc_feature
<222> LOCATION: (1)...(291)
<223> OTHER INFORMATION: n = A,T,C or G

<400> SEQUENCE: 52
ctcacatcct gggtccggct gtagagctgc accatggtgc tgagcgcccc ctccagctcc        60
ttgtagatgt aaaggacggc gaaggagctg tagtctgtgt ccacgatgcg cacgtccagg       120
tagcccaagg ccgggactct gaagttgtcc ctcggagccc accttcangt actcgggcat       180
ccacctggtt acagccnttc gncctcggna actccatntg gactttacag gccgccctcc       240
tctgtgggcc tgatggncct tgcaggacat nggaacacgg gagctcnctt t                291

<210> SEQ ID NO 53
<211> LENGTH: 95
<212> TYPE: DNA
<213> ORGANISM: Homo sapien
<220> FEATURE:
<221> NAME/KEY: misc_feature
<222> LOCATION: (1)...(95)

<223> OTHER INFORMATION: n = A,T,C or G

<400> SEQUENCE: 53
gtctgtgcag tttctgacac ttgttgttga acatggntaa atacaatggg tatcgctgan    60
cactaagttg tanaanttaa caaatgtgct gnttg    95

<210> SEQ ID NO 54
<211> LENGTH: 66
<212> TYPE: DNA
<213> ORGANISM: Homo sapien
<220> FEATURE:
<221> NAME/KEY: misc_feature
<222> LOCATION: (1)...(66)
<223> OTHER INFORMATION: n = A,T,C or G

<400> SEQUENCE: 54
cctnaatnat ntnaatggta tcaatnnccc tgaangangg gancggngga agccggnttt    60
gtccgg    66

<210> SEQ ID NO 55
<211> LENGTH: 265
<212> TYPE: DNA
<213> ORGANISM: Homo sapien
<220> FEATURE:
<221> NAME/KEY: misc_feature
<222> LOCATION: (1)...(265)
<223> OTHER INFORMATION: n = A,T,C or G

<400> SEQUENCE: 55
atctttcttc tcagtgcctt ggccntgttg agtctatctg gtaacactgg agctgactcc    60
ctgggaagag aggccaaatg ttacaatgaa cttaatggat gcaccaagat atatgaccct   120
gtctgtggga ctgatggaaa tacttatccc aatgaatgcc gtgttatgtt tttgaaaatc   180
ggaaacgcca gacttctatc ctcattcaaa aatctgggcc ttnctgaaaa ccagggtttt   240
naaaatccca ttcnggtcnc cggcg    265

<210> SEQ ID NO 56
<211> LENGTH: 420
<212> TYPE: DNA
<213> ORGANISM: Homo sapien
<220> FEATURE:
<221> NAME/KEY: misc_feature
<222> LOCATION: (1)...(420)
<223> OTHER INFORMATION: n = A,T,C or G

<400> SEQUENCE: 56
gagcggccgc ccgggcaggt cctcgcggtg acctgatggg atttcaaaac cttggttctc    60
agcaaggccc agattttga atgangatag aagtctggcg tttccgattt tcaaaacata   120
acacgcattc attgggataa gtatttccat cagtcccaca gacngggtca tatatcttgg   180
gtgcatccat taagttcntt tgttaacatt tgggcctctc tttcccangg gaattcagct   240
cccagttgtt taccaanatt naactccacc ggggccaaag gcncttgaaa aaaaaaanaa   300
ttccttgttt accttccttg ggcttnaagt tctggcgtcc aaaagttcaa tttgaaaact   360
gcaccgcact taccacgtct cttcnagaan cctggggaca cctcggccgc gaccacgcta   420

<210> SEQ ID NO 57
<211> LENGTH: 170
<212> TYPE: DNA
<213> ORGANISM: Homo sapien

<400> SEQUENCE: 57

```
gaagcggagt tgcagcgcct ggtggccgcc gagcagcaga aggcgcagtt tactgcacag    60
gtgcatcact tcatggagtt atgttgggat aaatgtgtgg agaagccagg gaatcgccta   120
gactctcgca ctgaaaattg tctctccaga cctcggccgc gaccacgcta             170

<210> SEQ ID NO 58
<211> LENGTH: 193
<212> TYPE: DNA
<213> ORGANISM: Homo sapien

<400> SEQUENCE: 58
attttcagtg cgagagtcta ggcgattccc tggcttctcc acacatttat cccaacataa    60
ctccatgaag tgatgcacct gtgcagtaaa ctgcgccttc tgctgctcgg cggccaccag   120
gcgctgcaac tccgcttcat cggcttcgcc cagctccgcc attgttcgcc acctgcccgg   180
gcggccgctc gaa                                                     193

<210> SEQ ID NO 59
<211> LENGTH: 229
<212> TYPE: DNA
<213> ORGANISM: Homo sapien

<400> SEQUENCE: 59
cgcaactctc gagcatttat atacaatagc aaatcatcca gtgtgttgta cagtctataa    60
tactccaaca gtctcccatc tgtattcaat ggcgccaccc aatacagtcc tttgtttgga   120
tgctggggag agtaatccct accccaagca ccatatagat aagaaaaccc tctccagttg   180
agctgaacca cagacggttt gctgatacct gcccgggcgg ccgctcgaa               229

<210> SEQ ID NO 60
<211> LENGTH: 340
<212> TYPE: DNA
<213> ORGANISM: Homo sapien

<400> SEQUENCE: 60
tcgagcggcc gcccgggcag gtcctctaaa gatcaaaaca ccctgtcgt ccaccctcct     60 cccactccag ggaagctgtg gtcatggtgg tgtggtgaac atcagcaaac cgtctgtggt   120
tcagctcaac tggagagggt tttcttatct atatggtgct tggggtaggg attactctcc   180
ccagcatcca aacaaaggac tgtattgggt ggcgccattg aatacagatg ggaaactgtt   240
ggagtattat aaactggtac aacacactgg atgatttgct attgtatata aatgctcgag   300
aattgcggat cacctatgga cctcggccgc gaccacgctg                         340

<210> SEQ ID NO 61
<211> LENGTH: 179
<212> TYPE: DNA
<213> ORGANISM: Homo sapien
<220> FEATURE:
<221> NAME/KEY: misc_feature
<222> LOCATION: (1)...(179)
<223> OTHER INFORMATION: n = A,T,C or G

<400> SEQUENCE: 61
tttttgtgac ggacgnttgg agtacatgtc ccaggatcac atccagcagc tagagtggct    60
gggacaagct ggcggnggcc aagcactgtt gaaacnatag gggtctgggn gnactcgggt   120
tnaagtggtt ggtccgantn ttnataacct tgtcngaacc nancatctcg gttgncang   179

<210> SEQ ID NO 62
```

<211> LENGTH: 78
<212> TYPE: DNA
<213> ORGANISM: Homo sapien
<220> FEATURE:
<221> NAME/KEY: misc_feature
<222> LOCATION: (1)...(78)
<223> OTHER INFORMATION: n = A,T,C or G

<400> SEQUENCE: 62

| | | | | | | |
|---|---|---|---|---|---|---|
| agggcgttcg | taacgggaat | gccgaagcgt | gggaaaaagg | gagcggtggc | nggaagacgg | 60 |
| ggatgagctt | angacaga | | | | | 78 |

<210> SEQ ID NO 63
<211> LENGTH: 410
<212> TYPE: DNA
<213> ORGANISM: Homo sapien
<220> FEATURE:
<221> NAME/KEY: misc_feature
<222> LOCATION: (1)...(410)
<223> OTHER INFORMATION: n = A,T,C or G

<400> SEQUENCE: 63

| | | | | | | |
|---|---|---|---|---|---|---|
| cccagttact | tggggaggct | gaggcaggga | gaatcctttg | aacccggngg | gtgggaggtt | 60 |
| gcagtgagcc | cgagatagca | ccattgcact | tccancatgg | ggtggacaga | gtgagactct | 120 |
| atctcaaaaa | aaagaaaag | aaaggaaag | agattagatt | aagattaagt | acctacttcc | 180 |
| tntcccattt | caagtcctga | aaatagagga | tcagaaatgt | tgaggaattc | tttaggatag | 240 |
| aaagggagat | gggattttac | ttatgggaa | agaccgcaaa | taaagactgn | aacttaacca | 300 |
| cattccccaa | gtgnaaggtg | ttacccaaga | agtaggaacc | cttttggctn | ttaccttacc | 360 |
| ttccngaaaa | aaacttattn | cttaaaatgg | aaacccttaa | agcccgggca | | 410 |

<210> SEQ ID NO 64
<211> LENGTH: 199
<212> TYPE: DNA
<213> ORGANISM: Homo sapien
<220> FEATURE:
<221> NAME/KEY: misc_feature
<222> LOCATION: (1)...(199)
<223> OTHER INFORMATION: n = A,T,C or G

<400> SEQUENCE: 64

| | | | | | | |
|---|---|---|---|---|---|---|
| cttgttctca | aaaaggtcaa | agggagcccg | acaggaata | aatagcaatg | ccctgaattc | 60 |
| caactgacct | tctacagaaa | agtgcttgac | tgccaagtgg | tcttcccagt | cattagtgag | 120 |
| gctcttgtag | aattctccat | actcctcttg | ggngangnca | tnagggtttn | nggcccaaat | 180 |
| aggntgggcc | tngttaagt | | | | | 199 |

<210> SEQ ID NO 65
<211> LENGTH: 125
<212> TYPE: DNA
<213> ORGANISM: Homo sapien
<220> FEATURE:
<221> NAME/KEY: misc_feature
<222> LOCATION: (1)...(125)
<223> OTHER INFORMATION: n = A,T,C or G

<400> SEQUENCE: 65

| | | | | | | |
|---|---|---|---|---|---|---|
| agcggtacag | ttctgtcctg | gcatcatcat | tcattgtagt | atggtcaata | ggtgccatga | 60 |
| aactcagtag | cttgctaagg | acatgaaacc | gaagtttcct | gcctttgctg | gcctngtngn | 120 |
| gggta | | | | | | 125 |

<210> SEQ ID NO 66
<211> LENGTH: 204
<212> TYPE: DNA
<213> ORGANISM: Homo sapien

<400> SEQUENCE: 66

```
attcagaatt ctggcatcgg tatttctata aagtccatca gttagagcag gagcaggccc    60
ggagggacgc cctgaagcag cgggcggaac agagcatctc tgaagagccc ggctgggagg   120
aggaggaaga ggagctcatg ggcatttcac ccatatctcc aaaagaggca aaggttcctg   180
tggacctcgg ccgcgaccac gcta                                          204
```

<210> SEQ ID NO 67
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 67

```
tcagggcctc caggcagcca gttttgcagg anattcagca cctagngtct tcctgcctna    60
cgctcccaag aacctgctcc tgcaggggga acatcagaac tcgtccttga tgtcaaaatg   120
gggctggtct tnaggcttga agtccaggtt agggctgcca tcctcattga gaattctccg   180
ggcagtgtan ccgacgatgg ggtatttggc tttgtacact ttggtgaaaa cctnatccag   240
ggcctccagt tccttggccg tganacccgt antgtcatgg gtgaggtctg caggatccaa   300
ggacatcttg gctacccctc tagtggagtc cttccccgtc aaggcattgt aagggggctcc   360
tcgtccataa aactcctttt cgg                                           383
```

<210> SEQ ID NO 68
<211> LENGTH: 99
<212> TYPE: DNA
<213> ORGANISM: Homo sapien

<400> SEQUENCE: 68

```
tcacatctcc ttttttttt aacttttttca aattttttgtg ttaaatagaa ggctaaaggg    60
ttagatttaa gtttctgcta cattgaccct atttaccta                           99
```

<210> SEQ ID NO 69
<211> LENGTH: 37
<212> TYPE: DNA
<213> ORGANISM: Homo sapien
<220> FEATURE:
<221> NAME/KEY: misc_feature
<222> LOCATION: (1)...(37)
<223> OTHER INFORMATION: n = A,T,C or G

<400> SEQUENCE: 69

```
gagaaggacn tacggncctg ntantananng aatctcc                            37
```

<210> SEQ ID NO 70
<211> LENGTH: 222
<212> TYPE: DNA
<213> ORGANISM: Homo sapien
<220> FEATURE:
<221> NAME/KEY: misc_feature
<222> LOCATION: (1)...(222)
<223> OTHER INFORMATION: n = A,T,C or G

<400> SEQUENCE: 70

```
gtgggtcatt tttgctgtca ccagcaacgt tgccacgacg aacatccttg acagacacat        60
tcttgacatt gaagcccaca ttgtccccag gaagagcttc actcaaagct tcatggcgca       120
tttcgacaga ttttacttcc gttgtaacgt tgactggagc aaaggtgacc accataccgg       180
gtttgagaac acccantcac ctgccccggg cggccgctcg aa                         222
```

```
<210> SEQ ID NO 71
<211> LENGTH: 428
<212> TYPE: DNA
<213> ORGANISM: Homo sapien
<220> FEATURE:
<221> NAME/KEY: misc_feature
<222> LOCATION: (1)...(428)
<223> OTHER INFORMATION: n = A,T,C or G

<400> SEQUENCE: 71
caggagtatt ttgtagaaaa gccagaagag cattagtaga tgtatggaaa tatacggtag        60
ggcacacgct gacagtactt ttcccaagcc acgccgtatt tcttcttaca gtggtactcg       120
tcacgagctt ctcggtggac aagcaacatg gtgaaataaa ttatgtagaa ataaggcaga       180
atgtggttaa aaccacatgg gagggaccac gccaaggcca tgatgagatc acccaagtaa       240
ttggggtggc gaacaaagcc ccaccatcca gaaactagaa naatttttcc cgttgaaata       300
tgaatggntt ttaaatgtgc aagctttgga tcactgggaa ttttcccgaa tgccttttc       360 tganaattgc accttnggaa gantccttac cccaagnttc agaccattat ttnaaaagcn       420
ttggaact                                                               428
```

```
<210> SEQ ID NO 72
<211> LENGTH: 264
<212> TYPE: DNA
<213> ORGANISM: Homo sapien
<220> FEATURE:
<221> NAME/KEY: misc_feature
<222> LOCATION: (1)...(264)
<223> OTHER INFORMATION: n = A,T,C or G

<400> SEQUENCE: 72
gaataaagag cttactggaa tccagcaggg ttttctgccc aaggatttgc aagctgaagc        60
tctctgcaaa cttgatagga gagtaaaaag ccacaataga gcagtttatg aagatcttgg       120
aggagattga cacacttgat cctgccagaa aatttcaaag acagtagatt gaaaaggaaa       180
ggctttggta aaaaaaggtt caggcattcc tagccgantg tgacacagtg agcanaaca       240 tctgcangag actgancggc tgca                                             264
```

```
<210> SEQ ID NO 73
<211> LENGTH: 442
<212> TYPE: DNA
<213> ORGANISM: Homo sapien
<220> FEATURE:
<221> NAME/KEY: misc_feature
<222> LOCATION: (1)...(442)
<223> OTHER INFORMATION: n = A,T,C or G

<400> SEQUENCE: 73
ggcgaatccg gcgggtatca gagccatcag aaccgccacc atgacggtgg gcaagagcag        60
caagatgctg cagcatattg attacaggat gaggtgcatc ctgcaggacg gccggatctt       120
cattggcacc ttcaaggctt ttgacaagca catgaatttg atcctctgtg actgtgatga       180
gttcagaaag atcaagccaa agaacttcaa acaagcagaa agggaagaga agcgagtcct       240 cggtctgggng ctgctgccaa gggagaatct ggtctcaatg acngtagaag gaccttcttc       300
```

```
caaagatact ggnattgctc gagttccact tgctggaact tcccggggcc caaggatcgc    360
aaggcttctg gcaaaagaaa tccanacttn ggccgggacc acctaancca attcacacac    420
tggcggccgt actagtggat cc                                             442

<210> SEQ ID NO 74
<211> LENGTH: 337
<212> TYPE: DNA
<213> ORGANISM: Homo sapien
<220> FEATURE:
<221> NAME/KEY: misc_feature
<222> LOCATION: (1)...(337)
<223> OTHER INFORMATION: n = A,T,C or G

<400> SEQUENCE: 74
ggtagcagcg tctccagagc ctgatctggg gtcccagata cccaggcagc agcagccctg     60
gaggtaaagg gcaagctccc caatgtgagg ggagacccca ttcctggtca gccaggcttt    120
cagaggagat agcaggtcga gggagccaac gaagaagaga ctgccancag gggaaggact    180
gtcccgccaa ggacagaact gattcagggg ggtcaatgct cctctagaga agagccacac    240
agaactgggg ggtccaggaa ccatgaanct tggctgtggt ctaaggagcc aggaatctgg    300
acagtgttct gggtcatacc aggattctgg aattgta                             337

<210> SEQ ID NO 75
<211> LENGTH: 588
<212> TYPE: DNA
<213> ORGANISM: Homo sapien
<220> FEATURE:
<221> NAME/KEY: misc_feature
<222> LOCATION: (1)...(588)
<223> OTHER INFORMATION: n = A,T,C or G

<400> SEQUENCE: 75
catgatgagt tctgagctac ggaggaaccc tcatttcctc aaaagtaatt tattttttaca    60 gcttctggtt tcacatgaaa ttgtttgcgc tactgagact gttactacaa acttttttaag  120 acatgaaaag gcgtaatgaa aaccatcccg tccccattcc tcctcctctc tgagggactg   180
gagggaagcc gtgcttctga ggaacaactc taattagtac acttgtgttt gtagatttac   240
actttgtatt atgtattaac atggcgtgtt tattttttgta tttttctctg gttgggagta  300
tgatatgaag gatcaagatc ctcaactcac acatgtagac aaacattagc tctttactct   360
ttctcaaccc cttttatgat tttaataatt ctcacttaac taattttgta agcctgagat   420
caataagaaa tgttcaggag agangaaaga aaaaaaatat atgttcccca tttatattta   480
gagagagacc cttantcttg cctgcaaaaa gtccacctt catagtagta ngggccacat    540
attacattca gttgctatag gncagcactg aactgcatta cctgggca                588

<210> SEQ ID NO 76
<211> LENGTH: 196
<212> TYPE: DNA
<213> ORGANISM: Homo sapien

<400> SEQUENCE: 76
gcggtatcac agcctggccc ccatgtacta tcgggggggcc caggctgcca tcgtggtcta    60
tgacatcacc aacacagata catttgcacg ggccaagaac tgggtgaagg agctacagag   120
gcaggccagc cccaacatcg tcattgcact cgcgggtaac aaggcagacc tggacctgcc   180
cgggcggccg ctcgaa                                                   196
```

<210> SEQ ID NO 77
<211> LENGTH: 458
<212> TYPE: DNA
<213> ORGANISM: Homo sapien
<220> FEATURE:
<221> NAME/KEY: misc_feature
<222> LOCATION: (1)...(458)
<223> OTHER INFORMATION: n = A,T,C or G

<400> SEQUENCE: 77

| | | | | | |
|---|---|---|---|---|---|
| agtagagatg | gggtttcact | gtgttaacca | ggatggtctt | gatctcctgg | cctcgtgatc | 60 |
| tgcccgcctc | ggcctcccaa | agtgttggga | ttacaggcgt | gaaccaccgc | acccggccag | 120 |
| aaatgttagt | ttttccctat | tctctctcct | ttttcctatt | atatacttgg | tcaaccagac | 180 |
| agccatccta | ccccanaatg | gtaatgcctc | ttcattcctc | atatgaggga | ataaaagaga | 240 |
| aaaaagcttt | tggaaaacat | ccacttatct | aatcatccca | aatatgtaat | caaaagtata | 300 |
| caactcatgt | gaagaataca | ctggtaaaat | gttantatag | gccaaggtat | cttgaattcc | 360 |
| tatatagaaa | gctggtaaat | gccctttcgg | ctggaaccgc | catcttccnn | taattcnccc | 420 |
| aaaatgacca | aacacaaagg | gnaagangan | aagccccc | | | 458 |

<210> SEQ ID NO 78
<211> LENGTH: 464
<212> TYPE: DNA
<213> ORGANISM: Homo sapien
<220> FEATURE:
<221> NAME/KEY: misc_feature
<222> LOCATION: (1)...(464)
<223> OTHER INFORMATION: n = A,T,C or G

<400> SEQUENCE: 78

| | | | | | |
|---|---|---|---|---|---|
| tccgcaaatt | tcctgccggc | aaggtcccag | catttgaggg | tgatgatgga | ttctgtgtgt | 60 |
| ttgagagcaa | cgccattgcc | tactatgtga | gcaatgagga | gctgcgggga | agtactccag | 120 |
| aggcagcagc | ccaggtggtg | cagtgggtga | gctttgctga | ttccgatata | gtgcccccag | 180 |
| ccagtacctg | ggtgttcccc | accttgggca | tcatgcacca | caacaaacag | gccactgaga | 240 |
| atgcaaagga | ggaagtgagg | cgaattctgg | ggctgctgga | tgcttacttg | aagacgagga | 300 |
| cttttctggt | gggcgaacga | gtgacattgg | ctgacatcac | agttgtctgc | accctgttgt | 360 |
| ggctctataa | gcaggntcta | gaaccttctt | ttcgcangac | cttcggccgg | accacgctta | 420 |
| acccaaattc | cacacacttg | cnggccgtac | taanggaatc | ccac | | 464 |

<210> SEQ ID NO 79
<211> LENGTH: 380
<212> TYPE: DNA
<213> ORGANISM: Homo sapien
<220> FEATURE:
<221> NAME/KEY: misc_feature
<222> LOCATION: (1)...(380)
<223> OTHER INFORMATION: n = A,T,C or G

<400> SEQUENCE: 79

| | | | | | |
|---|---|---|---|---|---|
| ctgtatgacc | agtttttcca | tctccttcac | ttctaccttg | atcagctcga | agtccagttc | 60 |
| agtgtaagaa | atggtatcct | tctccatgat | gtcaattcgg | acagttaggt | ttaacagttt | 120 |
| cttttcatac | acactaatta | attggacata | ttccctcact | ttanaaagtt | ctttctcaaa | 180 |
| cttctganaa | aagaacatga | actgtgaatt | ccaagcgttc | ccactctgtc | cacgggaaaa | 240 |
| ggtggtgtct | ggcagggaaa | cagaacactg | gcaggtccac | ggtcatccac | ggagccggtg | 300 |
| aaattgggaa | acaactggg | acacagaacc | tccgctgcct | aagctgcggn | tgggagcttg | 360 | gaacccgacc tggaactgga                                                    380

<210> SEQ ID NO 80
<211> LENGTH: 360
<212> TYPE: DNA
<213> ORGANISM: Homo sapien
<220> FEATURE:
<221> NAME/KEY: misc_feature
<222> LOCATION: (1)...(360)
<223> OTHER INFORMATION: n = A,T,C or G

<400> SEQUENCE: 80
tcgagcggcc gcccgggcag gtcctcagag agctgtttgt tncgcttctt caaaaactcc        60
tattctccac ttctgctaaa ggactggatg acatcaattg tgatagcaat atttgtgggt       120
gttctgtcan ncancatcgc actcctgaac aaagtagatg ttggattgga tcagtctctt       180
tccacccaga tgactcctan atggtggatn atttcaaatc catcantcag tacctgcatg       240
cgnggtccgc ctgtgtnctt tgtcctgcag gangggcnct actacacttc ttccnagggg       300
canaacatgg tgtgcngcgg ccatgggctg gcaacantga ttcnctgctg cacccanatn       360

<210> SEQ ID NO 81
<211> LENGTH: 440
<212> TYPE: DNA
<213> ORGANISM: Homo sapien
<220> FEATURE:
<221> NAME/KEY: misc_feature
<222> LOCATION: (1)...(440)
<223> OTHER INFORMATION: n = A,T,C or G

<400> SEQUENCE: 81
acgtggtccg gcgagtctga cctgcagata tgaactcctt gggaaaccta cattctgcct        60
cagacatact gggggcaaat ggctttaaaa gtctggctca gggagccaag attacagaaa       120
nccgttgagt cnccatacat ggacactgac aaaggaactg aagatatcca acaagccct        180 cctggtcccg ngcctgcata aagatcggga ncggaacggt accngacgtc tgtggtcagg       240
ggttgtggaa aattggaaaa aaccagtcct gcccacattg acagggaagc ctcaacggaa       300
attgaacaga tngtcttatc accagtctcc cctcctggat cntgtctcgg ctcnggggan       360
tcagtgatca gtcctttcag gtggaagaag caaagaagat caacaanaag cngatcctct       420
cacctgntac cagcatatgg                                                    440

<210> SEQ ID NO 82
<211> LENGTH: 264
<212> TYPE: DNA
<213> ORGANISM: Homo sapien
<220> FEATURE:
<221> NAME/KEY: misc_feature
<222> LOCATION: (1)...(264)
<223> OTHER INFORMATION: n = A,T,C or G

<400> SEQUENCE: 82
agcgtggtcg cggccgangt cctgacattc ctgccttctt atattaatta tacnaataaa        60
acaaaatagt gttgaagtgt tggagcggcg aaaattttg ggggtggta tggacagaga         120 atgggcgatn ttctcanggc tgcttcaagt gggattgggg cngcgtggga tcatncagtg       180
gganagattn cnctgaccgg antctnttgg tanggatnat cttgtgggga tgtgcaagag       240
ncattcgtct cctgaatgan tggt                                               264

<210> SEQ ID NO 83

<211> LENGTH: 410
<212> TYPE: DNA
<213> ORGANISM: Homo sapien
<220> FEATURE:
<221> NAME/KEY: misc_feature
<222> LOCATION: (1)...(410)
<223> OTHER INFORMATION: n = A,T,C or G

<400> SEQUENCE: 83

```
ancgtggtcg cggccgangt ccacagttgt gggagagcca gccattgtgg gggcagctcc      60
acaggtaaga ctcgtgtcct gagcagcgca catcatccag acaatgggt cctgagccct     120
gaccaaaccg ggcatttcct ggggctgaca tggcccagcc acagcccant tgcctgcaga    180
cgaaattggc atcattggtg tcccagtant catcacacac ggtgcccag gaacctccgg     240
tatangaact ccactcggcc tcnanacctg tcgcctccat tccncagcct caggggggcaa   300
actgggattc agatccttct gtgggtacag gtggtgatat cctgacaggc caactttctg   360
gcctgagtgt tgactgangc tgggcagacc tgcccgggcg gccgctcgaa               410
```

<210> SEQ ID NO 84
<211> LENGTH: 320
<212> TYPE: DNA
<213> ORGANISM: Homo sapien
<220> FEATURE:
<221> NAME/KEY: misc_feature
<222> LOCATION: (1)...(320)
<223> OTHER INFORMATION: n = A,T,C or G

<400> SEQUENCE: 84

```
tcgaacggcc gcccgggcag gtctgcccca ggtgtatcca tttgccgccg atctctatca      60
naaggagctg gctaccctgc nncgacgaan tcctgaaanat aatctcaccc nccagatct    120
ctctgtcgca atggagatgt cgtcatcggt ggncctgatc acagggcatt ggactcagag    180
anangtnanc acagtgtnga agcgattgan nnagttcagt tgctggtctt acccgatntt    240
ggaaggaagg aaaacgtgtt angacgtatc tcgatgnant tgaccaaanc tgaangctnc    300
aggggggcatc gcaaaganan                                               320
```

<210> SEQ ID NO 85
<211> LENGTH: 218
<212> TYPE: DNA
<213> ORGANISM: Homo sapien
<220> FEATURE:
<221> NAME/KEY: misc_feature
<222> LOCATION: (1)...(218)
<223> OTHER INFORMATION: n = A,T,C or G

<400> SEQUENCE: 85

```
tcgagcggcc gcccgggcag gtctgctgcc cgtgctggtg ccattgcccc atgtgaagtc      60
actgtgccag cccagaacac tggtctcggg cccgagaaga ctcctttctc caggctntan   120
gtatcaccac taaaatctcc agggggcacca tnganatcct gggtgtccgc aatgttgcca   180
atgtctgtcc gcnnattggc tacccaactg ttgcatca                            218
```

<210> SEQ ID NO 86
<211> LENGTH: 283
<212> TYPE: DNA
<213> ORGANISM: Homo sapien
<220> FEATURE:
<221> NAME/KEY: misc_feature
<222> LOCATION: (1)...(283)
<223> OTHER INFORMATION: n = A,T,C or G

<400> SEQUENCE: 86

```
tcgacttctt gtgaaggttt tgganaaata tgtatcagtt cgttttattt gggtattcaa    60
taatatcctt ggtgataatg ctgactccat ggcttctgac cccaaaaatt gaccctgctg   120
ccactggttg tagccctgag attgattttt gtagccacga ttgtttcctc gtcctctgaa   180
gtnctggttg tanttccctc tgtngggcat tcccctctgt tgtanttccc tctgtttgan   240
taactaccac ggccaggaaa aacagggggca cgaaggtatg gat                    283
```

<210> SEQ ID NO 87
<211> LENGTH: 179
<212> TYPE: DNA
<213> ORGANISM: Homo sapien
<220> FEATURE:
<221> NAME/KEY: misc_feature
<222> LOCATION: (1)...(179)
<223> OTHER INFORMATION: n = A,T,C or G

<400> SEQUENCE: 87

```
agcgtggtcc cggccgatgt ctttctgtgt aagtgcataa cactccacat acttgacatc    60
cttcangtca cgggccagct nttcagcant ctctggagtg ataggctact gtntgttctn   120
ggcaagtgtc tcaanaatac agggtcntc tctgagatga ntttcagtcc cgaaccctc    179
```

<210> SEQ ID NO 88
<211> LENGTH: 512
<212> TYPE: DNA
<213> ORGANISM: Homo sapien
<220> FEATURE:
<221> NAME/KEY: misc_feature
<222> LOCATION: (1)...(512)
<223> OTHER INFORMATION: n = A,T,C or G

<400> SEQUENCE: 88

```
tcgagcggcc gcccgggcag gtcctancan agaatcacca aatttatgga gagttaacag    60
gggtttaaca ggaangaagt gcctttagta agttctcaag ccagangctg gaggcagcag   120
ctaaatcaga ggacaggatc ctcagtgaaa gtgagccatt cggggtggca tgtcactcca   180
ggaataagca caacttanaa acaaatgatt tcgtangata gcacagtgac attggtgcac   240
ttgtgaacct gaggccactg tgtcaaactg tgcactggtt gtgaataggg aganccaaaa   300
attatgtcct actgggtaat gagctttcaa tgggctcgat cctctcacnc tgaaagctct   360
gtagagcagc tcagaaccac aaccactccc aacattgacc cttctggggg tactgtctgt   420
ggcacccaca ggaaggagct ggagatcccc attaggactg tccacccaca cttgaagcca   480
caaaactgca cctcggccgc gaccaccgct ta                                 512
```

<210> SEQ ID NO 89
<211> LENGTH: 358
<212> TYPE: DNA
<213> ORGANISM: Homo sapien
<220> FEATURE:
<221> NAME/KEY: misc_feature
<222> LOCATION: (1)...(358)
<223> OTHER INFORMATION: n = A,T,C or G

<400> SEQUENCE: 89

```
tcgagcgggc cgcccgggca ggtctgccag tccccatccc agacattctt tgcatctaag    60
ctgangtctg aactgagtgg ggtgggctgg tgtttccatc ctcacaactc cagtgagccg   120
ggtgtggccg tggcctgcgt ctctctggcg gttagtgatg ttggcatcat ccaccttttt   180
caaaacaaaa gcactggact gaagaanaat cccncccctgt ntccacccag tccatggttt   240
```

```
ttaataaaag ggttatnnaa gttgancaag ncatcaccac acacaancct aagaacnttt      300
ttcatcnntc cccaaaacaa acccncaccc tgggaactcc gggcgcgaac cacgccta        358
```

<210> SEQ ID NO 90
<211> LENGTH: 250
<212> TYPE: DNA
<213> ORGANISM: Homo sapien
<220> FEATURE:
<221> NAME/KEY: misc_feature
<222> LOCATION: (1)...(250)
<223> OTHER INFORMATION: n = A,T,C or G

<400> SEQUENCE: 90

```
cgagcggccg cccgggcagg tctggatggg gagacggact ggaactgcgg cttcccgtgg      60
cctgcacgca caaggctccc cacggccgcc gaccttcttc agattcgatc gtatgtgtac     120
gcacnaagag ccaaatattg acattcacaa cttcgtggga atnttacccc anaagactgc    180 gacccccga tcaggcgana gcctgagcat agaagaacac cgctgtgggc ttggcactgt     240 gggncccatc                                                            250
```

<210> SEQ ID NO 91
<211> LENGTH: 133
<212> TYPE: DNA
<213> ORGANISM: Homo sapien
<220> FEATURE:
<221> NAME/KEY: misc_feature
<222> LOCATION: (1)...(133)
<223> OTHER INFORMATION: n = A,T,C or G

<400> SEQUENCE: 91

```
tcgagcggcc gnccgggcag gtcccgggtg gttgtttgcc gaaatgggca agttcntnaa     60
ncctgggaag gtggtgcntg tnctggctgg acgctactcc ggacgcnaag ctgtcntcgt    120
gangancatt gat                                                        133
```

<210> SEQ ID NO 92
<211> LENGTH: 232
<212> TYPE: DNA
<213> ORGANISM: Homo sapien
<220> FEATURE:
<221> NAME/KEY: misc_feature
<222> LOCATION: (1)...(232)
<223> OTHER INFORMATION: n = A,T,C or G

<400> SEQUENCE: 92

```
agcgtggtcg cggccgangt ctgtcacttt gcggggtag cggtcaattc cagccaccag      60
agcatggctg tagggcgat ctgaggtgcc atcatcaatg ttcttcacga tgacaagctt     120
tgcgtccgga gtagcgtcca gccaggacaa gcaccacctt cccacgtntt cangaactng   180
cccatttcgg cataaccacc cgggacctgc ccgggcggnc gctcgaaaag cc             232
```

<210> SEQ ID NO 93
<211> LENGTH: 480
<212> TYPE: DNA
<213> ORGANISM: Homo sapien
<220> FEATURE:
<221> NAME/KEY: misc_feature
<222> LOCATION: (1)...(480)
<223> OTHER INFORMATION: n = A,T,C or G

<400> SEQUENCE: 93

```
agcgtgggtc gcggccgang tctgtangct caccggccag agaagaccac tgtgagcatt     60
ttgccgtata tcctgccctg ccatttgttc acttttttaaa ctaaaatagg aacatccgac   120
```

```
acacaccgtt tgcatcgtct tctcccttga tattttaagc attttcccat gtcgtgagtt     180
tctcagaaac atgtttttaa caattgtact atttagtcat ngtccattta ctataattta     240
tctgaccatt tccctactgt taaaatactt aagacggttt ctgattttc cactatttaa      300 ataatgctgt gatgaatatc tttaaaatct tctgatttct tacttttttc cccttagat     360 gcctggaagt ggtattttga ggtgaaagag tttgttcatt ttgaanatat ttctgtctct    420
ctctcgacct gatgtgtana cgctcacttc cagttagcag aaccaccttta gtttgtgtct   480
```

<210> SEQ ID NO 94
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 94

```
tcgagcggnc gcccgggcag ggtctgatgt cantcacaac ttgaagggat gccaatgatg      60
taccaatccn atgtgaaatc tctcctctta tctcctatgc tgganaaggg attacaaagt    120
tatgtggcng ataannaatt ccatgcacct ctantcatcg atgagaatgg agttcatgan    180
ctggtgaacn atggtatctg aacccgatac cangttttgt ttgccacgat angantagct    240 tttattttg atagaccaac tgtgaaccta ccacacgtct tggacnactg anntctaact     300
atccncaggg ttttatttg cttgttgaac tcttncagct nttgcaaact tcccaagatc    360
canatgactg antttcagat agcattttta tgattcccan ctcattgaag gtcttatnta   420
tntcnttttt tccaagccaa ggagaccatt ggacctcggc cgcgaccacc tn            472
```

<210> SEQ ID NO 95
<211> LENGTH: 309
<212> TYPE: DNA
<213> ORGANISM: Homo sapien
<220> FEATURE:
<221> NAME/KEY: misc_feature
<222> LOCATION: (1)...(309)
<223> OTHER INFORMATION: n = A,T,C or G

<400> SEQUENCE: 95

```
tcgagcggcc gcccgggcag agtgtcgagc cagcgtcgcc gcgatggtgt tgttggagag      60
cgagcagttc ctgacggaac tgaccagact ttttccanaag tgccggacgt cgggcancgt    120
ctatatcacc ttgaagaant atgacggtcg aaccaaaccc attccaaaga aangtactgt    180
gganggcttt ganccccgcag acaacnagtg tctgttaaga actaccgatn ggaaanaana   240
anatcagcac tgtgggtgag ctccnaggga agttaataan tttcggatgg gcttattcna    300
acctcctta                                                             309
```

<210> SEQ ID NO 96
<211> LENGTH: 371
<212> TYPE: DNA
<213> ORGANISM: Homo sapien
<220> FEATURE:
<221> NAME/KEY: misc_feature
<222> LOCATION: (1)...(371)
<223> OTHER INFORMATION: n = A,T,C or G

<400> SEQUENCE: 96

```
tcgagcggcc gcccgggcag gtccaccact cacctactcc ccgtctctat agatttgcct     60
```

| | |
|---|---|
| gttctgggca gttctcagca atggaatcct actgtgtatc tttttgtgac tggttcttta | 120 |
| actcagcatc acattttcaa ggttcatcca tgctgcagcc tggctccgta ctggtgacag | 180 |
| tacttcattt ctctctccct tttgttcaga ccaaggtctc cctctgtccc caaggctaaa | 240 |
| gtgcagttgg tgtgatcatg gctcactgca gcctcaaact cctggactca aacagtcctc | 300 |
| ccatctcagc ctcccaaagt gctgatntta taagttgcaa gccctgcacc cagcctgtat | 360 |
| ctccagtttg t | 371 |

<210> SEQ ID NO 97
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 97

| | |
|---|---|
| tcgancggcc gcccgggcag gtttnttttn tttnttttt nnnngntagt atttaaagan | 60 |
| atttattaaa tcatcttatc accaaaatgg aaacatnttc caactagaaa catgcnacca | 120 |
| tcatcttccc cagtccagtc ncaangtcca atattttnct tgcctctgca gataaaaagt | 180 |
| tcnnattttt atacccactc ttactccccc ccaaaatttt aattcngtcc tnccctaaaa | 240 |
| ttncnccggg taacaantta ccaaaatggc naaccaatta ttttaaanaa aagttgcncn | 300 |
| ttnaaaangg aaactttntg gcaanttanc ctcttttccc ttcccacccc ccantttaag | 360 |
| gggaaaacaa tggcactttg ctcttgcttn aacccaaaat tgtcttccaa aaactattaa | 420 |
| aaatgttnaa | 430 |

<210> SEQ ID NO 98
<211> LENGTH: 307
<212> TYPE: DNA
<213> ORGANISM: Homo sapien
<220> FEATURE:
<221> NAME/KEY: misc_feature
<222> LOCATION: (1)...(307)
<223> OTHER INFORMATION: n = A,T,C or G

<400> SEQUENCE: 98

| | |
|---|---|
| tcnaacggcc gcccnggcnn gtctngcngc acctgtgcct canccgtcga tacctggtcg | 60 |
| attgggacan ggaanacaat ntggttttca gggaggccac anatttggag aaacggatga | 120 |
| attctccttt attccgaant cagctccttg gtctccgtag anggtgatct tgaaattctc | 180 |
| ctgttttgaa aactttcttg aanaaacctt acctgctggt tgtatttggt ctcccactcg | 240 |
| gacaagtact cgttatccnn ggtactctta atgtgcccac gtnaactccc cgggntggca | 300 |
| actggaa | 307 |

<210> SEQ ID NO 99
<211> LENGTH: 207
<212> TYPE: DNA
<213> ORGANISM: Homo sapien
<220> FEATURE:
<221> NAME/KEY: misc_feature
<222> LOCATION: (1)...(207)
<223> OTHER INFORMATION: n = A,T,C or G

<400> SEQUENCE: 99

| | |
|---|---|
| gtccnggacc gatgttgcna aganntttct tggtccanta ggttcnaaaa aatgataanc | 60 |
| naggtntanc acgtgaagat ntntatanag tcttantnaa aacncntaga tctgnatgac | 120 |

```
gataantcga anacnggggg agggntgag gngaggtggn gtganggaag anntgttgat    180
aaaagannna gntgataaga anngagc                                      207
```

<210> SEQ ID NO 100
<211> LENGTH: 200
<212> TYPE: DNA
<213> ORGANISM: Homo sapien
<220> FEATURE:
<221> NAME/KEY: misc_feature
<222> LOCATION: (1)...(200)
<223> OTHER INFORMATION: n = A,T,C or G

<400> SEQUENCE: 100

```
acntnnacta gaantaacag ncnttctang aacactacca tctgtnttca catgaaatgc    60
cacacacata naaactccaa catcaatttc attgcacaga ctgactgtaa ttaattttgt   120
cacaggaatc tatggactga atctaatgcn nccccaaatg ttgttngttt gcaatntcaa   180
acatnnttat tccancagat                                              200
```

<210> SEQ ID NO 101
<211> LENGTH: 51
<212> TYPE: DNA
<213> ORGANISM: Homo sapien
<220> FEATURE:
<221> NAME/KEY: misc_feature
<222> LOCATION: (1)...(51)
<223> OTHER INFORMATION: n = A,T,C or G

<400> SEQUENCE: 101

```
tcgagcggcc gcccgggcag gtctgaccag tgganaaatg cccagttatt g             51
```

<210> SEQ ID NO 102
<211> LENGTH: 385
<212> TYPE: DNA
<213> ORGANISM: Homo sapien
<220> FEATURE:
<221> NAME/KEY: misc_feature
<222> LOCATION: (1)...(385)
<223> OTHER INFORMATION: n = A,T,C or G

<400> SEQUENCE: 102

```
aacgtggtcg cggccgaagt ccatggtgct gggattaatc cactgtgacn gtgactctga    60
gttgagttgt ttttcaatct tctccaagcc tgtggactca tcctccacat ccttgggtag   120
taggatgaac atgctgaaga tgctnatttt gaaaaggaac tctatgaatc ttacaattga   180
atactgtcaa tgtttcccca tnacagaacg tggnccccca aggttccatc atctgcactg   240
ggtttgggtg ttctgtcttg gttgactctt gaaaaggac atttctttt gttttcttga    300 attcanggaa attttcttca tccactttgc ccacaaaagt taggcagcat ttaaccccca   360
anggattttg ggtctgggtc cttcc                                        385
```

<210> SEQ ID NO 103
<211> LENGTH: 189
<212> TYPE: DNA
<213> ORGANISM: Homo sapien
<220> FEATURE:
<221> NAME/KEY: misc_feature
<222> LOCATION: (1)...(189)
<223> OTHER INFORMATION: n = A,T,C or G

<400> SEQUENCE: 103

```
agcgtggtcg cggccgaagt ctgcagcctg ggactgaccg ggaagctctg attatttacc    60
```

```
caccacaggt angttgtgtt ctgaatctca agttcacagg ttaaggctac agcatcctca      120
tcctccacgg ggttggantt gttgctggtg atgaanggtt tggggtggct ctgcataact      180
gttgatctc                                                              189

<210> SEQ ID NO104
<211> LENGTH: 181
<212> TYPE: DNA
<213> ORGANISM: Homo sapien
<220> FEATURE:
<221> NAME/KEY: misc_feature
<222> LOCATION: (1)...(181)
<223> OTHER INFORMATION: n = A,T,C or G

<400> SEQUENCE: 104
tcgagcggcc gcccgggcag gtccaggtct ccaccaangc accaccgtgg gaagctggta      60
attgatgccc accttgaagc cnntggggca ccatccncca actggatgct gcgcttggtt     120
ttgatggtgg caatggcaca ttgactcttt tgggaaccac ttcaccacgg tacaacaggc     180
a                                                                      181

<210> SEQ ID NO105
<211> LENGTH: 327
<212> TYPE: DNA
<213> ORGANISM: Homo sapien
<220> FEATURE:
<221> NAME/KEY: misc_feature
<222> LOCATION: (1)...(327)
<223> OTHER INFORMATION: n = A,T,C or G

<400> SEQUENCE: 105
tcgagcggcc gcccgggcag gtcttctgtg gagtctgcgt gggcatcgtg ggcagtgggg      60
ctgccctggc cgatgctcan aaccccagcc tctttgtaaa gattctcatc gtgganatct     120
ttggcagcgc cattggcctc tttggggtca tcgtcgcaat tcttcanacc tccanaatga     180
anatgggtga ctanataata tgtgtgggtn gggccgtgcc tcacttttat ttattgctgg     240
ttttcctggg acagaactcg ggcgcgaaca cgcttanccg aattccaaca cactggcggg     300
cgttactagt ggatccgagc tcggtac                                          327

<210> SEQ ID NO 106
<211> LENGTH: 268
<212> TYPE: DNA
<213> ORGANISM: Homo sapien
<220> FEATURE:
<221> NAME/KEY: misc_feature
<222> LOCATION: (1)...(268)
<223> OTHER INFORMATION: n = A,T,C or G

<400> SEQUENCE: 106
agcgtggtcg cggccgangt ctggcgtgtg ccacatcggt cccacctcgc tttacaaaac      60
agtcctgaac ttnatctaat aaaattattg tacacnacat ttacattaga aaaaganagc     120
tgggtgtang aaaccgggcc tggtgttccc tttaagcgaa ngtggctcca cagttggggc     180
atcgtcgctt cctcnaagca aaaacgccaa tgaaccccna aggggaaaa aggaatgaag      240 gaactgnccn gggangnccg ctccgaaa                                         268

<210> SEQ ID NO 107
<211> LENGTH: 353
<212> TYPE: DNA
<213> ORGANISM: Homo sapien
<220> FEATURE:
<221> NAME/KEY: misc_feature
```

<222> LOCATION: (1)...(353)
<223> OTHER INFORMATION: n = A,T,C or G

<400> SEQUENCE: 107

| tcgagcggcc gcccgggcag gtggccaggc catgttatgg gatctcaacg aaggcaaaca | 60 |
| cctttacacn ctagatggtg gggacatcat caacgccctg tgcttcagcc ctaaccgcta | 120 |
| ctggctgtgt gctgccgcag gccccagcat caagatctgg gatttanagg gaaagatcnt | 180 |
| tgtnnatgaa ctgaancnta aattatcagt tccannacca ngcaaaaacc acccngtgca | 240 |
| ctccctggcc tggtctgctg atgggacctc gggcgcgaac acgctnancc caattccanc | 300 |
| acactgggcg gncgttacta ntggatccga actcnggtac caancttggc gtt | 353 |

<210> SEQ ID NO 108
<211> LENGTH: 360
<212> TYPE: DNA
<213> ORGANISM: Homo sapien
<220> FEATURE:
<221> NAME/KEY: misc_feature
<222> LOCATION: (1)...(360)
<223> OTHER INFORMATION: n = A,T,C or G

<400> SEQUENCE: 108

| agcgtggtcg cggccgaagt cctggcctca catgaccctg ctccagcaac ttgaacagga | 60 |
| naagcagcag ctacatcctt aaggtccgga aagttagatg aagatttgga tcctgcattg | 120 |
| ncctgcctcc cacctatctc tcccnaatta taaacagcct ccttgggaag cagcagaatt | 180 |
| taaaaactct cccnctgccc tnttgaacta cacaccnacc gggaaaacct ttttcanaat | 240 |
| ggcacaaaaa tncnagggaa tgcatttcca tgaangaana aactgggtta cccaaaatta | 300 |
| ttgggttggg gaaatccngg gggggttttn aaaaaagggc aanccnccaa anaaaaaaac | 360 |

<210> SEQ ID NO 109
<211> LENGTH: 101
<212> TYPE: DNA
<213> ORGANISM: Homo sapien
<220> FEATURE:
<221> NAME/KEY: misc_feature
<222> LOCATION: (1)...(101)
<223> OTHER INFORMATION: n = A,T,C or G

<400> SEQUENCE: 109

| atcgtggtcn cggccgaagt cctgtgtcct ggatgggccg tgtgcancga atccgttggc | 60 |
| gactcctaac taccaanaaa angactctcg gaagaaattt c | 101 |

<210> SEQ ID NO 110
<211> LENGTH: 300
<212> TYPE: DNA
<213> ORGANISM: Homo sapien
<220> FEATURE:
<221> NAME/KEY: misc_feature
<222> LOCATION: (1)...(300)
<223> OTHER INFORMATION: n = A,T,C or G

<400> SEQUENCE: 110

| ccanggaaac ccagagtcac atgagatagg gtggctttcg ggacaggggg tcagangaat | 60 |
| ggtacatgga tctcagcccc tgatggacac ggaacaggtg tggtcagaac tcccangatt | 120 |
| ctgcatccan gatccagtct ctatagaagt tatggatcat tccttcattt cattcccccc | 180 |
| ttcatgaaaa aacttctgaa caagcctttt ttctcacttt ggggccctgt ttggcncaag | 240 |
| gtnttnantt ggggaaaaaa aaacaaatcc nttccnttan ccctccgtgg ggaatgacct | 300 |

<210> SEQ ID NO 111
<211> LENGTH: 366
<212> TYPE: DNA
<213> ORGANISM: Homo sapien
<220> FEATURE:
<221> NAME/KEY: misc_feature
<222> LOCATION: (1)...(366)
<223> OTHER INFORMATION: n = A,T,C or G

<400> SEQUENCE: 111

| | | | | | | |
|---|---|---|---|---|---|---|
| cgagcggccg | cccgggcagg | tccttgtgtt | gccatctgtt | ancattgatt | tctggaatgg | 60 |
| aacancttc | tcaaagtttg | gtcttgctan | tcatgaagtc | atgtcagtgt | cttaagtcac | 120 |
| tgctgctcac | ttccttaccc | aggaatata | ctgcataagt | ttctgaacac | ctgttttcan | 180 |
| tattcactgt | tcctctcctg | cccaaaattg | gaagggacct | catttaaaaa | tcaaatttga | 240 |
| atcctgaaan | aaaaacngga | aatntttctc | ttggaatttg | gaatagaatt | attcanttga | 300 |
| ataacatgtt | tttcccctt | gccttgctct | tcncaanaac | atctggacct | cggccgcgac | 360 |
| acctta | | | | | | 366 |

<210> SEQ ID NO 112
<211> LENGTH: 405
<212> TYPE: DNA
<213> ORGANISM: Homo sapien
<220> FEATURE:
<221> NAME/KEY: misc_feature
<222> LOCATION: (1)...(405)
<223> OTHER INFORMATION: n = A,T,C or G

<400> SEQUENCE: 112

| | | | | | | |
|---|---|---|---|---|---|---|
| ctgactncta | aacttctaat | tcnatcaana | taactactct | ccttccgtct | tncagagtgt | 60 |
| tcacaataaa | tctgtgaatc | tggcatacac | agttgctgga | aaattgttct | tcctccacna | 120 |
| aaaggtcaat | tgttcnccnc | atgaaanaag | ataaattgtt | catccatcac | tnctgaacca | 180 |
| tccaaaacgc | cggcggaatt | attncccgt | tattatgggg | aacggaattt | tnaataaatt | 240 |
| tgggaangaa | tggggcttt | attgttttgt | tttccccctt | tcttggcatt | gattgggccg | 300 |
| caatgggccc | cctcgctcan | aanntgcccc | ggggccggcc | gctccaaaac | cgaaattccc | 360 |
| anccacactt | ggcgggccgt | tactanttgg | atccgaactc | ggtta | | 405 |

<210> SEQ ID NO 113
<211> LENGTH: 401
<212> TYPE: DNA
<213> ORGANISM: Homo sapien

<400> SEQUENCE: 113

| | | | | | | |
|---|---|---|---|---|---|---|
| ggatagaaga | gtatatgggt | ttggcaccac | ggggtggata | ggcaaaacat | ttggttgata | 60 |
| aggcgcagat | tctgaactaa | cttgtaaggc | ttgtctggtt | ttaggacagg | taaaatgggg | 120 |
| gaatggtaag | gagagtttat | aggttttagg | agcccatgct | gtagcaggca | agtgataaca | 180 |
| ggctttaatc | ctttcaaagc | atgctgtggg | atgagatatt | ggcatttgag | cggggtaagg | 240 |
| gtgattaggt | tttaatgaga | tggtaagggg | tgcatgatcc | ggtccgccaa | ggaagggaag | 300 |
| tagaggtatc | ttatacttgt | ggggttaagg | tgggggggat | ataagaggga | ggacgccaaa | 360 |
| ggaggctttg | gattaggaat | aagggcggc | aatgagatgc | a | | 401 |

<210> SEQ ID NO 114
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 114

| | | | | | |
|---|---|---|---|---|---|
| angtccacag | gangcangag | gccaggctcc | gtcccancca | gtccatgatg | ttgaagagga | 60 |
| ggaagcagca | catggggttg | aagaactgac | tccacttccc | aggactggtg | gagctggtca | 120 |
| ccatggctgt | ggtggcgggg | aagacggaca | gggtgacttc | tggaagacag | tgaagactga | 180 |
| aggttttcct | ggcttctggg | gctcatctgg | ctctgattcc | ggctccttct | ccaggtcaag | 240 |
| atccagggtt | cagagctact | ttcttggggg | actactnggg | aatcccgttc | tcatctgggg | 300 |
| gtngagggggg | gacggggnaa | gggncatgct | tgtgacccag | gtttcccacc | tcggcccgcg | 360 |
| accacgctaa | ggcccgaatt | ncagcacact | tggcggcccg | t | | 401 |

<210> SEQ ID NO 115
<211> LENGTH: 401
<212> TYPE: DNA
<213> ORGANISM: Homo sapien

<400> SEQUENCE: 115

| | | | | | |
|---|---|---|---|---|---|
| atccctgtaa | gtctattaaa | tgtaaataat | acatacttta | caacttctct | tagtcggccc | 60 |
| ttggcagatt | aaatctttgc | aaaattccat | atgtgctatt | gaaaaatgaa | ataaaacctc | 120 |
| agatgtctga | attcttattt | caaatacagt | tatataatta | ttttaaatta | caatatacaa | 180 |
| tttctgttaa | atacaactgt | taagggattc | tgagaacaat | tataagatta | taataatata | 240 |
| tacaaactaa | cttctgaaat | gacatggggtt | gtttccttcc | caccctccta | ccctctcaaa | 300 |
| gagttttttgc | atttgctgtt | cctggttgca | aaaggcaaaa | gaaaatctaa | aaatagtctg | 360 |
| tgtgtgtcca | cgacatgctc | gctcctttga | gaatctcaaa | c | | 401 |

<210> SEQ ID NO 116
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 116

| | | | | | |
|---|---|---|---|---|---|
| ngatttaatt | gnnagcttct | ttttaatgga | atnnttggct | aaaatgaatt | gatgattatg | 60 |
| aatatcccta | ggaggagtta | gcatggannn | tgatcatttt | cttngnactc | ctttangaca | 120 |
| nggaaacagg | natcagcatg | anggtancan | aaaccttatn | accnangcgc | acganctgac | 180 |
| ttcttccaaa | gagttgnggt | tccgggcagc | ggtcattgcc | gtgcccattg | ctggagggct | 240 |
| gattctagtg | ntgcttatta | tgctggcct | gaggatgctt | ccaanatgaa | aataagangc | 300 |
| t | | | | | | 301 |

<210> SEQ ID NO 117
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 117

-continued

| aattgcaact ggactttat tgggcagtta cnacaacnaa tgttttcana aaaatatttg | 60 |
| gaaaaatat accacttcat agctaagtct tacagagaan aggatttgct aataaaactt | 120 |
| aagttttgaa aattaagatg cnggtanagc ttctgaacta atgccacag ctccaaggaa | 180 |
| nacatgtcct atttagttat tcaaatacca gttgagggca ttgtgattaa gcaaacaata | 240 |
| tatttgttan aactttgntt ttaaattact gntncttgac attacttata aaggagnctc | 300 |
| taactttcga tttctaaaac tatgtaatac aaaagtatan ntttccccat tttgataaaa | 360 |
| gggccnanga tactgantag gaa | 383 |

<210> SEQ ID NO 118
<211> LENGTH: 301
<212> TYPE: DNA
<213> ORGANISM: Homo sapien

<400> SEQUENCE: 118

| ctgctagaat cactgccgct gtgctttcgt ggaaatgaca gttccttgtt ttttttgttt | 60 |
| ctgttttgt tttacattag tcattggacc acagccattc aggaactacc ccctgcccca | 120 |
| caaagaaatg aacagttgta gggagaccca gcagcacctt tcctccacac accttcattt | 180 |
| tgaagttcgg gttttgtgt taagttaatc tgtacattct gtttgccatt gttacttgta | 240 |
| ctatacatct gtatatagtg tacggcaaaa gagtattaat ccactatctc tagtgcttga | 300 |
| c | 301 |

<210> SEQ ID NO 119
<211> LENGTH: 401
<212> TYPE: DNA
<213> ORGANISM: Homo sapien

<400> SEQUENCE: 119

| taaggacatg gaccccggc tgattgcatg gaaaggaggg gcagtgttgg cttgtttgga | 60 |
| tacaacacag gaactgtgga tttatcagcg agagtggcag cgctttggtg tccgcatgtt | 120 |
| acgagagcgg gctgcgtttg tgtggtgaat ggggaggaaa tgtcactgcc gaagaccaaa | 180 |
| aacaagcttc ttggtataaa agactcttac agaatatgtg tattgtaatt tattgatctg | 240 |
| gatgcttaag tgtcatggac agtaaatgaa tttgaacttt atgtttgagg acatgacatt | 300 |
| gggtttgaaa atataaactg cttttgagca gtttaagtca gggcatttga gaataaaata | 360 |
| ggaactttct cttcagtttg taaaactctc ttgccctctc t | 401 |

<210> SEQ ID NO 120
<211> LENGTH: 301
<212> TYPE: DNA
<213> ORGANISM: Homo sapien

<400> SEQUENCE: 120

| tccagagata ccacagtcaa acctggagcc aaaaaggaca caaggactc tcgacccaaa | 60 |
| ctgccccaga ccctctccag aggttggggt gaccaactca tctggactca gacatatgaa | 120 |
| gaagctctat ataaatccaa gacaagcaac aaaccttga tgattattca tcacttgggt | 180 |
| gagtgcccac acagtcaagc tttaaagaaa gtgtttgctg aaaataaaga aatccagaaa | 240 |
| ttggcagagc agtttgtcct cctcaatctg gtttatgaaa caactgacaa acacctttct | 300 |
| c | 301 |

<210> SEQ ID NO 121
<211> LENGTH: 2691

<212> TYPE: DNA
<213> ORGANISM: Homo sapien

<400> SEQUENCE: 121

| | |
|---|---|
| gcttgcccgt cggtcgctag ctcgctcggt gcgcgtcgtc ccgctccatg gcgctcttcg | 60 |
| tgcggctgct ggctctcgcc ctggctctgg ccctgggccc cgccgcgacc ctggcgggtc | 120 |
| ccgccaagtc gccctaccag ctggtgctgc agcacacgcag gctccggggc cgccagcacg | 180 |
| gccccaacgt gtgtgctgtg cagaaggtta ttggcactaa taggaagtac ttcaccaact | 240 |
| gcaagcagtg gtaccaaagg aaaatctgtg gcaaatcaac agtcatcagc tacgagtgct | 300 |
| gtcctggata tgaaaaggtc cctggggaga agggctgtcc agcagcccta ccactctcaa | 360 |
| acctttacga gaccctggga gtcgttggat ccaccaccac tcagctgtac acggaccgca | 420 |
| cggagaagct gaggcctgag atggaggggc ccggcagctt caccatcttc gcccctagca | 480 |
| acgaggcctg ggcctccttg ccagctgaag tgctggactc cctggtcagc aatgtcaaca | 540 |
| ttgagctgct caatgccctc cgctaccata tggtgggcag gcgagtcctg actgatgagc | 600 |
| tgaaacacgg catgacCCTC acctctatgt accagaattc caacatccag atccaccact | 660 |
| atcctaatgg gattgtaact gtgaactgtg cccggctcct gaaagccgac caccatgcaa | 720 |
| ccaacgggg ggtgcacctc atcgataagg tcatctccac catcaccaac aacatccagc | 780 |
| agatcattga gatcgaggac acctttgaga cccttcgggc tgctgtggct gcatcagggc | 840 |
| tcaacacgat gcttgaaggt aacggccagt acacgctttt ggccccgacc aatgaggcct | 900 |
| tcgagaagat ccctagtgag actttgaacc gtatcctggg cgacccagaa gccctgagag | 960 |
| acctgctgaa caaccacatc ttgaagtcag ctatgtgtgc tgaagccatc gttgcggggc | 1020 |
| tgtctgtaga gaccctggag ggcacgacac tggaggtggg ctgcagcggg gacatgctca | 1080 |
| ctatcaacgg gaaggcgatc atctccaata aagacatcct agccaccaac ggggtgatcc | 1140 |
| actacattga tgagctactc atcccagact cagccaagac actatttgaa ttggctgcag | 1200 |
| agtctgatgt gtccacagcc attgaccttt tcagacaagc cggcctcggc aatcatctct | 1260 |
| ctggaagtga gcggttgacc ctcctggctc ccctgaattc tgtattcaaa gatggaaccc | 1320 |
| ctccaattga tgcccataca aggaatttgc ttcggaacca cataattaaa gaccagctgg | 1380 |
| cctctaagta tctgtaccat ggacagaccc tggaaactct gggcggcaaa aaactgagag | 1440 |
| ttttgttta tcgtaatagc ctctgcattg agaacagctg catcgcggcc cacgacaaga | 1500 |
| gggggaggta cgggaccctg ttcacgatgg accgggtgct gaccccccca atggggactg | 1560 |
| tcatggatgt cctgaaggga gacaatcgct ttagcatgct ggtagctgcc atccagtctg | 1620 |
| caggactgac ggagaccctc aaccgggaag gagtctacac agtctttgct cccacaaatg | 1680 |
| aagccttccg agccctgcca ccaagagaac ggagcagact cttgggagat gccaaggaac | 1740 |
| ttgccaacat cctgaaatac cacattggtg atgaaatcct ggttagcgga ggcatcgggg | 1800 |
| ccctggtgcg gctaaagtct ctccaaggtg acaagctgga agtcagcttg aaaaacaatg | 1860 |
| tggtgagtgt caacaaggag cctgttgccg agcctgacat catggccaca aatgcgtgg | 1920 |
| tccatgtcat caccaatgtt ctgcagcctc cagccaacag acctcaggaa gaggggatg | 1980 |
| aacttgcaga ctctgcgctt gagatcttca acaagcatc agcgttttcc agggcttccc | 2040 |
| agaggtctgt gcgactagcc cctgtctatc aaaagttatt agagaggatg aagcattagc | 2100 |
| ttgaagcact acaggaggaa tgcaccacgg cagctctccg ccaatttctc tcagatttcc | 2160 |
| acagagactg tttgaatgtt ttcaaaacca agtatcacac tttaatgtac atgggccgca | 2220 |

-continued

```
ccataatgag atgtgagcct tgtgcatgtg ggggaggagg gagagagatg tacttttaa    2280 atcatgttcc ccctaaacat ggctgttaac ccactgcatg cagaaacttg gatgtcactg    2340
cctgacattc acttccagag aggacctatc ccaaatgtgg aattgactgc ctatgccaag    2400
tccctggaaa aggagcttca gtattgtggg gctcataaaa catgaatcaa gcaatccagc    2460
ctcatgggaa gtcctggcac agttttgta aagcccttgc acagctggag aaatggcatc    2520
attataagct atgagttgaa atgttctgtc aaatgtgtct cacatctaca cgtggcttgg    2580
aggcttttat ggggccctgt ccaggtagaa aagaaatggt atgtagagct tagatttccc    2640
tattgtgaca gagccatggt gtgtttgtaa taataaaacc aaagaaacat a             2691
```

<210> SEQ ID NO 122
<211> LENGTH: 683
<212> TYPE: PRT
<213> ORGANISM: Homo sapien

<400> SEQUENCE: 122

```
Met Ala Leu Phe Val Arg Leu Leu Ala Leu Ala Leu Ala Leu
1               5                   10                  15

Gly Pro Ala Ala Thr Leu Ala Gly Pro Ala Lys Ser Pro Tyr Gln Leu
            20                  25                  30

Val Leu Gln His Ser Arg Leu Arg Gly Arg Gln His Gly Pro Asn Val
        35                  40                  45

Cys Ala Val Gln Lys Val Ile Gly Thr Asn Arg Lys Tyr Phe Thr Asn
    50                  55                  60

Cys Lys Gln Trp Tyr Gln Arg Lys Ile Cys Gly Lys Ser Thr Val Ile
65                  70                  75                  80

Ser Tyr Glu Cys Cys Pro Gly Tyr Glu Lys Val Pro Gly Glu Lys Gly
                85                  90                  95

Cys Pro Ala Ala Leu Pro Leu Ser Asn Leu Tyr Glu Thr Leu Gly Val
            100                 105                 110

Val Gly Ser Thr Thr Thr Gln Leu Tyr Thr Asp Arg Thr Glu Lys Leu
        115                 120                 125

Arg Pro Glu Met Glu Gly Pro Gly Ser Phe Thr Ile Phe Ala Pro Ser
    130                 135                 140

Asn Glu Ala Trp Ala Ser Leu Pro Ala Glu Val Leu Asp Ser Leu Val
145                 150                 155                 160

Ser Asn Val Asn Ile Glu Leu Leu Asn Ala Leu Arg Tyr His Met Val
                165                 170                 175

Gly Arg Arg Val Leu Thr Asp Glu Leu Lys His Gly Met Thr Leu Thr
            180                 185                 190

Ser Met Tyr Gln Asn Ser Asn Ile Gln Ile His His Tyr Pro Asn Gly
        195                 200                 205

Ile Val Thr Val Asn Cys Ala Arg Leu Leu Lys Ala Asp His His Ala
    210                 215                 220

Thr Asn Gly Val Val His Leu Ile Asp Lys Val Ile Ser Thr Ile Thr
225                 230                 235                 240

Asn Asn Ile Gln Gln Ile Ile Glu Ile Glu Asp Thr Phe Glu Thr Leu
                245                 250                 255

Arg Ala Ala Val Ala Ala Ser Gly Leu Asn Thr Met Leu Glu Gly Asn
            260                 265                 270

Gly Gln Tyr Thr Leu Leu Ala Pro Thr Asn Glu Ala Phe Glu Lys Ile
        275                 280                 285

Pro Ser Glu Thr Leu Asn Arg Ile Leu Gly Asp Pro Glu Ala Leu Arg
```

```
                290                 295                 300
Asp Leu Leu Asn Asn His Ile Leu Lys Ser Ala Met Cys Ala Glu Ala
305                 310                 315                 320

Ile Val Ala Gly Leu Ser Val Glu Thr Leu Glu Gly Thr Thr Leu Glu
                325                 330                 335

Val Gly Cys Ser Gly Asp Met Leu Thr Ile Asn Gly Lys Ala Ile Ile
                340                 345                 350

Ser Asn Lys Asp Ile Leu Ala Thr Asn Gly Val Ile His Tyr Ile Asp
                355                 360                 365

Glu Leu Leu Ile Pro Asp Ser Ala Lys Thr Leu Phe Glu Leu Ala Ala
            370                 375                 380

Glu Ser Asp Val Ser Thr Ala Ile Asp Leu Phe Arg Gln Ala Gly Leu
385                 390                 395                 400

Gly Asn His Leu Ser Gly Ser Glu Arg Leu Thr Leu Leu Ala Pro Leu
                405                 410                 415

Asn Ser Val Phe Lys Asp Gly Thr Pro Pro Ile Asp Ala His Thr Arg
                420                 425                 430

Asn Leu Leu Arg Asn His Ile Ile Lys Asp Gln Leu Ala Ser Lys Tyr
            435                 440                 445

Leu Tyr His Gly Gln Thr Leu Glu Thr Leu Gly Gly Lys Lys Leu Arg
450                 455                 460

Val Phe Val Tyr Arg Asn Ser Leu Cys Ile Glu Asn Ser Cys Ile Ala
465                 470                 475                 480

Ala His Asp Lys Arg Gly Arg Tyr Gly Thr Leu Phe Thr Met Asp Arg
                485                 490                 495

Val Leu Thr Pro Pro Met Gly Thr Val Met Asp Val Leu Lys Gly Asp
                500                 505                 510

Asn Arg Phe Ser Met Leu Val Ala Ala Ile Gln Ser Ala Gly Leu Thr
            515                 520                 525

Glu Thr Leu Asn Arg Glu Gly Val Tyr Thr Val Phe Ala Pro Thr Asn
            530                 535                 540

Glu Ala Phe Arg Ala Leu Pro Pro Arg Glu Arg Ser Arg Leu Leu Gly
545                 550                 555                 560

Asp Ala Lys Glu Leu Ala Asn Ile Leu Lys Tyr His Ile Gly Asp Glu
                565                 570                 575

Ile Leu Val Ser Gly Gly Ile Gly Ala Leu Val Arg Leu Lys Ser Leu
                580                 585                 590

Gln Gly Asp Lys Leu Glu Val Ser Leu Lys Asn Asn Val Val Ser Val
            595                 600                 605

Asn Lys Glu Pro Val Ala Glu Pro Asp Ile Met Ala Thr Asn Gly Val
            610                 615                 620

Val His Val Ile Thr Asn Val Leu Gln Pro Pro Ala Asn Arg Pro Gln
625                 630                 635                 640

Glu Arg Gly Asp Glu Leu Ala Asp Ser Ala Leu Glu Ile Phe Lys Gln
                645                 650                 655

Ala Ser Ala Phe Ser Arg Ala Ser Gln Arg Ser Val Arg Leu Ala Pro
                660                 665                 670

Val Tyr Gln Lys Leu Leu Glu Arg Met Lys His
            675                 680

<210> SEQ ID NO 123
<211> LENGTH: 1205
<212> TYPE: DNA
<213> ORGANISM: Homo sapien
```

<400> SEQUENCE: 123

```
ccagtcagca gagggacagg aatcattcgg ccactgttca gacgggagcc acacccttct      60
ccaatccaag cctggcccca gaagatcaca aagagccaaa gaaactggca ggtgtccacg     120
cgctccaggc cagtgagttg gttgtcactt acttttctg tggggaagaa attccatacc      180
ggaggatgct gaaggctcag agcttgaccc tgggccactt aaagagcag ctcagcaaaa      240
agggaaatta taggtattac ttcaaaaaag caagcgatga gtttgcctgt ggagcggtgt     300
ttgaggagat ctgggaggat gagacggtgc tcccgatgta tgaaggccgg attctgggca    360
aagtggagcg gatcgattga gccctgcggt ctggctttgg tgaactgttg gagcccgaag    420
ctcttgtgaa ctgtcttggc tgtgagcaac tgcgacaaaa cattttgaag gaaaattaaa    480
ccaatgaaga agacaaagtc taaggaagaa tcggccagtg ggccttcggg agggcggggg    540
gaggttgatt ttcatgattc atgagctggg tactgactga gataagaaaa gcctgaacta    600
tttattaaaa acatgaccac tcttggctat tgaagatgct gcctgtattt gagagactgc    660
catacataat atatgacttc ctagggatct gaaatccata aactaagaga aactgtgtat    720
agcttacctg aacaggaatc cttactgata tttatagaac agttgatttc ccccatcccc    780
agtttatgga tatgctgctt taaacttgga aggggggagac aggaagtttt aattgttctg   840
actaaactta ggagttgagc taggagtgcg ttcatggttt cttcactaac agaggaatta   900
tgctttgcac tacgtccctc caagtgaaga cagactgttt tagacagact ttttaaaatg   960
gtgccctacc attgacacat gcagaaattg gtgcgttttg tttttttttc ctatgctgct  020
ctgttttgtc ttaaaggtct tgaggattga ccatgttgcg tcatcatcaa cattttgggg   080
gttgtgttgg atgggatgat ctgttgcaga gggagaggca gggaaccctg ctccttcggg  1140
ccccaggttg atcctgtgac tgaggctccc cctcatgtag cctccccagg cccagggccc  1200
tgagg                                                               1205
```

<210> SEQ ID NO 124
<211> LENGTH: 583
<212> TYPE: DNA
<213> ORGANISM: Homo sapien

<400> SEQUENCE: 124

```
ccaagaagca gtggccttat tgcatcccaa accacgcctc ttgaccaggc tgcctcccctt     60
gtggcagcaa cggcacagct aattctactc acagtgcttt taagtgaaaa tggtcgagaa     120
agaggcacca ggaagccgtc ctggcgcctg gcagtccgtg ggacgggatg gttctggctg    180
tttgagattc tcaaaggagc gagcatgtcg tggacacaca cagactattt ttagattttc    240
ttttgccttt tgcaaccagg aacagcaaat gcaaaaactc tttgagaggg taggagggtg    300
ggaaggaaac aaccatgtca tttcagaagt tagtttgtat atattattat aatcttataa    360
ttgttctcag aatcccttaa cagttgtatt taacagaaat tgtatattgt aatttaaaat    420
aattatataa ctgtatttga aataagaatt cagacatctg aggttttatt tcattttca    480
atagcacata tggaattttg caaagattta atctgccaag ggccgactaa gagaagttgt   540
aaagtatgta ttatttacat ttaatagact tacagggata agg                     583
```

<210> SEQ ID NO 125
<211> LENGTH: 783
<212> TYPE: DNA
<213> ORGANISM: Homo sapien

<400> SEQUENCE: 125

```
tcaaccatac atactgcttc cactagctaa taccaaatgc aggttctcag atccagacaa     60
atggaggaaa agaacattta tgcttccgtt tcagaaagcc aagtcgtagt tttggccctt    120
cctttctcta aagtttattc ccaaaaacag gtagcattcc tgattgggca gagaagagga    180
tattttcagc ccacatctgc tgcaggtatg tcattttctc ccatcttcac tgtgactagt    240
aaagatctca ccacttctct tggaatttc caactttgct tgtgattgaa tgtcacttcg     300
tgaatttgta ttatgtcaga tcacttggca ttgctcttcc atatgcatca agttgccagg    360
cactgttgcg ctgtcgggcc cactggaatc cacggggtg aaacaaattc aattatgctt     420
ttacagatcc tgctcaaaaa aggtttcaac tgcttaacca agtacagctc attcttccac    480
cttcttactc tgcaaccaaa ccaagtgccc catactacag gtaggtgccg agaaattccg    540
cagcagaaaa tccaaaatca tttctgaaac ctccttgcta acaaagttc tttttttctc     600
caaacagcat ataaaatgat caagtcttga agagaaaag aagcaaagta gcaaatacat      660
caacaattca ctatcagaaa cacataaaat cccagagaga gagaaggcag tatctctgaa    720
tcatggatgg acttggaaag ttcggaagga ttccgagtgc ttcctttcag aaagacaatt    780
ctg                                                                  783
```

<210> SEQ ID NO 126
<211> LENGTH: 604
<212> TYPE: DNA
<213> ORGANISM: Homo sapien

<400> SEQUENCE: 126

```
cctgctagaa tcactgccgc tgtgctttcg tggaaatgac agttccttgt ttttttgtt      60
tctgttttg ttttacatta gtcattggac cacagccatt caggaactac cccctgcccc     120
acaaagaaat gaacagttgt agggagaccc agcagcacct ttcctccaca caccttcatt    180
ttgaagttcg ggttttttgtg ttaaagttaa tctgtacatt ctgtttgcca ttgttacttg    240
tactatacat ctgtatatag tgtacggcaa aagagtatta atccactatc tctagtgctt    300
gactttaaat cagtacagta cctgtacctg cacggtcacc cgctccgtgt gtcgccctat    360
attgagggct caagctttcc cttgtttttt gaaaggggtt tatgtataaa tatatttat     420
gccttttat tacaagtctt gtactcaatg acttttgtca tgacattttg ttctacttat     480
actgtaaatt atgcattata aagagttcat ttaaggaaaa ttacttggta caataattat    540
tgtaattaav agatgtagcc tttattaaaa ttttatattt ttcaaaaaaa aaaaaaaaa     600
aaaa                                                                 604
```

<210> SEQ ID NO 127
<211> LENGTH: 417
<212> TYPE: DNA
<213> ORGANISM: Homo sapien

<400> SEQUENCE: 127

```
ctgagcctct gtcaccagag aaggctgagg ccccaatggc acacctcaga aacctacacc      60
ccgaggctgg acggctggac tcctgagcac aagctccctc tcgcacccttt tgccagacag    120
tttgtctcca atttcaaact gacctaaggc tcttactcct ggatttttg tttttaaacc     180
ttctcccagc cagtcttcgg gagggcatga ttagagaagt gctcctttgc tgatggagga    240
ggggacctaa ggaagaaggt ggatcccagg tgcctcctct ctaattgatc ctccccacct    300
agtttccttt gcctctcttc cttctaccag gtcatgtttt ttactctctg ccccttctgc    360
```

```
ctcctagcat ttcaaaaact gtagagtgca ccccatagtg dcatttttta gtccagg      417
```

<210> SEQ ID NO 128
<211> LENGTH: 657
<212> TYPE: DNA
<213> ORGANISM: Homo sapien

<400> SEQUENCE: 128

```
ccacactgaa atgcagttta atgtggaaac ttttctaaat acatattgta gcatctttgg    60
acatcaacgt gtggcctgaa atttttatta ttgttccctc ttctcctcca ttaaaaaaaa   120
aatctccttg tggtatttag tcatttacca ttaacacata ttatggctta aaaagggcca   180
tcccttcctt ttctgagctg gagttcttca cgctcacctt tgatgcatgg ccttagctgg   240
ttactttgcc ttggtttggt catgaacatt ggggttagtg gcctggcaac ttgaatgcat   300
atggaaagaa caatgccaag tgatctgaca taatacaaat tccgaagtga cattcaatca   360
caagcaaagt tggaaattcc aaagagaagt ggtgagatct ttactagtca cagtgaagat   420
gggagaaaat gacatacctg cagcagatgt gggctgaaaa tatcctcttc tctgcccaat   480
caggaatgct acctgttttt gggaataaac tttagagaaa ggaagggcca aaactacgac   540
ttggctttct gaaacggaag cataaatgtt cttttcctcc atttgtctgg atctgagaac   600
ctgcatttgg tattagctag tggaagcagt atgtatggtt gaagtgcatt gctgcag       657
```

<210> SEQ ID NO 129
<211> LENGTH: 1220
<212> TYPE: DNA
<213> ORGANISM: Homo sapien

<400> SEQUENCE: 129

```
cgcgtgctcg gctcacacca acaaggcaag ccaaaggcgc ccctcccccag agggatccct    60
aacgtgccca gcatgtagat tctggactaa cagacaacat acattcaccg ctggtcaccc   120
agatcctcat tcaaacccac tgctggcaca tcccttttcct tactttgccc tgtgctacca   180
gccacggaag gagcctctct tgttttttct ataaaatggg taggcaggag aaaagcaggt   240
gccctaagat tgctctaagg cccagcatgt ggttacagtt ctctgacttg cagaacctgc   300
caggtgtatg gctacaagtt atcctcgtgc tgatctgtct cattactaag ttaatggaga   360
agacagaaag gtaaaaatca cgtgtagcaa gaacaactct tatttcacaa actcaggtat   420
gaaacgaaac gcctgtcctt catggaactg cttttagctc ctgtcttttc aaaatggcag   480
agggagttcc tacacacact ttttccctgg aggccaaggt ctaggggtag aaaggggagg   540
ggtggggcta ccaggtagca gttgacaacc caaggtcaga ggagtggccc tcagtgtcat   600
ctgtccacag tgatacctgc caagatgacc actgacccac atctggtctt agtcattggt   660
ctcctcgat ttctggggcc acctgcaagc cccattccat tcctacagat ctctcagcca   720
cctgtaagtc ctttgtgaag atgtgggtga cacaggggga caggaaaacc catttctcaa   780
cccagatcca tgtctccact gcttctactc tgggttggga ttcaggaaga caggcacagt   840
cctctctgtt catagaaaca cctgccagtg tcaaggattc cagtcaggtg tctatcccaa   900
ctggtcaggg agagaaggc agacccattc tcaaagacca ccatgtccaa ggtctgacag   960
ctcccactg gctgccccca caggggcttt aggctggtct gggtcatggg aagcgtccc   020
tcttatcgct ggtctgtgtt ctcctggatt tggtatctat gttggtacga ctcctggcct   080
tttatctaaa ggactttggc ttttgtaaat cacaagccaa taatagactt ttttctcccc  1140
```

```
ctctgtttt  tgctgtgtca  tctctgcctt  gagactgcct  tgagacagtg  cttgccttga    1200
gagagtgagc  caattaacag                                                  1220
```

<210> SEQ ID NO 130
<211> LENGTH: 1274
<212> TYPE: DNA
<213> ORGANISM: Homo sapien

<400> SEQUENCE: 130

```
ccatatgagt  ttgccatctc  catggatgcc  atttcaatgc  cttcagggta  atcattctct      60
ccccaaagac  tgcccacggg  gtcatcactc  ctgtgacgaa  atgagggctg  gattgaagat    120
gttctgctga  gcaccccct   ggtcatcttt  ggggtctcag  aagagccata  atcatgacca    180
ttctcagcat  ctgaataatc  aggttctctc  caagtgcttg  gcaagttctg  attgtcctca    240
gcactgggat  agtctggctc  cccaaaaaag  ggtggagagt  taggttgaat  gtcagcgcct    300
ggataatcag  gctttcccag  agagtctgcg  tatggattga  ttctaaaact  tgtatgttcc    360
agattctttc  tggatcctgg  atggttcaaa  ttggctctgg  gtccaggatg  atcagagttg    420
ctctgagctc  cagggtagtc  cggttctaag  gagccaaaat  gatctggatg  tgttctggag    480
cctgcatagt  ttccactgct  gctggagcct  gcaaaatcag  gatttcgttg  agatccaggg    540
tagtctggtt  gtctggatga  tgctcggtgg  tagggatgac  tctgaaattc  actataatct    600
ggctctggta  gagaggtagg  atggtctggg  cttgttctag  aggctgcaga  gtatgcattg    660
cttctggtgc  cagaatagtc  tggattactc  agagatctag  gataatttgg  ttctgccaga    720
gacccaggat  agtctggacg  tgttctggag  gctacagagt  atggattgct  cctggtgccg    780
gggtaatctg  gattgttcag  aggacctgga  acatctggat  aaccttgagt  tttcaaaatac    840 ccctgcgtac  ggttctgaga  ccctgaatag  tcagggtaat  ctgggtcttc  ctcagaccag    900
ttattcctgt  agtaggcaga  catgttggta  tggactcttc  accctggagt  ggtaaactgt    960
cccagcattt  gcaattactc  agggatcttt  ttttttttcac  ttttttgccc  ttattgttct   1020
tgctttgtcc  caagtagatg  caaatgttgt  gcaaaccaac  ttgatcttaa  gatgttgtta   1080
agaacactgg  agtcacgtgt  ccatgggtcc  ttcaggctgg  cttttgatgg  gagctgggat   1140
gcagatgatt  tacggagggt  tataatctgt  gatgctggtc  tgaagtctga  atattccaag   1200
ttgctgactg  caggcagagc  ctcatgtcct  cctggcgctc  ctgttgccgc  tgcttgcgct   1260
ggccctcggg  tcga                                                        1274
```

<210> SEQ ID NO 131
<211> LENGTH: 554
<212> TYPE: DNA
<213> ORGANISM: Homo sapien
<220> FEATURE:
<221> NAME/KEY: misc_feature
<222> LOCATION: (1)...(554)
<223> OTHER INFORMATION: n = A,T,C or G

<400> SEQUENCE: 131

```
ctgtaattct  gccttttcta  ccttcattcc  atccttcctc  tgcccagata  aagkccagca      60
gaaattcctc  ctttctacct  ctctgggact  ctgagacagg  aaatcttcaa  ggaggagttt    120
ttccctcccc  actattctta  ttctcaaccc  ccagaggaac  caaggctgct  gtacccacct    180
cagggacaga  actccacact  atagtgggaa  agcttcaggg  acccctcctt  ttagtgctca    240
gggctcacct  atgctactgg  tccttttggc  aaaaaaggaa  aatgatagag  ccagggttgc    300
ccctgatgta  gcagccttac  tgtggagggg  ccaaagctgg  tgttcagagc  tcacccaagg    360
```

```
agggaggtga taaggtgtca tgcgttctgc tgaacccact ggntggtatg aacatgaggc    420
ttggggtgag ggaaaccaag tagggggttgg agaaggagca gcacctttgt macacctggc   480
tacccatagc tagctttctg ccctcaaaaa ctcagccttc aagggatcca gcccacacac    540
gccacaggca gcag                                                     554

<210> SEQ ID NO 132
<211> LENGTH: 787
<212> TYPE: DNA
<213> ORGANISM: Homo sapien

<400> SEQUENCE: 132
ctggtcaccc aactcttgtg gaagagggga attgagatcg agtactgaat atctggcaga     60
gaggctggaa tccttcagcc ccagagccca ggaccactc cagtagatgc agagaggggc    120
ctgcccaggg gtcagggcag tgggtatcac tggtgacatc aagaatatca gggctgggga   180
ggcatctttg tttcctggtg ccctcctcaa agttgctgac actttgggga cgggaagggg   240
tagaagtagg gctgctcctt ttggagctgg agggaataga cctggagaca gagttgaggc   300
agtcgggctg tccaggttct aagcatcaca gcttctgcac tgggctctga ggagattctc   360
agccagagga tcccagcctc ctcctccctc aaatgtcagt ccaagcaaat accaaagcaa   420
cgcatcgatt ttgtggaagt caattagaga tgtggggagc tatcggagac aagcactatt   480 gtacctttc acctccacac ttgtcacaag caggggactgt ctcctcccca ctttgcttgc   540
cacgcctgcc atggcttgag ctggggtgag gagtggtctt tatcttcttt gggagatcct   600
gactggttgc gcacttgcta agggcaggaa gtctggaggg ctgcaggaat ggtgccgttg   660
ataaacaggt ggacttataa tcatcatgca ctgcaattgt agaacatagt ctcctgcctt   720
ttctcatttg tataattgtc tgggtcaata ttctcccaat attgggaggg gctctgcagc   780
cctccag                                                             787

<210> SEQ ID NO 133
<211> LENGTH: 219
<212> TYPE: DNA
<213> ORGANISM: Homo sapien
<220> FEATURE:
<221> NAME/KEY: misc_feature
<222> LOCATION: (1)...(219)
<223> OTHER INFORMATION: n = A,T,C or G

<400> SEQUENCE: 133
tactgctcta agttttgtna aatttttcat attttaattt caagcttatt ttggagagat     60
aggaaggtca tttccatgta tgcataataa tcctgcaaag tacaggtact ttgtctaaga   120
aacattggaa gcaggttaaa tgttttgtaa actttgaaat atatggtcta atgtttaagc   180
agaattggaa nagactaata tcggttaaca aataacaac                          219

<210> SEQ ID NO 134
<211> LENGTH: 234
<212> TYPE: DNA
<213> ORGANISM: Homo sapien

<400> SEQUENCE: 134 attttaaaa acatcatgac tttgaactga aaaacataca cgtttagcac acaaatattg     60 aatatgaat gaactccaac tccatttgaa aacatgtgaa tcaaagtaca gttttagaag    120 tagtaattc acatttaagc aagttagcgc cttgctgaat acagcctttg taaaaaagag   180
``` cttagtgca tattttaatg gtacattgtg gttttgtacc atttggttga gttg 234

<210> SEQ ID NO 135
<211> LENGTH: 414
<212> TYPE: DNA
<213> ORGANISM: Homo sapien

<400> SEQUENCE: 135

| ctccagcctg gctatatccg gtcccgctat aacctgggca tcagctgcat caacctcggg | 60 |
| gctcaccggg aggctgtgga gcactttctg gaggccctga acatgcagag gaaaagccgg | 120 |
| ggcccccggg gtgaaggagg tgccatgtcg gagaacatct ggagcaccct gcgtttggca | 180 |
| ttgtctatgt taggccagag cgatgcctat ggggcagccg acgcgcggga tctgtccacc | 240 |
| ctcctaacta tgtttggcct gccccagtga cagtgggacg ggctgccctg tgagtgtcca | 300 |
| cctgggatt aaatatgtct tcaacaaggg aggcctggct tctacaatgg tttaggtaaa | 360 |
| ggggcctttg aagtagttct ggccaggctt gcaatacaca caacacaaga gcca | 414 |

<210> SEQ ID NO 136
<211> LENGTH: 461
<212> TYPE: DNA
<213> ORGANISM: Homo sapien

<400> SEQUENCE: 136

| gaagtgatta taggtttat ttgcatatac acagagaaga gtcagcattg ttgggtgaga | 60 |
| agaggcaggc tgtgaggagg taaggcttca gcagaggaag gcaccttgac agacaacacg | 120 |
| agactcctat taaatcagca cagttgcaaa cttcacctgc ctcaagccaa cagctcattg | 180 |
| aactcatatg tcgattgaga atcatttaca aaaccaggag agaaacaatg ggaagagcaa | 240 |
| cggtctctca tccctggacc tgacactcaa acattatgt acaggatgca ggaacaaaat | 300 |
| ctgtctgatc agtgccctct cctgctggga aaaacaccca tcacggaaga atttggggat | 360 |
| taaatatgtc ttcaacaagg gaggcctggc ttctacaatg gtttaggtaa aggggccttt | 420 |
| gaagtagttc tggccaggct tgcaatacac acaacacaag a | 461 |

<210> SEQ ID NO 137
<211> LENGTH: 269
<212> TYPE: DNA
<213> ORGANISM: Homo sapien

<400> SEQUENCE: 137

| atagcaaatg gacacaaatt acaaatgtgt gtgcgtggga cgaagacatc tttgaaggtc | 60 |
| atgagtttgt tagtttaaca tcatatattt gtaatagtga aacctgtact caaaatataa | 120 |
| gcagcttgaa actggcttta ccaatcttga aatttgacca caagtgtctt atatatgcag | 180 |
| atctaatgta aaatccagaa cttggactcc atcgttaaaa ttatttatgt gtaacattca | 240 |
| aatgtgtgca ttaaatatgc ttccacagt | 269 |

<210> SEQ ID NO 138
<211> LENGTH: 452
<212> TYPE: DNA
<213> ORGANISM: Homo sapien
<220> FEATURE:
<221> NAME/KEY: misc_feature
<222> LOCATION: (1)...(452)
<223> OTHER INFORMATION: n = A,T,C or G

<400> SEQUENCE: 138

```
ctccatggga ggcaaaatat agagaattta tggtgcccaa ctcttatgta atcactggac      60
taatcttccc tggtaactat gcaacatttg acagaaagg cacacaaaaa agtttaaata     120
tttcatgtgc caatctggaa aaaataatt taaatcaaca gaacagacag tacatctaca     180
caaatgagga aagcagaaaa gatacctcac attcatttat ctcaggtttc aaagtggctt     240
caatgctaaa gtaaatgtat taacatttgg aaaatacaag acaattttt tgtttgtttt     300 caattttttt agctctatac aatgattaca acataagaca aaaaaaaaa aaaacacaa     360 aaaacaaaac aaaaaggag ttcaggactt gttatcagtg tccaagtggc taanaactgg     420
ttcccataac aagcattgaa agttaaggcc cc                                   452
```

<210> SEQ ID NO 139
<211> LENGTH: 474
<212> TYPE: DNA
<213> ORGANISM: Homo sapien

<400> SEQUENCE: 139

```
tgtgcctcat tgaggttaca attgaaacag atgtgagcac ctgagagact ttccctgatt      60
atattcctcc acaaaccact gtaccatatt accttatttt atcttcttga aattcttatt     120
cattggcttg tttgttgtct ctttgcatta gatatatgta agctccttgg cataaatttg     180
acattggtag gggactgaca ttctaacctg gcccaggccc taggagagag ataactccac     240
aaagcagcac atactatctt aggttagcag ggagctaact caccatgtag cagatgaaaa     300
aaaccaaacc cagcactgtg cataaatacc acttgccaag aagtcaggtc ctcggcaacc     360
gagaatcaac ctcagcacaa acgcaggtgg ctgggctctg ttccccctta gccaccacct     420
cagcctctcc cctcccctgc cccaagtgcc caagagcttg ctctctgtg cttt            474
```

<210> SEQ ID NO 140
<211> LENGTH: 487
<212> TYPE: DNA
<213> ORGANISM: Homo sapien

<400> SEQUENCE: 140

```
cttccctgcc tcgtgttcct gagaaacgga ttaatagccc tttatccccc tgcaccctcc      60
tgcaggggat ggcactttga gccctctgga gccctcccct tgctgagcct tactctcttc     120
agactttctg aatgtacagt gccgttggtt gggatttggg gactggaagg gaccaaggac     180 actgaccccca agctgtcctg cctagcgtcc agcgtcttct aggagggtgg ggtctgcctg     240
tcctggtgtg gttggtttgg ccctgttttgc tgtgactacc ccccccctc cccgaaccga     300 gggacggctg ccttttgtctc tgcctcagat gccacctgcc ccgcccatgc tccccatcag     360
cagcatccag actttcagga aggcagggc cagccagtcc agaaccgcat ccctcagcag     420
ggactgataa gccatctctc ggagggcccc ctaataccca agtggagtct ggttcacacc     480
ctggggg                                                               487
```

<210> SEQ ID NO 141
<211> LENGTH: 248
<212> TYPE: DNA
<213> ORGANISM: Homo sapien
<220> FEATURE:
<221> NAME/KEY: misc_feature
<222> LOCATION: (1)...(248)
<223> OTHER INFORMATION: n = A,T,C or G

<400> SEQUENCE: 141

-continued

```
ttaaagatgg ggaaatgagg cctgnaaata gaaaagattt gcctagagtc acacacactg      60
tcaggtcagg tagagtcaaa atcaggcacc ccgactcaca gactgcttca cattgccatc     120
agagattgtc ctgcaacaat attatgttta gttctactgc agaatgataa ctggatctta     180 cccccttttgc ctgatctggc cacaaacttg tttttcaggt ctttccatta ggctctcttc    240
agctaatt                                                              248
```

<210> SEQ ID NO 142
<211> LENGTH: 173
<212> TYPE: DNA
<213> ORGANISM: Homo sapien

<400> SEQUENCE: 142

```
tactaagatt gtccaagcct ccctcttaaa actttctttc cctttagagg aatcattact      60
tcgtattaaa agtttctact tccttgtaga atatctacat ccaatgggcc atggcacaaa    120
atttaagtct agaaagaatc ttaaaggctc atcttatagt aaccagaggc agg           173
```

<210> SEQ ID NO 143
<211> LENGTH: 511
<212> TYPE: DNA
<213> ORGANISM: Homo sapien
<220> FEATURE:
<221> NAME/KEY: misc_feature
<222> LOCATION: (1)...(511)
<223> OTHER INFORMATION: n = A,T,C or G

<400> SEQUENCE: 143

```
cctcgtcaga ggggtggttc ctggtnacct gtactccacg gacctcggtg aagcaaaagc      60
ttcagggcag agggaatgag gcaacccagt ggcagcccg ctgggcccg tggctcctgc     120 tctcctattg gacgtagagg caggggagag acttctctat acaaatattc tcatcacaga    180
agggatgatc cttgctgctc tgccgtaggg ttttgatgc tgagctatgc tgcacatgac     240
gttaacctaa agaacttgga ctgagctttt aaaaaggac agcaaacaat tttataatcc     300
ttaaagtgta atagacggtt acactagtgc agggtattgg ggaggctctt tgggtgtgga   360
ggctgtcact tgtatttatt gtgactctaa atctttgata gtaaaacaaa tgtaaaaga   420 aatgtttgcc accagatggg aatagaagtt ccaataagca ggctggaatg ggtggctata    480
cgttgtatca cgaggaagtt ttagactctg a                                   511
```

<210> SEQ ID NO 144
<211> LENGTH: 190
<212> TYPE: DNA
<213> ORGANISM: Homo sapien

<400> SEQUENCE: 144

```
cattcttctg tcacatgcca attcagttgt caatcccatt gtctatgctt accggaaccg      60
agacttccgc tacactttc acaaaattat ctccaggtat cttctctgcc aagcagatgt    120
caagagtggg aatggtcagg ctggggtaca gcctgctctc ggtgtgggcc tatgatctag    180
gctctcgcct                                                            190
```

<210> SEQ ID NO 145
<211> LENGTH: 169
<212> TYPE: DNA
<213> ORGANISM: Homo sapien

<400> SEQUENCE: 145

```
gatgtggtta tctcctcaga tggccagttt gccctctcag gctcctggga tggaaccctg      60
```

```
cgcctctggg atctcacaac gggcaccacc acgaggcgat tgtgggcca taccaaggat    120 gtgctgagtg tggccttctc ctctgacaac cggcagattg tctctggat               169
```

<210> SEQ ID NO 146
<211> LENGTH: 511
<212> TYPE: DNA
<213> ORGANISM: Homo sapien

<400> SEQUENCE: 146

```
atctagagaa gatttgggaa acacatgata gctatggtta aatacttaac agggcaatca    60
cagggaagat gactagattt cctaacatcc atgagtgaaa tttatagaag tatactctct   120
gacttgatat aaaggaagat tttaaaaaac atgactgttc aggagtgttc aagtagggtc   180
agatgaccag tgattgggaa tacttcgtaa gcaggagcaa gtaagatctg agccactgtt   240
ctatcggtag ggtgtctgtg gtattccttg gtcaaagaag tactctaagc aacttcagtc   300
tcacgaatta ctatcaccct cgtgggcata catgatggtt accctaaaga ggaagtttca   360
gaaggcagta atattggatc ctggaatagt cagacaggag ccttcatgca gatacccttt   420
tcagttctcc atacacccat tcacaagtgg tcacaaaaac acccagtacc tttacttggc   480
tttacccact taacaatatg ctcaatatga g                                  511
```

<210> SEQ ID NO 147
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 147

```
gaccagttga gttcttcctg gctattgtat aatccacagc cacactgtga aagcaaatct    60
ggccagttag caacacaggg agaatctgcc tgaactgacc aaaggtgtcc atacttcatg   120
tcagtgagaa tttcacctcc atcatgttct aaagagccaa caacagattc tagggcactg   180
caaaatgctt cagcaattaa ttgaagttct gtttgagtac attcatcatc tttgagaatg   240
ctttctgggt cgttgtgagt cttgtgtctg atatatgcag ccaaatgagt ttcagtacag   300
ccacctccca acaaagccca tggttccttg agtgttaact gcaggacatg cagtgccgtc   360
tgacacgtga gcttcagctc atcccangca gtgtcatttc tgttgcagag aagccaagct   420
g                                                                   421
```

<210> SEQ ID NO 148
<211> LENGTH: 237
<212> TYPE: DNA
<213> ORGANISM: Homo sapien

<400> SEQUENCE: 148

```
acacaccact gttggccttc catctgggtt aagtcaactg tgagtagaaa ccgaagataa    60
cagttttgta ttcataatgg cctttttcata ctccaagtac ttttgagcac agagcctctt   120
gcttctgacc tggcacttgg aacacagata tatatatctt ttgttctgtc cctgggaaac   180
tgatatttgt gtaagacaac caccagatat tttctctaat aaaatcttct aaaatta       237
```

<210> SEQ ID NO 149
<211> LENGTH: 168
<212> TYPE: DNA

-continued

<213> ORGANISM: Homo sapien

<400> SEQUENCE: 149

```
agagaaagtt aaagtgcaat aatgtttgaa gacaataagt ggtggtgtat cttgtttcta      60
ataagataaa cttttttgtc tttgctttat cttattaggg agttgtatgt cagtgtataa     120
aacatactgt gtggtataac aggcttaata aattctttaa aaggagag                  168
```

<210> SEQ ID NO 150
<211> LENGTH: 68
<212> TYPE: DNA
<213> ORGANISM: Homo sapien
<220> FEATURE:
<221> NAME/KEY: misc_feature
<222> LOCATION: (1)...(68)
<223> OTHER INFORMATION: n = A,T,C or G

<400> SEQUENCE: 150

```
ggtggggttt ggcagagatg antttaagtg ctgtggccag aagcgggggg ggggtttggt      60
ggaaattt                                                               68
```

<210> SEQ ID NO 151
<211> LENGTH: 421
<212> TYPE: DNA
<213> ORGANISM: Homo sapien

<400> SEQUENCE: 151

```
aggtgacacg tattcgggat gaaagtataa tagtcattcc ttcaacccctt gcatttatgg     60
actctggaaa tcgaagatcc acagtgagta aagatgttcg tccaaagaca aaaatagaa     120
acagctcaac aaagcgagag acaaaaaaac aaaatgcac tgtggctctg cctttgaagt     180
ctgggctcca gcagagggct gatcttccca caggagacga gacggcctat gacactctcc     240
agaactgttg tcagtgccga attttacttc ccttgcccat tctaaatgag caccaggaga     300
agtgccagag gttagctcac caaaagaaac tccagtgggg ctggtgagat ggctcagcgg     360
gtaagagcac ccgactgctc ttccgaaggt ccggagttca atcccagca accacatggt     420
g                                                                     421
```

<210> SEQ ID NO 152
<211> LENGTH: 507
<212> TYPE: DNA
<213> ORGANISM: Homo sapien
<220> FEATURE:
<221> NAME/KEY: misc_feature
<222> LOCATION: (1)...(507)
<223> OTHER INFORMATION: n = A,T,C or G

<400> SEQUENCE: 152

```
gaattcggca cnagctcgtg ccgccagggt nggtccnttt tttgctccgc ctcgccanga      60
cttcctacag ctatcgccag tcgtcggcca cgtcntcctt cngaggcctg ggcggcggct     120
ccgtgcgttn tgggccgggg gtcgcctttc nctcncccag cattcacggg ggctccggcg     180
gccgcggcgt atccgtgtcc tccgcccgct ntgtgtcctc gtcctcctcn ggggcctacg     240
gctngctgct acngcggctt cctgaccgct tccacgggc tgctggcngg caacgagaag     300
ctaaccatgc agaacctnaa cnaccgcctg gcctcctacc tgnacaaggt gcgcnccctg     360
taggcggcca acggcnagct agaggtgaag atccnctact gggtaccaga agcaggggcc     420
tgggccctgc ccgactacag ccactnctnc acnaccatgc agtacctgcn gggnaaagat     480
tntngggngc caccatngag aactgca                                         507
```

<210> SEQ ID NO 153
<211> LENGTH: 513
<212> TYPE: DNA
<213> ORGANISM: Homo sapien

<400> SEQUENCE: 153

| | | | | | |
|---|---|---|---|---|---|
| gaattcggca | cgaggtggct | cagatgtcca | ctactgggag | tatggtcgaa | ttgggaattt | 60 |
| tattgtgaaa | agcccatgg | tgctgggaca | tgaagcttcg | ggaacagtcg | aaaaagtggg | 120 |
| atcatcggta | aagcacctaa | aaccaggtga | tcgtgttgcc | atcgagcctg | gtgctccccg | 180 |
| agaaaatgat | gaattctgca | agatgggccg | atacaatctg | tcaccttcca | tcttcttctg | 240 |
| tgccgcgccc | cccgatgacg | ggaacctctg | ccggttctat | aagcacaatg | cagccttttg | 300 |
| ttacaagctt | cctgacaatg | tcacctttga | ggaaggcgcc | ctgatcgagc | cactttctgt | 360 |
| ggggatccat | gcctgcagga | gaggcggagt | taccctggga | cacaaggtcc | ttgtgtgtgg | 420 |
| agctgggcca | atcgggatgg | tcactttgct | cgtggccaaa | gcaatgggag | cagctcaagt | 480 |
| agtggtgact | gatctgtctg | ctacccgatt | gtc | | | 513 |

<210> SEQ ID NO 154
<211> LENGTH: 507
<212> TYPE: DNA
<213> ORGANISM: Homo sapien
<220> FEATURE:
<221> NAME/KEY: misc_feature
<222> LOCATION: (1)...(507)
<223> OTHER INFORMATION: n = A,T,C or G

<400> SEQUENCE: 154

| | | | | | |
|---|---|---|---|---|---|
| ggcacgagct | cgtgccgaat | tcggcncgag | cagacacaat | ggtaagaatg | gtgcctgtcc | 60 |
| tgctgtctct | gctgctgctt | ctgggtcctg | ctgtccccca | ggagaaccaa | gatggtcgtt | 120 |
| actctctgac | ctatatctac | actgggctgt | ccaagcatgt | tgaagacgtc | ccgcgtttc | 180 |
| aggcccttgg | ctcactcaat | gacctccagt | tctttagata | caacagtaaa | gacaggaagt | 240 |
| ctcagcccat | gggactctgg | agacaggtgg | aaggaatgga | ggattggaag | caggacagcc | 300 |
| aacttcagaa | ggccagggag | gacatcttta | tggagaccct | gaaagacatc | gtggagtatt | 360 |
| acaacgacag | taacgggtct | cacgtattgc | agggaaggtt | tggttgtgag | atcgagaata | 420 |
| acagaagcag | cggagcattc | tggaaatatt | actatgatgg | aaaggactac | attgaattca | 480 |
| acaaagaaat | cccagcctgg | gtcccct | | | | 507 |

<210> SEQ ID NO 155
<211> LENGTH: 507
<212> TYPE: DNA
<213> ORGANISM: Homo sapien
<220> FEATURE:
<221> NAME/KEY: misc_feature
<222> LOCATION: (1)...(507)
<223> OTHER INFORMATION: n = A,T,C or G

<400> SEQUENCE: 155

| | | | | | |
|---|---|---|---|---|---|
| ggcacgagga | gacctaaggg | ctgagtntcg | ggaacaggag | aaagctctgt | tggccctcca | 60 |
| gcagcagtgt | gctgagcagg | cacaggagca | tgaggtggag | accagggccc | tgcaggacag | 120 |
| ctggctgcag | gcccaggcag | tgctcaagga | acgggaccag | gagctggaag | ctctgcgggc | 180 |
| agaaagtcag | tcctcccggc | atcaggagga | ggctgccgg | gccgggctg | aggctctgca | 240 |
| ggaggccctt | ggcaaggctc | atgctgccct | gcaggggaaa | gagcagcatc | tcctcgagca | 300 |

| | |
|---|---|
| ggcagaattg agccgcagtc tggaggccag cactgcaacc ctgcaagcct ccctggatgc | 360 |
| ctgccaggca cacagtcggc agctggagga ggctctgagg atacaagaag gtgagatcca | 420 |
| ggaccaggat ctccgatacc aggaggatgt gcagcagctg cagcaggcac ttgcccagag | 480 |
| ggatgaagag ctgagacatc agcagga | 507 |

<210> SEQ ID NO 156
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 156

| | |
|---|---|
| ggcacgagga cagagagaac cctgtngaaa gagcgttacc aggaggtcct ggacaaacag | 60 |
| aggcaagtgg agaatcagct ccaagtgcaa ttaaagcagc ttcagcaaag gagagaagag | 120 |
| gaaatgaaga atcaccagga gatattaaag gctattcagg atgtgacaat aaagcgggaa | 180 |
| gaaacaaaga agaagataga gaaagagaag aaggagtttt tgcagaagga gcaggatctg | 240 |
| aaagctgaaa ttgagaagct ttgtgagaag ggcagaagag aggtgtggga atggaactg | 300 |
| gatagactca agaatcagga tggcgaaata aataggaaca ttatgaagaa gactgaacgg | 360 |
| gcctggaagg cagagatctt atcactagag agccggaaag agttactggt actgaaacta | 420 |
| gaagaagcag aaaagaggc agaattgcac cttacttacc tcaagtcaac tcccccaaca | 480 |
| ctggagacag ttcgttccaa acaggagtg | 509 |

<210> SEQ ID NO 157
<211> LENGTH: 507
<212> TYPE: DNA
<213> ORGANISM: Homo sapien

<400> SEQUENCE: 157

| | |
|---|---|
| ggcacgaggg cagccctcct accggcgcac gtggtgccgc cgctgctgcc tcccgctcgc | 60 |
| cctgaaccca gtgcctgcag ccatggctcc cggccagctc gccttattta gtgtctctga | 120 |
| caaaaccggc cttgtggaat tgcaagaaa cctgaccgct cttggtttga atctggtcgc | 180 |
| ttccggaggg actgcaaaag ctctcaggga tgctggtctg gcagtcagag atgtctctga | 240 |
| gttgacggga tttcctgaaa tgttgggggg acgtgtgaaa actttgcatc ctgcagtcca | 300 |
| tgctggaatc ctagctcgta atattccaga agataatgct gacatggcca gacttgattt | 360 |
| caatcttata agagttgttg cctgcaatct ctatccctt gtaaagacag tggcttctcc | 420 |
| aggtgtaagt gttgaggagg ctgtggagca aattgacatt ggtggagtaa ccttactgag | 480 |
| agctgcagcc aaaaaccacg ctcgagt | 507 |

<210> SEQ ID NO 158
<211> LENGTH: 507
<212> TYPE: DNA
<213> ORGANISM: Homo sapien
<220> FEATURE:
<221> NAME/KEY: misc_feature
<222> LOCATION: (1)...(507)
<223> OTHER INFORMATION: n = A,T,C or G

<400> SEQUENCE: 158

| | |
|---|---|
| ggcacgagtc gagctgtgcc tattcgngtc aatccaagag tgagtaatgt gaagtctgtc | 60 |
| tacaaaaccc acattgatgt cattcattat cggaaaacgg atgcaaaacg tctgcatggc | 120 |

```
cttgatgaag aagcagaaca gaaactttt tcagagaaac gtgtggaatt gcttaaggaa      180 cttccagga aaccagacat ttatgagagg cttgcttcag ccttggctcc aagcatttat      240
gaacatgaag atataaagaa gggaatttg cttcagctct ttggcgggac aaggaaggat      300
tttagtcaca ctggaagggg caaatttcgg gctgagatca acatcttgct gtgtggcgac      360
cctggtacca gcaagtccca gctgctgcag tacgtgtaca acctcgtccc cagggccag      420 tacacgtntg ggaagggctc cagtgcannt ggcctnactg cntacgtaat gaaagaccct      480
gagacaaggn anctggnnct gnnacag                                        507
```

<210> SEQ ID NO 159
<211> LENGTH: 508
<212> TYPE: DNA
<213> ORGANISM: Homo sapien
<220> FEATURE:
<221> NAME/KEY: misc_feature
<222> LOCATION: (1)...(508)
<223> OTHER INFORMATION: n = A,T,C or G

<400> SEQUENCE: 159

```
ggcacnanaa accaggatta tggtnnggat ccaaagattg ctaatgcaat aatgaaggca      60
gcagatgagg tagctgaagg taaattaaat gatcattttc ctctcgtggt atggcagact     120
ggatcaggaa ctcagacaaa tatgaatgta aatgaagtca ttagcaatag agcaattgaa     180
atgttaggag gtgaacttgg cagcaagata cctgtgcatc ccaacgatca tgttaataaa     240
agccagagct caaatgatac ttttcccaca gcaatgcaca ttgctgctgc aatagaagtt     300
catgaagtac tgttaccagg actacagaag ttacatgatg ctcttgatgc aaaatccaaa     360
gagtttgcac agatcatcaa gattggacgt actcatactc aggatgctgt tccacttact     420
cttgggcagg aatttagtgg ttatgttcaa caagtaaaat atgcaatgac aagaataaaa     480
gctgccatgc caagaatcta tgagctcg                                       508
```

<210> SEQ ID NO 160
<211> LENGTH: 508
<212> TYPE: DNA
<213> ORGANISM: Homo sapien
<220> FEATURE:
<221> NAME/KEY: misc_feature
<222> LOCATION: (1)...(508)
<223> OTHER INFORMATION: n = A,T,C or G

<400> SEQUENCE: 160

```
ggcacgagct tggagcaaag tcatctnaag gaattagagg acacacttca ggttaggcac      60
atacaagagt ttgagaaggt tatgacagac cacagagttt ctttggagga attaaaaaag     120 gaaaccaac aaataattaa tcaaatacaa gaatctcatg ctgaaattat ccaggaaaaa     180 gaaaacagt tacaggaatt aaaactcaag gtttctgatt tgtcagacac gagatgcaag     240
ttagaggttg aacttgcgtt gaaggaagca gaaactgatg aaataaaaat tttgctggaa     300
gaaagcagag cccagcagaa ggagaccttg aaatctcttc ttgaacaaga dacagaaaat     360
ttgagaacag aaattagtaa actcaaccaa aagattcagg ataataatga aaattatcag     420
gtgggcttag cagagctaag aactttaatg acaattgaaa aagatcagtg tatttccgag     480
ttaattagta gacatgaaga agaatcta                                       508
```

<210> SEQ ID NO 161
<211> LENGTH: 507
<212> TYPE: DNA

<213> ORGANISM: Homo sapien

<400> SEQUENCE: 161

| | | | | | |
|---|---|---|---|---|---|
| ggcacgagcg | ctaccggcgc | ctcctctgcg | gccactgagc | cggagccggc | ctgagcagcg | 60 |
| ctctcggttg | cagtacccac | tggaaggact | taggcgctcg | cgtggacacc | gcaagcccct | 120 |
| cagtagcctc | ggcccaagag | gcctgctttc | cactcgctag | ccccgccggg | ggtccgtgtc | 180 |
| ctgtctcggt | ggccggaccc | gggcccgagc | ccgagcagta | gccggcgcca | tgtcggtggt | 240 |
| gggcatagac | ctgggcttcc | agagctgcta | cgtcgctgtg | gcccgcgccg | gcggcatcga | 300 |
| gactatcgct | aatgagtata | gcgaccgctg | cacgccggct | tgcatttctt | ttggtcctaa | 360 |
| gaatcgttca | attggagcag | cagctaaaag | ccaggtaatt | tctaatgcaa | agaacacagt | 420 |
| ccaaggattt | aaaagattcc | atggccgagc | attctctgat | ccatttgtgg | aggcagaaaa | 480 |
| atctaacctt | gcatatgata | ttgtgca | | | | 507 |

<210> SEQ ID NO 162
<211> LENGTH: 507
<212> TYPE: DNA
<213> ORGANISM: Homo sapien
<220> FEATURE:
<221> NAME/KEY: misc_feature
<222> LOCATION: (1)...(507)
<223> OTHER INFORMATION: n = A,T,C or G

<400> SEQUENCE: 162

| | | | | | |
|---|---|---|---|---|---|
| ggcacgagca | gctgtgcacc | gacatgntct | cagtgtcctg | agtaagacca | aagaagctgg | 60 |
| caagatcctc | tctaataatc | ccagcaaggg | actggccctg | ggaattgcca | aagcctggga | 120 |
| gctctacggc | tcacccaatg | ctctggtgct | actgattgct | caagagaagg | aaagaaacat | 180 |
| atttgaccag | cgtgccatag | agaatgagct | actggccagg | aacatccatg | tgatccgacg | 240 |
| aacatttgaa | gatatctctg | aaaagggtgc | tctggaccaa | gaccgaaggc | tgtttgtgga | 300 |
| tggccaggaa | attgctgtgg | tttacttccg | ggatggctac | atgcctcgtc | agtacagtct | 360 |
| acagaattgg | gaagcacgtc | tactgctgga | gaggtcacat | gctgccaagt | gcccagacat | 420 |
| tgccacccag | ctggctggga | ctaagaaggt | gcagcaggag | ctaagcaggc | cgggcatgct | 480 |
| ggagatgttg | ctccctggcc | agcctga | | | | 507 |

<210> SEQ ID NO 163
<211> LENGTH: 460
<212> TYPE: DNA
<213> ORGANISM: Homo sapien

<400> SEQUENCE: 163

| | | | | | |
|---|---|---|---|---|---|
| ggcacgagaa | ataactttat | ttcattgtgg | gtcgcggttc | ttgtttgtgg | atcgctgtga | 60 |
| tcgtcacttg | acaatgcaga | tcttcgtgaa | gactctgact | ggtaagacca | tcaccctcga | 120 |
| ggttgagccc | agtgacacca | tcgagaatgt | caaggcaaag | atccaagata | ggaaggcat | 180 |
| ccctcctgac | cagcagaggc | tgatctttgc | tggaaaacag | ctggaagatg | ggcgcaccct | 240 |
| gtctgactac | aacatccaga | aagagtccac | cctgcacctg | gtgctccgtc | tcagaggtgg | 300 |
| gatgcaaatc | ttcgtgaaga | cactcactgg | caagaccatc | acccttgagg | tggagcccag | 360 |
| tgacaccatc | gagaacgtca | agcaaagat | ccaggacaag | gaaggcattc | ctcctgacca | 420 |
| gcagaggttg | atctttgccg | gaaagcagct | ggaagatggg | | | 460 |

<210> SEQ ID NO 164
<211> LENGTH: 462

<212> TYPE: DNA
<213> ORGANISM: Homo sapien

<400> SEQUENCE: 164

```
ggcacgagcc ggatctcatt gccacgcgcc cccgacgacc gcccgacgtg cattcccgat      60
tccttttggt tccaagtcca atatggcaac tctaaaggat cagctgattt ataatcttct     120
aaaggaagaa cagaccccccc agaataagat tacagttgtt ggggttggtg ctgttggcat    180
ggcctgtgcc atcagtatct taatgaagga cttggcagat gaacttgctc ttgttgatgt     240
catcgaagac aaattgaagg gagagatgat ggatctccaa catggcagcc ttttccttag     300
aacaccaaag attgtctctg caaagacta taatgtaact gcaaactcca agctggtcat      360
tatcacggct ggggcacgtc agcaagaggg agaaagccgt cttaatttgg tccagcgtaa    420
cgtgaacatc tttaaattca tcattcctaa tgttgtaaaa ta                          462
```

<210> SEQ ID NO 165
<211> LENGTH: 462
<212> TYPE: DNA
<213> ORGANISM: Homo sapien

<400> SEQUENCE: 165

```
ggcacgagga agccatgagc agcaaagtct ctcgcgacac cctgtacgag gcggtgcggg      60
aagtcctgca cgggaaccag cgcaagcgcc gcaagttcct ggagacggtg gagttgcaga    120
tcagcttgaa gaactatgat ccccagaagg acaagcgctt ctcgggcacc gtcaggctta     180
agtccactcc ccgccctaag ttctctgtgt gtgtcctggg ggaccagcag cactgtgacg     240
aggctaaggc cgtggatatc ccccacatgg acatcgaggc gctgaaaaaa ctcaacaaga     300
ataaaaaact ggtcaagaag ctggccaaga agtatgatgc gttttttggcc tcagagtctc    360
tgatcaagca gattccacga atcctcggcc caggtttaaa taaggcagga aagttccctt    420
ccctgctcac acacaacgaa aacatggtgg ccaaagtgga tg                         462
```

<210> SEQ ID NO 166
<211> LENGTH: 459
<212> TYPE: DNA
<213> ORGANISM: Homo sapien
<220> FEATURE:
<221> NAME/KEY: misc_feature
<222> LOCATION: (1)...(459)
<223> OTHER INFORMATION: n = A,T,C or G

<400> SEQUENCE: 166

```
gcacgagag ggacctgtnt gaatggntcc actagggttn anntgnctct tacttttaac       60
antnaaatn gacctgcccg tgaanangcg ggcntgacac annaaaacga gaagaccta      120
ggagcttta atttattaat gcanacagna cctaacaaac ccacangtcc taaactacca    180
gcctgcatt aaaaatttcg gntggggcna cctcnnagca naacccaacc tccgagcaac    240
catgctaag acttcaccag tcaaagctga actactatac tcaattgatc caataacttg     300
accaacagan caagntaccc tagggataac ancacaatcc tattctagac cccttatnac     360
caatangntt tacacctcna tngnggaacc aggacatccg atggggcagn cgttattaaa    420
gttngttgnt aacataaaag tctacgtgat ctgagttag                             459
```

<210> SEQ ID NO 167
<211> LENGTH: 464
<212> TYPE: DNA
<213> ORGANISM: Homo sapien

```
<220> FEATURE:
<221> NAME/KEY: misc_feature
<222> LOCATION: (1)...(464)
<223> OTHER INFORMATION: n = A,T,C or G

<400> SEQUENCE: 167
gaattgggac caacganaan cntgcggntc ttnttttgcn tccanngccc agctnattgc      60
tcagacacac atgggaagg tnaaggtcgg gagtcaacng atttggtngt attgnagcgt     120
ttggtcacca gngctgcttt taactctggn aaagtggata ttgttgtcat naatgacccc    180
tncattgacc tnaactacat ggtttacatg ttccaatatg attccaccca tggcaaattc    240
catngcaccg tnaaggctga gaacgggaag cttgtnatca atggaaatcc catcaccatc    300
tttcangaac ganatccntn caaaaatcaa anttgggggc gatgcttggc cncttgaagt    360
accgttcaan gggaannncc ccactttggc cgntntttnc aancccaccc caatttgggn    420
aaaaaaaaag gggnntttgg gggggggcct tttannttt tttt                      464

<210> SEQ ID NO 168
<211> LENGTH: 462
<212> TYPE: DNA
<213> ORGANISM: Homo sapien
<220> FEATURE:
<221> NAME/KEY: misc_feature
<222> LOCATION: (1)...(462)
<223> OTHER INFORMATION: n = A,T,C or G

<400> SEQUENCE: 168
ggcacgaggn nnaacctncg gggctggggc agcacgcctt gngcaancct gcactgcact     60
gaagacccgg tgccggaagc cgnnggcngc nacatgcagn aactgaacca gctgggcgcg    120
cancagttct cagacctgac agaggtgctt ttacacttcc taactgatcc anantangtg    180
gaaatattnt tngttnatnt catntgaatn atccancncc aatcatanca nntttnattn    240
cctcataanc nttgagaana gcnnccttnt gnttncanan ggtgctntga anangagtct    300
cacangcaan caggtccaag cggatttnnt aactntgggt cttantgang agaaagncac    360
ttacttttct gaaancngga agcagaatgc tcccacccct gctcgatggg ccatacgtca    420
agactctgat gattaaccag ctttanatat ggacnggaaa tt                       462

<210> SEQ ID NO 169
<211> LENGTH: 460
<212> TYPE: DNA
<213> ORGANISM: Homo sapien
<220> FEATURE:
<221> NAME/KEY: misc_feature
<222> LOCATION: (1)...(460)
<223> OTHER INFORMATION: n = A,T,C or G

<400> SEQUENCE: 169
ggcacgaggg acagcagacn agacagtcac agcagccttg acaaaacgtt cctggaactc     60
aagntcttnt ncncaaagga ggacagagca nacagcagag accatggant ctncctcggc    120
ccctccccac agatggtgca tccctggca naggctcctg ctcacagcct cacttctaac    180
cttctggaac ccgcccacca ctgccaagct cactattgaa tccacgccgt tcaatgnntc    240
ntaggggaag gaggngcttt ctactnttnc acaatctgan ccccttcttn tttggttact    300
ancatggctc tncatgtnaa aatactggna tggntaacct gtcaaattta taggnantnt    360
gctaattggg aaactnccnn tngtctaccc caggggnccc agattcctnn gttncataa    420 cnattaattt aaccctaat gncaanccct tngttaaaga                            460
```

<210> SEQ ID NO 170
<211> LENGTH: 508
<212> TYPE: DNA
<213> ORGANISM: Homo sapien
<220> FEATURE:
<221> NAME/KEY: misc_feature
<222> LOCATION: (1)...(508)
<223> OTHER INFORMATION: n = A,T,C or G

<400> SEQUENCE: 170

| | | | | | |
|---|---|---|---|---|---|
| ggcacgaggg | ggatttttag | gtggtcnggt | gtggtatcag | gaataatgtg | ggaggccaga | 60 |
| ttgaagtcca | ggccaggaac | aatggtaatt | gtgggactta | agaaagtgtg | agtacagctg | 120 |
| aatgagccgg | ggagcagaaa | gtatatgcgt | caggtatgag | gaagaaaata | gattttggaa | 180 |
| gttatgagaa | atgtagagag | tgagttgagc | atagtttgtg | attttgaggg | cctctaacag | 240 |
| tattaaagca | gcggcagcgg | ctgcacacag | acatgatggc | taggctaaaa | caggaaggtc | 300 |
| aagttgtttg | gacagaaagg | ctacaggtg | cagtcctggc | tcttgtgtaa | gaattctgac | 360 |
| cacactaacc | atgcctagga | aggaaaggag | ttgttctttt | gtaagggatt | gaggtttggg | 420 |
| agattaatcg | gacacgatca | gcagggagag | cacctgtgtt | tttatgagaa | ttatgctgag | 480 |
| ataggtaaca | gatgaggatg | aaatttgg | | | | 508 |

<210> SEQ ID NO 171
<211> LENGTH: 507
<212> TYPE: DNA
<213> ORGANISM: Homo sapien
<220> FEATURE:
<221> NAME/KEY: misc_feature
<222> LOCATION: (1)...(507)
<223> OTHER INFORMATION: n = A,T,C or G

<400> SEQUENCE: 171

| | | | | | |
|---|---|---|---|---|---|
| ggcacgagac | cagccactag | cgcagnctcg | agcgatggcc | tatgtccccg | caccgggcta | 60 |
| ccagcccacc | tacaacccga | cgctgcctta | ctaccagccc | atcccgggcg | ggctcaacgt | 120 |
| gggaatgtct | gtttacatcc | aaggagtggc | cagcgagcac | atgaagcggt | tcttcgtgaa | 180 |
| ctttgtggtt | gggcaggatc | cgggctcaga | cgtcgccttc | cacttcaatc | cgcggtttga | 240 |
| cggctgggac | aaggtggtct | tcaacacgtt | gcagggcggg | aagtggggca | gcgaggagag | 300 |
| gaagaggagc | atgcccttca | aaaagggtgc | cgcctttgag | ctggtcttca | tagtcctggc | 360 |
| tgagcactac | aagtggtgg | taatggaaa | tcccttctat | gagtacgggc | accggcttcc | 420 |
| cctacagatg | gtcacccacc | tgcaagtgga | tgggatctg | caacttcaat | caatcaactt | 480 |
| catcggaggc | cagcccctcc | ggcccca | | | | 507 |

<210> SEQ ID NO 172
<211> LENGTH: 409
<212> TYPE: DNA
<213> ORGANISM: Homo sapien

<400> SEQUENCE: 172

| | | | | | |
|---|---|---|---|---|---|
| ggcacgagct | ggagtgtctg | ctgccacccc | ctcgtcctct | gcagaaatgt | ctgtcaccta | 60 |
| cgatgactct | gtgggagtgg | aagtgtccag | cgacagcttc | tgggaggttg | ggaactacaa | 120 |
| acggactgtg | aagcggattg | acgatggcca | ccgcctgtgt | ggtgacctca | tgaactgtct | 180 |
| gcatgagcgg | gcacgcatcg | agaaggcgta | tgcacagcag | ctcactgagt | gggcccgacg | 240 |
| ctggaggcag | ctggtagaga | aggaccaca | gtatgggacc | gtggagaagg | cctggatagc | 300 |
| tgtcatgtct | gaagcagaga | gggtgagtga | actgcacctg | gaagtgaagg | catcactgat | 360 |

```
gaatgaagac tttgagaaga tcaagaactg gcagaaggaa gcctttcac          409
```

<210> SEQ ID NO 173
<211> LENGTH: 409
<212> TYPE: DNA
<213> ORGANISM: Homo sapien

<400> SEQUENCE: 173

```
ggcacgaggg cagctagagg aagagtccaa ggccaagaac gcactggccc acgccctgca    60
gtcagctcgc catgactgtg acctgctgcg gaacagtat gaagaggagc aggaagccaa    120
ggctgagctg cagagggcca tgtccaaggc caacagcgag gtagcccagt ggaggacgaa    180
atatgagacg gatgccatcc agcgcacaga ggagctggaa gaggccaaga agaagctggc    240
tcagcgtctg caggatgctg aggaacatgt agaagctgtg aattccaaat gcgcttctct    300
tgaaaagacg aagcagcgac ttcagaatga agtggaggac ctcatgattg acgtggagag    360
gtctaatgct gcctgcgctg cgcttgataa gaagcagagg aactttgac               409
```

<210> SEQ ID NO 174
<211> LENGTH: 407
<212> TYPE: DNA
<213> ORGANISM: Homo sapien

<400> SEQUENCE: 174

```
ggcacgagcc ggggcggggc gcggcgctcc ggctcgaggc attcggagct gcgggagccg    60
ggctggcagg agcaggatgg cggcggcggc ggctgcaggc gaggcgcgcc gggtgctggt    120
gtacggcggc aggggcgctc tgggttctcg atgcgtgcag gcttttcggg cccgcaactg    180
gtgggttgcc agcgttgatg tggtggagaa tgaagaggcc agcgctagca tcattgttaa    240
aatgacagac tcgttcactg agcaggctga ccaggtgact gctgaggttg aaaagctctt    300
gggtgaagag aaggtggatg caattctttg cgttgctgga ggatgggccg ggggcaatgc    360
caaatccaag tctctctttta agaactgtga cctgatgtgg aagcaga               407
```

<210> SEQ ID NO 175
<211> LENGTH: 407
<212> TYPE: DNA
<213> ORGANISM: Homo sapien

<400> SEQUENCE: 175

```
ggcacgagct tgcccgtcgg tcgctagctc gctcggtgcg cgtcgtcccg ctccatggcg    60
ctcttcgtgc ggctgctggc tctcgccctg gctctggccc tgggcccgc cgcgaccctg    120
gcgggtcccg ccaagtcgcc ctaccagctg gtgctgcagc acagcaggct ccggggccgc    180
cagcacggcc ccaacgtgtg tgctgtgcag aaggttattg gcactaatag gaagtacttc    240
accaactgca gcagtggta ccaaaggaaa atctgtggca atcaacagt catcagctac    300
gagtgctgtc ctggatatga aaaggtccct ggggagaagg gctgtccagc agccctacca    360
ctctcaaacc tttacgagac cctgggagtc gttggatcca ccaccac               407
```

<210> SEQ ID NO 176
<211> LENGTH: 409
<212> TYPE: DNA
<213> ORGANISM: Homo sapien

<400> SEQUENCE: 176

```
ggcacgagtg gtgccaaaac gggaccatgc cctcctggag gagcagagca agcagcagtc    60
```

```
caacgagcac ctgcgccgcc agttcgccag ccaggccaat gttgtgggc cctggatcca      120 gaccaagatg gaggagatcg ggcgcatctc cattgagatg aacgggaccc tggaggacca      180
gctgagccac ctgaagcagt atgaacgcag catcgtggac tacaagccca acctggacct      240
gctggagcag cagcaccagc tcatccagga ggccctcatc ttcgacaaca agcacaccaa      300
ctataccatg gagcacatcc gcgtgggctg ggagcagctg ctcaccacca ttgcccgcac      360
catcaacgag gtggagaacc agatcctcac ccgcgacgcc aagggcatc                  409
```

<210> SEQ ID NO 177
<211> LENGTH: 408
<212> TYPE: DNA
<213> ORGANISM: Homo sapien

<400> SEQUENCE: 177

```
ggcacgaggt ccaggtaact gcaaaaacaa tggctcagca tgaagaactg atgaagaaaa      60
ctgaaacaat gaatgtagtt atggagacca ataaaatgct aagagaagag aaggagcagg     120
tttcaaaaat ggcatcagtc cgtcagcatt tggaagaaac aacacagaaa gcagaatcac     180
agttgttgga gtgtaaagca tcttgggagg aaagagagag aatgttaaag gatgaagttt     240
ccaaatgtgt atgtcgctgt gaagatctgg agaaacaaaa cagattactt catgatcaga     300
tcgaaaaatt aagtgacaag gtcgttgcct ctgtgaagga aggtgtacaa ggtccactga     360
atgtatctct cagtgaagaa ggaaaatctc aagaacaaat tttggaaa                  408
```

<210> SEQ ID NO 178
<211> LENGTH: 92
<212> TYPE: DNA
<213> ORGANISM: Homo sapien

<400> SEQUENCE: 178

```
ggcacgagaa gaaattaaga gctaaagaca aggagaatga aaatatggtt gcaaagctga      60
acaaaaaagt taaagagcta agaggaga tg                                      92
```

<210> SEQ ID NO 179
<211> LENGTH: 411
<212> TYPE: DNA
<213> ORGANISM: Homo sapien

<400> SEQUENCE: 179

```
ggcacgagga gacacgccac ctataccaca gttctcagaa tgaattagct aagttggaat      60
cagaacttaa gagtctcaaa gaccagttga ctgatttaag taactctttta gaaaaatgta    120 aggaacaaaa aggaaacttg gaagggatca taaggcagca agaggctgat attcaaaatt     180
ctaagttcag ttatgaacaa ctggagactg atcttcaggc ctccagagaa ctgaccagta     240
ggctgcatga agaaataaat atgaaagagc aaaagattat aagcctgctt tctggcaagg     300
aagaggcaat ccaagtagct attgctgaac tgcgtcagca acatgataaa gaaattaaag     360
agctggaaaa cctgctgtcc caggaggaag aggagaatat tgttttagaa g              411
```

<210> SEQ ID NO 180
<211> LENGTH: 411
<212> TYPE: DNA
<213> ORGANISM: Homo sapien

<400> SEQUENCE: 180

```
ggcacgaggt tgttcggagc gggcgagcgg agttagcagg gctttactgc agagcgcgcc      60
gggcactcca gcgaccgtgg ggatcagcgt aggtgagctg tggccttttg cgaggtgctg     120
```

| | |
|---|---|
| cagccatagc tacgtgcgtt cgctacgagg attgagcgtc tccacccatc ttctgtgctt | 180 |
| caccatctac ataatgaatc ccagtatgaa gcagaaacaa gaagaaatca aagagaaatat | 240 |
| aaagactagt tctgtcccaa gaagaactct gaagatgatt cagccttctg catctggatc | 300 |
| tcttgttgga agagaaaatg agctgtccgc aggcttgtcc aaaaggaaac atcggaatga | 360 |
| ccacttaaca tctacaactt ccagccctgg ggttattgtc ccagaatcta g | 411 |

<210> SEQ ID NO 181
<211> LENGTH: 411
<212> TYPE: DNA
<213> ORGANISM: Homo sapien

<400> SEQUENCE: 181

| | |
|---|---|
| ggcacgaggc gggacagggc gaagcggcct gcgcccacgg agcgcgcgac actgcccgga | 60 |
| agggaccgcc acccttgccc cctcagctgc ccactcgtga tttccagcgg cctccgcgcg | 120 |
| cgcacgatgc cctcggccac cagccacagc gggagcggca gcaagtcgtc cggaccgcca | 180 |
| ccgccgtcgg gttcctccgg gagtgaggcg gccgcgggag ccggggccgc cgcgccggct | 240 |
| tctcagcacc ccgcaaccgg caccggcgct gtccagaccg aggccatgaa gcagattctc | 300 |
| ggggtgatcg acaagaaact tcggaacctg gagaagaaaa agggtaagct tgatgattac | 360 |
| caggaacgaa tgaacaaagg ggaaaggctt aatcaagatc agctggatgc c | 411 |

<210> SEQ ID NO 182
<211> LENGTH: 411
<212> TYPE: DNA
<213> ORGANISM: Homo sapien

<400> SEQUENCE: 182

| | |
|---|---|
| ggcacgagcc gacatggagc tgttcctcgc gggccgccgg gtgctggtca ccggggcagg | 60 |
| caaaggtata gggcgcggca cggtccaggc gctgcacgcg acgggcgcgc gggtggtggc | 120 |
| tgtgagccgg actcaggcgg atcttgacag ccttgtccgc gagtgcccgg ggatagaacc | 180 |
| cgtgtgcgtg gacctgggtg actgggaggc caccgagcgg gcgctgggca gcgtgggccc | 240 |
| cgtggacctg ctggtgaaca acgccgctgt cgccctgctg cagcccttcc tggaggtcac | 300 |
| caaggaggcc tttgacagat cctttgaggt gaacctgcgt gcggtcatcc aggtgtcgca | 360 |
| gattgtggcc aggggcttaa tagcccgggg agtcccaggg gccatcgtga a | 411 |

<210> SEQ ID NO 183
<211> LENGTH: 409
<212> TYPE: DNA
<213> ORGANISM: Homo sapien

<400> SEQUENCE: 183

| | |
|---|---|
| ggcacgagcc tacactctgg ccagagatac cacagtcaaa cctggagcca aaaggacac | 60 |
| aaaggactct cgacccaaac tgccccagac cctctccaga ggttggggtg accaactcat | 120 |
| ctggactcag acatatgaag aagctctata taaatccaag acaagcaaca aaccccttgat | 180 |
| gattattcat cacttggatg agtgcccaca cagtcaagct ttaaagaaag tgtttgctga | 240 |
| aaataaagaa atccagaaat tggcagagca gtttgtcctc ctcaatctgg tttatgaaac | 300 |
| aactgacaaa caccttttctc ctgatggcca gtatgtcccc aggattatgt tgttgacccc | 360 |
| atctctgaca gttagagccg atatcactgg aagatattca aatcgtctc | 409 |

<210> SEQ ID NO 184

<211> LENGTH: 410
<212> TYPE: DNA
<213> ORGANISM: Homo sapien

<400> SEQUENCE: 184

| | | |
|---|---|---|
| ggcacgaggt cattccagca ccaacaggat ccaagccaga ttgattgggc tgcattggcc | 60 | |
| caagcttgga ttgcccaaag agaagcttca ggacagcaaa gcatggtaga acaaccacca | 120 | |
| ggaatgatgc caaatggaca agatatgtct acaatggaat ctggtccaaa caatcatggg | 180 | |
| aatttccaag gggattcaaa cttcaacaga atgtggcaac cagaatgggg aatgcatcag | 240 | |
| caaccccac accccctcc agatcagcca tggatgccac caacaccagg cccaatggac | 300 | |
| attgttcctc cttctgaaga cagcaacagt caggacagtg gggaatttgc ccctgacaac | 360 | |
| aggcatatat ttaaccagaa caatcacaac tttggtgac cacccgataa | 410 | |

<210> SEQ ID NO 185
<211> LENGTH: 411
<212> TYPE: DNA
<213> ORGANISM: Homo sapien
<220> FEATURE:
<221> NAME/KEY: misc_feature
<222> LOCATION: (1)...(411)
<223> OTHER INFORMATION: n = A,T,C or G

<400> SEQUENCE: 185

| | | |
|---|---|---|
| ggcacgagca cagatgtagt tttctctgcg cgtgtgcgtt ttccctcctc ccccgccctc | 60 | |
| agggtccacg gccaccatgg cgtattaggg gcagcagtgc ctgcggcagc attggccttt | 120 | |
| gcagcggcgg cagcagcacc aggctctgca gcggcaaccc ccagcggctt aagccatggc | 180 | |
| gcttctcacg gcattcagca gcagcgttgc tgtaaccgac aaagacacct tcgaattaag | 240 | |
| cacattcctc gattccagca aagcaccgca acatgaccga atgagcttc ctgagcagcg | 300 | |
| aggtgttggt gggggacttg atgtccccct tcgacccgtc gggtttgggg gctgaagaaa | 360 | |
| gcctangtct cttagatgat tacctggagg tggccaagca cttcaaacct c | 411 | |

<210> SEQ ID NO 186
<211> LENGTH: 410
<212> TYPE: DNA
<213> ORGANISM: Homo sapien

<400> SEQUENCE: 186

| | | |
|---|---|---|
| ggcacgagct tctagtcccg ccatggccgc tctcacccgg gaccccagt tccagaagct | 60 | |
| gcagcaatgg taccgcgagc accgctccga gctgaacctg cgccgcctct tcgatgccaa | 120 | |
| caaggaccgc ttcaaccact tcagcttgac cctcaacacc aaccatgggc atatcctggt | 180 | |
| ggattactcc aagaacctgg tgacggagga cgtgatgcgg atgctggtgg acttggccaa | 240 | |
| gtccagggc gtggaggccg cccggagcg gatgttcaat ggtgagaaga tcaactacac | 300 | |
| cgagggtcga gccgtgctgc acgtggctct gcggaaccgg tcaaacacac ccatcctggt | 360 | |
| agacggcaag gatgtgatgc cagaggtcaa caaggttctg gacaagatga | 410 | |

<210> SEQ ID NO 187
<211> LENGTH: 506
<212> TYPE: DNA
<213> ORGANISM: Homo sapien

<400> SEQUENCE: 187

| | | |
|---|---|---|
| ctttcgtggc tcactccctt tcctctgctg ccgctcggtc acgcttgtgc ccgaaggagg | 60 | |
| aaacagtgac agacctggag actgcagttc tctatccttc acacagctct ttcaccatgc | 120 | |

```
ctggatcact tcctttgaat gcagaagctt gctggccaaa agatgtggga attgttgccc      180
ttgagatcta ttttccttct caatatgttg atcaagcaga gttggaaaaa tatgatggtg      240
tagatgctgg aaagtatacc attggcttgg gccaggccaa gatgggcttc tgcacagata      300
gagaagatat taactctctt tgcatgactg tggttcagaa tcttatggag agaaataacc      360
tttcctatga ttgcattggg cggctggaag ttggaacaga gacaatcatc gacaaatcaa      420
agtctgtgaa gactaattg atgcagctgt ttgaagagtc tgggaataca gatatagaag      480
gaatcgacac aactaatgca tgctat                                           506

<210> SEQ ID NO 188
<211> LENGTH: 506
<212> TYPE: DNA
<213> ORGANISM: Homo sapien

<400> SEQUENCE: 188
gccacagagg cggcggagag atggccttca gcggttccca ggctccctac ctgagtccag       60
ctgtcccctt ttctgggact attcaaggag gtctccagga cggacttcag atcactgtca      120
atgggaccgt tctcagctcc agtggaacca ggtttgctgt gaactttcag actggcttca      180
gtggaaatga cattgccttc cacttcaacc ctcggtttga agatggaggg tacgtggtgt      240
gcaacacgag gcagaacgga agctgggggc ccgaggagag aagacacac atgcctttcc       300 agaaggggat gccctttgac ctctgcttcc tggtgcagag ctcagatttc aaggtgatgg      360
tgaacgggat cctcttcgtg cagtacttcc accgcgtgcc cttccaccgt gtggacacca      420
tctccgtcaa tggctctgtg cagctgtcct acatcagctt ccagcctccc ggcgtgtggc      480
ctgccaaccc ggctcccatt acccag                                           506

<210> SEQ ID NO 189
<211> LENGTH: 399
<212> TYPE: DNA
<213> ORGANISM: Homo sapien

<400> SEQUENCE: 189
ctggacagga gaagagcctg gctgctgaag gcagggctga cacgaccacg ggcagcattg       60
ctggagcccc agaggatgaa agatcgcaga gcacagcccc ccaggcacca gagtgcttcg      120
accctgccgg accggctggg ctcgtgaggc cgacatctgg cctttcccag ggcccaggaa      180
aggaaaccct ggaaagtgct ctaatcgctc tagactctga aaaacccaag aaacttcgct      240
tccacccaaa gcagctgtac ttctctgcca ggcagggtga gctgcagaag gtgcttctca      300
tgctggttga tggaattgat cccaacttca aaatggagca ccaaagtaag cgttccccat      360
tacatgctgc tgcggaggct ggccacgtgg acatctgcc                             399

<210> SEQ ID NO 190
<211> LENGTH: 401
<212> TYPE: DNA
<213> ORGANISM: Homo sapien

<400> SEQUENCE: 190
cggcgacggt ggtggtgact gagcggagcc cggtgacagg atgttggtgt tggtattagg       60
agatctgcac atcccacacc ggtgcaacag tttgccagct aaattcaaaa aactcctggt      120
gccaggaaaa attcagcaca ttctctgcac aggaaacctt tgcaccaaag agagtttatga     180 ctatctcaag actctggctg gtgatgttca tattgtgaga ggagacttcg atgagaatct      240
```

| | |
|---|---|
| gaattatcca gaacagaaag ttgtgactgt tggacagttc aaaattggtc tgatccatgg | 300 |
| acatcaagtt attccatggg gagatatggc cagcttagcc ctgttgcaga ggcaatttga | 360 |
| tgtggacatt cttatctcgg gacacacaca caaatttgaa g | 401 |

<210> SEQ ID NO 191
<211> LENGTH: 406
<212> TYPE: DNA
<213> ORGANISM: Homo sapien

<400> SEQUENCE: 191

| | |
|---|---|
| tggcagccta agccgtggga gggttccagt cgagaatggg aagatgaaag acttcagatg | 60 |
| gaacagaaat aaatgccttt tttgacaaac gcagcagtgc gtgcctctag cttgcaagag | 120 |
| cgttactccc cttcatagct ttaaaaggtt ttcgcactgc gtgcagttag agtagctaaa | 180 |
| tcttgtgtga cgctccacaa acacttgtaa gaattttgca gagaaagata accgttgcca | 240 |
| cccaatgccc cccacaggca ttctactccc cagtacctct tagggtggga gaaatggtga | 300 |
| agagttgttc ctacaacttg ctaacctagt ggacagggta gtagattagc atcatccgga | 360 |
| tagatgtgaa gaggacggct gtttggataa taattaagga taaaat | 406 |

<210> SEQ ID NO 192
<211> LENGTH: 316
<212> TYPE: DNA
<213> ORGANISM: Homo sapien

<400> SEQUENCE: 192

| | |
|---|---|
| ccggggagg ccctggtcat aaaactttaa attttactag tgttacttaa tgtatattct | 60 |
| aaaagagaa tgcagtaact aatgccctaa atgtttgatc tctgtttgtc attactttt | 120 |
| aaaattatt ttttctgta aagtataata tataaaactt cttgcttaaa ttgaatttct | 180 |
| tattagtgg ttaattgcag tttattaaag ggatcattat cagtaatttc atagcaactg | 240 |
| tctagtgtt ttgtgttttt aaaacagaat taggaatttg agatatctga ttatattttt | 300 |
| atatgaatc acagac | 316 |

<210> SEQ ID NO 193
<211> LENGTH: 146
<212> TYPE: DNA
<213> ORGANISM: Homo sapien

<400> SEQUENCE: 193

| | |
|---|---|
| gaaacatgga ctgcccctta aattttgact gtcctaaaaa cctatttctg atttataata | 60 |
| tgctgcctga taaagtgaca ctagatgtac cagctgagtg tttaatcttc ccatcacaga | 120 |
| tcagatttga gcattaacag gtattt | 146 |

<210> SEQ ID NO 194
<211> LENGTH: 405
<212> TYPE: DNA
<213> ORGANISM: Homo sapien

<400> SEQUENCE: 194

| | |
|---|---|
| cggatgtgct cactgacatt ctactccaag tcggagatgc agatccactc caagtcacac | 60 |
| accgagacca agccccacaa gtgcccacat tgctccaaga ccttcgccaa cagctcctac | 120 |
| ctggcccagc acatccgtat acactcaggg gctaagccct acagttgtaa cttctgtgag | 180 |
| aaatccttcc gccagctctc ccaccttcag cagcacaccc gaatccacac tggtgataga | 240 |
| ccatacaaat gtgcacaccc aggctgtgag aaagccttca cacaactctc caatctgcag | 300 |

| | |
|---|---|
| tcccacagac ggcaacacaa caaagataaa cccttcaagt gccacaactg tcatcgggcg | 360 |
| tacacggatg cagcctcact agaggtgcac ctgtctacgc acaca | 405 |

<210> SEQ ID NO 195
<211> LENGTH: 421
<212> TYPE: DNA
<213> ORGANISM: Homo sapien

<400> SEQUENCE: 195

| | |
|---|---|
| agaattcggc acgagctact ccttgcgcgc tggcactccg cagcctttaa ggttcgcgcg | 60 |
| ggggccaggc aagagttagc catgaagagc ctcaagtccc gcctgaggag gcaggacgtg | 120 |
| cccggccccg cgtcgtctgg cgccgccgcc gccagcgcgc atgcagcaga ttggaataaa | 180 |
| tatgatgacc gattgatgaa agcagcagaa agggggatg tagaaaaagt gacgtcaatc | 240 |
| cttgctaaaa aggggtcaa tccaggcaaa ctagatgtgg aaggcagatc tgtcttccat | 300 |
| gttgtgacct caaaggggaa tcttgagtgt ttgaatgcca tccttataca tggagttgat | 360 |
| attacaacca gtgacactgc aggagaaat gctcttcacc tggctgctaa gtatggacat | 420 |
| g | 421 |

<210> SEQ ID NO 196
<211> LENGTH: 476
<212> TYPE: DNA
<213> ORGANISM: Homo sapien

<400> SEQUENCE: 196

| | |
|---|---|
| agaattgatc tatagattta atgcaatgcc tactaaaatc ccagtacgat tttttacagg | 60 |
| catagacaat agacatagcc aaaacttatt ctaaaataca tatgaagatg cacaggccct | 120 |
| agttatacaa tcttgacaaa gaagaataaa gtgggaagaa tctatttgat tttaaggctt | 180 |
| accatgtaac tacagtcatc aagagagtgt ggtatcggca gacggtcaga catacagatc | 240 |
| aatggaatgt aacagaggac ccagaaatag gcccacacag atatgctcaa tggatatttg | 300 |
| acaagcgtgc aaaacaattc aatggaagaa taagctttca aaaaaatggc gttggagcaa | 360 |
| ccggacatcc ataggaaaaa atgaacccat acctaaacca taaaccttat ataaaaataa | 420 |
| acacaaaatg aatcataggc ttaaatgtaa gctataaaac ttttagagaa aaacac | 476 |

<210> SEQ ID NO 197
<211> LENGTH: 503
<212> TYPE: DNA
<213> ORGANISM: Homo sapien

<400> SEQUENCE: 197

| | |
|---|---|
| tagccctcgg tgaagcccca gaccacagct atgagtccct tcgtgtgacg tctgcgcaga | 60 |
| aacatgttct gcatgtccag ctcaaccggc ccaacaagag gaatgccatg aacaaggtct | 120 |
| tctggagaga gatggtagag tgcttcaaca gatttcgag agacgctgac tgtcgggcgg | 180 |
| tggtgatctc tggtgcagga aaaatgttca ctgcaggtat tgacctgatg gacatggctt | 240 |
| cggacatcct gcagcccaaa ggagatgatg tggcccggat cagctggtac ctccgtgaca | 300 |
| tcatcactcg ataccaggag accttcaacg tcatcgagag gtgccccaag ccgtgattg | 360 |
| ctgccgtcca tgggggctgc attggcggag gtgtggacct tgtcaccgcc tgtgacatcc | 420 |
| ggtactgtgc ccaggatgct ttcttccagg tgaaggaggt ggacgtgggt ttggctgccc | 480 |
| atgtaggaac actgcagcgc ctg | 503 |

<210> SEQ ID NO 198
<211> LENGTH: 168
<212> TYPE: PRT
<213> ORGANISM: Homo sapien

<400> SEQUENCE: 198

Phe Val Ala His Ser Leu Ser Ser Ala Ala Arg Ser Arg Leu Cys
1               5                   10                  15

Pro Lys Glu Glu Thr Val Thr Asp Leu Glu Thr Ala Val Leu Tyr Pro
            20                  25                  30

Ser His Ser Ser Phe Thr Met Pro Gly Ser Leu Pro Leu Asn Ala Glu
        35                  40                  45

Ala Cys Trp Pro Lys Asp Val Gly Ile Val Ala Leu Glu Ile Tyr Phe
50                  55                  60

Pro Ser Gln Tyr Val Asp Gln Ala Glu Leu Glu Lys Tyr Asp Gly Val
65                  70                  75                  80

Asp Ala Gly Lys Tyr Thr Ile Gly Leu Gly Gln Ala Lys Met Gly Phe
                85                  90                  95

Cys Thr Asp Arg Glu Asp Ile Asn Ser Leu Cys Met Thr Val Val Gln
            100                 105                 110

Asn Leu Met Glu Arg Asn Asn Leu Ser Tyr Asp Cys Ile Gly Arg Leu
        115                 120                 125

Glu Val Gly Thr Glu Thr Ile Ile Asp Lys Ser Lys Ser Val Lys Thr
130                 135                 140

Asn Leu Met Gln Leu Phe Glu Glu Ser Gly Asn Thr Asp Ile Glu Gly
145                 150                 155                 160

Ile Asp Thr Thr Asn Ala Cys Tyr
                165

<210> SEQ ID NO 199
<211> LENGTH: 168
<212> TYPE: PRT
<213> ORGANISM: Homo sapien

<400> SEQUENCE: 199

His Arg Gly Gly Gly Glu Met Ala Phe Ser Gly Ser Gln Ala Pro Tyr
1               5                   10                  15

Leu Ser Pro Ala Val Pro Phe Ser Gly Thr Ile Gln Gly Gly Leu Gln
            20                  25                  30

Asp Gly Leu Gln Ile Thr Val Asn Gly Thr Val Leu Ser Ser Ser Gly
        35                  40                  45

Thr Arg Phe Ala Val Asn Phe Gln Thr Gly Phe Ser Gly Asn Asp Ile
50                  55                  60

Ala Phe His Phe Asn Pro Arg Phe Glu Asp Gly Gly Tyr Val Val Cys
65                  70                  75                  80

Asn Thr Arg Gln Asn Gly Ser Trp Gly Pro Glu Glu Arg Lys Thr His
            85                  90                  95

Met Pro Phe Gln Lys Gly Met Pro Phe Asp Leu Cys Phe Leu Val Gln
            100                 105                 110

Ser Ser Asp Phe Lys Val Met Val Asn Gly Ile Leu Phe Val Gln Tyr
        115                 120                 125

Phe His Arg Val Pro Phe His Arg Val Asp Thr Ile Ser Val Asn Gly
        130                 135                 140

Ser Val Gln Leu Ser Tyr Ile Ser Phe Gln Pro Pro Gly Val Trp Pro
145                 150                 155                 160

```
Ala Asn Pro Ala Pro Ile Thr Gln
            165
```

<210> SEQ ID NO 200
<211> LENGTH: 132
<212> TYPE: PRT
<213> ORGANISM: Homo sapien

<400> SEQUENCE: 200

```
Gly Gln Glu Lys Ser Leu Ala Ala Glu Gly Arg Ala Asp Thr Thr Thr
 1               5                  10                  15

Gly Ser Ile Ala Gly Ala Pro Glu Asp Glu Arg Ser Gln Ser Thr Ala
             20                  25                  30

Pro Gln Ala Pro Glu Cys Phe Asp Pro Ala Gly Pro Ala Gly Leu Val
         35                  40                  45

Arg Pro Thr Ser Gly Leu Ser Gln Gly Pro Gly Lys Glu Thr Leu Glu
     50                  55                  60

Ser Ala Leu Ile Ala Leu Asp Ser Glu Lys Pro Lys Lys Leu Arg Phe
65                  70                  75                  80

His Pro Lys Gln Leu Tyr Phe Ser Ala Arg Gln Gly Glu Leu Gln Lys
                 85                  90                  95

Val Leu Leu Met Leu Val Asp Gly Ile Asp Pro Asn Phe Lys Met Glu
            100                 105                 110

His Gln Ser Lys Arg Ser Pro Leu His Ala Ala Ala Glu Ala Gly His
        115                 120                 125

Val Asp Ile Cys
    130
```

<210> SEQ ID NO 201
<211> LENGTH: 120
<212> TYPE: PRT
<213> ORGANISM: Homo sapien

<400> SEQUENCE: 201

```
Met Leu Val Leu Val Leu Gly Asp Leu His Ile Pro His Arg Cys Asn
 1               5                  10                  15

Ser Leu Pro Ala Lys Phe Lys Lys Leu Leu Val Pro Gly Lys Ile Gln
             20                  25                  30

His Ile Leu Cys Thr Gly Asn Leu Cys Thr Lys Glu Ser Tyr Asp Tyr
         35                  40                  45

Leu Lys Thr Leu Ala Gly Asp Val His Ile Val Arg Gly Asp Phe Asp
     50                  55                  60

Glu Asn Leu Asn Tyr Pro Glu Gln Lys Val Val Thr Val Gly Gln Phe
65                  70                  75                  80

Lys Ile Gly Leu Ile His Gly His Gln Val Ile Pro Trp Gly Asp Met
                 85                  90                  95

Ala Ser Leu Ala Leu Leu Gln Arg Gln Phe Asp Val Asp Ile Leu Ile
            100                 105                 110

Ser Gly His Thr His Lys Phe Glu
        115                 120
```

<210> SEQ ID NO 202
<211> LENGTH: 135
<212> TYPE: PRT
<213> ORGANISM: Homo sapien

<400> SEQUENCE: 202

```
Arg Met Cys Ser Leu Thr Phe Tyr Ser Lys Ser Glu Met Gln Ile His
```

```
                1               5                  10                 15
        Ser Lys Ser His Thr Glu Thr Lys Pro His Lys Cys Pro His Cys Ser
                        20                  25                  30
        Lys Thr Phe Ala Asn Ser Ser Tyr Leu Ala Gln His Ile Arg Ile His
                        35                  40                  45
        Ser Gly Ala Lys Pro Tyr Ser Cys Asn Phe Cys Glu Lys Ser Phe Arg
         50                      55                  60
        Gln Leu Ser His Leu Gln Gln His Thr Arg Ile His Thr Gly Asp Arg
         65                  70                  75                  80
        Pro Tyr Lys Cys Ala His Pro Gly Cys Glu Lys Ala Phe Thr Gln Leu
                        85                  90                  95
        Ser Asn Leu Gln Ser His Arg Arg Gln His Asn Lys Asp Lys Pro Phe
                        100                 105                 110
        Lys Cys His Asn Cys His Arg Ala Tyr Thr Asp Ala Ala Ser Leu Glu
                        115                 120                 125
        Val His Leu Ser Thr His Thr
                        130                 135

<210> SEQ ID NO 203
<211> LENGTH: 135
<212> TYPE: PRT
<213> ORGANISM: Homo sapien

<400> SEQUENCE: 203

Leu Leu Leu Ala Arg Trp His Ser Ala Ala Phe Lys Val Arg Ala Gly
         1               5                  10                 15
        Ala Arg Gln Glu Leu Ala Met Lys Ser Leu Lys Ser Arg Leu Arg Arg
                        20                  25                  30
        Gln Asp Val Pro Gly Pro Ala Ser Ser Gly Ala Ala Ala Ala Ser Ala
                        35                  40                  45
        His Ala Ala Asp Trp Asn Lys Tyr Asp Asp Arg Leu Met Lys Ala Ala
                        50                  55                  60
        Glu Arg Gly Asp Val Glu Lys Val Thr Ser Ile Leu Ala Lys Lys Gly
         65                  70                  75                  80
        Val Asn Pro Gly Lys Leu Asp Val Glu Gly Arg Ser Val Phe His Val
                        85                  90                  95
        Val Thr Ser Lys Gly Asn Leu Glu Cys Leu Asn Ala Ile Leu Ile His
                        100                 105                 110
        Gly Val Asp Ile Thr Thr Ser Asp Thr Ala Gly Arg Asn Ala Leu His
                        115                 120                 125
        Leu Ala Ala Lys Tyr Gly His
                        130                 135

<210> SEQ ID NO 204
<211> LENGTH: 167
<212> TYPE: PRT
<213> ORGANISM: Homo sapien

<400> SEQUENCE: 204

Ala Leu Gly Glu Ala Pro Asp His Ser Tyr Glu Ser Leu Arg Val Thr
         1               5                  10                 15
        Ser Ala Gln Lys His Val Leu His Val Gln Leu Asn Arg Pro Asn Lys
                        20                  25                  30
        Arg Asn Ala Met Asn Lys Val Phe Trp Arg Glu Met Val Glu Cys Phe
                        35                  40                  45
        Asn Lys Ile Ser Arg Asp Ala Asp Cys Arg Ala Val Val Ile Ser Gly
```

```
                  50                  55                  60
Ala Gly Lys Met Phe Thr Ala Gly Ile Asp Leu Met Asp Met Ala Ser
 65                  70                  75                  80

Asp Ile Leu Gln Pro Lys Gly Asp Asp Val Ala Arg Ile Ser Trp Tyr
                 85                  90                  95

Leu Arg Asp Ile Ile Thr Arg Tyr Gln Glu Thr Phe Asn Val Ile Glu
                100                 105                 110

Arg Cys Pro Lys Pro Val Ile Ala Ala Val His Gly Cys Ile Gly
            115                 120                 125

Gly Gly Val Asp Leu Val Thr Ala Cys Asp Ile Arg Tyr Cys Ala Gln
        130                 135                 140

Asp Ala Phe Phe Gln Val Lys Glu Val Asp Val Gly Leu Ala Ala His
145                 150                 155                 160

Val Gly Thr Leu Gln Arg Leu
                165

<210> SEQ ID NO 205
<211> LENGTH: 381
<212> TYPE: DNA
<213> ORGANISM: Homo sapien

<400> SEQUENCE: 205
aaatttggga tcatcgcctg ttctgaaaac tagatgcacc aaccgtatca ttatttgttt    60
gaggaaaaaa agaaatctgc attttaattc atgttggtca aagtcgaatt actatctatt   120
tatcttatat cgtagatctg ataaccctat ctaaaagaaa gtcacacgct aaatgtattc   180
ttacatagtg cttgtatcgt tgcatttgtt ttaatttgtg gaaagtatt gtatctaact    240
tgtattactt tggtagtttc atctttatgt attattgata tttgtaattt tctcaactat   300
aacaatgtag ttacgctaca acttgcctaa acattcaaa cttgttttct tttttctgtt    360
gttttctttg ttaattcatt t                                             381

<210> SEQ ID NO 206
<211> LENGTH: 514
<212> TYPE: DNA
<213> ORGANISM: Homo sapien

<400> SEQUENCE: 206
aaaagtaaat tgcataaaat tacatccaat ttctttctct aaaccaacat attcttcacc    60
ttcacaaagc aaacacatgg tgcactgaaa ccgaggtgtt accagcttta catactgttc   120
tgccatttgt gggggtgca accacaacat aagtcagaaa aaaagctatc cagcttttcg    180
tggaatctgg tgaagtttac acttagcgat aagcctctaa gcctgaactt agcagggcta   240
gcaaaacttt atttatttcc taactcctat tattttagaa tggttttcaa ataatactg    300
caagttccta attgaaatac aaaacagaac aaaaagctgt gagaaatctt tttttttctt   360
tggctcctta aagacttgga ataatttata ttagtgttgc atacatttta ccttctacat   420
tttgatgtac ttgctcttga aagcactaga acaaattaat tgaaataaaa cctctctgaa   480
accatttgaa tctttgatcc taccatagag tttt                                514

<210> SEQ ID NO 207
<211> LENGTH: 522
<212> TYPE: DNA
<213> ORGANISM: Homo sapien
<220> FEATURE:
<221> NAME/KEY: misc_feature
<222> LOCATION: (1)...(522)
```

<223> OTHER INFORMATION: n = A,T,C or G

<400> SEQUENCE: 207

```
caagcttttg gtgcatagca gccngcctgg aagcattctg agtgctctgt ctgccctggt      60
gggtttcatt atcctgtctg tcaaacaggc caccttaaat cctgcctcac tgcagtgtga    120
gttggacaaa aataatatac caacaagaag ttatgtttct tacttttatc atgattcact    180
ttataccacg gactgctata cagccaaagc cagtctggct ggaactctct ctctgatgct    240
gatttgcact ctgctggaat tctgcctagc tgtgctcact gctgtgctgc ggtggaaaca    300
ggcttactct gacttccctg ggagtgtact tttcctgcct cacagttaca ttggtaattc    360
tggcatgtcc tcaaaaatga ctcatgactg tggatatgaa gaactattga cttcttaaga    420
aaaaagggag aaatattaat cagaaagttg attcttatga taatatggaa aagttaacca    480
ttatagaaaa gcaaagcttg agtttcctaa atgtaagctt tt                       522
```

<210> SEQ ID NO 208
<211> LENGTH: 278
<212> TYPE: DNA
<213> ORGANISM: Homo sapien

<400> SEQUENCE: 208

```
aaatgcact accccttttt tccaacacgg agcttaaaac aaattaatga aagagtggaa       60
attcaaaat aagggcaaga gataaggttt tttttttttt tcctttaaga tagactcagg      120
taggtagat agctttcact gatgtagatg tggaataaat tattacttca ggaaaaaaat      180
cccaaacat cttatgaaaa agtatacaac tctacttcaa aatatgctat ttactcactg      240
caaagacag ttttatttga aatcttgttt ctgtattt                              278
```

<210> SEQ ID NO 209
<211> LENGTH: 234
<212> TYPE: DNA
<213> ORGANISM: Homo sapien
<220> FEATURE:
<221> NAME/KEY: misc_feature
<222> LOCATION: (1)...(234)
<223> OTHER INFORMATION: n = A,T,C or G

<400> SEQUENCE: 209

```
cctcccaaat ttagcaggtg ctgggnagga ccctagggag tggtttatgg gggctagctg      60
gtgaaactgc cctttccttt ctgttctatg agtgtgatgg tgtttgagaa aatgtggggc    120
tatggttcag gcgcacttca catgtgcaaa gatggagaaa gcactcacct acacgtttag    180
gctcagaatg ttgattgaaa cattttgaat gatcaaaaat aaaatgttat tttt          234
```

<210> SEQ ID NO 210
<211> LENGTH: 186
<212> TYPE: DNA
<213> ORGANISM: Homo sapien
<220> FEATURE:
<221> NAME/KEY: misc_feature
<222> LOCATION: (1)...(186)
<223> OTHER INFORMATION: n = A,T,C or G

<400> SEQUENCE: 210

```
aaaataactg atggcaaaat aaaanattta catcacatca tactgtgtaa acatgtaagg      60
tctctgtaca aagaaatata catgcaaaat aatgtaaaaa tttaactgaa ataataaaag    120
aaacaataca caaataaaaa ttatgaggtt acgaatacac atccagtttc gaatccaatt    180
tctttt                                                               186
```

<210> SEQ ID NO 211
<211> LENGTH: 403
<212> TYPE: DNA
<213> ORGANISM: Homo sapien

<400> SEQUENCE: 211

| | | | | | |
|---|---|---|---|---|---|
| aaaaattggt | aaaatattta | agtacaaaat | aagtagcttc | cagcgaggtt | tttataccat | 60 |
| agtaagagca | cacaatagat | attactagca | cacatgggtt | atctgggagc | gctatagcta | 120 |
| caataaacct | aattatggaa | cagaaatttg | cattctgttt | ccagtgctac | tacactccta | 180 |
| ctttctcaaa | agtctgctct | attaatatca | gctcagtgca | gtttactatg | aatagtttat | 240 |
| gtctgtgatg | caaagcatta | attgttctct | ttttacaaac | atacattttt | ttcataagga | 300 |
| agactgggggg | aaaacccaga | aacatacaga | gaaaaggaaa | gcatcatcaa | atatatgtta | 360 |
| aaaattaaga | tgatgtttac | tactagtcat | cctacaacaa | ttt | | 403 |

<210> SEQ ID NO 212
<211> LENGTH: 345
<212> TYPE: DNA
<213> ORGANISM: Homo sapien

<400> SEQUENCE: 212

| | | | | | |
|---|---|---|---|---|---|
| ctctttatg | agttcattac | tgctgttcag | tctcggcaca | cagacacccc | tgtgcaccgg | 60 |
| gtgtacttt | ctactctgat | cgctgggcct | gtggttgaga | taagtcacca | gctacggaag | 120 |
| tttctgacg | tagaagagct | taccccctcca | gagcatcttt | ctgatcttcc | accatttttca | 180 |
| ggtgtttaa | taggaataat | aataaagtct | tcgaatgtgg | tcaggtcatt | tttggatgaa | 240 |
| taaaggcat | gtgtggcttc | taatgatatt | gaaggcattg | tgtgcctcac | ggctgctgtg | 300 |
| atattatcc | tggttattaa | tgcaggtaaa | cataaaagct | caaaa | | 345 |

<210> SEQ ID NO 213
<211> LENGTH: 318
<212> TYPE: DNA
<213> ORGANISM: Homo sapien

<400> SEQUENCE: 213

| | | | | | |
|---|---|---|---|---|---|
| aaatgtttt | attattttga | aaataatgtt | gtaattcatg | ccagggactg | acaaaagact | 60 |
| gagacagga | tggttattct | tgtcagctaa | ggtcacattg | tgccttttttg | acctttttctt | 120 |
| ctggactat | tgaaatcaag | cttattggat | taagtgatat | ttctatagcg | attgaaaggg | 180 |
| aatagttaa | agtaatgagc | atgatgagag | tttctgttaa | tcatgtatta | aaactgattt | 240 |
| tagctttac | aaatatgtca | gtttgcagtt | atgcagaatc | caaagtaaat | gtcctgctag | 300 |
| tagttaagg | attgttttt | | | | | 318 |

<210> SEQ ID NO 214
<211> LENGTH: 462
<212> TYPE: DNA
<213> ORGANISM: Homo sapien

<400> SEQUENCE: 214

| | | | | | |
|---|---|---|---|---|---|
| aaacacatct | ggttctggca | gcaagttata | ttatgcattt | agagcaatag | gtgccctgaa | 60 |
| agttattgtt | gcttttttttg | tttttttttt | cagtttgtgc | gtgtcacttg | aatcagaaac | 120 |
| caaacacatg | taaaaaaata | tcatcctcaa | tgcccccccat | taactctctc | tccagaaggt | 180 |
| gacaatgtta | gtgaactcaa | gactctcact | gatgatggta | ttttacaatg | aaaacacaag | 240 |

```
gaaacccttt gaggtccaat tttcacatca tattctccaa atagtaaaat agcagctcta      300
catgttgatg aaaagaaatt tcaatttctt cctatttgtt tttactcata tcaacattaa      360
tatgtatctg gatttattaa tttccaaaaa gaaaatttta gttaccaaat atttcagaaa      420
tttaataaag cattatatat atgtaattag cacttatcta cc                        462
```

<210> SEQ ID NO 215
<211> LENGTH: 280
<212> TYPE: DNA
<213> ORGANISM: Homo sapien

<400> SEQUENCE: 215

```
aactttttct gaaacgatta gctgtagcca aattatgtgg ttacgttttg ctacattaga       60 tttgaaaat gcaatatgtg tggtaaatct actgtttgaa atttataatg gtctctgata      120 gattcgaat tttggtaact tttgaaagtt attttccccc tttagtcatg gatttctatt      180 gttttttaa tgttaatttt tctagaaagc atctgaattg actaggcttt tcctatataa      240 aaactcaaa acttgttaac tctgtacttt aataaaattt                            280
```

<210> SEQ ID NO 216
<211> LENGTH: 210
<212> TYPE: DNA
<213> ORGANISM: Homo sapien

<400> SEQUENCE: 216

```
aaaatctctg gcttcaaagt ttcttgggga aaggtcggtt tacctcacat tttttgtttc       60
cattagtaat attctaggta cctcacaaaa tgtattatgg tgccatggct gttagttttt      120
agtgagtgct gtaggattaa ttcgaaaata ggcagaattc cattcctccc aaggtggcaa      180
aaattagcta tactgatgta attgtcattt                                      210
```

<210> SEQ ID NO 217
<211> LENGTH: 398
<212> TYPE: DNA
<213> ORGANISM: Homo sapien

<400> SEQUENCE: 217

```
ctggagctgc tagaacttga gatgagggca agagcgatta aagccctaat gaaagctggt       60
gatataaaaa agccagccta ggtatttaac ttgattttga attttaggta tgtttgaaca      120
aagccacatc atttaatttt gtatctaaaa tttatttggg gtcttatatg ttatttctca      180
tgtaaccctt attaggactc attttagccc taaattacct gtggctgttt cttttttattt      240 ttttgactac ttttatatta taaatgtgtg ttactgtctt atgaattcat ggcaatatag      300
ttggatagcc tggatacttt gttagatgag tatttagctg tgtctgcaaa tcttaaaagc      360
cattagcaaa gagtcgtggt attttttttct ttattttt                            398
```

<210> SEQ ID NO 218
<211> LENGTH: 487
<212> TYPE: DNA
<213> ORGANISM: Homo sapien

<400> SEQUENCE: 218

```
ctgccgccgg tcaggctggt taaagatcag gtcccccagg accttgcgat ttatgtcgcc       60
attctccagc aagacctcag tgccgaagac ctctacgatg cgccggtggg cagggtatcc      120
tggctgcacg acgtgccggg ccatcacgtc cacgtcaatc accgcacagc ccagtttcag      180
```

-continued

```
tgtttttaca cattatattg ttataatctc acaataacta taaattaggt agaacaggaa    240
atgaggtttg gagaagatac ttgacttatc cgaccatctg tacttgtccc atagtaagga    300
gcctcaagca gagacaaagg aggaagttgc ctatgttgta tggtttacag gccataaatg    360
aatgtcatct ttttcctccc ctggggaaaa atgtctcaaa atcccacca taggacatga    420 catctccaga acctctatta caaaatacac atttcctgta gagggtaac aaatttgggt    480 taacctg                                                             487
```

<210> SEQ ID NO 219
<211> LENGTH: 390
<212> TYPE: DNA
<213> ORGANISM: Homo sapien

<400> SEQUENCE: 219

```
aaaaaataca ccacacgata caactcaata caggagtatt tcttctcaaa ttcttctagc     60
accatcaaca ttcttcaagt atctgaaata ctattaatta gcacctttgt attatgaaca    120
aaacaaaaca aggacctcag ttcatctctg tctaggtcag cacctaacaa tgtggatcac    180
actcatggga aagtgttttg aggtagttta aacctttgga agtttgggtt ttaaacttcc    240
ctctgtggaa gatattcaaa agccacaagt ggtgcaaatg tttatggttt ttatttttca    300 attttttattt tggttttctt acaaaggttg acatttttcca taacaggtgt aagagtgttg    360
aaaaaaaagt tcaaatttttt gggggagcgg                                    390
```

<210> SEQ ID NO 220
<211> LENGTH: 341
<212> TYPE: DNA
<213> ORGANISM: Homo sapien
<220> FEATURE:
<221> NAME/KEY: misc_feature
<222> LOCATION: (1)...(341)
<223> OTHER INFORMATION: n = A,T,C or G

<400> SEQUENCE: 220

```
aaacaggca aagttttaca gagaggatac atttaataaa actgcgagga catcaaagtg     60 taaatactg tgaaataccct tttctnnnca aaaggcaaat attgaagttg tttatcaact    120 cgctagaaa aaaaaaaaca cttggcatac aaaatattta agtgaaggag aagtctaacg    180 tgaactnnn aatgaaggga aattgtttat gtgttatgaa catccaagtc tttcttcttt    240 ttaagttgt caagaagct tccacaaaat tagaaaggac aacagttctg agctgtaatt    300 cgccttaaa ctctggacac tctatatgta gtgcattttt a                        341
```

<210> SEQ ID NO 221
<211> LENGTH: 234
<212> TYPE: DNA
<213> ORGANISM: Homo sapien

<400> SEQUENCE: 221

```
ccagggggaa ttgagggagg ctctaagcta ggggcactgc atggtgggac aggatggccc     60
cttgaggact gaaccctggg gagaagacaa acagtaataa taaaaacaaa taacaagtac    120
tttaagaatg gattgtatga cctatagtga cagatgacat cactaatact gaaagcttct    180
tatattaata attttggcaa aatgtcattt tgtaatatag tatatgcttt ccag          234
```

<210> SEQ ID NO 222
<211> LENGTH: 186
<212> TYPE: DNA
<213> ORGANISM: Homo sapien -continued

<400> SEQUENCE: 222

```
aaattttcat tgagttgtcc atctccagca tatagggctt caggagcaga gcagaccttg      60
tttttagtgg ttccatggga taaaatggga ttggaggagc tagaagaatt cagggtctgg     120
tccaatctgc cagtcttcct gaaatatcga aaatacacca gggctgctat atcagagcca    180
ccctgg                                                                186
```

<210> SEQ ID NO 223
<211> LENGTH: 486
<212> TYPE: DNA
<213> ORGANISM: Homo sapien

<400> SEQUENCE: 223

```
ccataagcag ataagtagca gttcaactgg atgtctctct tctccaaatg ctacagtaca      60
aagccctaag catgagtgga aaatcgttgc ttcagaaaag acttcaaata acacttactt    120
gtgcctggct gtgctggatg gtatattctg tgtcattttt cttcatggga gaaacagccc    180
acagagctca ccaacaagta ctccaaaact aagtaagagt ttaagctttg agatgcaaca    240
agatgagcta atcgaaaagc ccatgtctcc tatgcagtac gcacgatctg gtctgggaac    300
agcagagatg aatggcaaac tcatagctgc aggtggctat aacagagagg aatgtcttcg    360
aacagtcgaa tgctataatc cacatacaga tcactggtcc tttcttgctc ccatgagaac    420
accaagagcc cgatttcaaa tggctgtact catgggccag ctctatgtgg taggtggatc    480
aaatgg                                                                486
```

<210> SEQ ID NO 224
<211> LENGTH: 322
<212> TYPE: DNA
<213> ORGANISM: Homo sapien

<400> SEQUENCE: 224

```
aatgttcac tatgtcattt agtgtccaac tttacggata ggttgactat ctaaataggc       60
tttttagtc attaaaaaaa aatctagtca ccaggaggat ccctataact caaaataact      120
gtttgtaaa agaaaatttg tttacttacc cattagtaag ttcctgcata ttcattataa     180
atggcaaat caaacttttc taggatgaag acagcttatt tttaagttgt atagtcttag     240
tggtttagg gtctcaattt taattaataa aatacttggt ttttatttgc ttgtccttttt    300
aattcctgt tttaataatt tt                                               322
```

<210> SEQ ID NO 225
<211> LENGTH: 489
<212> TYPE: DNA
<213> ORGANISM: Homo sapien

<400> SEQUENCE: 225

```
aaatgtagga ataaaatggc tggcatctaa gcactttagt aaaagaggtt tttacaaata     60
actaaggatt gtagagcttc cttctctttt tttttctttt tctttctttt gttttacatg    120
aactcaactt attcctaaca tttgtctacc tcaaagaaat ttcaagatta tttagataac    180
atggatatgt gccaaatcct ttgagctgtt aagatgataa tttcctgctt tcctcctaca    240
tcttctcctc ccactccctc ctttggtgtg aatattggct tcccaattaa gacctttttt    300
ttttttttcc agtttgtttt agcttattat aggttttgga ggaactttgc cattttgtaa    360
tctttcaaat cattcttcac ccttcctcac atcagcttcc tgcttttccc agtgttttac    420
```

-continued

| tgtaaattgt gtagcatatg acaaatcttg agctgacttt cctcttcact gatgtcatct | 480 |
| tgagctctt | 489 |

<210> SEQ ID NO 226
<211> LENGTH: 398
<212> TYPE: DNA
<213> ORGANISM: Homo sapien

<400> SEQUENCE: 226

| caagggccca ccgcagagca cacctatgct atggggagcc ctgctggcag ccccgagagc | 60 |
| catgccatgg cctgcaggag ccaggctcct gtgtggatga agtccctctt cctctgtgcc | 120 |
| ttgatccctt gggggtgcct ttggtcatct cttctgtcct ttcctgtctc tgaaatagtc | 180 |
| atcactcccc ttgactctct ctgttcacgt cttctcagtc tgcagagtta acttctgtaa | 240 |
| ggagtttaat ctggggttcc aagaaaacaa gttccttgtt aacatagcac tgactttgca | 300 |
| acaatagaaa actaacaaat gagcaacaat ataaagagta gaggtagttc tcattgggtg | 360 |
| taacttcaac ccattctgct tgtggttaga atttataa | 398 |

<210> SEQ ID NO 227
<211> LENGTH: 535
<212> TYPE: DNA
<213> ORGANISM: Homo sapien

<400> SEQUENCE: 227

| ctgctgcata gaaatatgc taacatacaa cagtcaagtt taagcctgtg catagagaag | 60 |
| ataaagcact tatggtaact gcaaatggta acgagtcctt aaggtttgta caacctagta | 120 |
| tgggtccata aggaaaaact gtagtagaaa tggttaggac aaacaataaa gtagaaacag | 180 |
| gggggaaact tgagaagaga agaaagaagc aagaaaaaaa gactttcaat tgtataaaat | 240 |
| tcacaaacca gtaaagtata aagacaccat ggagaaatgg ttaactctgc cccaaacacc | 300 |
| caacagcaaa caaaaccaga atgaataagc ctttggcaga caattttaga aatttgaatg | 360 |
| ttacatttct caataattca caaacaatat attatatggt atatttatat taatattgg | 420 |
| gaaaccaatg ttgtaaattt gatgcttata atgctttagc caatgagagc acaatgatat | 480 |
| caatcaagct aaatgaatgc tggtgttatc acaacagtgc tcatttatga aacaa | 535 |

<210> SEQ ID NO 228
<211> LENGTH: 301
<212> TYPE: DNA
<213> ORGANISM: Homo sapien

<400> SEQUENCE: 228

| aaacaataaa caccatcaac cttattgact ttattgtccc ttaaattata ttgactgttg | 60 |
| tgattccatc aagtttgtac actcttttct ctccctgttt tgcagcaaca aattgcgaag | 120 |
| tgcttttgtt tgtttgtttt cgtttggtta aagcttattg ccatgctggt gcggctatgg | 180 |
| agactgtctg gaaggcttgg aatggtttat tgcttatggt aaaatttgcc tgatttctta | 240 |
| caggcagcgt ttggaaacct tttattatat agttgtttac atacttataa gtctatcatt | 300 |
| t | 301 |

<210> SEQ ID NO 229
<211> LENGTH: 420
<212> TYPE: DNA
<213> ORGANISM: Homo sapien

<400> SEQUENCE: 229

```
aaagttgctt tgctggaagt ttttataagg aatctcagat taaacccttta gaagtttaat      60 tgacactagg aagccaaacc aaggctgact tcagactttg tttgtagtac ctgtgggttt     120
attacctatg ggtttatatc ctcaaatacg acattctagt caaagtcttg gtaatataac     180
caatgttttc aaatgtattc tgtcatacaa agagcagatt tttattgaac ttgtgcaata     240
actatattac catacaatat aaatattcat gaatagtttc ccaagtctgg agcgaccaca     300
tagggagaaa atgcaaatgt ctcaattttt gttcacaaaa gtatatttta tcaaattgct     360
gtaagctgtg gatagcttaa aagaaaaaaa gtttcctgaa atctgggaaa caagacattt     420
```

<210> SEQ ID NO 230
<211> LENGTH: 419
<212> TYPE: DNA
<213> ORGANISM: Homo sapien

<400> SEQUENCE: 230

```
gtgaagtcct aaagcttgca ttccaccagc ttctacaata gccggcttat tactagagca      60
gacagatagc accttcagca ctctgcttgt ggtccacagt agttttttcgt aagtataggt     120 cctcattata tttactaaag cttggggtcc accactagcc agtatgatga gcttgctttc     180
ttggttgcca taagctaaaa tttgaaggca gtctgtcgta atagccaaga atttaacatt     240
tgttttgttg agcaaggcaa ccatttctg cagcccacca gctaaacgca ctgccatttt     300
agctccttct tgatgtaata aaaggttgtg gagagttgta atggcataaa acaacacaga     360
atccactggt gaaccaagca ttttcaccag ggcaggaatg cctccagact taaagatgg      419
```

<210> SEQ ID NO 231
<211> LENGTH: 389
<212> TYPE: DNA
<213> ORGANISM: Homo sapien

<400> SEQUENCE: 231

```
ttgttcagag ccctggtgga tcttgcaatc cagtgcccta caaaggctag aacactacag      60
gggatgaatt cttcaaatag gagccgatgg atctgtggtc ctttgggact catcaaagcc     120
ttggtttagc attttgtcag ttttatcttc agaaattctc tgcgattaag aagataattt     180
attaaaggtg gtccttccta cctctgtggt gtgtgtcgcg cacacagctt agaagtgcta     240
taaaaaagga aagagctcca aattgaatca cctttataat ttacccatttt ctatacaaca     300 ggcagtggaa gcagtttcag agaacttttt gcatgcttat ggttgatcag ttaaaaaaga     360
atgttacagt aacaaataaa gtgcagttt                                       389
```

<210> SEQ ID NO 232
<211> LENGTH: 397
<212> TYPE: DNA
<213> ORGANISM: Homo sapien

<400> SEQUENCE: 232

```
ccaggataat atacacaggt ttgcagctaa aactgtgcac agtgggtcat tgatgctagt      60
cacagtggaa ctgaaggaag gctctacagc ccagcttatc ataaacactg agaaaactgt     120
gattggctct gttctgctgc gggaactgaa gcctgtcctg tctcagggggt aacctgctta     180 catctggact ttagaatctg gcacacaaca aaagtgcctg gcatccacta ctgctgcctt     240
tcatttataa taatagccct tccatctggc agtgggggaa gaatacactc ttgacattct     300
tgtctcctgc tttagaatgc tagtgtgtat ctatcatgta tgcaatactt tccccctttt     360
```

```
tgctttgcta accaaagagc atatatttta ctgtcag                                 397

<210> SEQ ID NO 233
<211> LENGTH: 508
<212> TYPE: DNA
<213> ORGANISM: Homo sapien

<400> SEQUENCE: 233
cgaggagtcg cttaagtgcg aggacctcaa agtgggacaa tatatttgta aagatccaaa        60
aataaatgac gctacgcaag aaccagttaa ctgtacaaac tacacagctc atgtttcctg       120
ttttccagca cccaacataa cttgtaagga ttccagtggc aatgaaacac attttactgg       180
gaacgaagtt ggttttttca agcccatatc ttgccgaaat gtaaatggct attcctacaa       240
agtggcagtc gcattgtctc tttttcttgg atggttggga gcagatcgat tttaccttgg       300
ataccctgct ttgggtttgt taaagttttg cactgtaggg ttttgtggaa ttgggagcct       360
aattgatttc attcttattt caatgcagat tgttggacct tcagatggaa gtagttacat       420
tatagattac tatggaacca gacttacaag actgagtatt actaatgaaa catttagaaa       480
aacgcaatta tatccataaa tatttttt                                          508

<210> SEQ ID NO 234
<211> LENGTH: 358
<212> TYPE: DNA
<213> ORGANISM: Homo sapien

<400> SEQUENCE: 234
aaatgttggt attcaaaacc aaagatataa ccgaaaggaa aaacagatga gacataaaat        60
gatttgcaag atgggaaata tagtagttta tgaatgtaaa ttaaattcca gttataatag       120
tggctacaca ctctcactac acacacagac cccacagtcc tatatgccac aaacacattt       180
ccataacttg aaaatgagta ttttgcatat ctcagttcag gatatgtttt ttacaagtta       240
atcctaaagt cataaagcaa gaagctattc atagtacaag attttatttg ctaagcttta       300
caaattaaac tctaaaaaat tattacaatg atactgaaag atattttatt ggccttttt       358

<210> SEQ ID NO 235
<211> LENGTH: 482
<212> TYPE: DNA
<213> ORGANISM: Homo sapien

<400> SEQUENCE: 235
gaagaaagtt agatttacgc cgatgaatat gatagtgaaa tggattttgg cgtaggtttg        60
gtctagggtg tagcctgaga ataggggaaa tcagtgaatg aagcctccta tgatggcaaa       120
tacagctcct attgatagga catagtggaa gtgagctaca acgtagtacg tgtcgtgtag       180
tacgatgtct agtgatgagt ttgctaatac aatgccagtc aggccaccta cggtgaaaag       240
aaagatgaat cctagggctc agagcactgc agcagatcat ttcatattgc ttccgtggag       300
tgtggcgagt cagctaaata ctttgacgcc ggtgggggata gcgatgatta tggtagcgga       360
ggtgaaatat gctcgtgtgt ctacgtctat tcctactgta aatatatggt gtgctcacac       420
gataaaccct aggaagccaa ttgatatcat agctcagacc ataccatgt atccaaatgg       480 tt                                                                     482

<210> SEQ ID NO 236
<211> LENGTH: 149
<212> TYPE: DNA
<213> ORGANISM: Homo sapien
```

<400> SEQUENCE: 236

```
cctcttcatt gttcacatgt cacaggagga ggctctgagc aaaggccact ggcaagttag      60
ggcaacacca agaaggctct gcggagagac tccctgtggg ttggggcctg gcaggaacgg     120
tgcctgtgga ctgtttatgg tctgtccag                                       149
```

<210> SEQ ID NO 237
<211> LENGTH: 391
<212> TYPE: DNA
<213> ORGANISM: Homo sapien

<400> SEQUENCE: 237

```
gaagctaaat ccaaagaaat atgaaggtgg ccgtgaatta agtgatttta ttagctatct      60
acaaagagaa gctacaaacc ccctgtaat tcaagaagaa aaacccaaga agaagaagaa     120
ggcacaggag gatctctaaa gcagtagcca aacaccactt tgtaaaagga ctcttccatc     180
agagatggga aaaccattgg ggaggactag gacccatatg ggaattatta cctctcaggg     240
ccgagaggac agaatggata taatctgaat cctgttaaat tttctctaaa ctgtttctta     300
gctgcactgt ttatggaaat accaggacca gtttatgttt gtggttttgg gaaaaattat     360
ttgtgttggg ggaaatgttg tgggggtggg g                                    391
```

<210> SEQ ID NO 238
<211> LENGTH: 374
<212> TYPE: DNA
<213> ORGANISM: Homo sapien

<400> SEQUENCE: 238

```
aaaaaacaaa acaatgtaag taaggatat ttctgaatct taaaattcat cccatgtgtg      60
atcataaact cataaaaata attttaagat gccggaaaag gatactttga ttaaataaaa     120
acactcatgg atatgtaaaa actgtcaaga ttaaaattta atagtttcat ttatttgtta     180
ttttatttgt aagaaatagt gatgaacaaa gatccttttt catactgata cctggttgta     240
tattatttga tgcaacagtt ttctgaaatg atatttcaaa ttgcatcaag aaattaaaat     300
catctatctg agtagtcaaa atacaagtaa aggagagcaa ataaacaaca tttggaaaaa     360
aaaaaaaaaa aaaa                                                       374
```

<210> SEQ ID NO 239
<211> LENGTH: 200
<212> TYPE: DNA
<213> ORGANISM: Homo sapien

<400> SEQUENCE: 239

```
aaagatgtct ttgaccgcat atgtactgga aatttcaaac gtggatcttc ccaggttgta      60
gtctttgtgt tatgatcaat gaagaagggc cggccgtttg gcgctatcct catttcccag     120
ccgggtggca agaagctctg tgtgactttg tgttgtggtt tgggggagtt gtaaggtgat     180
ggctgtgggg actgtgggtt                                                 200
```

<210> SEQ ID NO 240
<211> LENGTH: 314
<212> TYPE: DNA
<213> ORGANISM: Homo sapien
<220> FEATURE:
<221> NAME/KEY: misc_feature
<222> LOCATION: (1)...(314)
<223> OTHER INFORMATION: n = A,T,C or G

```
<400> SEQUENCE: 240
ctggtaaact gtccaaaaca aggttccaaa taacacctct tactgattta ccctacccat    60
acatatncca natagntttt gatcaaaaac atgaaatana tccacctgct tattttaagc   120
atattaaaaa ggaaactaat tggaccattt tctatttgtc tattttatac aaaaaggcta   180
cacaattgat acactctatt cagataacaa tcaattagag tgantatgaa ttactggcga   240
caccatcact caattcttaa aaattagaaa ttgctgtagc agtattcact ataacttaac   300
actaccgaga gact                                                    314

<210> SEQ ID NO 241
<211> LENGTH: 375
<212> TYPE: DNA
<213> ORGANISM: Homo sapien
<220> FEATURE:
<221> NAME/KEY: misc_feature
<222> LOCATION: (1)...(375)
<223> OTHER INFORMATION: n = A,T,C or G

<400> SEQUENCE: 241
ccaagtcctt ggagttatag gatattcatt acttcctctc attgtaatag ccctgtact    60 tttggtggtt ggatcatttg aagtggtgtc tacacttata aaactgtttg gtgtgttttg   120
ggctgcctac agtgctgctt cattgttagt gggtgaagaa ttcaagacca aaaagcctct   180
tctgatttat ccaatctttt tattatacat ttatcttttg tcgttatata ctggtgtgtg   240
atccaagtta tacatgaata gaaaaagatg gtgttaaatt tgtgtgtagg ctgggaattc   300
tngctaaagg aatggnaaaa aacctgtnnt tgnaaaattn acntgtccca aagnnaagga   360
anctaaacgc ttttt                                                  375

<210> SEQ ID NO 242
<211> LENGTH: 387
<212> TYPE: DNA
<213> ORGANISM: Homo sapien

<400> SEQUENCE: 242
aaaggcattc tctgatttac atgagaattg agaaactgag atgtatgatt tgtctgttag    60
tcaatttcac acccttcat tctcataagc cccaatttt gctcagttaa ggagcttgct    120
ttaggcccac ctatgtaagt ctgttatact agctaatgtg cccatttgaa tagttcaagg   180
gtcagctaat gctctgagct tcatggctcc agtataaaga acaaatttaa caaaattaag   240
ctgttactgt agccgagtta cccttctgct ccacacatat gtagtgggat cttgcaggat   300
ttccatagtg ccaattatca aaggccttga ctacttagca ttgctgtatt acagatgtgc   360
aaactgaggc actgaaaagt caaattt                                     387

<210> SEQ ID NO 243
<211> LENGTH: 536
<212> TYPE: DNA
<213> ORGANISM: Homo sapien
<220> FEATURE:
<221> NAME/KEY: misc_feature
<222> LOCATION: (1)...(536)
<223> OTHER INFORMATION: n = A,T,C or G

<400> SEQUENCE: 243
aaaccaaaag gacgaagaaa aaacactttn aaaaaaaaaa aaaaaaaaga aaaaccaaac    60
catattttgc cacacatgtgag agtacggtca agcagtattt acaaaaaggt taacggaaca  120
acactctgac acatgctctg agaatactgg gactgctgtt tcaaaaaaaa aggttcaaac   180
```

```
ttattgtcac agcatcatca caaaatagag gatcaccatt ggtttgcttg gcttttcttt      240
ttttttttcc cccaagtgag gacctaactc caaataatac aatagaatat gcaaattatc      300
ttcacatcaa gagtacccca agaaaaacga aatccatggc acanacactg tacaagggtg      360
cagggcaggg ctctgagggg cccaaacccc attttgccaa ctcgattttc tagcattgaa      420
gggagcaagg ggtcaggcat atgatggaga tgatactgaa atgatttatc caaaatccat      480
gcaaatcaag ttctttggat agaggtgaan aacttggaca tggctgtttc aggcag         536
```

<210> SEQ ID NO 244
<211> LENGTH: 397
<212> TYPE: DNA
<213> ORGANISM: Homo sapien

<400> SEQUENCE: 244

```
ccaggataat atacacaggt ttgcagctaa aactgtgcac agtgggtcat tgatgctagt       60
cacagtggaa ctgaaggaag gctctacagc ccagcttatc ataaacactg agaaaactgt      120
gattggctct gttctgctgc gggaactgaa gcctgtcctg tctcagggt aacctgctta      180 catctggact ttagaatctg cacacaaca aaagtgcctg gcatccacta ctgctgcctt      240
tcatttataa taatagccct tccatctggc agtgggggaa gaatacactc ttgacattct      300
tgtctcctgc tttagaatgc tagtgtgtat ctatcatgta tgcaatactt tccccctttt      360
tgctttgcta accaaagagc atatatttta ctgtcag                              397
```

<210> SEQ ID NO 245
<211> LENGTH: 508
<212> TYPE: DNA
<213> ORGANISM: Homo sapien

<400> SEQUENCE: 245

```
cgaggagtcg cttaagtgcg aggacctcaa agtgggacaa tatatttgta aagatccaaa       60
aataaatgac gctacgcaag aaccagttaa ctgtacaaac tacacagctc atgtttcctg      120
ttttccagca cccaacataa cttgtaagga ttccagtggc aatgaaacac attttactgg      180
gaacgaagtt ggttttttca agcccatatc ttgccgaaat gtaaatgct attcctacaa      240 agtggcagtc gcattgtctc ttttttcttgg atggttggga gcagatcgat tttaccttgg      300 atacccttgct ttgggttttgt taaagttttttg cactgtaggg ttttgtggaa ttgggagcct      360
aattgatttc attcttattt caatgcagat tgttggacct tcagatggaa gtagttacat      420
tatagattac tatggaacca gacttacaag actgagtatt actaatgaaa catttagaaa      480
aacgcaatta tatccataaa tattttt                                         508
```

<210> SEQ ID NO 246
<211> LENGTH: 358
<212> TYPE: DNA
<213> ORGANISM: Homo sapien

<400> SEQUENCE: 246

```
aaatgttggt attcaaaacc aaagatataa ccgaaaggaa aaacagatga gacataaaat       60
gatttgcaag atgggaaata tagtagttta tgaatgtaaa ttaaattcca gttataatag      120
tggctacaca ctctcactac acacacagac cccacagtcc tatatgccac aaacacattt      180
ccataacttg aaaatgagta ttttgcatat ctcagttcag gatatgtttt ttacaagtta      240
atcctaaagt cataaagcaa gaagctattc atagtacaag attttatttg ctaagcttta      300
```

```
caaattaaac tctaaaaaat tattacaatg atactgaaag atattttatt ggcctttt        358
```

```
<210> SEQ ID NO 247
<211> LENGTH: 673
<212> TYPE: DNA
<213> ORGANISM: Homo sapen
<220> FEATURE:
<221> NAME/KEY: misc_feaure
<222> LOCATION: (1)...(673)
<223> OTHER INFORMATION: n = A,T,C or G

<400> SEQUENCE: 247
gaagaaagtt agatttacgc cgatgaatat gatagtgaaa tggattttgg cgtaggtttg       60
gtctagggtg tagcctgaga ataggggaaa tcagtgaatg aagcctccta tgatggcaaa      120
tacagctcct attgatagga catagtggaa gtgagctaca acgtagtacg tgtcgtgtag      180
tacgatgtct agtgatgagt ttgctaatac aatgccagtc aggccaccta cggtgaaaag      240
aaagatgaat cctagggctc agagcactgc agcagatcat ttcatattgc ttccgtggag      300
tgtggcgagt cagctaaata ctttgacgcc ggtgggata gcgatgatta tggtagcgga       360
ggtgaaatat gctcgtgtgt ctacgtctat tcctactgta aatatatggt gtgctcacac      420
gataaaccct aggaagccaa ttgatatcat agctcagacc ataccatgt atccaaatgg      480 ttctttttt ccggagtagt aagttacaat atgggagatt attccgaagc ctggtaggat      540
aagaatataa acttcagggt gaccgaaaaa tcagaatagg tgttggtata gaatggggtc      600
tcctnctccg cggggtcnaa gaaggtggtg ttgangttgc cggnctgtta ntagtatagn     660
gatgccanca gct                                                        673
```

```
<210> SEQ ID NO 248
<211> LENGTH: 149
<212> TYPE: DNA
<213> ORGANISM: Homo sapien

<400> SEQUENCE: 248
cctcttcatt gttcacatgt cacaggagga ggctctgagc aaaggccact ggcaagttag       60
ggcaacacca agaaggctct gcggagagac tccctgtggg ttggggcctg gcaggaacgg      120
tgcctgtgga ctgtttatgg tctgtccag                                       149
```

```
<210> SEQ ID NO 249
<211> LENGTH: 458
<212> TYPE: DNA
<213> ORGANISM: Homo sapien
<220> FEATURE:
<221> NAME/KEY: misc_feature
<222> LOCATION: (1)...(458)
<223> OTHER INFORMATION: n = A,T,C or G

<400> SEQUENCE: 249
gaagctaaat ccaaagaaat atgaaggtgg ccgtgaatta agtgatttta ttagctatct       60
acaaagagaa gctacaaacc ccctgtaat tcaagaagaa aaacccaaga agaagaagaa      120
ggcacaggag gatctctaaa gcagtagcca acaccactt tgtaaaagga ctcttccatc      180
agagatggga aaaccattgg ggaggactag gacccatatg ggaattatta cctctcaggg     240
ccgagaggac agaatggata taatctgaat cctgttaaat tttctctaaa ctgtttctta     300
gctgcactgt ttatggaaat accaggacca gtttatgttt gtggttttgg gaaaaattat     360
ttgtgttggg ggaaatgttg tgggggtggg gttgagttgg gggtattttc taattttttt     420
tgtacatttg gaacagtgac aataaatgan accccttt                             458
```

<210> SEQ ID NO 250
<211> LENGTH: 374
<212> TYPE: DNA
<213> ORGANISM: Homo sapien

<400> SEQUENCE: 250

| aaaaaacaaa acaatgtaag taaaggatat ttctgaatct taaaattcat cccatgtgtg | 60 |
| atcataaact cataaaaata attttaagat gccggaaaag gatactttga ttaaataaaa | 120 |
| acactcatgg atatgtaaaa actgtcaaga ttaaaattta atagtttcat ttatttgtta | 180 |
| ttttatttgt aagaaatagt gatgaacaaa gatccttttt catactgata cctggttgta | 240 |
| tattatttga tgcaacagtt ttctgaaatg atatttcaaa ttgcatcaag aaattaaaat | 300 |
| catctatctg agtagtcaaa atacaagtaa aggagagcaa ataaacaaca tttggaaaaa | 360 |
| aaaaaaaaaa aaaa | 374 |

<210> SEQ ID NO 251
<211> LENGTH: 356
<212> TYPE: DNA
<213> ORGANISM: Homo sapien

<400> SEQUENCE: 251

| aaagatcttc tctaacaagc tatgggaatt tggcttcata ctctttcttt gcaacagcag | 60 |
| tgttctgggt gataattttg aattgatacc tgttcctttt tctggttttt gttggctttt | 120 |
| tgaaaaattg tctttcctta tcattggtgg gaggcttggt agcaaagtaa cattttttgg | 180 |
| aaaagaggac agaaaaattg aactacagct tgagaacgta ttctttttttt cctactttgt | 240 |
| tattgcaaat tgaggaatca cttttaactg ttttaggtgt gtgtgtccag agtgagcaag | 300 |
| gattatgttt tggattgtc aaagaggatg cttagtctta aaataaaaat aaattt | 356 |

<210> SEQ ID NO 252
<211> LENGTH: 484
<212> TYPE: DNA
<213> ORGANISM: Homo sapien

<400> SEQUENCE: 252

| ctggtaaact gtccaaaaca aggttccaaa taacacctct tactgattta ccctacccat | 60 |
| acatatccca aatagttttt gatcaaaaac atgaaataga tccacctgct tatttaagc | 120 |
| atattaaaaa ggaaactaat tggaccattt tctatttgtc tattttatac aaaaaggcta | 180 |
| cacaattgtt acactttatt cagattacaa ttaattagag tgattatgaa ttagtgttct | 240 |
| acaccattac tcaattctta aaaattagaa attgctgtag cagtattcac tataacttaa | 300 |
| cactacgaga gacttaaaaa acagttactg caaaaaaaaa aaagagctac ttcaaagcaa | 360 |
| gcaaagtcag taccattaca gatattctta aaaaaaaaaa aaaatttaac aagcaaggct | 420 |
| agggtttgat aaaattccatc ttgtgatcca ttcttgtgca ttcttcactt cttgagtcac | 480 |
| tccc | 484 |

<210> SEQ ID NO 253
<211> LENGTH: 379
<212> TYPE: DNA
<213> ORGANISM: Homo sapien

<400> SEQUENCE: 253

| aaaaagcgct tagacttccc tttccatctg gaacatgtaa aatttttgcag caacaggttt | 60 |

```
tctccaattc cttcagcaag aattcccagc ctacacacaa atttaacacc atctttttct      120
attcatgtat aacttggatc acacaccagt atataacgac aaaagataaa tgtataataa      180
aaagattgga taaatcagaa gaggcttttt ggtcttgaat tcttcaccca ctaacaatga      240
agcagcactg taggcagccc aaaacacacc aaacagtttt ataagtgtag acaccacttc      300
aaatgatcca accaccaaaa gtacaggggc tattacaatg agaggaagta atgaatatcc      360
tataactcca aggacttgg                                                  379

<210> SEQ ID NO 254
<211> LENGTH: 387
<212> TYPE: DNA
<213> ORGANISM: Homo sapien
<220> FEATURE:
<221> NAME/KEY: misc_feature
<222> LOCATION: (1)...(387)
<223> OTHER INFORMATION: n = A,T,C or G

<400> SEQUENCE: 254
aaatttgact tttcagtgcc tcagtttgca catctgtaat acagcaatgc taagtagtca       60
aggccnttga taattggcac tatggaaatc ctgcaagatc ccactacata tgtgtggagc      120
agaagggtaa ctcggctaca gtaacagctt aattttgtta aatttgttct ttatactgga      180
gccatgaagc tcagagcatt agctgaccct tgaactattc aaatgggcac attagctagt      240
ataacagact tacataggtg ggcctaaagc aagctcctta actgagcaaa atttggggct      300
tatgagaatg aaagggtgtg aaattgacta acagacaaat catacatctc agtttctcaa      360
ttctcatgta aatcagagaa tgcctttt                                        387

<210> SEQ ID NO 255
<211> LENGTH: 225
<212> TYPE: DNA
<213> ORGANISM: Homo sapien
<220> FEATURE:
<221> NAME/KEY: misc_feature
<222> LOCATION: (1)...(225)
<223> OTHER INFORMATION: n = A,T,C or G

<400> SEQUENCE: 255
aaatgtcttg tttcccagat ttcaggaaan ttttttttctt ttaagctatc cacagcttac      60
agcacctttg ataaaatata cttttgtgaa caaaaattga gacatttaca ttttctccct      120
atgtggtcgc tccagacttg ggaaactatt catgaatatt tatattgtat ggtaatatag      180
ttattgcaca agttcaataa aaatctgctc tttgtatgac agaat                     225

<210> SEQ ID NO 256
<211> LENGTH: 544
<212> TYPE: DNA
<213> ORGANISM: Homo sapien
<220> FEATURE:
<221> NAME/KEY: misc_feature
<222> LOCATION: (1)...(544)
<223> OTHER INFORMATION: n = A,T,C or G

<400> SEQUENCE: 256
ccttgcttaa agcccagaag tggtttaggc ntttggaaaa tctggttcac atcataaaga       60
acttgatttg aaatgttttc tatagaaaca agtgctaagt gtaccgtatt atacttgatg      120
ttggtcattt ctcagtccta tttctcagtt ctattatttt agaacctagt cagttcttta      180
agattataac tggtcctaca ttaaaataat gcttctcgat gtcagatttt acctgtttgc      240
tgctgagaac atctctgcct aatttaccaa agccagacct tcagttcaac atgcttcctt      300
```

```
agcttttcat agttgtctga catttccatg aaaacaaagg aaccaacttt gttttaacca      360
aactttgttt ggttacagtt ttcaggggag cgtttcttcc atgacacaca gcaacatccc      420
aaagaaataa acaagtgtga caaanaaaaa aacaaaccta aatgctactg ttccaaagag      480
caacttgatg gtttttttta atactgagtg caaaaggnca cccaaattcc tatgatgaaa      540
tttt                                                                   544

<210> SEQ ID NO 257
<211> LENGTH: 420
<212> TYPE: DNA
<213> ORGANISM: Homo sapien

<400> SEQUENCE: 257
aaatgtcttg tttcccagat ttcaggaaac ttttttctt ttaagctatc cacagcttac        60
agcaatttga taaatatac ttttgtgaac aaaaattgag acatttacat tttctcccta      120
tgtggtcgct ccagacttgg gaaactattc atgaatattt atattgtatg gtaatatagt     180
tattgcacaa gttcaataaa aatctgctct ttgtatgaca gaatacattt gaaaacattg      240
gttatattac caagactttg actagaatgt cgtatttgag gatataaacc cataggtaat     300
aaacccacag gtactacaaa caaagtctga agtcagcctt ggtttggctt cctagtgtca     360
attaaacttc taaagtttta atctgagatt ccttataaaa acttccagca aagcaacttt     420

<210> SEQ ID NO 258
<211> LENGTH: 736
<212> TYPE: DNA
<213> ORGANISM: Homo sapien

<400> SEQUENCE: 258
aaacaaaatg ctaaacctaa aaacattgtt ctgtcagttc ccaaattaaa tctacttaga       60
acaaaaacaa aaatttatag ctcggtcaca tactacttaa ataatattgt tcaggcatct     120
ctaaaatcct ccatgttttc aagtatggaa atagaactca aatattccac aatacagtac     180
taaacagatg gagtatttag gaaagacttt gttgtcatat ggcacaatat taatattttg      240
ttgcttcaat acgttttgaa ataaatatca gattttttgtt ttttttttcct aaaagaccaa    300 aattataatc tacattaaga taattctgac tgtggttaag acttaagagt gtaaaataca    360
acatcaatat tttatcacaa aagtaaagct ggtaacaaat tataaaagga gccagtactc     420
tactgagaca ggctcggaga ttaaagctca tcatgataga aatagtcatc atggagctgt    480
ctgccataat ctgtggcttc actggtgaga aacaagtccg ggttttccag aatctcttct     540
tcagagagct ttttgtcacc attcaaatcc atttcatcaa ttagatgaag cgcctcctct    600
tgtgcaatgc cctgattatt aggtctaccc aaggtaacag ctcttgggga tcaagcctgc     660
catcgttatc tttgtcataa tcattcaccg aatctgtctt tctcacaagt atcccattct     720
ggatcttcat ttgcag                                                     736

<210> SEQ ID NO 259
<211> LENGTH: 437
<212> TYPE: DNA
<213> ORGANISM: Homo sapien
<220> FEATURE:
<221> NAME/KEY: misc_feature
<222> LOCATION: (1)...(437)
<223> OTHER INFORMATION: n = A,T,C or G

<400> SEQUENCE: 259
```

| | |
|---|---|
| aaaaccatac tgaaatcatt taccaaataa cnaagatctt aatctaaaag atagtgaata | 60 |
| catcatcatc atgaaatctg gttttatgtg ctctatgaag tacttggaga attgcttttt | 120 |
| tattttctt ttgctttatt aggtcacaca aacagaatg aattagcaga aaaatgtatg | 180 |
| ttataaaaca gcatttacta cttcaattta attttttta ctaacaattg tggaccttt | 240 |
| tgatgacact tatgtatgtt tttaataaat tatgtactta ttagtactta atgagccctt | 300 |
| cctgcctcaa tataaaatta ctaaacttgg agaattacag attttattgt aggccctgat | 360 |
| gttagtcact ttggagaagc taaaaatttg gaaatgatgt aattcccact gtaatagcat | 420 |
| agggattttg gaagcag | 437 |

<210> SEQ ID NO 260
<211> LENGTH: 592
<212> TYPE: DNA
<213> ORGANISM: Homo sapien

<400> SEQUENCE: 260

| | |
|---|---|
| ttttttttt gaaaaatata aaattttaat aaaggctaca tctcttaatt acaataatta | 60 |
| ttgtaccaag taattttcct taaatgaact ctttataatg cataatttac agtataagta | 120 |
| gaacaaaatg tcatgacaaa agtcattgag tacaagactt gtaataaaaa ggcataaaat | 180 |
| atatttatac ataaacccct ttcaaaaaac aagggaaagc ttgagccctc aatatagggc | 240 |
| gacacacgga gcgggtgacc gtgcaggtac aggtactgta ctgatttaaa gtcaagcact | 300 |
| agagatagtg gattaatact cttttgccgt acactatata cagatgtata gtacaagtaa | 360 |
| caatggcaaa cagaatgtac agattaactt aacacaaaaa cccgaacatc aaaatgaagg | 420 |
| tgtgtggagg aaaggtgctg ctgggtctcc ctacaactgt tcatttcttt gtggggcagg | 480 |
| gggtagttcc tgaatggctg tggtccaatg actaatgtaa aacaaaaaca gaaacaaaaa | 540 |
| aaacaaggaa ctgtcatttc cacgaaagca cagcggcagt gattctagca gg | 592 |

<210> SEQ ID NO 261
<211> LENGTH: 450
<212> TYPE: DNA
<213> ORGANISM: Homo sapien

<400> SEQUENCE: 261

| | |
|---|---|
| gtggcagggc ccagccccga accagacaag ggacccctca aggagcttca ttctagcatg | 60 |
| agaaaattga gaagtaaacc agaaagttac agaatgtctg aaggggacag tgtgggagaa | 120 |
| tccgtccatg ggaaaccttc ggtggtgtac agattttca caagacttgg acagatttat | 180 |
| cagtcctggc tagacaagtc cacaccctac acggctgtgc gatgggtcgt gacactgggc | 240 |
| ctgagctttg tctacatgat tcgagtttac ctgctgcagg gttggtacat tgtgacctat | 300 |
| gccttgggga tctaccatct aaatcttttc atagcttttc tttctcccaa agtggatcct | 360 |
| tccttaatgg aagactcaga tgacggtcct tcgctaccca ccaaacagaa cgaggaattc | 420 |
| cgccccttca ttcgaaggct cccagagttt | 450 |

<210> SEQ ID NO 262
<211> LENGTH: 239
<212> TYPE: DNA
<213> ORGANISM: Homo sapien
<220> FEATURE:
<221> NAME/KEY: misc_feature
<222> LOCATION: (1)...(239)
<223> OTHER INFORMATION: n = A,T,C or G

<400> SEQUENCE: 262

```
taactttgat gacaaaatct aaaattaaag anttagtctt aaaagcctat agtgacttgt      60
ttacttgcat aaataatatt ttcacttagt acaggctatt aatataagta atgagaattt     120
aagtattaac tcaaaaaaag atagaggctc caaacttttc taagaaatta atgcattttc     180
aaagtaataa tataatcaat ctgtaagtca aaagtaattt catattcatt gccaaattt      239
```

<210> SEQ ID NO 263
<211> LENGTH: 376
<212> TYPE: DNA
<213> ORGANISM: Homo sapien
<220> FEATURE:
<221> NAME/KEY: misc_feature
<222> LOCATION: (1)...(376)
<223> OTHER INFORMATION: n = A,T,C or G

<400> SEQUENCE: 263

```
aaaaaaaaaa aaaaaaaatt ccttgtngtt tnttagagga aaaaagaaa accccaact       60 tttancactg atactacata ttgctctgtt aaagaatttt ctctgccaaa aaaagaaaa     120 aacaaaaaaa cgcttaaagc tggagtttga cattctgctt tcagatgctg tcttttatt    180 agtgagtgat gatggtttgc taataatcaa taggtaataa ttttttgtaa tcccatcaag    240
tggctccata tgtttctgct ctctcgtgac tgtgttaatg tttaactgtt gtaccttaaa    300
gccgaaatca gtaactatgc atactgtaac caaggtattg ggcttacaga gttgtttgtt    360
gnataaagaa aatttt                                                     376
```

<210> SEQ ID NO 264
<211> LENGTH: 207
<212> TYPE: DNA
<213> ORGANISM: Homo sapien

<400> SEQUENCE: 264

```
aaattagcat tccacaaata tacaggtaat ttaataatta ttgtgcatga atacatacac     60
aatgcttata tatacaaatt ccagtttgtt ttcatgtgct ggcaagggat ttgtatacaa    120
tcataagctg tgttcatatt ggtcccattg aatattcaca atacaaaagc acaaaagaac    180
cattgattta caaaggaaa tctattt                                          207
```

<210> SEQ ID NO 265
<211> LENGTH: 388
<212> TYPE: DNA
<213> ORGANISM: Homo sapien
<220> FEATURE:
<221> NAME/KEY: misc_feature
<222> LOCATION: (1)...(388)
<223> OTHER INFORMATION: n = A,T,C or G

<400> SEQUENCE: 265

```
naactgcact ttatttgtta ctgtaacatt nttttttaac tgatcaacca taagcatgca     60
aaagnccnct gaaactgctt ccactgcctg ttgtatagaa atgggtaaat tataaaggtg    120
attcaatttg gagctccttc cttttttata gcacttctaa gctgtgtgcg cgacacacac    180
cacagaggta ggaaggacca cctttaataa attatcttct taatcgcaga gaatttctga    240
agataaaact gacaaaatgc taaaccaagg ctttgatgag tcccaaagga ccacagatcc    300
atcggctcct atttgaagaa ttcatcccct gtagtgttct agcctttgta gggcactgga    360
ttacaagatc caccagggct ctgaacaa                                        388
```

<210> SEQ ID NO 266

```
<211> LENGTH: 616
<212> TYPE: DNA
<213> ORGANISM: Homo sapien
<220> FEATURE:
<221> NAME/KEY: misc_feature
<222> LOCATION: (1)...(616)
<223> OTHER INFORMATION: n = A,T,C or G

<400> SEQUENCE: 266
aaatacagag tcaaaagatg atttataaaa tntaaaacat tttctgcttg gccgtatttg      60
aagacaagct gaatacatat ctatgttctg aataagtcca ctatggatat atataggaag     120
agatatacat atatccatcc acagatacac acacacatat atatttctgc atgtatatat     180
acataattct ttctatagtt acaggaaata cttcttctat aattctgatt ttgactccca     240
tcctccacca tttactcatc cactcattac ctaaatcttg gctttctttc ctatattgta     300
aataatccat ccaaacttct agccagtact gtcaggaggg ttcttgctcg agtgagctgt     360
taatactatt ttccactgac aacttctgca catcgaggac acagtgtatc tgaagactcc     420
gctgtatact tccaacaacg ggggcatttt tctttcgtag tcggcatgac aattacttta     480
taggaagact cttcacgaat atcaccacct tctaagttga tgaggaattt cccttttaagc    540
tcgattacat ctgcagtcat ctctcgtggt tcctgaccag taaagttgac tcagaagcca     600
tcattaattc attcaa                                                     616

<210> SEQ ID NO 267
<211> LENGTH: 341
<212> TYPE: DNA
<213> ORGANISM: Homo sapien

<400> SEQUENCE: 267 cattatgta tgtatttctct tgaaaaatac ttatttcagc tacttatttt taatagttac      60
tattcttgt tgtattgtca tttgagtttt gtatatattt ttgatattaa ccccttgtca      120
atgtataat ttgcaaatat tttctcccctt tttttagttg tcacattctg ttcattgtat      180
agattctgt gcagcagctt tttaatttga agtgatctga ctgacttgtt cttccttttg      240
gtcctggga tatttaggtt aaatcaaaaa acttgctgcc cagaccaatg ttatggggct      300
tcactctat tttttggtag tagtagttta agagttttag g                          341

<210> SEQ ID NO 268
<211> LENGTH: 367
<212> TYPE: DNA
<213> ORGANISM: Homo sapien
<220> FEATURE:
<221> NAME/KEY: misc_feature
<222> LOCATION: (1)...(367)
<223> OTHER INFORMATION: n = A,T,C or G

<400> SEQUENCE: 268
ttgtagattg gaatagcaaa agtgaatgct ntgaccaaaa ttttgccct cctaaataaa       60
gacgtntcct tctagagagc aaatctatca taaaatgtca aaactagaag agaataaaat     120
gaaaggaaaa aacctagaaa aatatcctaa aatatcaaat gcagtcattt ctaaatataa     180
gccataatta tagcttttacc tattgttctt attgttccta tgctgcttct acaatgttac    240
atcaactata cttagcttta ctctcccaaa atcttggtga tgaagccttc tgagtgtgct     300
ttccaatgtg ccagaaccag aagggcattc caaggcttcc ccacatttcc tccatttacg     360
gagacag                                                               367
```

<210> SEQ ID NO 269
<211> LENGTH: 270
<212> TYPE: DNA
<213> ORGANISM: Homo sapien
<220> FEATURE:
<221> NAME/KEY: misc_feature
<222> LOCATION: (1)...(270)
<223> OTHER INFORMATION: n = A,T,C or G

<400> SEQUENCE: 269

| | | | | |
|---|---|---|---|---|
| caaatctctc cctcactaga cgtaagccnt tnctcactc tctcaatctt atgcatcata | | | | 60 |
| gnaangcngn tgaggtggat taaaccaaac ccagctacgc aaaatcttag catactcctc | | | | 120 |
| aattacccac ataggatgaa taatagcagt tctaccgtac aaccctaaca taaccattct | | | | 180 |
| taatttaact atttatatta tcctaactac taccgcatcc ctactactca acttaaactc | | | | 240 |
| cagcaccacg accctactac tatntcgcac | | | | 270 |

<210> SEQ ID NO 270
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 270

| | | | | |
|---|---|---|---|---|
| ctgaatcatg aataacacta tataatagag tntaaggaac acaagcatta gatgtgatcc | | | | 60 |
| ttgccccata cccttagatt atgtcagact aaagctgaca attctgccag gctctgaacc | | | | 120 |
| cctagtgccc ccaacccaaa tcttggaagc aaagaatatg ccctgtcata caactttgta | | | | 180 |
| caagttgtag taaaacaaag cttaagtttt ctcatctttc tacagcaaat ggtcagttat | | | | 240 |
| ttaataaaca ctaaaatgct cctaagaatc cattttgagt tgtttacca aacacattgt | | | | 300 |
| gcaagaactg actacacaaa agttcctttt gaaatttggt ccacaaattc acttaaggtt | | | | 360 |
| ggaaattt | | | | 368 |

<210> SEQ ID NO 271
<211> LENGTH: 313
<212> TYPE: DNA
<213> ORGANISM: Homo sapien
<220> FEATURE:
<221> NAME/KEY: misc_feature
<222> LOCATION: (1)...(313)
<223> OTHER INFORMATION: n = A,T,C or G

<400> SEQUENCE: 271

| | | | | |
|---|---|---|---|---|
| aaatttatat aaaactctgt acatgttcac tttattattg cataaacagc ataatcttca | | | | 60 |
| agacaanngt ttgcaaacac atgtccaatt caggaaaaaa aatttcacgt ttctcgtctg | | | | 120 |
| gcttttttct tctttttat ttgtttggga gattcccagc tagtttcaga cttggtctgt | | | | 180 |
| gaaggaggca cactattttg cttggtattt gacttggatt tatctgtctc ttgtagtatt | | | | 240 |
| ggcggcactt gggaagagct cttgtcagaa tcacttttg ataagattac agatggctcg | | | | 300 |
| gtagaagtag cag | | | | 313 |

<210> SEQ ID NO 272
<211> LENGTH: 462
<212> TYPE: DNA
<213> ORGANISM: Homo sapien
<220> FEATURE:
<221> NAME/KEY: misc_feature
<222> LOCATION: (1)...(462)

<223> OTHER INFORMATION: n = A,T,C or G

<400> SEQUENCE: 272

| | | | | | |
|---|---|---|---|---|---|
| aaaaaacatt | tattttaata | agactattgc | naacacatta | aaaaaactaa | atagtaatat | 60 |
| tacaaaatct | atatacttgc | acatttagta | tttgtcaatg | tgccagaggt | tttcttcatg | 120 |
| aaatttgact | tctttgaagt | gaaggctttt | ttctatcatc | tcttatagct | ctgactgaat | 180 |
| aagtcttaat | gctttcttca | tgttttctat | caatagggt | aaatcccgag | gctcatatgt | 240 |
| gtacaatctg | ttagagtatc | ttccagctat | gtcagctcta | actgttaaag | aagggtctac | 300 |
| aaacatgatt | ctaggcacat | attgcccatc | aggtgataaa | ttcttatcag | tggtttcatg | 360 |
| cataaggttt | agcatgatga | acttattctg | agccatttct | tgtatttctt | cattttgggc | 420 |
| aaatactttc | tttagtgctt | gagagtattg | acaatcctcc | ag | | 462 |

<210> SEQ ID NO 273
<211> LENGTH: 282
<212> TYPE: DNA
<213> ORGANISM: Homo sapien
<220> FEATURE:
<221> NAME/KEY: misc_feature
<222> LOCATION: (1)...(282)
<223> OTHER INFORMATION: n = A,T,C or G

<400> SEQUENCE: 273

| | | | | | |
|---|---|---|---|---|---|
| ctgatcaaag | catgggatat | tttaatagtn | ttatacataa | tatttttaca | tagaaaactt | 60 |
| tacatnncat | ttcatattat | ataattctgc | ttattctttc | aaaaatttat | acatccattg | 120 |
| ggcaaggaat | ggttttcatt | aaattaccaa | tattaaatgc | acttaatcat | tgtgtatagg | 180 |
| ttaaaccaaa | gtaactatta | actaactttt | aggcatttta | aggaggtaaa | acatacattt | 240 |
| tacacataag | tatttgatgc | aaatatgcag | ataaaatttt | tt | | 282 |

<210> SEQ ID NO 274
<211> LENGTH: 125
<212> TYPE: DNA
<213> ORGANISM: Homo sapien
<220> FEATURE:
<221> NAME/KEY: misc_feature
<222> LOCATION: (1)...(125)
<223> OTHER INFORMATION: n = A,T,C or G

<400> SEQUENCE: 274

| | | | | | |
|---|---|---|---|---|---|
| cagccctaga | cctcaactac | ctaaccaacn | ttncttaaaa | taaaatcccc | actatgcaca | 60 |
| ttnaatcnct | ccaacatact | cggattctac | cctagcatca | cacaccgcac | aatcccctat | 120 |
| ctagg | | | | | | 125 |

<210> SEQ ID NO 275
<211> LENGTH: 528
<212> TYPE: DNA
<213> ORGANISM: Homo sapien
<220> FEATURE:
<221> NAME/KEY: misc_feature
<222> LOCATION: (1)...(528)
<223> OTHER INFORMATION: n = A,T,C or G

<400> SEQUENCE: 275

| | | | | | |
|---|---|---|---|---|---|
| aaagctgtgg | aaaagcttta | ttatagattt | ttntacagaa | ttaaaaaagt | tcaaacaata | 60 |
| ataagccngg | aaccacaaat | aattaaaagg | aaacacagca | atcccataaa | caagcattct | 120 |
| ggcatctgtt | agaaattttc | cctcaaatta | tgaaatgtag | ctctccatgc | tttccaatga | 180 |
| ttgttataat | acccacaaat | atctgtgatt | tcagtggaat | actttaacaa | agttttctt | 240 |

```
tttaaggcat gatcctgatt cattttttct tcaatatctc agtcatttca ggaactacct    300
taaataaatc tgcaactatt ccataatctg ccacttggaa aattggagct tctgggtctt    360
tattaattgc cacaattgtc ttgctgtctt tcatcccagc taaatgttgg atggctccag    420
atattccaac agcaatataa agttctggtg ctactatttt tcccgtctgn ccaacttgca    480
tgtcattggg aacaaagcca gcatcaacag cagcacggga agcaccaa                528
```

```
<210> SEQ ID NO 276
<211> LENGTH: 420
<212> TYPE: DNA
<213> ORGANISM: Homo sapien
<220> FEATURE:
<221> NAME/KEY: misc_feature
<222> LOCATION: (1)...(420)
<223> OTHER INFORMATION: n = A,T,C or G

<400> SEQUENCE: 276
aaatgtcttg tttcccagat ttcaggaaan ttttttttct ttaagctatc cacagcttac     60
agaaacctga taaaatatac ttttgtgaac aaaaattgag acatttacat tttctcccta    120
tgtggtcgct ccagacttgg gaaactattc atgaatattt atattgtatg gtaatatagt    180
tattgcacaa gttcaataaa aatctgctct ttgtatgaca gaatacattt gaaaacattg    240
gttatattac caagactttg actagaatgt cgtatttgag gatataaacc cataggtaat    300
aaacccacag gtactacaaa caaagtctga agtcagcctt ggtttggctt cctagtgtca    360
attaaacttc taaaagttta atctgagatt ccttataaaa acttccagca aagcaacttt    420
```

```
<210> SEQ ID NO 277
<211> LENGTH: 668
<212> TYPE: DNA
<213> ORGANISM: Homo sapien
<220> FEATURE:
<221> NAME/KEY: misc_feature
<222> LOCATION: (1)...(668)
<223> OTHER INFORMATION: n = A,T,C or G

<400> SEQUENCE: 277
ccagggtggc tctgatatag cagccctggt ntattttcga tatttcagga agactggcag     60
atngcaccag accctgaatt cttctagctc ctccaatccc attttatccc atggaaccac    120
taaaaacaag gtctgctctg ctcctgaagc cctatatgct ggagatggac aactcaatga    180
aaatttaaag ggaaacccct caggcctgag gtgtgtgcca ctcagagact tcacctaact    240
agagacaggc aaactgcaaa ccatggtgag aaattgacga cttcacacta tggacagctt    300
ttcccaagat gtcaaaacaa gactcctcat catgataagg ctcttacccc cttttaattt    360
gtccttgctt atgcctgcct ctttcgcttg gcaggatgat gctgtcatta gtatttcaca    420
agaagtagct tcagagggta acttaacaga gtatcagatc tatcttgtca atcccaacgt    480
tttacataaa ataagagatc ctttagtgca cccagtgact gacattagca gcatctttaa    540
cacagccgtg tgttcaaatg tacagnggtc cttttcagag ttggacttct agactccacct    600 gttctcactc cctgttttaa ttcaacccag ccatgcaatg ccaaataata gaaattgctc    660
cctaccag                                                              668
```

```
<210> SEQ ID NO 278
<211> LENGTH: 202
<212> TYPE: DNA
<213> ORGANISM: Homo sapien
<220> FEATURE:
<221> NAME/KEY: misc_feature
```

```
<222> LOCATION: (1)...(202)
<223> OTHER INFORMATION: n = A,T,C or G

<400> SEQUENCE: 278
aaattggtat cgacggcaac caggggaagn tnctaaactc ctaatctatt ctggatccaa      60
ttngcnaagt ggggtcccat caaggttcag tggcagtgga tctgggacag atttcactct     120
cacgatcagc agtctgcaac ccgaagattt tgcaacttac tactgtcaac agagttacat     180
gtccccgtac acttttggac cc                                              202

<210> SEQ ID NO 279
<211> LENGTH: 694
<212> TYPE: DNA
<213> ORGANISM: Homo sapien
<220> FEATURE:
<221> NAME/KEY: misc_feature
<222> LOCATION: (1)...(694)
<223> OTHER INFORMATION: n = A,T,C or G

<400> SEQUENCE: 279
ctgtacttgg acaaaataag ttaattctat ttggttgtcc attaaagttt tatgtggcta      60
tgnacccact ggagctaaaa attggctttt aactgtttcc aaatcagaac tagcagagga     120
gagaagtaaa taaagccaat ggcactccct tcagaggctc aaaatggtta gattttgatg     180
cagatttaac cttagcgagt ttcagtcagt ccatttagat gatcctgtag gttcatacaa     240
atacactgaa ccgttggttt aacttctctt ccttcctcaa agtttatgat aaagagactc     300
atccctgtat tgggagtgac tgacataagt tcagatctgc tcagagtggc tggtaaggaa     360
cacttaaggt cagtcagaaa ataatcaaac agacttctca tgtaagcacc gtgactcaca     420
actaagacac tggctgctaa tcctggaata ccgctgtctg aattaacttt agagctgtga     480
ttttttccta aggaaatat ctctgccaaa gaagtttcca gacagntgct tgggagatcc     540
ttggggaaaa ctggtctttt tgatccggtt ctttcangan taggtngaca aaagaaatnc     600
aaaaaagnct atcccacgcn tttntcacct gggcccagcg gnnctcctcc nggggggggn     660
aaacacangg gactcttccc ngggctngct tnng                                 694

<210> SEQ ID NO 280
<211> LENGTH: 441
<212> TYPE: DNA
<213> ORGANISM: Homo sapien

<400> SEQUENCE: 280
aaaaaacttc catgcaactt ctggtttatt gtttggcaac tccacatgat aaaaaaataa      60
aaacagccca accgagtttc ggaattaagt attcttctag taagtgattc aaacttgtaa     120
tatttgccac aggactgact tatttattta ctagctagaa gctcttaagt tcacttgttt     180
atcagggcat atacagaagg gtttgttaaa actcgatgtt aactttacaa ctttctgacc     240
tggtgcatga attctcaagt actgtatttc actgtgttgg tgtgtctgat ggaaatttcg     300
aggtggtccc acaaaaatat tttatgtagt gtgccttcaa agagaaccat ttatttctct     360
tcacttatcg tcccacaaag tcacatttgg tggtggtcag ccaagtcgca tctggtctag     420
ttttactctt gtcccaattt t                                               441

<210> SEQ ID NO 281
<211> LENGTH: 398
<212> TYPE: DNA
<213> ORGANISM: Homo sapien
```

```
<400> SEQUENCE: 281
aaatttgtta ggtctgaaga atctaaaact gttaatttaa cccttaactt gtgcctagaa      60
actacagcac atataaaata tgtaaacacc agcctgttgc tgtacttttc tgcttatttt     120
acagcctcaa atatttctca ttatcttgtc acttagttct tcatgtttct ccttctgact    180
tttaataatg gtaataggaa aacaaaaccc aaagcttttc agaacttcag tgtgaggttt    240
cctattttga caagttaact tgtaaatact caggttttac gatgtataat ttacctaata    300
gaccaaacta actcatggag atattttgaa ctattattta ggtacaaact ttataaagaa    360
tgttagtatg tcataaaata taacattaca gcttattt                            398

<210> SEQ ID NO 282
<211> LENGTH: 226
<212> TYPE: DNA
<213> ORGANISM: Homo sapien
<220> FEATURE:
<221> NAME/KEY: misc_feature
<222> LOCATION: (1)...(226)
<223> OTHER INFORMATION: n = A,T,C or G

<400> SEQUENCE: 282
aaaacaatat tctcttttg aaaatagtat naacaggcca tgcatataat gtacagtgta      60
ttacnccaat atgtaaagat tcttcaaggt aacaaggggt tgggttttga aataaacatc    120
tggatcttat agaccgttca tacaatggtt ttagcaagtt catagtaaga caaacaagtc    180 ctatctttt ttttggctgg ggtgggggcg cccaggccga ggctgg                   226

<210> SEQ ID NO 283
<211> LENGTH: 358
<212> TYPE: DNA
<213> ORGANISM: Homo sapien

<400> SEQUENCE: 283 aacaaaaat actcaagatc atttatattt ttttggagag aaaactgtcc taatttagaa      60 ttccctcaa atctgaggga cttttaagaa atgctaacag attttctgg aggaaattta     120 acaaaacaa tgtcatttag tagaatattt cagtatttaa gtggaatttc agtatactgt    180 ctatccttt ataagtcatt aaaataatgt ttcatcaaat ggttaaatgg accactggtt    240 cttagagaa atgtttttag gcttaattca ttcaattgtc aagtacactt agtcttaata    300 actcaggtt tgaacagatt attctgaata ttaaaattta atccattctt aatatttt      358

<210> SEQ ID NO 284
<211> LENGTH: 288
<212> TYPE: DNA
<213> ORGANISM: Homo sapien

<400> SEQUENCE: 284
aaaacttttg ttaagaaaaa ctgccagttt gtgcttttga aatgtctgtt ttgacatcat     60
agtctagtaa aattttgaca gtgcatatgt actgttacta aaagctttat atgaaaattat    120 taatgtgaag ttttcattt ataattcaag gaaggatttc ctgaaaacat ttcaagggat    180
ttatgtctac atatttgtgt gtgtgtgtgt gtatatatat gtaatatgca tacacagatg    240
catatgtgta tatataatga aatttatgtt gctggtattt tgcatttt                288

<210> SEQ ID NO 285
<211> LENGTH: 629
<212> TYPE: DNA
<213> ORGANISM: Homo sapien
```

```
<220> FEATURE:
<221> NAME/KEY: misc_feature
<222> LOCATION: (1)...(629)
<223> OTHER INFORMATION: n = A,T,C or G

<400> SEQUENCE: 285
cctaaaagca gccaccaatt aacaaagcgt ncannctcaa cacccactac ctaaaaaatc      60
ccaaacatat aactgaactc ctcacaccca attggaccaa tctatcaccc tatanaagaa     120
ctaatgttag tataagtaac atgaaaacat tctcctctgc ataagcctgc gtcagattaa     180
aacactgaac tgacaattaa cagcccaata tctacaatca accaacaagt cattattacc     240
ctcactgtca acccaacaca ggcatgctca taaggaaagg ttaaaaaaag taaaaggaac     300
tcggcaaatc ttaccccgcc tgtttaccaa aaacatcacc tctagcatca ccagtattag     360
aggcaccgcc tgcccagtga cacatgttta acggccgcgg taccctaacc gtgcaaaggt     420
agcataatca cttgntcctt aattagggac ctgtatgaat ggcttcacga gggttcagct     480
gtctcttact tttaaccagt gaaattgacc tgcccgtgaa gaggcnggca tgacacagca     540
agacgagaag accctatgga gctttaattt attaatgcaa acagnaccta acaaacccca     600
caggtcctaa acttacccaa accctggca                                       629

<210> SEQ ID NO 286
<211> LENGTH: 485
<212> TYPE: DNA
<213> ORGANISM: Homo sapien

<400> SEQUENCE: 286
aaatgtactt gctcagctca actgcatttc agttgtatta tagtccagtt cttatcaaca      60
ttaaaaccta tagcaatcat ttcaaatcta ttctgcaaat tgtataagaa taaagttaga     120
attaacaatt ttattttgta caacagtgga attttctgtc atggataatg tgcttgagtc     180
cctataatct atagacatgt gatagcaaaa gaaacaaaca aaagccagga aaacactcat     240
tttcgccttg aatatgtaaa tgggattaat tttgtcctgt gccttatgtg aaaggaact      300 tctttggttt tcctttttg ttctggtgga agcatgtgca ggagacatat catccaaaca     360
taaaccatta aaatgtttgt ggtttgcttg gctgtaattt tcaaagtagt taattgagga     420
caaagggtaa tgcagaagtg atagctttgg tttgctgagt cttgttttaa gtggccttga     480
tattt                                                                  485

<210> SEQ ID NO 287
<211> LENGTH: 340
<212> TYPE: DNA
<213> ORGANISM: Homo sapien

<400> SEQUENCE: 287
cctggagtcc aataaccacc ccctcatacc acaccctgtg catacaccag ccaagccttt      60
cctggtctgg gaagggaaga gaaaaaagac gcaggccacc tgggggttct gcagtctttg     120
gtcagtccag ccttctatct tagctgcctt tggcttccgc agtgtaaacc ttgcctgccc     180
ggaggcagga ggcccagctg gacctccgag ggccatgagc aggcagcagc catcttggcc     240
tcaagcttgc ctttcccttg agtccctctc tcccctcggc tctagccaga ggtgtagcct     300
gcagatctag gaagagaaga gctggggagg aggatgaagg                            340

<210> SEQ ID NO 288
<211> LENGTH: 290
<212> TYPE: DNA
```

<213> ORGANISM: Homo sapien

<400> SEQUENCE: 288

| aaacagtctc tcctcggtgt tctccttgtc aaactgttca tcccagtttc ctctgaaata | 60 |
|---|---|
| gacagcattc accagaacca gccttgtcaa tggatccact gagcccggag agagcaactc | 120 |
| cgcaatttta ccttctgtct tttcagctac ccaggtgttt atgtgttttc tggacttctc | 180 |
| tacggcgctg ataaagtcaa gctcctccat ctctgcttgg tagaattttt ggcaggaatc | 240 |
| tctaaaagat gagaggaaat cacaagactt tcccccaaag agcctgttgg | 290 |

<210> SEQ ID NO 289
<211> LENGTH: 404
<212> TYPE: DNA
<213> ORGANISM: Homo sapien

<400> SEQUENCE: 289

| ccacccacgc ttaggttccc atcacactga tgactccggg tttggcgagc acaggagcgc | 60 |
|---|---|
| aaaccttttc acattctttc tgtgatccaa atttgttttc gtttccacca caacctccat | 120 |
| accagaatct tgcacagctt tggtgtttg gatcatagta ccattttaat atgaaatccc | 180 |
| tgcaagttcc ttcgtctttc ggcaacttgc atatatctgt ttcagtgaga gccaatggtt | 240 |
| ctgtgctcac cattagattg atggttgaac tagaagctga ccttgctggc tgtggaggtg | 300 |
| ggggctgaga tttctttgta ctgaaacttc cgtggtaggt ggctctgacc tgagacctca | 360 |
| ggtagcagac cacagccaca tggtatgtct gcccagcgag cagg | 404 |

<210> SEQ ID NO 290
<211> LENGTH: 384
<212> TYPE: DNA
<213> ORGANISM: Homo sapien
<220> FEATURE:
<221> NAME/KEY: misc_feature
<222> LOCATION: (1)...(384)
<223> OTHER INFORMATION: n = A,T,C or G

<400> SEQUENCE: 290

| ccaggcgctc cttgtcggca tcagggaggg tggccttgaa ctgctcatgg gctgtggtca | 60 |
|---|---|
| gtccctggat ctcctcaatg gtgtgcacaa tgaaggtgtc ctgcaggtcc tccatggccc | 120 |
| cctccatcca gttgttgaag ggtgcagccc gcttggcata ctccaagtac agctggtcaa | 180 |
| tggtctccag cagtttctcg gtccgctcca gagcttccct tcgcttctga gttagggccc | 240 |
| ccagattgtc ccactggtca cagatctttt ggcaacgggc gttgacactg ggtgagtcat | 300 |
| aatantccag ctcattgagc tcctgtgcga tggcggcaat ctgctccaca cggtcctggt | 360 |
| gggcagccag gccactctcg aagg | 384 |

<210> SEQ ID NO 291
<211> LENGTH: 278
<212> TYPE: DNA
<213> ORGANISM: Homo sapien

<400> SEQUENCE: 291

| aaagtttatt tttactattt ctttatcact ttattgtatc atcaccattg gtttcataat | 60 |
|---|---|
| gtaaatacta tatgttgaac aaattaaatg tcaaattttt ttattaccat agtccatgtt | 120 |
| aatagtgggg ctttcaggtg tttagagatt ttttttgttg ttgttaacat tcattgcaaa | 180 |
| agtactagat ggtgtataac tctagagttg aattttaagg gattccctaa tatgtatact | 240 |
| atcttttat ctgaagtaat aaataaacaa tgatcttg | 278 |

<210> SEQ ID NO 292
<211> LENGTH: 177
<212> TYPE: DNA
<213> ORGANISM: Homo sapien

<400> SEQUENCE: 292

```
ccttggcccg gtcattcttg tccagtttga taggttcagg aaattcgttg tacagctcca      60
cctccgtttc ctgcttaagt gcattccgtg caatcgtctg gaacgcctgc tccacgttga     120
tggcctcctt ggcactggtc tcaaagtagg gaatgttgtt tttgctgtag caccagg       177
```

<210> SEQ ID NO 293
<211> LENGTH: 403
<212> TYPE: DNA
<213> ORGANISM: Homo sapien

<400> SEQUENCE: 293

```
aaaaagaagg acttagggtg tcgttttcac atatgacaat gttgcattta tgatgcagtt      60
tcaagtacca aaacgttgaa ttgatgatgc agttttcata tatcgagatg ttcgctcgtg     120
cagtactgtt ggttaaatga caatttatgt ggattttgca tgtaatacac agtgagacac     180
agtaatttta tctaaattac agtgcagttt agttaatcta ttaatactga ctcagtgtct     240
gcctttaaat ataaatgata tgttgaaaac ttaaggaagc aaatgctaca tatatgcaat     300
ataaatagt aatgtgatgc tgatgctgtt aaccaaaggg cagaataaat aagcaaaatg      360
ccaaaagggg tcttaattga aatgaaaatt taattttgtt ttt                      403
```

<210> SEQ ID NO 294
<211> LENGTH: 305
<212> TYPE: DNA
<213> ORGANISM: Homo sapien
<220> FEATURE:
<221> NAME/KEY: misc_feature
<222> LOCATION: (1)...(305)
<223> OTHER INFORMATION: n = A,T,C or G

<400> SEQUENCE: 294

```
aaagcaatct ggcatggtgt cctgtagtga agcagaggat cataacataa gtaaactctc      60
tatgggtgga agttggagag aaggacattt tggctttgta catgaaaaga ctctccagat     120
agaaacagat tctgcccata agtgaaataa aatgctttgt gggggtaatg agtgacttat     180
agtattcagg cagatgttac ataactgcta attaagtttc cctggattga ntttanncaa     240
anaattgaaa gtngatttg gtcangtgtc agnaaactac tgcctataaa cccatatcnt      300
accca                                                                305
```

<210> SEQ ID NO 295
<211> LENGTH: 397
<212> TYPE: DNA
<213> ORGANISM: Homo sapien
<220> FEATURE:
<221> NAME/KEY: misc_feature
<222> LOCATION: (1)...(397)
<223> OTHER INFORMATION: n = A,T,C or G

<400> SEQUENCE: 295

```
cctatctggt tggcctttttt gaagacacca acctgtgtgc tatccatgcc aaacgtgtaa     60
caattatgcc aaaagacatc cagctagcac gccgcatacg tggagaacgt gcttaagaat    120
ccactatgat gggaaacatt tcattcccaa aaaaaaaaaa aaaaaaaaat ttctcttctt    180
```

```
cctgttattg gtagttctga acgttagata tttttttttcc atggggtcaa aaggtaccta    240
agtatatgat tgccgagtgg aaaaataggg gacagaaatc aggtattggc agttttttcca   300 tttncatttg tgggngaatt tttaatataa atgcggagac gtaaagcatt aatgcnagtt    360
aaaatgtttc agtgaacaag tttcagcggt tcaactt                              397

<210> SEQ ID NO 296
<211> LENGTH: 447
<212> TYPE: DNA
<213> ORGANISM: Homo sapien

<400> SEQUENCE: 296
ccatcctcga tgttgaagtt gtcgtggggc ccgaagacgt tggtggggat gacagcggtg     60
aaggtgcagc cgtactgctg gaagtaggcc ctgttctgca cgtcgatcat cctcttggca   120
tacgagtacc caaaattgct gttgtgggga ggcccattgt ggatcatggt ctcatctatc   180
gggtaggtcg tcttgtcagg gaagatacag gtggacaggc aggacaccac cttgcgggcg   240
cccacctcga aggccgagtg caggacgttg tcgttcatgt gcacgttttt cctccagaag   300
tccaaattgt atttgatatt ccggaacagg ccccccacca ttgcagcaag atggatgacg   360
tgtgtgagtt ggaccttctc aaacagggcg cgggtctgtg ctgtatccgt gagatcggcg   420
tctttagagg agacaaacac ccagtcc                                         447

<210> SEQ ID NO 297
<211> LENGTH: 681
<212> TYPE: DNA
<213> ORGANISM: Homo sapien
<220> FEATURE:
<221> NAME/KEY: misc_feature
<222> LOCATION: (1)...(681)
<223> OTHER INFORMATION: n = A,T,C or G

<400> SEQUENCE: 297
aaataacagc atgtaaaata ttaaaataca agctttcaaa aataaataca taaataagta     60
gaaccctcgt aagaaatagt caaacacatt aagtccttttc cagctgtccc tagaaagctg  120
ctgttctctt tttcattttc agctctggta agggcaggga ccaccctgca ggaagtgtca   180
atgatacgct gataagcttc ttacttctct cctgtcagtt ggtgctcccc ctgtgatgag   240
aaaagggtta ctgttgcagg tgctaaggaa ggctgctctt ctgtcactct gaagttgctt   300
ggagggatgt ccccatgcag actctctccc agccctccac tcagggaagg tctgtctgta   360
cccactgcct tctatagcag aaaacttgca ctcctgaatg cttttttttt ttttcaagaa   420
agaagnggct gnggactcaa ctagattctt ggtttgaaaa agccaaaaca tattggtcac   480
tgattgtcac attgggttag aaatgtccat tcatgatctc ccttaagctg cacacaaccc   540
tatgaaataa ctaccattat ctaccctatt ttgctaaagc tcaaagagat taaataatgt   600
tgacagggat cttagccttg aactcactga aggngttact gcaaagttct gctcttcacc   660
aagaaggntt acaggccaaa g                                              681

<210> SEQ ID NO 298
<211> LENGTH: 353
<212> TYPE: DNA
<213> ORGANISM: Homo sapien
<220> FEATURE:
<221> NAME/KEY: misc_feature
<222> LOCATION: (1)...(353)
<223> OTHER INFORMATION: n = A,T,C or G

<400> SEQUENCE: 298
```

```
cctggcttaa gaccagacat ttgaagaagg ctccaggcag ggaaaggaaa ggagaggcca    60
gccccacnct gncccctccc tgccccacg  tctccagcaa cacaaggcgg ccagtggacc   120
gtgaaccatt tatttccaaa ctataaagaa acctgctctc tgagaaaana cactgcccag   180
gngatgaagc tccagcccct ggaggtccaa aacccagtcc aaactcagtc cctttagaaa   240
gctgctgtgc cttggaaatg annntcggnt gtcanagcct gggaagtggt gggaagaacc   300
agcccactcc cctctcctgc tgcgattcca gcgcncgttg ggnccagatc tgg          353
```

<210> SEQ ID NO 299
<211> LENGTH: 560
<212> TYPE: DNA
<213> ORGANISM: Homo sapien

<400> SEQUENCE: 299

```
aaagttcaag gactaacctt atttatttgg gaaaggggag gaggaaggaa atgatatggt    60
acccagacac tgggctaggc tgcaacttta tctcatttaa tactcccagc tgtcatgtga   120
gaaagaaagc aggctaggca tgtgaaatca ctttcatgga ttattaatgg atttaagagg   180
gcatcaatca gctcaactca agatttcata atcattttta gtatttagat tgtgcctcaa   240
agttgtagta cctcacaata cctccactgg tttcctgttg taaaaacctt cagtgagttt   300
gaccattgtg ctcttggctc ttgggctgga gtaccgtggt gagggagtaa acactagaag   360
tctttagtac aaaactgctc tagggacacc tggtgattcc tacacaagtg atgtttatat   420
ttctcataaa gagtcttccc tatcccaagg tcttcatgat gccagtagcc atatatgata   480
aattatgttc agtgataact tagttatcag aaatcagctc agtggtcttc cccgccatga   540
ttcacatttg atgagttttt                                               560
```

<210> SEQ ID NO 300
<211> LENGTH: 165
<212> TYPE: DNA
<213> ORGANISM: Homo sapien
<220> FEATURE:
<221> NAME/KEY: misc_feature
<222> LOCATION: (1)...(165)
<223> OTHER INFORMATION: n = A,T,C or G

<400> SEQUENCE: 300

```
aaaaactaca tagggtgtg  tgtgtgtgtg tatgtttatt ttatacacac atatttgtat    60
attctaatat attactaagg caattttaat gaattaccat gtatataaaa aaatatctgn   120
cacttggcac acaggtttgt atgtatgtgt atatatatat gtatg                   165
```

<210> SEQ ID NO 301
<211> LENGTH: 438
<212> TYPE: DNA
<213> ORGANISM: Homo sapien

<400> SEQUENCE: 301

```
aaaatatatg tatttaaaaa caaaaagcaa cagtaatcta tgtgtttctg taacaaattg    60
ggatctgtct tggcattaaa ccacatcatg gaccaaatgt gccatactaa tgatgagcat   120
ttagcacaat ttgagactga aatttagtac actatgttct aggtcagtct aacagtttgc   180
ctgctgtatt tatagtaacc attttcccttt ggactgttca agcaaaaaag gtaactaact   240
gcttcatctc cttttgcgct tatttggaaa ttttagttat agtgtttaac tggcatggat   300
taatagagtt ggagttttat tttaagaaaa aattcacaag ctaacttcca ctaatccatt   360
```

-continued

| | |
|---|---|
| atcctttatt ttattgaaat gtataattaa cttaactgaa gaaaaggttc ttcttgggag | 420 |
| tatgttgtca taacattt | 438 |

<210> SEQ ID NO 302
<211> LENGTH: 172
<212> TYPE: DNA
<213> ORGANISM: Homo sapien

<400> SEQUENCE: 302

| | |
|---|---|
| ccaaaacagg agtcctgggt gatatcatca tgagacccag ctgtgctcct ggatggtttt | 60 |
| accacaagtc caattgctat ggttacttca ggaagctgag gaactggtct gatgccgagc | 120 |
| tcgagtgtca gtcttacgga aacggagccc acctggcatc tatcctgagt tt | 172 |

<210> SEQ ID NO 303
<211> LENGTH: 552
<212> TYPE: DNA
<213> ORGANISM: Homo sapien

<400> SEQUENCE: 303

| | |
|---|---|
| ccagcctgtt gcaggctgct tcgtagcggg cgtcggctgc ggacttccct tcccgggtct | 60 |
| ggatcttttc atcctaccag atgagaaagg gaatgagtga atggagtgac cccgcaccct | 120 |
| gtcactttcc tgagacatga ctgccaggaa gaagagctgc tctggtctcc atcagggctg | 180 |
| gcaggacaaa ctgaccagtg agtcagtagg cagagttcac actgaaaaag ggcacaaggg | 240 |
| ctgtcccaca atgggaggaa atgggtctc agaacttcta cttctctgaa aactaagaca | 300 |
| caattgggac aaccaccacc cccgtgtgag atttctcacc tcgagacagg acaagatgaa | 360 |
| gttcacggct tcttctgggg taaagacctt gaagagccca tcacaggcca acaaaatgaa | 420 |
| cctacaacac cagggagaaa tataaacggg ttttaggccc aaccaaaaaa taaaaaataa | 480 |
| aaaagggcc tggagatgga gataaaataa atatttgtcc aactattcaa aggctaaggt | 540 |
| tttttttttct tt | 552 |

<210> SEQ ID NO 304
<211> LENGTH: 601
<212> TYPE: DNA
<213> ORGANISM: Homo sapien

<400> SEQUENCE: 304

| | |
|---|---|
| cctttgattc ttggtagtac attgcatgta aatgtttat aagaagctac ttttccttca | 60 |
| tgggaagaaa ttcccacatg agattcataa attcttagac tccgtggctt ctttggtccg | 120 |
| gaatgcttaa actcatatga gtgttctgga tcccagtgta tccaatcata attcacatta | 180 |
| tcaccttcac gaaccacata ctttgcccac ggtgaaatac gatacaagat ctctccgctt | 240 |
| ttactagtaa taactacctt taatttggat ccatgaggca cgagtacaga tttattctgc | 300 |
| tttggtggga tatacagctc ccattttcca taatccagtt ttttgtatgg gtacgaaaat | 360 |
| ggattccaac cattaaaatc tccagtaaga aaaactcctt ctgctcccgg gcccattct | 420 |
| ttgcagtata accaccatc agcacatctg tggacgccaa atgattcata gcctctggaa | 480 |
| aacttatcaa taccaccttc attttctcca atgttcttca aaatttggct aaactgctta | 540 |
| tacctgcgct ggaagtccac ggcgtagggc ttcaagtacc ggtcgatctc caggagtctg | 600 |
| g | 601 |

<210> SEQ ID NO 305
<211> LENGTH: 401

```
<212> TYPE: DNA
<213> ORGANISM: Homo sapien

<400> SEQUENCE: 305
aaataacagc atgtaaaata ttaaaataca agctttcaaa aataaataca taaataagta      60
gaaccctcgt aagaaatagt caaacacatt aagtcctttc cagctgtccc tagaaagctg     120
ctgttctctt tttcattttc agctctggta agggcaggga ccaccctgca ggaagtgtca     180
atgatacgct gataagcttc ttacttctct cctgtcagtt ggtgctcccc ctgtgatgag     240
aaaagggtta ctgttgcagg tgctaaggaa ggctgctctt ctgtcactct gaagttgctt     300
ggagggatgt ccccatgcag actctctccc agccctccac tcaggaaggg tctgtctgta     360
cccactgcct tctatagcag aaaacttgca ctcctgaatg c                          401

<210> SEQ ID NO 306
<211> LENGTH: 313
<212> TYPE: DNA
<213> ORGANISM: Homo sapien

<400> SEQUENCE: 306
aaactgacta tggattcctt gaaggtctgg cagttgttga tgatggcgat catgtactga      60
acgtagcagt gagggtgctg ccgattcctc aggtgctctt cttttatacag ctgcgcttca    120 tctttatatc tgaggacaga caggcttcgg tcagacagca ctaagggcaa catggagctg     180
tttcaaatgc cacgctgacg tcacgcctgg cctgaaattt cacatcacta acatctgacc     240
ggatgagcct ctaaaaataa aacaatcttt agacgatcca gactaatgga aggacagaga     300
ggttgattac ttt                                                         313

<210> SEQ ID NO 307
<211> LENGTH: 366
<212> TYPE: DNA
<213> ORGANISM: Homo sapien
<220> FEATURE:
<221> NAME/KEY: misc_feature
<222> LOCATION: (1)...(366)
<223> OTHER INFORMATION: n = A,T,C or G

<400> SEQUENCE: 307
aaagatgctg ntaatgaaca ttacggacaa ttcatggtgt ggctagttgg taacacttca      60
gctgattttt cttatgagat ggaaaaaaaa aatcagccaa gtaagggcac atcttcactt     120
catttataag tcagcatcca aggtaaaaga attctctgtt ggacttgaca tcactcccat     180
cctctgatac tcgcctactc tcttctcaaa gaagttagnt cttttccttcc antgaaatat    240 tctcataaaa gtcaaatggg ttctctactc tgaaaacctt gctaaaaccc aattccagca     300
taagtttgtc tgncacaaac ncaatgnatt gcttcattaa antgcaattc atcccaatga     360
gcttcc                                                                 366

<210> SEQ ID NO 308
<211> LENGTH: 534
<212> TYPE: DNA
<213> ORGANISM: Homo sapien
<220> FEATURE:
<221> NAME/KEY: misc_feature
<222> LOCATION: (1)...(534)
<223> OTHER INFORMATION: n = A,T,C or G

<400> SEQUENCE: 308
ccagctatca gctgatcgtc ttctgtctgg acgctcgtcc tgcttctgac atcaaaatct      60
```

```
tctgtctcaa agtcagagtc atccaactcc tcaggggtcc ttatcatcag cactgctttc      120
ctgatgtccc ggatgccatc ataccaggg cgggaagcat cgataaactc attctcatcc       180
atgggctggg cagggtccga gctgagggct tccacggctg cttctacttg ctcagtaaaa     240
cgtggcatga ctgtgttgga gagcagctta gtggcttcca gaaccttctc tgtgtagact     300
cctggctcat agtcgtccat ctctgaggtg actacgtgaa tgacccgggc tgcccggcct     360
cgaattgcac cagctgtgcg gccaggccat ccacatcctt ctcttggaga gcaatgacac     420
atttggtcac atcttccaaa atgtgattct ctgagacagc caagaagtca tcaatggaag     480
taatgncatc gacagcatct gtgagaacac cgacttgttt ttccattgnt cttt            534

<210> SEQ ID NO 309
<211> LENGTH: 164
<212> TYPE: DNA
<213> ORGANISM: Homo sapien

<400> SEQUENCE: 309
catactcctt acactattcc tcatcaccca actaaaaata ttaaacacaa actaccacct      60
acctccctca ccaaagccca taaaaataaa aaattataac aaaccctgag aaccaaaatg    120
aacgaaaatc tgttcgcttc attcattgcc cccacaatcc tagg                      164

<210> SEQ ID NO 310
<211> LENGTH: 131
<212> TYPE: DNA
<213> ORGANISM: Homo sapien

<400> SEQUENCE: 310
aaaaatcatt tatctttcgg tgcttcaaca tgatgccaaa caaaaatcta ctgaataaaa      60
atagcaagga agggaatcaa acatttataa gatatattta ttattttttct gaccaaagtg    120 caatgattt t                                                           131

<210> SEQ ID NO 311
<211> LENGTH: 626
<212> TYPE: DNA
<213> ORGANISM: Homo sapien

<400> SEQUENCE: 311
cctatgtgcg ccagtttcag gtcatcgaca accagaacct cctcttcgag ctctcctaca      60
agctggaggc aaacagtcag tgagagtgga ggctccagtc agacccgcca gatccttggg    120
cacctggcac tcaagcactt tgcacgatgt ctcaaccaac atctgacatc tttcccgtgg    180
agcaacttcc tgctccacgg gaaagaggtc gatggattta cccctggacc cataagtctg    240
ttcatcctgc tgaagtcccc tccccattgc tccttcaagc caaaactaca ctttgctggt    300
tcctgtcccc tctgagaaag gggatagaaa gctccttcct ctatgtcctc ccatcgagat    360
ctgttctggg gatggagctt ccaacttcct cttgcagcag gaaagaatgc tgctcaccct    420
tctgtcttgc agagtgggat tgtgggaggg attggcagcc ttcttctcca ccacctgtcc    480
agcttcctcc tggtcagggc tgggaccccc aggaatatta tgttgccgtg tgtgtgtgtg    540
tgtgtgtgtg tcttcttttta gggagcagga gtgcatctgg taattgaggg tagatgttgt    600
gtgtgctggg gaggggtcct tctgtt                                          626

<210> SEQ ID NO 312
<211> LENGTH: 616
<212> TYPE: DNA
<213> ORGANISM: Homo sapien
```

<400> SEQUENCE: 312

```
aaaccaaaga aattaagaaa aaagacttca ttgcttgaat gacgcgaaca gctgtctgag      60
tcacctagac tttaacacca cctggggccc tgggaatgac gctgacgaga gatctgcaca     120
tagtaggcgt gggctccaaa tgtgctcatc agctgacttc acatcctcac aagtcagcct     180
cagatatgac ccaagggata cgtaccatct cttcttgaaa cagcgtgtca aattatatat     240
atgtatgcaa aaagagtaa tgtactaagc aaaccaagtt tcgtcttttt cttctgaatc      300
tggttttaat gtgacctgtc atcccatct ttcgaattta tgagctccat cttctctaga      360
ctgttaactt cttgaggaaa acatgctatt ttaccacctt tcactgctga atccctagcc     420
cttaagcaca gtctctggca cagaataaat acgaaatgaa tgagtgaatg aatggatgga     480
tgggtgaaga gaaaggcaa tgcacaagat ttacctatca aaatccacca atggtcctta      540
aaaatggttt tgtcagtaga gatgctgaat atattcatat aatacattta tttcaatact     600
attaagaatt ctagtg                                                     616
```

<210> SEQ ID NO 313
<211> LENGTH: 553
<212> TYPE: DNA
<213> ORGANISM: Homo sapien

<400> SEQUENCE: 313

```
aaaaaatggc agcattgtac ttgaatcaga aagcttactg ggatttcctc atcgaaagta      60
gagattgcag ctaatcctag taccttttgt tagtaattac ttaaggcaca gtgcaaagtt     120
gaaggactgt tttggtacaa actcaagcca gctacatgta tgcttgcctt ggtatccttg     180
ctagagcaca tgcgggtata ataccgtatt atacacaaca aggccaccct gttgtatctg     240
tgttacaatt aaacatcagt cccagaaagt gaacccctagt catttattat aggtgcccac     300
ctctgacttg aacaaaatg ccactccatt catgttcatt tttgtcctgg agaggattta      360
tttcctaaaa gattctgaaa gccaacaaat caatgtagtt cttcatagag aacttaagag     420
taaggctcaa aatggcctca aaatgggctt cttggatgac ttccaacagt gactggcctt     480
ctcaacactg cagatgtctg agcactacca taacctaacg aagtgaggaa ggaggaggca     540
aattggtatt ttt                                                        553
```

<210> SEQ ID NO 314
<211> LENGTH: 330
<212> TYPE: DNA
<213> ORGANISM: Homo sapien

<400> SEQUENCE: 314

```
ccagcgactc cagcggtggc agcaggcagt gcacgtactc tgggcctccc accagggtag      60
tgaaggttcc cagctgttct gccagggcca ggaggaccct atcttcatca tagatggtat     120
ctgtaaggaa aggcagaagc tcacttcggg tcctttcaac cccaagggcc aaggcgatgg     180
tggacagctt cttgatgctg ttgaggcgaa gctgaacgtc tcattgcgg agttcgtcta      240
tgagcaccgc gatggggtac agcgagtcgt cgccgtcggc cgccgccatc ttggctccgt     300
ccctttcctg tcagactgcg gccagcgctg                                      330
```

<210> SEQ ID NO 315
<211> LENGTH: 380
<212> TYPE: DNA
<213> ORGANISM: Homo sapien

<400> SEQUENCE: 315

```
aaaaatgaca ttgcgtttag cttattgtaa gaggttgaac ttttgtattt tgtaactatc      60
tttaagccct tcagtttata attcatataa aatgcctttt gtatttaaaa taatcctatt     120
ttaatcagtg catgaaattt gctttttttaa agttcatttg aatgattatt ccttccctct    180
aaagaaatga ttttggtaat gttgagaggt accttaccac aaatcctaac tgtaagtgta    240
ttcatggtta ttttcaaaag aattatgact cttccccaaa agaatcctaa aaaacttgta    300
ataaacctat aaagctgatt tgcatatttta caaaattttg aatagcaaat ataggcaact    360
catatatgta tataatttttt                                                380
```

<210> SEQ ID NO 316
<211> LENGTH: 222
<212> TYPE: DNA
<213> ORGANISM: Homo sapien

<400> SEQUENCE: 316

```
aaactacaga gggttttcca gctattattt cctttagttt ctaaaagtaa cgacttatat     60
taatgtttta taaagatag tgatgaaaaa aaggtaatgc tgaaataaag gcgcttttag    120
aaatatttaa ggacaacata aggtattaat attggaaaaa aactgtacat attttcaagc    180
acaacactga aatattgcag cagtgtttaa ctgaattgtt tt                        222
```

<210> SEQ ID NO 317
<211> LENGTH: 490
<212> TYPE: DNA
<213> ORGANISM: Homo sapien

<400> SEQUENCE: 317

```
ccttgaatga gcgtggagag cgattaggcc gagcagagga gaagacagaa gacctgaaga     60
acagcgccca gcagtttgca gaaactgcgc acaagcttgc catgaagcac aaatgttgag    120
aaactgccta tcctggtgac tcttcttaag agaaactgaa gagtttgttc agcagttttt    180
acaagaattc gggacctccg cttgcttctt ttttttccaat atttggacac ttagagtggt    240
ttttgttttt tcttttcaga tgttaatgtg aaagaaaggg tgttgcattt ttacatttcc    300
ctaatgatct tgctaataaa tgctacaata gcatcggctt catttttgggt ttttgcctcc    360
tcccactgtg tgtatgtgtg tatatgtatg ttttgaatat gttttctttta ttaaaaaata    420
ttttttgtag tttgaatatg aaatttggac caaatgataa actgcgctga gtctaaactg    480
gcaacatgta                                                            490
```

<210> SEQ ID NO 318
<211> LENGTH: 340
<212> TYPE: DNA
<213> ORGANISM: Homo sapien

<400> SEQUENCE: 318

```
cctggagtcc aataaccacc ccctcatacc acaccctgtg catacaccag ccaagccttt     60
cctggtctgg gaagggaaga gaaaaaagac gcaggccacc tgggggttct gcagtctttg    120
gtcagtccag ctttctatct tagctgcctt tggcttccgc agtgtaaacc ttgcctgccc    180
ggaggcagga ggcccagctg gacctccgag ggccatgagc aggcagcagc catcttggcc    240
tcaagcttgc ctttcccttg agtccctctc tcccctcggc tctagccaga ggtgtagcct    300
gcagatctag gaagagaaga gctgggggagg aggatgaagg                          340
```

<210> SEQ ID NO 319
<211> LENGTH: 373
<212> TYPE: DNA
<213> ORGANISM: Homo sapien

<400> SEQUENCE: 319

| | | | | | |
|---|---|---|---|---|---|
| aaagatgctg | ttaatgaaca | ttacggacaa | ttcatggtgt | ggctagttgg | taacacttca | 60 |
| gctgattttt | cttatgagat | ggaaaaaaaa | atcagccaag | taagggcaca | tcttcagttc | 120 |
| atttagaagt | cagcatccaa | ggtaaaagaa | ttctctgttg | gacttgacat | cactcccatc | 180 |
| ctctgatact | cgcctactct | cttctcaaag | aagttagtct | ttccttccag | tgaaatattc | 240 |
| tccataaagt | caaatgggtt | ctctactctg | aaaaccttgc | taaaacccag | ttccagcata | 300 |
| agtctgtctg | ccacaaactc | aatgtattgc | ttcattagag | tgcaattcat | gccaatgagc | 360 |
| ttcacaggca | agg | | | | | 373 |

<210> SEQ ID NO 320
<211> LENGTH: 509
<212> TYPE: DNA
<213> ORGANISM: Homo sapien

<400> SEQUENCE: 320

| | | | | | |
|---|---|---|---|---|---|
| aaaaacaaaa | ttaaattttc | atttcaatta | agaccccttt | tggcattttg | cttacttatt | 60 |
| ctgccctttg | gttaacagca | tcagcatcac | attactattt | tatattgcat | atatgtagca | 120 |
| tttgcttcct | taagttttca | acatatcatt | tatatttaaa | ggcagacact | gagtcagtat | 180 |
| taatagatta | actaaactgc | actgtaattt | agataaaatt | actgtgtctc | actgtgtatt | 240 |
| acatgcaaaa | tccacataaa | ttgtcattta | accaacagta | ctgcacgagc | gaacatctcg | 300 |
| atatatgaaa | actgcatcat | caattcaacg | ttttggtact | tgaaactgca | tcataaatgc | 360 |
| aacattgtca | tatgtgaaaa | cgacacccta | agtccttctt | tttaaaaatg | acattgcgtt | 420 |
| tagcttattg | taagaggttg | aacttttgta | ttttgtaact | atctttaagc | tcttcagttt | 480 |
| ataattcata | taaaatgcct | tttgtattt | | | | 509 |

<210> SEQ ID NO 321
<211> LENGTH: 617
<212> TYPE: DNA
<213> ORGANISM: Homo sapien

<400> SEQUENCE: 321

| | | | | | |
|---|---|---|---|---|---|
| ccaaggcccc | ttttgcagcc | cacggctatg | gtgccttcct | gactctcagt | atcctcgacc | 60 |
| gatactacac | accgactatc | tcacgtgaga | gggcagtgga | actccttagg | aaatgtctgg | 120 |
| aggagctcca | gaaacgcttc | atcctgaatc | tgccaacctt | cagtgttcga | atcattgaca | 180 |
| aaaatggcat | ccatgacctg | gataacattt | ccttccccaa | acagggctcc | taacatcatg | 240 |
| tcctccctcc | cacttgccag | ggaacttttt | tttgatgggc | tcctttattt | ttttctactc | 300 |
| ttttcaggcg | cactcttgat | aaatggttaa | ttcagaataa | aggtgactat | ggatataatt | 360 |
| gagccctctg | gtccaggtct | cagtttacct | aatattacct | cagaaaggat | atggagggaa | 420 |
| gatgatcttt | tgccaggtc | tgactttct | tcctgctccg | ccctccatta | acgctcagta | 480 |
| cccctttagca | gctgacggcc | ccacgttcta | ctccatgctt | ggcttccttt | ccaactagct | 540 |
| ctttcatata | ttttacttgc | tagtatctcc | attctctcta | aagtagtggt | tcttttttgcc | 600 |
| cttaaactta | aattttt | | | | | 617 |

<210> SEQ ID NO 322

```
<210> SEQ ID NO 322
<211> LENGTH: 403
<212> TYPE: DNA
<213> ORGANISM: Homo sapien

<400> SEQUENCE: 322
aaaaagaagg acttagggtg tcgttttcac atatgacaat gttgcattta tgatgcagtt      60
tcaagtacca aaacgttgaa ttgatgatgc agttttcata tatcgagatg ttcgctcgtg     120
cagtactgtt ggttaaatga caatttatgt ggattttgca tgtaatacac agtgagacac     180
agtaatttta tctaaattac agtgcagttt agttaatcta ttaatactga ctcagtgtct     240
gcctttaaat ataaatgata tgttgaaaac ttaaggaagc aaatgctaca tatatgcaat     300
ataaaatagt aatgtgatgc tgatgctgtt aaccaaaggg cagaataaat aagcaaaatg     360
ccaaaagggg tcttaattga aatgaaaatt taattttgtt ttt                       403

<210> SEQ ID NO 323
<211> LENGTH: 298
<212> TYPE: DNA
<213> ORGANISM: Homo sapien

<400> SEQUENCE: 323
ccagaattag ggaatcagaa tcaaaccagt gtaaggcagt gctggctgcc attgcctggt      60
cacattgaaa ttggtggctt cattctagat gtagcttgtg cagatgtagc aggaaaatag     120
gaaaacctac catctcagtg agcaccagct gcctcccaaa ggaggggcag ccgtgcttat     180 attttatgg ttacaatggc acaaaattat tatcaaccta actaaaacat tccttttctc     240 tttttcctg aattatcatg gagttttcta attctctctt ttggaatgta gattttttt      298

<210> SEQ ID NO 324
<211> LENGTH: 78
<212> TYPE: DNA
<213> ORGANISM: Homo sapien

<400> SEQUENCE: 324
ccatgggaag gtttaccagt agaatccttg ctaggttgat gtgggccata cattcccttta    60 ataaaccatt gtgtacat                                                   78

<210> SEQ ID NO 325
<211> LENGTH: 174
<212> TYPE: DNA
<213> ORGANISM: Homo sapien

<400> SEQUENCE: 325
ccatcatggt caggaactcc gggaagtcaa tggtcccgtt cccatctgca tccacctcat      60
tgatcatatc ctgcagctct gcttcagtgg ggttctgtcc cagggatctc atcactgtcc     120
ccaactcctt ggtggtgata gtgccatctc catccttgtc aaagagggag aagg           174

<210> SEQ ID NO 326
<211> LENGTH: 679
<212> TYPE: DNA
<213> ORGANISM: Homo sapien
<220> FEATURE:
<221> NAME/KEY: misc_feature
<222> LOCATION: (1)...(679)
<223> OTHER INFORMATION: n = A,T,C or G

<400> SEQUENCE: 326
aaaactgaaa tacctcttaa aataatttga tccccagcgt ttgctctttt tgaagtaacc      60
aacttactct taaaaaggat ggntgccaag atggaaagtc ttactgggtt ttcatgttaa     120
```

```
cctattctttt ggacataact atgaattttg tatacaatgc acttcatgaa aagttgtggc       180
tcccccagat tgcccacaag tgtgatcttg aagtcctaaa catttgtcca tgtaagcttc       240
aaaacagcgt taactgagtt attcaagtag cagtacttaa agatacaatt cttgaagcag       300
tttcaatggt ttctgatcca aataatcagt ttctgaacat tactacttca cataatagag       360
tccatcttca gtttcttctc actttctctt tccctttggg gtttcctttt tgtggcctga       420
ggccaccagt tctttgggta ctatcaagat acttccatca tgggtacact ggagagcata       480
gtggttggga ttgactggcc taccttggtc atctcttaat ctactaaaaa tatcatgata       540
aaggtcatgc agtttctgtt tcattatgtt aatagctttg gtacattgtg cttgctctct       600
cttaanagtt tccttctttg cttgcaagtt acatacatca tcttctaaat tcaaaattat       660
gtccattttg gcgtttacc                                                    679

<210> SEQ ID NO 327
<211> LENGTH: 619
<212> TYPE: DNA
<213> ORGANISM: Homo sapien
<220> FEATURE:
<221> NAME/KEY: misc_feature
<222> LOCATION: (1)...(619)
<223> OTHER INFORMATION: n = A,T,C or G

<400> SEQUENCE: 327
aaaataagtt actggtaaat ggagttgcat tctatagtca cttaataaat attaacaaaa        60
tatttataac tggaacctta atgaaatgta tcatcaaatc aggtaaaagc aacttgtccg       120
cagttaccaa agcctanata cgcgttagat gcgccttttc cggcctgtgc gtctgctctg       180
gttcctctca ggcagcaaag ctggggaagg aagctcaggc aggagcctcc ccgacgccac       240
aacggcacaa gcagcagcta aagcaccgca ctttgctcta ctaaccttt acttaaatga       300 ggttttgcca aatccacatc tggaaccgcg tcacacccat ttgcaaggat gtttgttctt       360
tgatgaaact gcatctctac tgcacatgag ggctttcatt gtaggacaag aggagagttc       420
gtttattttt gtaactgttt tacatgttcc gattagttaa tcggtagctt atgtcatttg       480
ctatgcctgn agncttctaa tctctcctta ctaaaacatt acttcaaatt tgaattgacc       540
cttggttata atttatttag ccgggatttg tgtgtcattg tagagcaact ctaattcaag       600
aatagtgaca acttttaag                                                   619

<210> SEQ ID NO 328
<211> LENGTH: 132
<212> TYPE: DNA
<213> ORGANISM: Homo sapien

<400> SEQUENCE: 328
aaatccaaat acaaaagcat agtctctgca agattttgtt ctttgaattt cttgatattg        60
taattgatta ttgataactg tcatcatgaa attatctctc aataataaga taaataaact       120
agcatatgaa tc                                                           132

<210> SEQ ID NO 329
<211> LENGTH: 854
<212> TYPE: DNA
<213> ORGANISM: Homo sapien
<220> FEATURE:
<221> NAME/KEY: misc_feature
<222> LOCATION: (1)...(854)
<223> OTHER INFORMATION: n = A,T,C or G
```

<400> SEQUENCE: 329

| | | | | | |
|---|---|---|---|---|---|
| ccttgaggta | actattgcaa | aatatacagt | gtaagttcag | tctgatggaa | accccagatt | 60
| catcaaggat | acaaatctac | agtagcccaa | tggcggtttc | atagtgtata | atttattatc | 120
| aataaaatta | actccgttac | aatcagcatt | catttcctcc | aattaaaatt | aagcataaac | 180
| cctaggtagt | aaccttctgc | acatatgtat | agctccgaat | ttcctcactg | ttcgtctggt | 240
| gcaaaaacaa | tattcaagct | tgtctgatta | tgcatatttt | ctttaatcat | atagattata | 300
| tatacaaatag | acaagacagg | actatataga | taatggacag | acttaaatgc | ccgcattttt | 360
| aaggtggaga | aaatgatgaa | tctatgcatc | cccgagaaca | cttaaaattt | tttttttattt | 420
| cactgggaaa | ttcttacagc | tactttacaa | tcataggtta | acagcctagt | tatacagaag | 480
| acatattcca | ctacagagct | atactctatg | caactgtttt | ttcccctcat | aaacaacctg | 540
| agttcaaatt | gaattctatc | ttccacaatc | acaatgggtg | catcacccag | tacacagaag | 600
| tttgaatcac | aaaacataat | taccacaata | aaacacagtg | ttcaagtatc | ttggcagagc | 660
| aatctgccgc | acaaactgca | aattaaatta | actacacaga | ctaaaaacta | tacagcctac | 720
| catcacagtt | gtgcattata | aaaaagggag | tttctttcct | ttggttttaa | gtcaggaaca | 780
| gggtaggatt | ttttaccctc | nggccgggga | ccacgctaaa | ggggcgaaat | tcttgccan | 840
| natattccnt | tcac | | | | | 854

<210> SEQ ID NO 330
<211> LENGTH: 299
<212> TYPE: DNA
<213> ORGANISM: Homo sapien

<400> SEQUENCE: 330

| | | | | | |
|---|---|---|---|---|---|
| ccaatgaata | actgacttta | taatcctggg | caatcagctt | ttggcgggtt | gtaagtgctt | 60
| ctcgacactt | ttcactcatg | gattcttcaa | atttatggtt | aaagaggcac | ttatacactc | 120
| tgccctcacc | agcttgtgta | ttttcacaaa | aacgctcccg | atcatctcgg | caagcaaaat | 180
| ataaatgccg | gtctaagtga | agtcatccg | atgacagctc | agccacccgg | agaatggctt | 240
| tcttgcagag | ttcagaaact | tgaatcttgg | gttctctttc | ttctgcttct | ttcaccagg | 299

<210> SEQ ID NO 331
<211> LENGTH: 573
<212> TYPE: DNA
<213> ORGANISM: Homo sapien

<400> SEQUENCE: 331

| | | | | | |
|---|---|---|---|---|---|
| aaagatatga | acagcttaat | tttccgtgtg | attatctaat | taaaaagaa | aaacaaaaca | 60
| agcaaaatgt | tcaagttaaa | aaaaaaacat | accgggtgag | caatgcacta | aaattatcca | 120
| catgaaaaca | aatggtctgt | aatcttataa | accaacatag | catttcactg | tcaacaatgt | 180
| gaaaatttaa | tatcttctca | aacaggcata | agatgaagaa | gtgctatttt | ttaattgtaa | 240
| aaggaactta | tgtaatgtaa | aattacatta | taattttca | ttccgaattg | acaaatgatt | 300
| tcaaaaacaa | ggatcaaagt | ttgactgcaa | atagtaatgc | aatataattt | cataaaaatc | 360
| cttcaatttc | tattttttc | cttttctgta | gttgacatat | gaagaccact | tcaatttcta | 420
| aaaagggaa | ccattccaat | tttccctccc | caagaaaatg | tctcacaatt | acaaagtaga | 480
| aaaacagccg | ttcataaatg | caaaaaaatt | ctgatttata | tatgaaataa | tttctagatc | 540
| aattcaacat | atttgatgac | atttgttgag | ttt | | | 573

<210> SEQ ID NO 332
<211> LENGTH: 555
<212> TYPE: DNA
<213> ORGANISM: Homo sapien

<400> SEQUENCE: 332

| | | | | | |
|---|---|---|---|---|---|
| aaatttgaaa | gttgtaagca | ctgatgttaa | tgtgattgat | cagcatgggc | atatgtaaaa | 60 |
| tgtccttttc | tggttgcctc | tctatgctat | tgtgttcaga | tacttacacc | ataattaaac | 120 |
| agtaagttat | agacttgctg | agtttggcat | agatagtgcg | ctcatttaat | ctgtgcctct | 180 |
| caaaacttca | gaatattagc | atattaccac | aaataatttt | tggtgaaact | attgagatat | 240 |
| taaaatttt | gaaatcacta | ctgttacctg | ttatagaaaa | tagtgttggc | ttagtctagt | 300 |
| ctctgtgtaa | ctggttacat | tttgatggtt | gtctatactc | aactggatat | gtgtatgtaa | 360 |
| attagaaaat | acatacctat | ccagacataa | atgctaagta | acatttttt | cttcctccaa | 420 |
| ctacataatt | tgtagctcat | cattttcct | taatccttc | ctaacttgtc | gcagcagttt | 480 |
| gaatttccca | gatatttatg | tttgaacata | atggctcaga | atacatattt | gaacatcata | 540 |
| gttgtatata | ttttt | | | | | 555 |

<210> SEQ ID NO 333
<211> LENGTH: 460
<212> TYPE: DNA
<213> ORGANISM: Homo sapien

<400> SEQUENCE: 333

| | | | | | |
|---|---|---|---|---|---|
| aatttctttt | caacagtcta | ttggggtcca | aaaagcatat | atcaaaacaa | aataacaaa | 60 |
| gcaaaacaa | aatgctacat | gtaaaagcta | agaaagaaa | atgcagcata | ttcaggttct | 120 |
| tttcttgag | gtacctatat | aaatttaatc | acctgcccca | aagtcctctc | gttaggttaa | 180 |
| aacacaatg | cgtcctgggg | agccaattgc | ccggcacgtc | ttattactga | gaaagtgcaa | 240 |
| aatgctgat | catcttatgc | agcatactaa | aggatgattt | actctttaca | aaatagagct | 300 |
| aagtatcaa | cctgatggaa | gttagaaaat | taaaacatt | taagtagaat | catctctctc | 360 |
| ctatttttg | agatcctgca | gcaaaaagcc | tcccaaatca | actttcaaag | ttctgccatt | 420 |
| aggaatgtt | ggttctcttg | taaaattcag | agatctcttt | | | 460 |

<210> SEQ ID NO 334
<211> LENGTH: 190
<212> TYPE: DNA
<213> ORGANISM: Homo sapien

<400> SEQUENCE: 334

| | | | | | |
|---|---|---|---|---|---|
| ccaaggaagg | ctgtgctcta | gcccatctga | ccctgtctgc | aaaccacctg | ggggacaagg | 60 |
| ctgatagaga | cctgtgcaga | tgtctctctc | tgtgcccctc | actcatctca | ctggatctgt | 120 |
| ctgccaaccc | tgagatcagc | tgtgccagct | tggaagagct | cctgtccacc | ctccaaaagc | 180 |
| ggccccaagg | | | | | | 190 |

<210> SEQ ID NO 335
<211> LENGTH: 394
<212> TYPE: DNA
<213> ORGANISM: Homo sapien

<400> SEQUENCE: 335

| | | | | | |
|---|---|---|---|---|---|
| aaatttggac | agactctag | cggacagtta | cttctcaaga | attttctata | caaaagctgt | 60 |
| gccaggcata | tatttctca | ccaggacaca | tggggcagcg | gacccctggt | gtcagtaaga | 120 |

```
acacacccag aatgtataa ccagatattt ttcagtttct aaattaaggc atattcaaaa      180
aattccatgt acaatttac accactttc taagttactc accaggtaat taaagcagat      240
tcacagatga attatctca gtttaactat atgcaacaac catgccaata actttctctc     300
taaattttgc ataaaatgg ttaaaaaaag tggtagttta actatcatgt tcacaattgt      360
catttttcaa ggcatagaa gaccaagaca tttt                                 394
```

<210> SEQ ID NO 336
<211> LENGTH: 429
<212> TYPE: DNA
<213> ORGANISM: Homo sapien

<400> SEQUENCE: 336

```
aaagctatc accattgtag tagaatcatc cttcttttt gaaatttgaa gcatcccagg       60 ttaaaatct tgtgtttcag aaagacagtt ataccatga ctgcttaatt atcccccaa      120 gaccttctg attgaagtca tgtacagttc agtggcctaa attctctgcc tttttaactt     180 ctttgcaag cctactctga aataagtta tttagtcaag ttattctcaa agatgtccca      240 ttgcctaga aaggatcaaa tggaacattt gacacacata ctcaaaaaa tgtaactgac      300 ataaacact ttaacctaat catctgtatc aaactttcta aaaatcaaat ctcaggattg     360 tccactta gagattctat gtaaagttta taactata cttgtcaaat agcacctatc        420
atgcattt                                                             429
```

<210> SEQ ID NO 337
<211> LENGTH: 373
<212> TYPE: DNA
<213> ORGANISM: Homo sapien

<400> SEQUENCE: 337

```
aaagatgctg ttaagaaca ttacggacaa ttcatggtgt ggctagttgg taacacttca       60
gctgattttt cttagagat ggaaaaaaaa atcagccaag taagggcaca tcttcagttc      120
atttagaagt cagctccaa ggtaaaagaa ttctctgttg gacttgacat cactcccatc       180
ctctgatact cgccactct cttctcaaag aagttagtct ttccttccag tgaaatattc      240
tccataaagt caagggtt ctctactctg aaaaccttgc taaaacccag ttccagcata      300
agtctgtctg ccacaactc aatgtattgc ttcatcagag tgcaattcat cccaatgagt      360
ttcacaggca agg                                                       373
```

<210> SEQ ID NO 338
<211> LENGTH: 366
<212> TYPE: DNA
<213> ORGANISM: Homo sapien

<400> SEQUENCE: 338

```
ccatcccctt atgacgggc gcagtgatta taggctttcg ctctaagatt aaaaatgccc       60
tagcccactt cttacacaa ggcacaccta caccccttat ccccatacta gttattatcg     120
aaaccatcag cctatcatt caaccaatag ccctggccgt acgcctaacc gctaacatta     180
ctgcaggcca cctatcatg cacctaattg gaagcgccac cctagcaata tcaaccatta    240
accttccctc tacattatc atcttcacaa ttctaattct actgactatc ctagaaatcg      300
ctgtcgcctt aatcaagcc tacgttttca cacttctagt aagcctctac ctgcacgaca      360
acacat                                                               366
```

```
<210> SEQ ID NO 339
<211> LENGTH: 319
<212> TYPE: DNA
<213> ORGANISM: Homo sapien

<400> SEQUENCE: 339
ccttccctcc ccaccaccat caacctcttc aaaacctact ccctccctct aagtatctct      60
caacacagta tgtctggggc tagatttcaa aacccacgta atgaaaaagt cagttttaca     120
agcctaattt tgttgttttt tttttttatat caattaacgt taaaaattgc atcaactatt    180
taattcatga ggatctttca tattaaaatt taaccttaag attcaaccgc catgtgcttt     240
tataaaggaa acattttta gagacgtctg agctcacttt tacatggtgg tgcctactgc      300
cgttaatgtt tgtgatttt                                                  319

<210> SEQ ID NO 340
<211> LENGTH: 278
<212> TYPE: DNA
<213> ORGANISM: Homo sapien
<220> FEATURE:
<221> NAME/KEY: misc_feature
<222> LOCATION: (1)...(278)
<223> OTHER INFORMATION: n = A,T,C or G

<400> SEQUENCE: 340
ctaataaaat gaattaacca ctcattcatn natctaccca cccnatccaa catctccnca      60
tgatgaaacn ncggctcact ccttggcgcc tgcctgatcc tccaantcac cacaggacta    120
ttcctagcca tgcactactn accagacncc tcaacngcct tttnatcaat nggncacatn    180
actcganacn taaatnatgg ctgaatcatc cgctacctnc acgccaatgg cagcctcaat    240
attctttatg ctgcctcttc ctacacatgc gggcgagg                             278

<210> SEQ ID NO 341
<211> LENGTH: 400
<212> TYPE: DNA
<213> ORGANISM: Homo sapien

<400> SEQUENCE: 341
ccagcatggg gctgagctg aacctcacct atgagaggaa ggacaacacg acggtgacaa       60
ggcttctcaa catcaccccc aacaagacct cggccagcgg gagctgcggc gcccacctgg    120
tgactctgga gctgacagc gagggcacca ccgtcctgct cttccagttc gggatgaatg     180
caagttctag ccggttttc ctacaaggaa ttcagttgaa tacaattctt cctgacgcca     240
gagaccctgc ctttaagct gccaacggct ccctgcgagc gctgcaggcc acagtcggca     300
attcctacaa gtgcacgcg gaggagcacg tccgtgtcac gaaggcgttt tcagtcaata     360
tattcaaagt gtggtccag gctttcaagg tggaaggtgg                            400

<210> SEQ ID NO 342
<211> LENGTH: 536
<212> TYPE: DNA
<213> ORGANISM: Homo sapien

<400> SEQUENCE: 342 aagaacaat gggaaaaaca agtccgtgtt ctcacagatg ctgtcgatga cattacttcc       60 ttgatgact tcttggctgt ctcagagaat cacatttggg aagatgtgaa caaatgtgtc     120 ttgctctcc aagagaagga tgtggatggc ctggaccgca cagctggtgc aattcgaggc     180 gggcagccc gggtcattca cgtagtcacc tcagagatgg acaactatga gccaggagtc     240
```

-continued

```
acacagaga aggttctgga agccactaag ctgctctcca acacagtcat gccacgtttt    300 ctgagcaag tagaagcagc cgtggaagcc ctcagctcgg accctgccca gcccatggat    360 agaatgagt ttatcgatgc ttcccgcctg gtatatgatg catccggga catcaggaaa    420 cagtgctga tgataaggac ccctgaggag ttggatgact ctgactttga gacagaagat    480 ttgatgtca gaagcaggac gagcgtccag acagaagacg atcagctgat agctgg       536
```

<210> SEQ ID NO 343
<211> LENGTH: 646
<212> TYPE: DNA
<213> ORGANISM: Homo sapien

<400> SEQUENCE: 343

```
aaaacttcta ttcatcaaaa gacataaaga aaacagtcaa gccacagact aggtgtaata    60
tctcaataca tatatccgac aagagaattg catctagaat gtataaagaa tttctatgac   120
ccaattatag ctatcaggga tatacaaatt aaaaccaaaa tgaaacatca ctacacaccg   180
attggaatgg ttaaaaagga aaatactga caacaccaat atttgtaaag acaggaggta   240
ccagaactct cattcattat attcataaat tgacaaatat aaaaactgct atagtagggc   300
agtcttcctt agaaagggat tgtgggcatg acagagaaca atattaatct gtccattata   360
ttccttaact gtaaaatgga gaccatatgt tccaccagct tcacttggta attatgatac   420
atggctatta agagactcaa atgactccat ttcatcaact aatatgccct gtcaattcta   480
cttctaaagt atcccatgtt ctatccaatg tcataccact atcataattt aagtgttcat   540
aactctctat aatatttcaa taatctaact ggtctcaatg cctgtagtag aaattgcaga   600
ttgggctccc caatttctgt tccctaggaa ggctgagaaa gcttt             646
```

<210> SEQ ID NO 344
<211> LENGTH: 383
<212> TYPE: DNA
<213> ORGANISM: Homo sapien

<400> SEQUENCE: 344

```
cctgcacccc agtataaggg cctccccagc tgagtaagaa gctgcttccc ctcctctcat    60
aggccaagcc tattgtgtga aaccatctca tggtcttggt gacgtagacc attttttgaaa  120 ccgtctcatg gtcttggtga cgtagaccgt ttgcttcttt aactccagcc gcggaatgac  180
attagtggaa ccgggctagg gaactgctgg aagttcagga tgccaccacc ttgaacacct   240
aggccaggga tccccaccat gtcccgggtt tctttcttcg agagtataga accgttcatt   300
cttgctttgt gtcccattcc atctcttgaa aaaatgtagt ctttgaatgt gtgaaaatct   360
agggacattc aatctagtct ttt                                         383
```

<210> SEQ ID NO 345
<211> LENGTH: 263
<212> TYPE: DNA
<213> ORGANISM: Homo sapien

<400> SEQUENCE: 345

```
cctcccttc ccctttgctg gtgggaggag ctcgtgtgct ccttggccgc ttactggaag    60 ggcgttttc agagctgcag ggacagggtg agcagctgaa gggctaggag ggaagccggc   120
ccccgctctg cagaagctgc atttcagctg aatctgtgtt tcagcctcag ttggttgcac   180
cgttagcccc tctcctcccg gatggtcatg tttttgtcac attagagaat aaacagccac   240
acacacattt tttttttttcc ttt                                         263
```

<210> SEQ ID NO 346
<211> LENGTH: 132
<212> TYPE: DNA
<213> ORGANISM: Homo sapien

<400> SEQUENCE: 346

```
aaatccaaat acaaaagcat agtctctgca agattttgtt ctttgaattt cttgatattg      60
taattgatta ttgataactg tcatcatgaa attatctctc aataataaga taaataaact     120
agcatatgaa tc                                                         132
```

<210> SEQ ID NO 347
<211> LENGTH: 564
<212> TYPE: DNA
<213> ORGANISM: Homo sapien
<220> FEATURE:
<221> NAME/KEY: misc_feature
<222> LOCATION: (1)...(564)
<223> OTHER INFORMATION: n = A,T,C or G

<400> SEQUENCE: 347

```
cctgggtatc cagggaggct ctgcagccct gctgaagggc cctaactaga gttctagagt      60
ttctgattct gtttctcagt agtccttta gaggcttgct atacttggtc tgcttcaagg     120
aggtcgacct tctaatgtat gaagaatggg atgcatttga tctcaagacc aaagacagat    180
gtcagtgggc tgctctggcc ctggtgtgca cggctgtggc agctgttgat gccagtgtcc    240
tctaactcat gctgtccttg tgattaaaca cctctatctc ccttgggaat aagcacatac    300
aggcttaagc tctaagatag ataggtgttt gtccttttac catcgagcta cttcccataa    360
taaccacttt gcatccaaca ctcttcaccc acctcccata cgcaagggga tgtggatact    420
tggcccaaag taactggtgg taggaatctt agaaacaaga ccacttatac tgtctgtctg    480
aggnagaaga taacagcagc atctcgacca gcctctgcct taaaggaaat ctttattaat    540
cacgtatggt tcacaagata attc                                          564
```

<210> SEQ ID NO 348
<211> LENGTH: 321
<212> TYPE: DNA
<213> ORGANISM: Homo sapien
<220> FEATURE:
<221> NAME/KEY: misc_feature
<222> LOCATION: (1)...(321)
<223> OTHER INFORMATION: n = A,T,C or G

<400> SEQUENCE: 348

```
gcncatgaac anggagcaac ganaagagat gtcgggctaa gggcccggga cgggcggcac      60
ccatcctgcn acggaacacn ttcgggttnt ggttttgatt ngttcacctc tgtttatatg    120
canctatttg ntcctcctcc cccacccag ncccaactt catgcttntc ttccgcnctc     180
agccnccctg ccctgtcctc gcggtgagtc antgaccacn gnttcccctg cangagccgc    240
cgggcgtgag acncgaccc tcnntgcata caccaggccg ggcccnngct ggctcccccn    300
gnggccctgt gaaanagctg g                                             321
```

<210> SEQ ID NO 349
<211> LENGTH: 255
<212> TYPE: DNA
<213> ORGANISM: Homo sapien

<400> SEQUENCE: 349

```
ccatgacagt gaaggggctg ttaggaatat caacaccacc gaagcgcaca tagatcacat      60
atgtgcccgg cttggcagct gtgtagaaga tgtcataggt tccatcttca ttctcaatga     120
catcggcctc ggcctcagtg ccatctgggg tcagaaccgt gcaggtcact ttacccttcc     180
cggcagtctt ggcatcaacc acaaagccta cttcttcgcc agttttcaca gtggaggcga     240
ttccaggacc cgtag                                                      255

<210> SEQ ID NO 350
<211> LENGTH: 496
<212> TYPE: DNA
<213> ORGANISM: Homo sapien
<220> FEATURE:
<221> NAME/KEY: misc_feature
<222> LOCATION: (1)...(496)
<223> OTHER INFORMATION: n = A,T,C or G

<400> SEQUENCE: 350 ggcttattn gctcacaaaa tcattcnctt ttggaactat ggccaattga agctacacac      60 gaatttatt aatacagcat taagtttctt tgtgtnaaaa aatctttgtn cncagtaata     120 aaaaagata aggcaagatg cattaaacat gaaaccttct ggctcttttc ctctgcgttt     180 tacagagcc actgatgact atctgcaaca aaagagttaa gtttctgatt ttccgtatca     240 gcatcttat gcctttgctg tggtaagaat tctggccaag caccctgaag acagatgct     300 gtgatggnc tttggcactt atgctggcaa actgagcttc tttcccttga gtacttttgn     360 atgtacaag tagaagaagt cacaagtata ggatggtctg gactacgccg gccaccacag     420 aatgaggtc aaagaagccc tcaaagnaga agcgnccaga tccagttgac aagatacaaa     480 cacgataga ggccca                                                     496

<210> SEQ ID NO 351
<211> LENGTH: 109
<212> TYPE: DNA
<213> ORGANISM: Homo sapien
<220> FEATURE:
<221> NAME/KEY: misc_feature
<222> LOCATION: (1)...(109)
<223> OTHER INFORMATION: n = A,T,C or G

<400> SEQUENCE: 351
ccatagtgaa gcctgggaat gagtgttact gcagcatctg ggctgccanc cacagggaag      60
ggccaagccc catgtagccc cagtcatcct gcccagcccc gcctcctgg                109

<210> SEQ ID NO 352
<211> LENGTH: 384
<212> TYPE: DNA
<213> ORGANISM: Homo sapien

<400> SEQUENCE: 352
ccttcgagag tgacctggct gcccaccagg accgtgtgga gcagattgcc gccatcgcac      60
aggagctcaa tgagctggac tattatgact cacccagtgt caacgcccgt tgccaaaaga     120
tctgtgacca gtgggacaat ctgggggccc taactcagaa gcgaagggaa gctctggagc     180
ggaccgagaa actgctggag accattgacc agctgtactt ggagtatgcc aagcgggctg     240 caccccttcaa caactggatg gagggggcca tggaggacct gcaggacacc ttcattgtgc     300
acaccattga gggagatccag ggactgacca cagcccatga gcagttcaag gccaccctcc     360
ctgatgccga caaggagcgc ctgg                                            384
```

<210> SEQ ID NO 353
<211> LENGTH: 345
<212> TYPE: DNA
<213> ORGANISM: Homo sapien
<220> FEATURE:
<221> NAME/KEY: misc_feature
<222> LOCATION: (1)...(345)
<223> OTHER INFORMATION: n = A,T,C or G

<400> SEQUENCE: 353

```
ccttggtcag gatgaagtng gctgacacac cttagcttgg ntttgcttat tcaaaagana      60
aaataactac acatggaaat gaaactagct gaagcctttt cttgttttan caactgaaaa     120
ttgnacttgg ncacttttgt gcttgaggag gcccattttc tgcctggcag ggggcaggta     180
tgtgccctcc cgctgactcc tgctgtgtcc tgaggtgcat ttcctgttgn ncacacaang     240
gccangntcc attctccctc ccttttcacc agngccacan cctnntctgg aaaaangacc     300
agnggtcccg gaggaaccca tttgngctct gcttggacag canag                    345
```

<210> SEQ ID NO 354
<211> LENGTH: 712
<212> TYPE: DNA
<213> ORGANISM: Homo sapien

<400> SEQUENCE: 354

```
ccatctacaa tagcatcaat ggtgccatca cccagttctc ttgcaacatc tcccacctca      60
gcagcctgat cgctcagcta aagagaagc agcagcagcc caccagggag ctcctgcagg     120
acattgggga cacattgagc agggctgaaa gaatcaggat tcctgaacct tggatcacac     180
ctccagattt gcaagagaaa atccacattt ttgcccaaaa atgtctattt ttgacggaga     240
gtctaaagca gttcacagaa aaaatgcagt cagatatgga gaaaatccaa gaattaagag     300
aggctcagtt atactcagtg gacgtgactc tggacccaga cacggcctac cccagcctga     360
tcctctctga taatctgcgg caagtgcggt acagttacct ccaacaggac ctgcctgaca     420
accccgagag gttcaatctg tttccctgtg tcttgggctc tccatgcttc atcgccggga     480
gacattattg ggaggtagag gtgggagata agccaagtg gaccataggt gtctgtgaag     540
actcagtgtg cagaaaaggt ggagtaacct cagcccccca gaatggattc tgggcagtgt     600
cttttgtggta tgggaaagaa tattgggctc ttacctccca atgactgccc taccctgcg     660
gaccccgctc cagcgggtgg gggattttct tggactatga tgctggggga gg            712
```

<210> SEQ ID NO 355
<211> LENGTH: 385
<212> TYPE: DNA
<213> ORGANISM: Homo sapien

<400> SEQUENCE: 355

```
cctcatagcc gcttagcaca gttacagaat gtctgaaggg gacagtgtgg gagaatccgt      60
ccatgggaaa ccttcggtgg tgtacagatt tttcacaaga cttggacaga tttatcagtc     120
ctggctagac aagtccacac cctacacggc tgtgcgatgc gtcgtgacac tgggcctgag     180
cttttgtctac atgattcgag tttacctgct gcagggttgg tacattgtga cctatgcctt     240
ggggatctac catctaaatc ttttcatagc ttttctttct cccaaagtgg atccttcctt     300
aatggaagac tcagatgacg gtccttcgct acccaccaaa cagaacgagg aattccgccc     360
cttcattcga aggctcccag agttt                                          385
```

<210> SEQ ID NO 356

<211> LENGTH: 347
<212> TYPE: DNA
<213> ORGANISM: Homo sapien

<400> SEQUENCE: 356

```
aaatgagata agaaagtct cctttgtttt ttagatggaa agaaagcac aagttttttc    60
tacctgtgaa tgactttgg tgacctatat gtgccattca tgcagcattt ttgttcatat   120
tggcttagaa ttcagtgcat gaatatcatt acattcttat atctaacatt cctagttagc   180
tttgattcaa aatatacaaa atctgataca tgaatacttt gctagattaa tgacttgatc   240
atctttggaa tgagtaggca agacgatttt tacctattat ttctatgttg tgggtaatgt   300
taaaactaaa tacagatgat aataattgct atttcacagt gatgttt                347
```

<210> SEQ ID NO: 357
<211> LENGTH: 313
<212> TYPE: DNA
<213> ORGANISM: Homo sapien

<400> SEQUENCE: 357

```
aaagtaatca acctctctgt ccttccatta gtctggatcg tctaaagatt gttttatttt    60
tagaggctca tccggtcaga tgttagtgat gtgaaatttc aggccaggcg tgacgtcagc   120
gtggcatttg aaacagctcc atgttgccct tagtgctgtc tgaccgaagc ctgtctgtcc   180
tcagatataa agatgaagcg cagctgtata aagaagagca cctgaggaat cggcagcacc   240
ctcactgcta cgttcagtac atgatcgcca tcatcaacaa ctgccagacc ttcaaggaat   300
ccatagtcag ttt                                                      313
```

<210> SEQ ID NO 358
<211> LENGTH: 403
<212> TYPE: DNA
<213> ORGANISM: Homo sapien

<400> SEQUENCE: 358

```
aaaaagaagg acttagggtg tcgttttcac atatgacaat gttgcattta tgatgcagtt    60
tcaagtacca aaacgttgaa ttgatgatgc agttttcata tatcgagatg ttcgctcgtg   120
cagtactgtt ggttaaatga caatttatgt ggattttgca tgtaatacac agtgagacac   180
agtaattta tctaaattac agtgcagttt agttaatcta ttaatactga ctcagtgtct   240
gcctttaaat ataaatgata tgttgaaaac ttaaggaagc aaatgctaca tatatgcaat   300
ataaaatagt aatgtgatgc tgatgctgtt aaccaaaggg cagaataaat aagcaaaatg   360
ccaaaagggg tcttaattga aatgaaaatt taattttgtt ttt                     403
```

<210> SEQ ID NO 359
<211> LENGTH: 411
<212> TYPE: DNA
<213> ORGANISM: Homo sapien

<400> SEQUENCE: 359

```
aaataaatac ttgaacacg acttggctcc tacaagcatc tggactctag gtctcagtac    60
tggagtgtct cacccatggg ccccacgcag ggacgccacg gttccctccc accccgtgat   120
caagacacgg aatcggctgc cgatggttgg atcgcaatgc gccctttc tagagccttc   180
cccggccatc tacaggcagg atgcggctgg gaaaagaca actggaattt ctcgaaggtt   240
gatggtccgc acggttgagg attctacgtg gttctcttgg ttccctggt gtgtgtgtgt   300
gtggaggagg ccgcggccct tagatcacct tcttgagctc gtcgtacagg accagcacga   360
```
aggcgccccc catgccccgc aggacgttgg accacgcacc cttgaagaag g    411

<210> SEQ ID NO 360
<211> LENGTH: 378
<212> TYPE: DNA
<213> ORGANISM: Homo sapien
<220> FEATURE:
<221> NAME/KEY: misc_feature
<222> LOCATION: (1)...(378)
<223> OTHER INFORMATION: n = A,T,C or G

<400> SEQUENCE: 360
cctcttcagg ggcccgagcc agggacaggg ccttggtttc cttctccctg gcttctgcct    60
cagctctgtc cctctcatcc gcgtatttgg aagagatgtt ttctcctcg gctaacaact    120
gatcaaattt cctctgcttc ttttccaggt tggacacgag ttgccgctgg ttgtccaaat    180
caacaaccag gtcgtccagc tcctgctgaa gcctgttctt ggtcttttcc agtttatcat    240
aagcggccgc cttctcctcg tactgctggg tgaggntctc gatctccttc tggaacctct    300
tcttcccctc ttccagagct tccacggngc tggcaaagtc ctgcagcttc ttcttcgagt    360
cggagagctg gatgttga    378

<210> SEQ ID NO 361
<211> LENGTH: 372
<212> TYPE: DNA
<213> ORGANISM: Homo sapien

<400> SEQUENCE: 361
aaatactggg ggccattaag agtggatgta gctaagagct tagctaacat tgccttttca    60
ctctatttt ctcagatatt gtaagcattc tgttttttcaa tattgtagtt aattttttgg    120
ctttcaacag cagccctagt aatggtggag ttgttaatta atgtgtatat tgtactgaat    180
ttctgtcagt taagggggttc actgctttgg tggaaattgg tggaaattgc tagcaggttc    240
cacgatgttt attttttttct ccatgttgta tatcattacc atttcacata cgcgtttcta    300
ttttcttcc tctcctcctg atctccttaa aaatgaatct agagttggtg gcttttttccc    360
cctcctcttt gg    372

<210> SEQ ID NO 362
<211> LENGTH: 544
<212> TYPE: DNA
<213> ORGANISM: Homo sapien

<400> SEQUENCE: 362
cctgagtcac ctagcatagg gttgcagcaa gccctggatt cagagtgtta aacagaggct    60
tgccctcttc aggacaacag ttccaattcc aaggagccta cctgaggtcc ctactctcac    120
tggggtcccc aggatgaaaa cgacaatgtg ccttttattatt attatttatt tggtggtcct    180
gtgttattta agagatcaaa tgtataacca cctagctctt ttcacctgac ttagtaataa    240
ctcatactaa ctggtttgga tgcctgggtt gtgacttcta ctgaccgcta gataaacgtg    300
tgcctgtccc ccaggtggtg ggaataattt acaatctgtc caaccagaaa agaatgtgtg    360
tgtttgagca gcattgacac atatctactt tgataagaga cttcctgatt ctctaggtcg    420
gttcgtggtt atcccattgt ggaaattcat cttgaatccc attgtcctat agtcctagca    480
ataagagaaa tttcctcaag tttccatgtg cggttctcct agctgcagca atactttgac    540
attt    544

<210> SEQ ID NO 363
<211> LENGTH: 328
<212> TYPE: DNA
<213> ORGANISM: Homo sapien

<400> SEQUENCE: 363

```
aaactggtta tgacaaaagc ctttagttgt gtttcttgaa ctataaagaa aacaaatttt      60
ggcagtcttt aagtatatat agcttaaaat ataatttta gcatttggca ccatatgtat      120
gccattatat ttgattttgc attactgttt cacaatgaag ctttctttaa ggctttgatt      180
tttatgatta tgaaagaaat aaggcacaac cacagttttt ctttcttaaa tttcatcact      240
gttgatgtgg ttcttttgtg ttaaaaaaaa aaagtgcaac tatcaaaact aaaaaattat      300
agagtaatat tgccgttctg ctgattttt                                       328
```

<210> SEQ ID NO 364
<211> LENGTH: 569
<212> TYPE: DNA
<213> ORGANISM: Homo sapien

<400> SEQUENCE: 364

```
cctgggcacc tctttgcttg aaatatggca agacttggaa aaatgtttgc ccttagaatc      60
tatctcacta ctttagttag ttgtctcctt tgggcctggg cacagttctg gccctgatct     120
ggaacagact ccctttcta aaactgaact tgaccacatc aaaagtttgt aaaacaatct      180
ccatggtaat taaacttgca ttcaacacca tatggtaaca gaagatggca aaggataaga    240
ttcagatctt agatctttcc aagtagggca tgttagatga tagaaggatt agttgcaagc    300
tggatctgag ctcaggcttg ggcatgaagg aaactgtctc ccatgtggtt tggaagagtt    360
aggggctccc tgagctctat tgtgaactat acgggtttca tccaaggaat ggtatgatgt    420
gggcataaaa ccattcttca gacaactgaa gatggtcccc ttctgtagcc agaaacacta    480
gctgtcctgc attgtccatt tcctttagcc ccaggcggtc ctgtgtgtac agggaggtct    540
cctgtaaggg aatggtttcc ttggcttgg                                      569
```

<210> SEQ ID NO 365
<211> LENGTH: 151
<212> TYPE: DNA
<213> ORGANISM: Homo sapien

<400> SEQUENCE: 365

```
aaaaaaaaaa atcctttat tatggaattt gtcaaacaca cacacaagca taacaaaccc      60
ctaggtaccc atctccaagt tttgaccccct attataattt catcttcagt gttttattat    120
ccacttcctc tctctctatc tttagtattt t                                    151
```

<210> SEQ ID NO 366
<211> LENGTH: 508
<212> TYPE: DNA
<213> ORGANISM: Homo sapien
<220> FEATURE:
<221> NAME/KEY: misc_feature
<222> LOCATION: (1)...(508)
<223> OTHER INFORMATION: n = A,T,C or G

<400> SEQUENCE: 366

```
agtataaaga tatattccat aaaagagttt ggcagtcaaa ganaagcatc gcacttccga      60
aaaacacaag cattcttctc ctagtctaca gagaattgng taaaaaaaaa aaaaaatcat     120
catcaacagc cnccantnta cnccacacta gaatgtacac tccggcaagt aaattaaggn    180
```

```
tgcagtccat ccctgaacga tganaagngg tctgagctat ggcaaagngt tanaaagtag      240
cccagctana caaatgcccc agctatcccc aggggagtta ttcagtactt aanacttcat      300
ttccaananc agccccggaa aagccctgac aggaaggggg gaccagngat caccgatntc      360
ccattagggg cggncaccaa aaacaaaatg cctggagctt ntgagcagct gcagcctggg      420
gttgtggcta ggcncngggn gnggttgcaa aaaacggct gtntccgggg agaggcaaat      480
ggcaggccag ccagccctgg gtacatgg                                         508
```

<210> SEQ ID NO 367
<211> LENGTH: 382
<212> TYPE: DNA
<213> ORGANISM: Homo sapien

<400> SEQUENCE: 367

```
cctgagcggc tagtctttaa gatgcgcttc tatcgtttgc tgcaaatccg agcagaagcc       60
ctcctggcgg caggcagcca tgtgatcatt ctgggtgacc tgaatacagc ccaccgcccc      120
attgaccact gggatgcagt caacctggaa tgctttgaag aggacccagg gcgcaagtgg      180
atggacagct tgctcagtaa cttggggtgc cagtctgcct ctcatgtagg gcccttcatc      240
gatagctacc gctgcttcca accaaagcag gaggggggcct tcacctgctg gtcagcagtc      300
actggcgccc gccatctcaa ctatggctcc cggcttgact atgtgctggg ggacaggacc      360
ctggtcatag acacctttca gg                                               382
```

<210> SEQ ID NO 368
<211> LENGTH: 174
<212> TYPE: DNA
<213> ORGANISM: Homo sapien

<400> SEQUENCE: 368

```
ccttctccct ctttgacaag gatggagatg gcactatcac caccaaggag ttggggacag       60
tgatgagatc cctgggacag aaccccactg aagcagagct gcaggatatg atcaatgagg      120
tggatgcaga tgggaacggg accattgact cccggagtt cctgaccatg atgg             174
```

<210> SEQ ID NO 369
<211> LENGTH: 216
<212> TYPE: DNA
<213> ORGANISM: Homo sapien

<400> SEQUENCE: 369

```
aaatctcatg ggttctatta aaaaaatata tatatagggc cccaatccat tgccatcaaa       60
ttgcccttgg acttttccaa ggtatattat ggggttttat gcaaaattcc aagctaccat      120 gtaactttt ttaaccattt aacaaggagg gggaactgtt tcctaccttc tttacatgtt      180
gtgcattgtt gtggtccaga aatgccaaac ctttttt                              216
```

<210> SEQ ID NO 370
<211> LENGTH: 344
<212> TYPE: DNA
<213> ORGANISM: Homo sapien

<400> SEQUENCE: 370

```
ccttggtcag gatgaagttg gctgacacag cttagcttgg ttttgcttat tcaaaagaga       60
aaataactac acatggaaat gaaactagct gaagcctttt cttgttttag caactgaaaa      120
ttgtacttgg tcactttgt gcttgaggag gcccattttc tgcctggcag ggggcaggtc      180
```

-continued

```
tgtgccctcc cgctgactcc tgctgtgtcc tgaggtgcat ttcctgttgt acacacaagg    240
gccaggctcc attctccctc cctttccacc agtgccacag cctcgtctgg aaaaaggacc    300
aggggtcccg gaggaaccca tttgtgctct gcttggacag cagg                     344

<210> SEQ ID NO 371
<211> LENGTH: 741
<212> TYPE: DNA
<213> ORGANISM: Homo sapien
<220> FEATURE:
<221> NAME/KEY: misc_feature
<222> LOCATION: (1)...(741)
<223> OTHER INFORMATION: n = A,T,C or G

<400> SEQUENCE: 371
aaattacata tctaattgtg tgatttgtta aatgcccatt tcttcatcta agtgctaagt     60
gctaagtgta gcagtttgtt ccctgctaca ctccaaggca caaggagtt caaggaatgt    120 gcaatggaaa tcagttagat gaatgtgtta ggaaccttcc ctttaataaa gctggatccc   180
acactagccc ctacaccctc tcatcaccaa atattcctgc ttcctctcac ctgcacttgc   240
tgttctctcc tctgccacac aaatctacct ctcaagccta ggtcccacct gcttcatgac   300
aactttccag actattccag aacctttaac catctctgac ctctcatcag atctatgttg   360
tacataacac caattaatga gatcattact gctttatgct ctaattgctt cctgtattca   420
aaatcttctc tccaaccaca taatgactcc ctaaacttct cttgtatttt ccaatgcctt   480
gtacaagcac agaactggtc aatcaataaa tactcactgg ttatttgagg aaaaaatgtt   540
gccaagcacc atctttatca gaaaataaat caattcttct aaacttggag aaatcaccct   600
attcctagta tgtgatctta attagaacaa ttcagattga gaangngaca gcatgctggc   660
agtcctcaga gccctcgctt gctctcggna cctccctgcc tgggctccca ctttggtggc   720
atttgaggag cccttcagcc t                                             741
```